United States Patent [19]

Or et al.

[11] Patent Number: 6,028,181

[45] Date of Patent: *Feb. 22, 2000

[54] 6-0-SUBSTITUTED ANTIBACTERIAL ERYTHROMYCIN KETOLIDES AND METHODS OF MAKING

[75] Inventors: Yat Sun Or, Libertyville; Zhenkun Ma, Gurnee; Richard F. Clark, Mundelein, all of Ill.; Daniel T. Chu, Santa Clara; Jacob J. Plattner, Berkeley, both of Calif.; George Griesgraber, Libertyville, Ill.

[73] Assignee: Abbott Laboratories, Abbott Park, Ill.

[ * ] Notice: This patent issued on a continued prosecution application filed under 37 CFR 1.53(d), and is subject to the twenty year patent term provisions of 35 U.S.C. 154(a)(2).

[21] Appl. No.: 09/186,395

[22] Filed: Nov. 4, 1998

Related U.S. Application Data

[60] Division of application No. 08/888,350, Jul. 3, 1997, Pat. No. 5,866,549, which is a continuation-in-part of application No. 08/707,776, Sep. 4, 1996, abandoned.

[51] Int. Cl.$^7$ .......................... C07H 17/08; A61K 31/70
[52] U.S. Cl. .................. 536/7.2; 536/7.4; 514/29
[58] Field of Search ................ 536/7.2, 7.4; 514/29

[56] References Cited

U.S. PATENT DOCUMENTS

| | | | |
|---|---|---|---|
| 5,350,839 | 9/1994 | Asaka et al. | 536/7.4 |
| 5,439,889 | 8/1995 | Agouridas et al. | 514/29 |
| 5,439,890 | 8/1995 | Agouridas et al. | 514/29 |
| 5,444,051 | 8/1995 | Agouridas et al. | 514/29 |
| 5,527,780 | 6/1996 | Agouridas et al. | 514/29 |
| 5,543,400 | 8/1996 | Agouridas et al. | 514/29 |
| 5,561,118 | 10/1996 | Agouridas et al. | 514/29 |
| 5,614,614 | 3/1997 | Agouridas et al. | 536/7.5 |
| 5,770,579 | 6/1998 | Agouridas et al. | 514/29 |

FOREIGN PATENT DOCUMENTS

| | | |
|---|---|---|
| 0487411 | 5/1992 | European Pat. Off. . |
| 0596802 | 5/1994 | European Pat. Off. . |
| 0565364 | 6/1995 | European Pat. Off. . |
| 0676409 | 10/1995 | European Pat. Off. . |
| 0680967 | 11/1995 | European Pat. Off. . |
| 2697524 | 5/1994 | France . |
| 2738571 | 3/1997 | France . |
| 9321200 | 10/1983 | WIPO . |
| 9209614 | 6/1992 | WIPO . |
| 9313116 | 7/1993 | WIPO . |
| 9313663 | 7/1993 | WIPO . |
| 9321199 | 10/1993 | WIPO . |
| 9710251 | 3/1997 | WIPO . |
| 9717356 | 5/1997 | WIPO . |
| 9830574 | 7/1998 | WIPO . |

OTHER PUBLICATIONS

Pestka et al. (I), "Effect of Erythromycin Analogues on Binding of [$^{14}$C]Erythromycin to *Escherichia coli* Ribosomes," *Antimicrobial Agents and Chemotherapy*, 6(4), 488–491 (Oct. 1974).

Pestka et al. (II), "Correlation of Effects of Erythromycin Analogues on Intact Bacteria and on [$^{14}$C]Erythromycin Binding to *Escherichia coli* Ribosomes," *Antimicrobial Agents and Chemotherapy*, 6(4), 488–491 (Oct. 1974).

Pestka et al. (III), "Inhibition of [$^{14}$C]Chloramphenicol Binding to *Escherichia coli* Ribosomes by Erythromycin Derivatives," *Antimicrobial Agents and Chemotherapy*, 6(1), 39–45 (Jul. 1974).

Pestka et al. (IV), "Induction of Erythromycin Resistance in *Staphylococcus aureus* by Erythromycin Derivatives," *Antimicrobial Agents and Chemotherapy*, 9(1), 128–130 (Jan. 1976).

LeMahieu et al., "Glycoside Cleavage Reactions on Erythromycin A. Preparation of Erythronolide A," *J. Medicinal Chem.*, 17(9), 953–956 (Sep. 1974).

Agouridas et al. (X), "Synthesis and Antibacterial Activity of Ketolides (6–0–Methyl–3–oxoerythromycin Derivatives): A New Class of Antibacterials Highly Potent Against Macrolide–Resistant and –Susceptible Respiratory Pathogens," *J. Medicinal Chemistry*, 41(21), 4080–4100 (Oct. 8, 1998).

*Primary Examiner*—L. Eric Crane
*Attorney, Agent, or Firm*—Mona Anand; Portia Chen

[57] ABSTRACT

Antimicrobial compounds having the formula

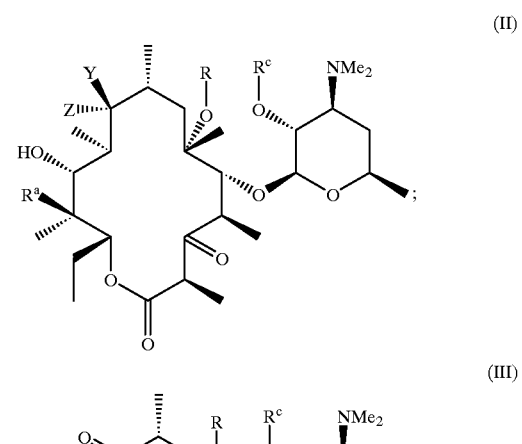

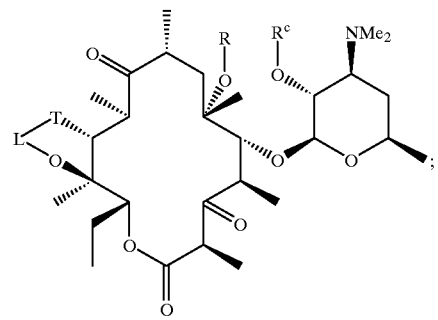

-continued
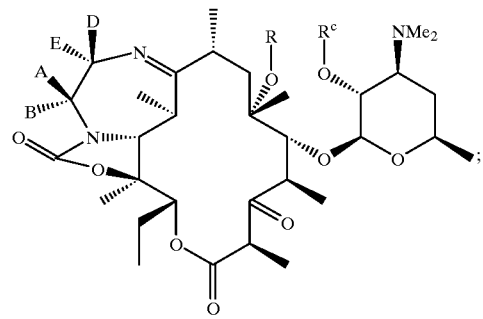
(IV)
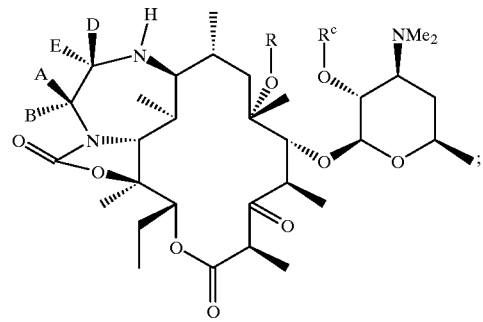
(IV-A)
-continued
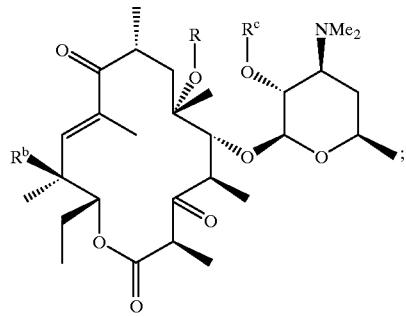
(V)
as well as pharmaceutically acceptable salts, esters or prodrugs thereof; pharmaceutical compositions comprising such compounds; methods of treating bacterial infections by the administration of such compounds; and processes for the preparation of the compounds.
9 Claims, No Drawings

6-0-SUBSTITUTED ANTIBACTERIAL ERYTHROMYCIN KETOLIDES AND METHODS OF MAKING

This is a divisional of U.S. patent application Ser. No. 08/888,350, filed Jul. 3, 1997, now U.S. Pat. No. 5,866,549, which is a continuation-in-part of U.S. application Ser. No. 08/707,776, filed Sep. 4, 1996, now abandoned.

TECHNICAL FIELD

This invention relates to novel semi-synthetic macrolides having antibacterial activity, to pharmaceutical compositions comprising these compounds, and to a medical method of treatment. More particularly, this invention concerns to 6-O-substituted erythromycin ketolide derivatives, compositions containing these compounds, and a method of treating bacterial infections.

BACKGROUND OF THE INVENTION

Erythromycins A through D, represented by formula (I),

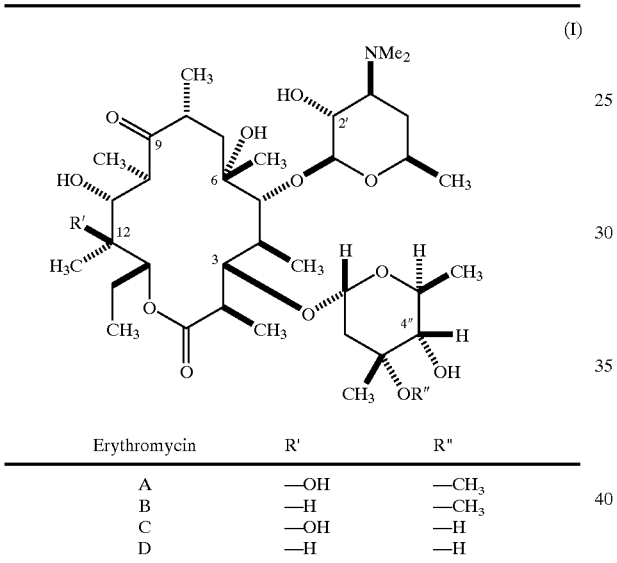

| Erythromycin | R' | R" |
|---|---|---|
| A | —OH | —$CH_3$ |
| B | —H | —$CH_3$ |
| C | —OH | —H |
| D | —H | —H | are well-known and potent antibacterial agents, used widely to treat and prevent bacterial infection. As with other antibacterial agents, however, bacterial strains having resistance or insufficient susceptibility to erythromycin have been identified. Also, erythromycin A has only weak activity against Gram-negative bacteria. Therefore, there is a continuing need to identify new erythromycin derivative compounds which possess improved antibacterial activity, which have less potential for developing resistance, which possess the desired Gram-negative activity, or which possess unexpected selectivity against target microorganisms. Consequently, numerous investigators have prepared chemical derivatives of erythromycin in an attempt to obtain analogs having modified or improved profiles of antibiotic activity.

U.S. Pat. No. 5,444,051 discloses 6-O-substituted-3-oxoerythromycin A derivatives in which the substituents are selected from alkyl, —$CONH_2$, —CONHC(O)alkyl and —$CONHSO_2$alkyl. PCT application WO 97/10251, published Mar. 20, 1997, discloses 6-O-methyl 3-descladinose erythromycin derivatives.

European Patent Application 596802, published May 11, 1994, discloses bicyclic 6-O-methyl-3-oxoerythromycin A derivatives.

PCT application WO 92/09614, published Jun. 11, 1992, discloses tricyclic 6-O-methylerythromycin A derivatives.

SUMMARY OF THE INVENTION

The present invention provides a novel class of 6-O-substituted erythromycin derivatives possessing increased acid stability relative to erythromycin A and 6-O-methyl erythromycin A and enhanced activity toward gram negative bacteria and macrolide resistant gram positive bacteria.

In one embodiment, the present invention provides compounds selected from the group consisting of

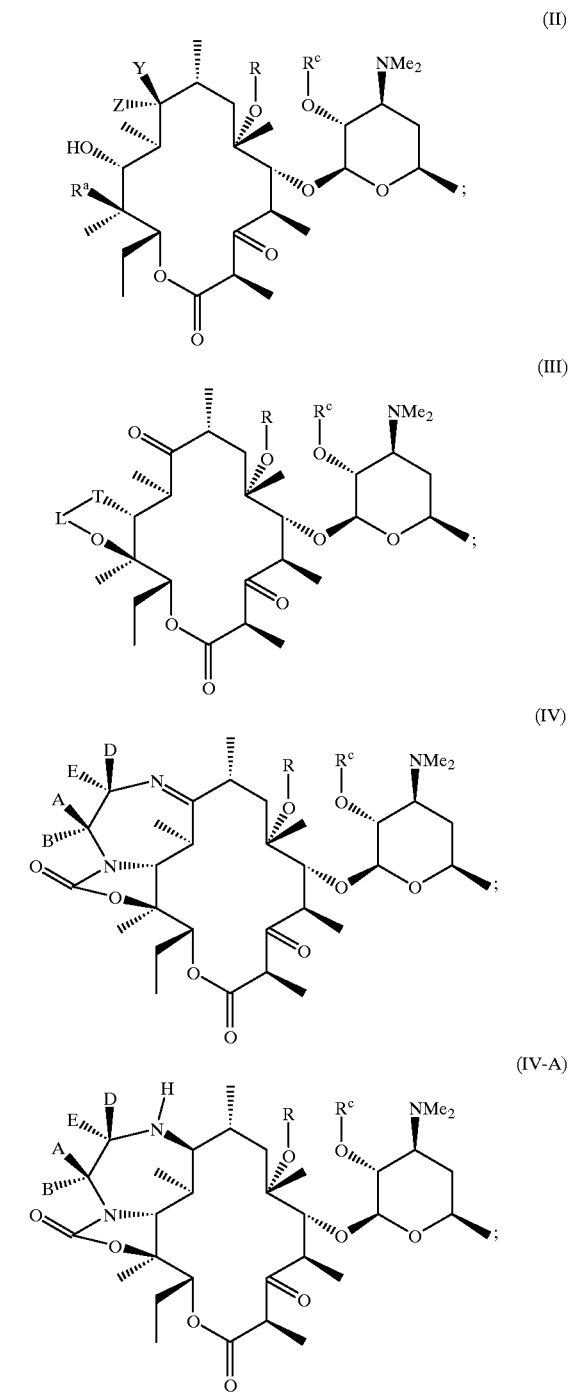

-continued
and

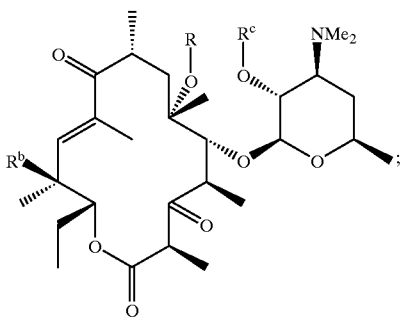

(V)

or a pharmaceutically acceptable salt, ester or prodrug thereof,
wherein either,
  Y and Z taken together define a group X,
wherein
  X is selected from the group consisting of
    (1) =O,
    (2) =N—OH,
    (3) =N—O—$R^1$ where $R^1$ is selected from the group consisting of
      (a) unsubstituted $C_1$–$C_{12}$-alkyl,
      (b) $C_1$–$C_{12}$-alkyl substituted with aryl,
      (c) $C_1$–$C_{12}$-alkyl substituted with substituted aryl,
      (d) $C_1$–$C_{12}$-alkyl substituted with heteroaryl,
      (e) $C_1$–$C_{12}$-alkyl substituted with substituted heteroaryl,
      (f) $C_3$–$C_{12}$-cycloalkyl, and
      (g) —Si—$(R^2)(R^3)(R^4)$ wherein $R^2$, $R^3$ and $R^4$ are each independently selected from $C_1$–$C_{12}$-alkyl and Aryl; and
    (4) =N—O—$C(R^5)(R^6)$—O—$R^1$ where $R^1$ is as previously defined and $R^5$ and $R^6$ are each independently selected from the group consisting of
      (a) hydrogen,
      (b) unsubstituted $C_1$–$C_{12}$-alkyl,
      (c) $C_1$–$C_{12}$-alkyl substituted with aryl,
      (d) $C_1$–$C_{12}$-alkyl substituted with substituted aryl,
      (e) $C_1$–$C_{12}$-alkyl substituted with heteroaryl, and
      (f) $C_1$–$C_{12}$-alkyl substituted with substituted heteroaryl, or
      $R^5$ and $R^6$ taken together with the atom to which they are attached form a $C_3$–$C_{12}$-cycloalkyl ring;
    or,
  one of Y and Z is hydrogen and the other is selected from a group consisting of
    (1) hydrogen,
    (2) hydroxy,
    (3) protected hydroxy, and
    (4) $NR^7R^8$ wherein $R^7$ and $R^8$ are independently selected from hydrogen and $C_1$–$C_6$-alkyl, or $R^7$ and $R^8$ are taken with the nitrogen atom to which they are connected to form a 3- to 7-membered ring which, when the ring is a 5- to 7-membered ring, may optionally contain a hetero function selected from the group consisting of —O—, —NH—, —N($C_1$–$C_6$-alkyl-)—, —N(aryl)—, —N(aryl-$C_1$–$C_6$-alkyl-)—, —N(substituted-aryl-$C_1$–$C_6$-alkyl-)—, —N(heteroaryl)—, —N(heteroaryl-$C_1$–$C_6$-alkyl-)—, —N(substituted-heteroaryl-$C_1$–$C_6$-alkyl-)—, and —S— or —S(O)$_n$—, wherein n is 1 or 2, $R^a$ is hydrogen or hydroxy;
$R^b$ is selected from the group consisting of hydroxy, —O—C(O)—$NH_2$ and —O—C(O)-imidazolyl;
$R^c$ is hydrogen or a hydroxy protecting group;
L is methylene or carbonyl, provided that when L is methylene, T is —O—,
T is selected from the group consisting of —O—, —NH—, and —N(W—$R^d$)—, wherein
  W is absent or is selected from the group consisting of —O—, —NH—CO—, —N=CH— and —NH—; and
$R^d$ is selected from the group consisting of
  (1) hydrogen,
  (2) $C_1$–$C_6$-alkyl optionally substituted with one or more substituents selected from the group consisting of
    (a) aryl,
    (b) substituted-aryl,
    (c) heteroaryl,
    (d) substituted-heteroaryl,
    (e) hydroxy,
    (f) $C_1$–$C_6$-alkoxy,
    (g) $NR^7R^8$, wherein $R^7$ and $R^8$ are as defined previously, and
    (h) —$CH_2$—M—$R^9$
      wherein M is selected from the group consisting of:
        (i) —C(O)—NH—,
        (ii) —NH—C(O)—,
        (iii) —NH—,
        (iv) —N=,
        (v) —N($CH_3$)—,
        (vi) —NH—C(O)—O—
        (vii) —NH—C(O)—NH—
        (viii) —O—C(O)—NH—
        (ix) —O—C(O)—O—
        (x) —O—,
        (xi) —S(O)$_n$—, wherein n is 0, 1 or 2,
        (xii) —C(O)—O—,
        (xiii) —O—C(O)—, and
        (xiv) —C(O)—, and
      $R^9$ is selected from the group consisting of:
        (i) $C_1$–$C_6$-alkyl, optionally substituted with a substituent selected from the group consisting of
          (aa) aryl,
          (bb) substituted-aryl,
          (cc) heteroaryl, and,
          (dd) substituted-heteroaryl,
        (ii) aryl,
        (iii) substituted-aryl,
        (iv) heteroaryl,
        (v) substituted-heteroaryl, and
        (vi) heterocycloalkyl,
  (3) $C_3$–$C_7$-cycloalkyl,
  (4) aryl,
  (5) substituted-aryl,
  (6) heteroaryl, and
  (7) substituted-heteroaryl;
R is selected from the group consisting of
  (1) methyl substituted with a moiety selected from the group consisting of
    (a) CN,
    (b) F,
    (c) —$CO_2R^{10}$ wherein $R^{10}$ is $C_1$–$C_3$-alkyl or aryl substituted $C_1$–$C_3$-alkyl, or heteroaryl substituted $C_1$–$C_3$-alkyl, (d) S(O)$_n$R$^{10}$ where n is 0, 1 or 2 and R$^{10}$ is as previously defined,
(e) NHC(O)R$^{10}$ where R$^{10}$ is as previously defined,
(f) NHC(O)NR$^{11}$R$^{12}$ wherein R$^{11}$ and R$^{12}$ are independently selected from hydrogen, C$_1$–C$_3$-alkyl, C$_1$–C$_3$-alkyl substituted with aryl, substituted aryl, heteroaryl, substituted heteroaryl,
(g) aryl,
(h) substituted aryl,
(i) heteroaryl, and
(j) substituted heteroaryl,
(2) C$_2$–C$_{10}$-alkyl,
(3) C$_2$–C$_{10}$-alkyl substituted with one or more substituents selected from the group consisting of
  (a) halogen,
  (b) hydroxy,
  (c) C$_1$–C$_3$-alkoxy,
  (d) C$_1$–C$_3$-alkoxy-C$_1$–C$_3$-alkoxy,
  (e) oxo,
  (f) —N$_3$,
  (g) —CHO,
  (h) O—SO$_2$-(substituted C$_1$–C$_6$-alkyl),
  (i) —NR$^{13}$R$^{14}$ wherein R$^{13}$ and R$^{14}$ are selected from the group consisting of
    (i) hydrogen,
    (ii) C$_1$–C$_{12}$-alkyl,
    (iii) substituted C$_1$–C$_{12}$-alkyl,
    (iv) C$_1$–C$_{12}$-alkenyl,
    (v) substituted C$_1$–C$_{12}$-alkenyl,
    (vi) C$_1$–C$_{12}$-alkynyl,
    (vii) substituted C$_1$–C$_{12}$-alkynyl,
    (viii) aryl,
    (ix) C$_3$–C$_8$-cycloalkyl,
    (x) substituted C$_3$–C$_8$-cycloalkyl,
    (xi) substituted aryl,
    (xii) heterocycloalkyl,
    (xiii) substituted heterocycloalkyl,
    (xiv) C$_1$–C$_{12}$-alkyl substituted with aryl,
    (xv) C$_1$–C$_{12}$-alkyl substituted with substituted aryl,
    (xvi) C$_1$–C$_{12}$-alkyl substituted with heterocycloalkyl,
    (xvii) C$_1$–C$_{12}$-alkyl substituted with substituted heterocycloalkyl,
    (xviii) C$_1$–C$_{12}$-alkyl substituted with C$_3$–C$_8$-cycloalkyl,
    (xix) C$_1$–C$_{12}$-alkyl substituted with substituted C$_3$–C$_8$-cycloalkyl,
    (xx) heteroaryl,
    (xxi) substituted heteroaryl,
    (xxii) C$_1$–C$_{12}$-alkyl substituted with heteroaryl, and
    (xxiii) C$_1$–C$_{12}$-alkyl substituted with substituted heteroaryl, or
  R$^{13}$ and R$^{14}$ are taken together with the atom to which they are attached form a 3–10 membered heterocycloalkyl ring which may be substituted with one or more substituents independently selected from the group consisting of
    (i) halogen,
    (ii) hydroxy,
    (iii) C$_1$–C$_3$-alkoxy,
    (iv) C$_1$–C$_3$-alkoxy-C$_1$–C$_3$-alkoxy,
    (v) oxo,
    (vi) C$_1$–C$_3$-alkyl,
    (vii) halo-C$_1$–C$_3$-alkyl, and
    (vii) C$_1$–C$_3$-alkoxy-C$_1$–C$_3$-alkyl,
  (j) —CO$_2$R$^{10}$ wherein R$^{10}$ is as previously defined,
  (k) —C(O)NR$^{11}$R$^{12}$ wherein R$^{11}$ and R$^{12}$ are as previously defined,
  (l) =N—O—R$^{10}$ wherein R$^{10}$ is as previously defined,
  (m) —C≡N,
  (n) O—S(O)$_n$R$^{10}$ wherein n is 0, 1 or 2 and R$^{10}$ is as previously defined,
  (o) aryl,
  (p) substituted aryl,
  (q) heteroaryl,
  (r) substituted heteroaryl,
  (s) C$_3$–C$_8$-cycloalkyl,
  (t) substituted C$_3$–C$_8$-cycloalkyl,
  (u) C$_1$–C$_{12}$-alkyl substituted with heteroaryl,
  (v) heterocycloalkyl,
  (w) substituted heterocycloalkyl,
  (x) NHC(O)R$^{10}$ where R$^{10}$ is as previously defined,
  (y) NHC(O)NR$^{11}$R$^{12}$ wherein R$^{11}$ and R$^{12}$ are as previously defined,
  (z) =N—NR$^{13}$R$^{14}$ wherein R$^{13}$ and R$^{14}$ are as previously defined,
  (aa) =N—R$^9$ wherein R$^9$ is as previously defined,
  (bb) =N—NHC(O)R$^{10}$ wherein R$^{10}$ is as previously defined, and
  (cc) =N—NHC(O)NR$^{11}$R$^{12}$ wherein R$^{11}$ and R$^{12}$ are as previously defined;
(4) C$_3$-alkenyl substituted with a moiety selected from the group consisting of
  (a) halogen,
  (b) —CHO,
  (c) —CO$_2$R$^{10}$ where R$^{10}$ is as previously defined,
  (d) —C(O)—R$^9$ where R$^9$ is as previously defined,
  (e) —C(O)NR$^{11}$R$^{12}$ wherein R$^{11}$ and R$^{12}$ are as previously defined,
  (f) —C≡N,
  (g) aryl,
  (h) substituted aryl,
  (i) heteroaryl,
  (j) substituted heteroaryl,
  (k) C$_3$–C$_7$-cycloalkyl, and
  (l) C$_1$–C$_{12}$-alkyl substituted with heteroaryl,
(5) C$_4$–C$_{10}$-alkenyl;
(6) C$_4$–C$_{10}$-alkenyl substituted with one or more substituents selected from the group consisting of
  (a) halogen,
  (b) C$_1$–C$_3$-alkoxy,
  (c) oxo,
  (d) —CHO,
  (e) —CO$_2$R$^{10}$ where R$^{10}$ is as previously defined,
  (f) —C(O)NR$^{11}$R$^{12}$ wherein R$^{11}$ and R$^{12}$ are as previously defined,
  (g) —NR$^{13}$R$^{14}$ wherein R$^{13}$ and R$^{14}$ are as previously defined,
  (h) =N—O—R$^{10}$ where R$^{10}$ is as previously defined,
  (i) —C≡N,
  (j) O—S(O)$_n$R$^{10}$ where n is 0, 1 or 2 and R$^{10}$ is as previously defined,
  (k) aryl,
  (l) substituted aryl,
  (m) heteroaryl,
  (n) substituted heteroaryl,
  (o) C$_3$–C$_7$-cycloalkyl,
  (p) C$_1$–C$_{12}$-alkyl substituted with heteroaryl,
  (q) NHC(O)R$^{10}$ where R$^{10}$ is as previously defined,
  (r) NHC(O)NR$^{11}$R$^{12}$ wherein R$^{11}$ and R$^{12}$ are as previously defined, (s) =N—NR$^{13}$R$^{14}$ wherein R$^{13}$ and R$^{14}$ are as previously defined,
(t) =N—R$^9$ wherein R$^9$ is as previously defined,
(u) =N—NHC(O)R$^{10}$ where R$^{10}$ is as previously defined, and
(v) =N—NHC(O)NR$^{11}$R$^{12}$ wherein R$^{11}$ and R$^{12}$ are as previously defined;
(7) C$_3$–C$_{10}$-alkynyl; and
(8) C$_3$–C$_{10}$-alkynyl substituted with one or more substituents selected from the group consisting of
  (a) trialkylsilyl,
  (b) aryl,
  (c) substituted aryl,
  (d) heteroaryl, and
  (e) substituted heteroaryl; and
A, B, D and E, with the provision that at least two of A, B, D and E are hydrogen, are independently selected from the group consisting of:
  (a) hydrogen;
  (b) C$_1$–C$_6$-alkyl, optionally substituted with one or more substituents selected from the group consisting of:
    (i) aryl;
    (ii) substituted-aryl;
    (iii) heteroaryl;
    (iv) substituted-heteroaryl;
    (v) heterocycloalkyl;
    (vi) hydroxy;
    (vii) C$_1$–C$_6$-alkoxy;
    (viii) halogen consisting of Br, Cl, F or I; and
    (ix) NR$^7$R$^8$, wherein R$^7$ and R$^8$ are as previously defined;
  (c) C$_3$–C$_7$-cycloalkyl;
  (d) aryl;
  (e) substituted-aryl;
  (f) heteroaryl;
  (g) substituted-heteroaryl;
  (h) heterocycloalkyl; and
  (i) a group selected from option (b) above further substituted with —M—R$^9$, wherein M and R$^9$ are as previously defined; or
any one pair of substituents, consisting of AB, AD, AE, BD, BE or DE, is taken together with the atom or atoms to which they are attached to form a 3- to 7-membered ring optionally containing a hetero function selected from the group consisting of —O—, —NH—, —N(C$_1$–C$_6$-alkyl-)—, —N(aryl-C$_1$–C$_6$-alkyl-)—, —N(substituted-aryl-C$_1$–C$_6$-alkyl-)—, —N(heteroaryl-C$_1$–C$_6$-alkyl-)—, —N(substituted-heteroaryl-C$_1$–C$_6$-alkyl-)—, —S— or —S(O)$_n$—, wherein n is 1 or 2, —C(O)—NH—, —C(O)—NR$^{12}$—, wherein R$^{12}$ is as previously defined, —NH—C(O)—, —NR$^{12}$—C(O)—, wherein R$^{12}$ is as previously defined, and —C(=NH)—NH—.

The present invention also provides pharmaceutical compositions which comprise a therapeutically effective amount of a compound as defined above in combination with a pharmaceutically acceptable carrier.

The invention further relates to a method of treating bacterial infections in a host mammal in need of such treatment comprising administering to a mammal in need of such treatment a therapeutically effective amount of a compound as defined above.

In a further aspect of the present invention are provided processes for the preparation of 6-O-substituted macrolide derivatives of Formula (II), (III), (IV), (IV-A) and (V) above.

DETAILED DESCRIPTION OF THE INVENTION

In one embodiment of the present invention are compounds having the formula II,

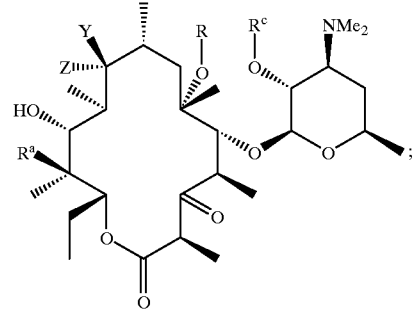

(II)

wherein

X, Y, R, Ra and Rc are as described previously.

A representative compound of formula II is the compound of Formula (II), R$^a$ is OH, R$^c$ is benzoyl, R is allyl.

In a preferred embodiment of the compounds of formula II of the invention are compounds wherein R$^a$ is hydroxy and R$^c$ is hydrogen.

In a more preferred embodiment of the compounds of formula II of the invention are compounds having the formula VIII,

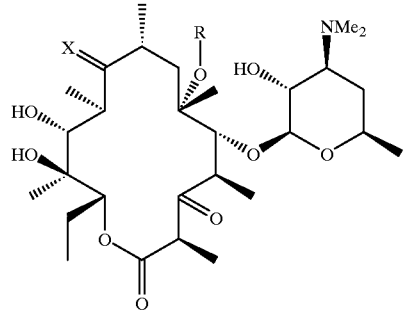

VIII wherein X is O or NOH, and R is as defined previously.

Compounds representative of this embodiment include, but are not limited to:

Compound of Formula (VIII): X is O, R is allyl;
Compound of Formula (VIII): X is NOH, R is allyl.;
Compound of Formula (VIII): X is O, R is propyl;
Compound of Formula (VIII): X is O, R is —CH$_2$CHO;
Compound of Formula (VIII): X is O, R is —CH$_2$CH=NOH;
Compound of Formula (VI,I): X is NOH, R is —CH$_2$CH=NOH;
Compound of Formula (VIII): X is O, R is —CH$_2$CN;
Compound of Formula (VIII): X is O, R is —CH$_2$CH$_2$NH$_2$;
Compound of Formula (VIII): X is O, R is —CH$_2$CH$_2$NHCH$_2$-Phenyl;
Compound of Formula (VIII): X is O, R is —CH$_2$CH$_2$NHCH$_2$CH$_2$-Phenyl;
Compound of Formula (VIII): X is O, R is —CH$_2$CH$_2$NHCH(CO$_2$CH$_3$)CH$_2$-Phenyl;
Compound of Formula (VIII): X is O, R is —CH$_2$CH$_2$NHCH$_2$-(4-pyridyl);

Compound of Formula (VIII): X is O, R is —CH$_2$CH$_2$NHCH$_2$-(4-quinolyl);
Compound of Formula (VIII): X is O, R is —CH$_2$CH═CH-Phenyl;
Compound of Formula (VIII): X is O, R is —CH$_2$CH$_2$CH$_2$-Phenyl;
Compound of Formula (VIII): X is O, R is —CH$_2$CH═CH-(4-methoxyphenyl);
Compound of Formula (VIII): X is O, R is —CH$_2$CH═CH-(4-chlorophenyl);
Compound of Formula (VIII): X is O, R is —CH$_2$CH═CH-(3-quinolyl);
Compound of Formula (VIII): X is O, R is —CH$_2$CH$_2$CH$_2$OH.;
Compound of Formula (VIII): X is O, R is —CH$_2$C(O)OH;
Compound of Formula (VIII): X is O, R is —CH$_2$CH$_2$NHCH$_3$;
Compound of Formula (VIII): X is O, R is —CH$_2$CH$_2$NHCH$_2$OH;
Compound of Formula (VIII): X is O, R is —CH$_2$CH$_2$N(CH$_3$)$_2$;
Compound of Formula (VIII): X is O, R is —CH$_2$CH$_2$-(1-morpholinyl);
Compound of Formula (VIII): X is O, R is —CH$_2$C(O)NH$_2$;
Compound of Formula (VIII): X is O, R is —CH$_2$NHC(O)NH$_2$;
Compound of Formula (VIII): X is O, R is —CH$_2$NHC(O)CH$_3$;
Compound of Formula (VIII): X is O, R is —CH$_2$F;
Compound of Formula (VIII): X is O, R is —CH$_2$CH$_2$OCH$_3$;
Compound of Formula (VIII): X is O, R is —CH$_2$CH$_3$;
Compound of Formula (VIII): X is O, R is —CH$_2$CH═CH(CH$_3$)$_2$;
Compound of Formula (VIII): X is O, R is —CH$_2$CH$_2$CH(CH$_3$)CH$_3$;
Compound of Formula (VIII): X is O, R is —CH$_2$CH$_2$OCH$_2$CH$_2$OCH$_3$;
Compound of Formula (VIII): X is O, R is —CH$_2$SCH$_3$;
Compound of Formula (VIII): X is O, R is -cyclopropyl;
Compound of Formula (VIII): X is O, R is —CH$_2$OCH$_3$;
Compound of Formula (VIII): X is O, R is —CH$_2$CH$_2$F;
Compound of Formula (VIII): X is O, R is —CH$_2$-cyclopropyl;
Compound of Formula (VIII): X is O, R is —CH$_2$CH$_2$CHO;
Compound of Formula (VIII): X is O, R is —C(O)CH$_2$CH$_2$CH$_3$;
Compound of Formula (VIII): X is O, R is —CH$_2$-(4-nitrophenyl);
Compound of Formula (VIII): X is O, R is —CH$_2$-(4-chlorophenyl);
Compound of Formula (VIII): X is O, R is —CH$_2$-(4-methoxyphenyl);
Compound of Formula (VIII): X is O, R is —CH$_2$-(4-cyanophenyl);
Compound of Formula (VIII): X is O, R is —CH$_2$CH═CHC(O)OCH$_3$;
Compound of Formula (VIII): X is O, R is —CH$_2$CH═CHC(O)OCH$_2$CH$_3$;
Compound of Formula (VIII): X is O, R is —CH$_2$CH═CHCH$_3$;
Compound of Formula (VIII): X is O, R is —CH$_2$CH═CHCH$_2$CH$_3$;
Compound of Formula (VIII): X is O, R is —CH$_2$CH═CHCH$_2$CH$_2$CH$_3$;
Compound of Formula (VIII): X is O, R is —CH$_2$CH═CHSO$_2$-phenyl;
Compound of Formula (VIII): X is O, R is —CH$_2$C≡C—Si(CH$_3$)$_3$;
Compound of Formula (VIII): X is O, R is —CH$_2$C≡CCH$_2$CH$_2$CH$_2$CH$_2$CH$_3$;
Compound of Formula (VIII): X is O, R is —CH$_2$C≡CCH$_3$;
Compound of Formula (VIII): X is O, R is —CH$_2$13 (2-pyridyl);
Compound of Formula (VIII): X is O, R is —CH$_2$-(3-pyridyl);
Compound of Formula (VIII): X is O, R is —CH$_2$-(4-pyridyl);
Compound of Formula (VIII): X is O, R is —CH$_2$-(4-quinolyl);
Compound of Formula (VIII): X is O, R is —CH$_2$NO$_2$;
Compound of Formula (VIII): X is O, R is —CH$_2$C(O)OCH$_3$;
Compound of Formula (VIII): X is O, R is —CH$_2$C(O)-phenyl;
Compound of Formula (VIII): X is O, R is —CH$_2$C(O)CH$_2$CH$_3$;
Compound of Formula (VIII): X is O, R is —CH$_2$Cl;
Compound of Formula (VIII): X is O, R is —CH$_2$S(O)$_2$-phenyl;
Compound of Formula (VIII): X is O, R is —CH$_2$CH═CHBr;
Compound of Formula (VIII): X is O, R is —CH$_2$CH═CH-(4-quinolyl);
Compound of Formula (VIII): X is O, R is —CH$_2$CH$_2$CH$_2$-(4-quinolyl);
Compound of Formula (VIII): X is O, R is —CH$_2$CH═CH-(5-quinolyl);
Compound of Formula (VIII): X is O, R is —CH$_2$CH$_2$CH$_2$-(5-quinolyl);
Compound of Formula (VIII): X is O, R is —CH$_2$CH═CH-(4-benzoxazolyl);
Compound of Formula (VIII): X is O, R is —CH$_2$CH═CH-(7-benzimidazolyl);
Compound of Formula (VIII): X is O, R is CH$_2$-(3-iodophenyl);
Compound of Formula (VIII): X is O, R is CH$_2$-(2-naphthyl);
Compound of Formula (VIII): X is O, R is CH$_2$—CH═CH-(4-fluorophenyl); and
Compound of Formula (VIII): X is O, R is CH$_2$—CH(OH)—CN.

Preferred compounds of formula VIII are selected from the group consisting of:
Compound of Formula (VIII): X is O, R is allyl;
Compound of Formula (VIII): X is O, R is —CH$_2$CH═CH-phenyl; and
Compound of Formula (VIII): X is O, R is —CH$_2$CH═CH-(3-quinolyl).

In one embodiment of the invention is a process for the preparation of 6-O-substituted macrolide compounds having the Formula:

(II)

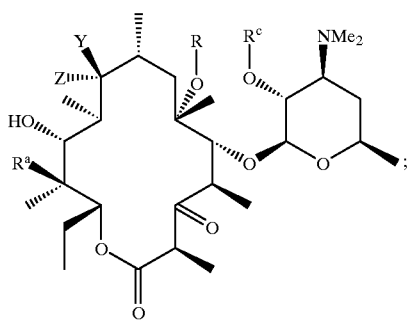

wherein either,
  Y, Z, $R^a$, $R^c$, and R are previously defined, the method comprising:
(a) treating a compound having the formula

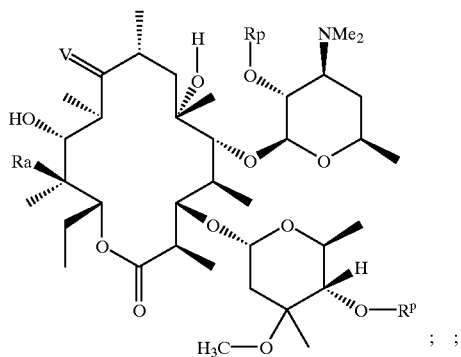

wherein
  RP is a hydroxy protecting group and V is $=N-O-R^1$ or $=N-O-C(R^5)(R^6)-O-R^1$
wherein
  $R^1$, $R^9$ and $R^{10}$ are as previously defined, with a base in an aprotic solvent followed by treatment with an alkylating agent to give a compound having the formula

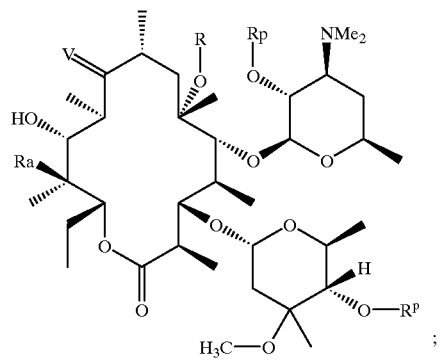

wherein
  $R^a$ and RP are as previously defined, V is $=N-O-R^1$ or $=N-O-C(R^5)(R^6)-O-R^1$
wherein
  $R^1$, $R^5$ and $R^6$ are as previously defined, and R is the "alkyl group" derived from the corresponding alkylating agent;

(b) deprotecting the 2'- and 4"-hydroxyl groups to give a compound of the formula

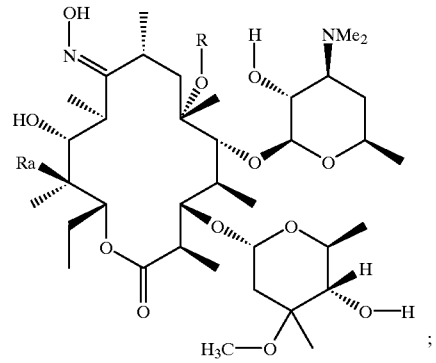

wherein
  $R^a$ is as previously defined and R is the "alkyl group" derived from the corresponding alkylating agent;
(c) deoximation in the presence of acid in a suitable solvent to give the desired intermediate having the formula

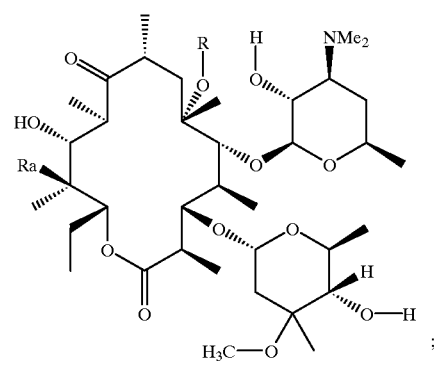

(d) removing the cladinose moiety by hydrolysis with acid, and protecting the 2' hydroxyl group by treatment with a hydroxy-protecting reagent to give a 3-hydroxy erythromycin compound having the formula

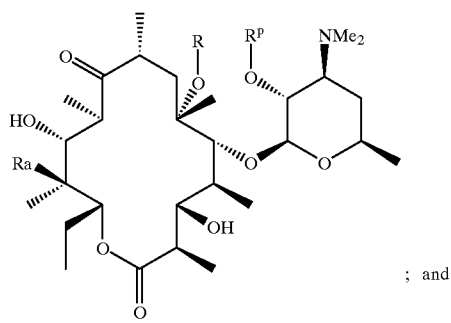

; and (e) oxidizing the 3-hydroxy group, optionally deprotecting the 2'-hydroxyl group, and isolating the desired compound.
  In a preferred embodiment of the process immediately above, in step (a) the base is selected from the group consisting of potassium hydroxide, cesium hydroxide, tetraalkylammonium hydroxide, sodium hydride, potassium hydride, potassium isopropoxide, potassium tert-butoxide and potassium isobutoxide, the alkylating agent is selected from the group consisting of allyl bromide, propargyl bromide, benzyl bromide, 2-fluoroethyl bromide, 4-nitrobenzyl bromide, 4-chlorobenzyl bromide, 4-methoxybenzyl bromide, α-bromo-p-tolunitrile, cinnamyl bromide, methyl 4-bromocrotonate, crotyl bromide, 1-bromo-2-pentene, 3-bromo-1-propenyl phenyl sulfone, 3-bromo-1-trimethylsilyl-1-propyne, 3-bromo-2-octyne, 1-bromo-2-butyne, 2-picolyl chloride, 3-picolyl chloride, 4-picolyl chloride, 4-bromomethyl quinoline, bromoacetonitrile, epichlorohydrin, bromofluoromethane, bromonitromethane, methyl bromoacetate, methoxymethyl chloride, bromoacetamide, 2-bromoacetophenone, 1-bromo-2-butanone, bromo chloromethane, bromomethyl phenyl sulfone, 1,3-dibromo-1-propene, allyl O-tosylate, 3-phenylpropyl-O-trifluoromethane sulfonate, and n-butyl-O-methanesulfonate, and the reaction is performed at a temperature from about −15° C. to about 50° C. for a period from 0.5 hours to 10 days; in step (b) deprotection is accomplished by use of acetic acid in water and acetonitrile; and in step (c) the deoximating reagent is an inorganic sulfur oxide compound is selected from the group consisting of sodium hydrogen sulfite, sodium pyrosulfate, sodium thiosulfate, sodium sulfate, sodium sulfite, sodium hydrosulfite, sodium metabisulfite, sodium dithionate, potassium thiosulfate, and potassium metabisulfite, or an inorganic nitrite salt in the presence of acid selected from the group consisting of sodium nitrite and potassium nitrite, and the solvent is selected from the group consisting of water, methanol, ethanol, propanol, isopropanol, trimethylsilanol or a mixture of one or more thereof; in step (d) the hydroxy protecting reagent is selected from the group consisting of a trialkysilyl halide, an acyl anhydride or an acyl halide; in step (e), the oxidizing is selected from N-chlorosuccinimide-dimethyl sulfide and carbodiimide-dimethylsulfoxide, and the optional deprotection is carried out by stirring in methanol.

In another embodiment of the present invention are compounds having formula III, (III)

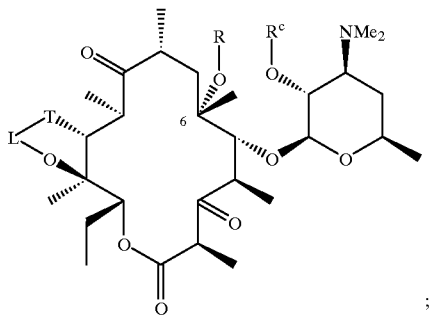

wherein

R, $R^c$, L and T are as described previously.

Preferred compounds of formula III are those selected from the group consisting of:
Compound of Formula (III); Rc is acetyl, L is CO, T is NH, R is —CH$_2$CH═CH$_2$;
Compound of Formula (III): $R^c$ is acetyl, L is CO, T is NH, R is —CH$_2$CH═CH-(3-quinolyl);
Compound of Formula (III): $R^c$ is benzoyl, L is CO, T is NH, R is —CH$_2$CH═CH-(3-quinolyl);
Compound of Formula (III): $R^c$ is propanoyl, L is CO, T is NH, R is —CH$_2$CH═CH-(3-quinolyl); and
Compound of Formula (III): $R^c$ is ethylsuccinoyl, L is CO, T is NH, R is —CH$_2$CH═CH-(3-quinolyl).

In a more preferred embodiment of the compounds of formula III of the invention are compounds having the formula IX.

(IX)

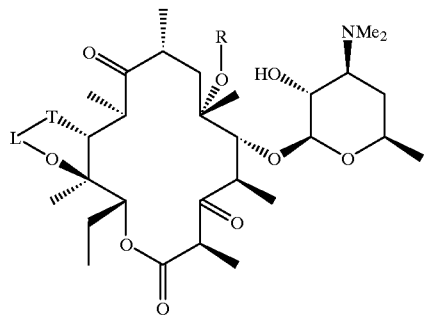

wherein L, T, and R are defined above.

Compounds representative of this embodiment include, but are not limited to:
Compound of Formula (IX): L is CO, T is O, R is —CH$_2$CH═CH$_2$;
Compound of Formula (IX): L is CO, T is O, R is —CH$_2$CH═CH-phenyl;
Compound of Formula (IX): L is CO, T is O, R is —CH$_2$CH$_2$CH$_2$-Phenyl;
Compound of Formula (IX): L is CO, T is O, R is —CH$_2$CH═CH-(4-chlorophenyl);
Compound of Formula (IX): L is CO, T is O, R is —CH$_2$CH═CH-(3-quinolyl);
Compound of Formula (IX): L is CO, T is O, R is —CH$_2$CH$_2$CH$_3$.;
Compound of Formula (IX): L is CO, T is O, R is —CH$_2$CH$_2$NH$_2$.;
Compound of Formula (IX): L is CO, T is O, R is —CH$_2$CH═NOH.;
Compound of Formula (IX): L is CO, T is O, R is —CH$_2$CH$_2$CH$_2$OH;
Compound of Formula (IX): L is CO, T is O, R is —CH$_2$F;
Compound of Formula (IX): L is CO, T is O, R is —CH$_2$CH$_2$-phenyl;
Compound of Formula (IX): L is CO, T is O, R is —CH$_2$CH$_2$-(4-pyridyl);
Compound of Formula (IX): L is CO, T is O, R is —CH$_2$CH$_2$-(4-quinolyl);
Compound of Formula (IX): L is CO, T is O, R is —CH$_2$CH(OH)CN;
Compound of Formula (IX): L is CO, T is O, R is —CH(C(O)OCH$_3$)CH$_2$-phenyl;
Compound of Formula (IX): L is CO, T is O, R is —CH$_2$CN;
Compound of Formula (IX): L is CO, T is O, R is —CH$_2$CH═CH-(4-methoxyphenyl);
Compound of Formula (IX): L is CO, T is O, R is —CH$_2$CH═CH-(4-fluorophenyl);
Compound of Formula (IX): L is CO, T is O, R is —CH$_2$CH═CH-(8-quinolyl);
Compound of Formula (IX): L is CO, T is O, R is —CH$_2$CH$_2$NHCH$_2$-phenyl;
Compound of Formula (IX): L is CO, T is O, R is —CH$_2$-phenyl;
Compound of Formula (IX): L is CO, T is O, R is —CH$_2$-(4-pyridyl);
Compound of Formula (IX): L is CO, T is O, R is —CH$_2$-(4-quinolyl);
Compound of Formula (IX): L is CO, T is O, R is —CH$_2$CH═CH-(4-pyridyl);

Compound of Formula (IX): L is CO, T is O, R is —CH₂CH₂CH₂-(4-pyridyl );
Compound of Formula (IX): L is CO, T is O, R is —CH₂CH═CH-(4-quinolyl );
Compound of Formula (IX): L is CO, T is O, R is —CH₂CH₂CH₂-(4-quinolyl);
Compound of Formula (IX): L is CO, T is O, R is —CH₂CH═CH-(5-quinolyl);
Compound of Formula (IX): L is CO, T is O, R is —CH₂CH₂CH₂-(5-quinolyl);
Compound of Formula (IX): L is CO, T is O, R is —CH₂CH═CH-(4-benzoxazolyl);
Compound of Formula (IX): L is CO, T is O, R is —CH₂CH═CH-(4-benzimidazolyl);
Compound of Formula (IX): L is CO, T is NH, R is —CH₂CH═CH₂;
Compound of Formula (IX): L is CO, T is NH, R is —CH₂CH═CH-Phenyl;
Compound of Formula (IX): L is CO, T is NH, R is —CH₂CH═CH-(3-quinolyl);
Compound of Formula (IX): L is CO, T is NH, R is —CH₂CH₂CH₃.;
Compound of Formula (IX): L is CO, T is NH, R is —CH₂CH₂NH₂.;
Compound of Formula (IX): L is CO, T is NH, R is —CH₂CH═NOH.;
Compound of Formula (IX): L is CO, T is NH, R is —CH₂CH₂CH₂OH;
Compound of Formula (IX): L is CO, T is NH, R is —CH₂F;
Compound of Formula (IX): L is CO, T is NH, R is —CH₂CH₂-phenyl;
Compound of Formula (IX): L is CO, T is NH, R is —CH₂CH₂-(4-pyridyl);
Compound of Formula (IX): L is CO, T is NH, R is —CH₂CH(OH)CN;
Compound of Formula (IX): L is CO, T is NH, R is —CH₂CH₂-(4-quinolyl);
Compound of Formula (IX): L is CO, T is NH, R is —CH(C(O)OCH₃)CH₂-phenyl;
Compound of Formula (IX): L is CO, T is NH, R is —CH₂CN;
Compound of Formula (IX): L is CO, T is NH, R is —CH₂CH═CH-(4-chlorophenyl);
Compound of Formula (IX): L is CO, T is NH, R is —CH₂CH═CH-(4-fluorophenyl);
Compound of Formula (IX): L is CO, T is NH, R is —CH₂CH₂CH₂-(4-methoxyphenyl);
Compound of Formula (IX): L is CO, T is NH, R is —CH₂CH═CH-(4-methoxyphenyl);
Compound of Formula (IX): L is CO, T is NH, R is —CH₂CH═CH-(3-chloro-6-quinolyl);
Compound of Formula (IX): L is CO, T is NH, R is —CH₂CH₂NHCH₂CH₂-(2-chlorophenyl);
Compound of Formula (IX): L is CO, T is NH, R is —CH₂-phenyl;
Compound of Formula (IX): L is CO, T is NH, R is —CH₂-(4-pyridyl);
Compound of Formula (IX): L is CO, T is NH, R is —CH₂-(4-quinolyl);
Compound of Formula (IX): L is CO, T is NH, R is —CH₂CH═CH-(4-pyridyl);
Compound of Formula (IX): L is CO, T is NH, R is —CH₂CH₂CH₂-(4-pyridyl);
Compound of Formula (IX): L is CO, T is NH, R is —CH₂CH═CH-(3-fluoro-6-quinolyl);
Compound of Formula (IX): L is CO, T is NH, R is —CH₂CH₂CH₂-(4-quinolyl);
Compound of Formula (IX): L is CO, T is NH, R is —CH₂CH═CH-(3-cyano-6-quinolyl);
Compound of Formula (IX): L is CO, T is NH, R is —CH₂CH₂CH₂-(5-quinolyl);
Compound of Formula (IX): L is CO, T is NH, R is —CH₂CH═CH-(4-benzoxazolyl);
Compound of Formula (IX): L is CO, T is NH, R is —CH₂CH═CH-(4-benzimidazolyl);
Compound of Formula (IX): L is CO, T is NH, R is —CH₂CH═CH-(3-methoxy-6-quinolyl);
Compound of Formula (IX): L is CO, T is NH, R is —CH₂-(2-naphthyl);
Compound of Formula (IX): L is CO, T is N(CH₃), R is —CH₂CH═CH₂;
Compound of Formula (IX): L is CO, T is N(CH₃), R is —CH₂CH═CH-(3-quinolyl);
Compound of Formula (IX): L is CO, T is N(CH₂CH₂N(CH₃)₂), R is —CH₂CH═CH₂;
Compound of Formula (IX): L is CO, T is N(CH₂CH₂N(CH₃)₂), R is —CH₂CH═CH-(3-quinolyl);
Compound of Formula (IX): L is CO, T is N(CH₂CH═CH₂), R is —CH₂CH═CH₂;
Compound of Formula (IX): L is CO, T is T is N(CH₂CH═C—(3-quinolyl)), R is —CH₂CH═CH-(3-quinolyl);
Compound of Formula (IX): L is CO, T is NH, R is —CH₂CH═CH-(3-pyridyl);
Compound of Formula (IX): L is CO, T is NH, R is —CH₂CH═CH-(2-naphthyl);
Compound of Formula (IX): L is CO, T is NH, R is —CH₂CH═CH-(4-isoquinolinyl);
Compound of Formula (IX): L is CO, T is NH, R is —CH₂CH═CH-(3,4-methylenedioxyphenyl);
Compound of Formula (IX): L is CO, T is NH, R is —CH₂CH═CH-(8-quinolyl);
Compound of Formula (IX): L is CO, T is NH, R is —CH₂CH═CH-(5-indolyl);
Compound of Formula (IX): L is CO, T is NH, R is —CH₂CH═CH-(6-chloro-3-quinolyl);
Compound of Formula (IX): L is CO, T is NH, R is —CH₂CH═CH-(3,4-ethylenedioxyphenyl);
Compound of Formula (IX): L is CO, T is NH, R is —CH₂CH═CH-(3-nitrophenyl);
Compound of Formula (IX): L is CO, T is NH, R is —CH₂CH═CH-(6-quinolyl);
Compound of Formula (IX): L is CO, T is NH, R is —CH₂CH═CH-(6-nitroquinolyl);
Compound of Formula (IX): L is CO, T is NH, R is —CH₂CH═CH-(5-quinolyl);
Compound of Formula (IX): L is CO, T is NH, R is —CH₂CH═CH-(2-methyl-6-quinolyl);
Compound of Formula (IX): L is CO, T is NH, $R^c$ is acetyl; R is —CH₂CH═CH-(3-quinolyl);
Compound of Formula (IX): L is CO, T is NH, R is —CH₂CH═CH-(5-isoquinolyl);
Compound of Formula (IX): L is CO, T is NH, R is —CH₂CH═CH-(7-nitro-6-quinoxalinyl);
Compound of Formula (IX): L is CO, T is NH, R is —CH₂CH═CH-(6-amino-3-quinolyl);
Compound of Formula (IX): L is CO, T is NH, R is —CH₂CH═CH-(1,8-naphthyridin-3-yl);
Compound of Formula (IX): L is CO, T is NH, R is —CH₂CH═CH-(6-(acetylamino)-3-quinolyl);
Compound of Formula (IX): L is CO, T is NH, R is —CH₂CH═CH-(3-carbazolyl);
Compound of Formula (IX): L is CO, T is NH, R is —CH₂CH═CH-(5-benzimidazolyl);

Compound of Formula (IX): L is CO, T is NH, R is —CH$_2$CH=CH-(3-hydroxy-2-(N-(2-methoxyphenyl)amido)-7-naphthyl);
Compound of Formula (IX): L is CO, T is NH, R is —CH$_2$CH=CH-(6-quinoxalinyl);
Compound of Formula (IX): L is CO, T is NH, R is —CH$_2$CH=CH-(6-hydroxy-3-quinolyl);
Compound of Formula (IX): L is CO, T is NH, R is —CH$_2$CH=CH-(6-methoxy-3-quinolyl);
Compound of Formula (IX): L is CO, T is NH, R is —CH$_2$CH=CH-(5-nitro-3-quinolyl);
Compound of Formula (IX): L is CO, T is NH, R is —CH$_2$CH=CH-(8-nitro-3-quinolyl);
Compound of Formula (IX): L is CO, T is NH, R is —CH$_2$CH=CH-(2-quinolyl);
Compound of Formula (IX): L is CO, T is NH, R is —CH$_2$CH=CH-(4-quinolyl);
Compound of Formula (IX): L is CO, T is NH, R is —CH$_2$CH=CH-(4-carboxyl-3-quinolyl);
Compound of Formula (IX): L is CO, T is NH, R is —CH$_2$CH=CH-(6-fluoro-3-quinolyl);
Compound of Formula (IX): L is CO, T is NH, R is —CH$_2$CH=CH-(6-methoxycarbonyl-3-quinolyl);
Compound of Formula (IX): L is CO, T is NH, R is —CH$_2$CH=CH-(6-aminocarbonyl-3-quinolyl);
Compound of Formula (IX): L is CO, T is NH, R is —CH$_2$CH=CH-(6-cyano-3-quinolyl);
Compound of Formula (IX): L is CO, T is NH, R is —CH$_2$CH=CH-(3-bromo-6-quinolyl);
Compound of Formula (IX): L is CO, T is NH, R is —CH$_2$C(O)H;
Compound of Formula (IX): L is CO, T is NH, R is —CH$_2$CH$_2$NHCH$_2$Phenyl;
Compound of Formula (IX): L is CO, T is NH, R is —CH$_2$CH$_2$NHCH$_2$CH$_2$Phenyl;
Compound of Formula (IX): L is CO, T is NH, R is —CH$_2$CH$_2$NHCH$_2$CH$_2$CH$_2$Phenyl;
Compound of Formula (IX): L is CO, T is NH, R is —CH$_2$CH$_2$NHCH$_2$CH$_2$CH$_2$CH$_2$Phenyl;
Compound of Formula (IX): L is CO, T is NH, R is —CH$_2$CH$_2$NHCH$_2$CH$_2$CH$_2$-(3-quinolyl);
Compound of Formula (IX): L is CO, T is NH, R is —CH$_2$CH$_2$NHCH$_2$(3-quinolyl);
Compound of Formula (IX): L is CO, T is NH, R is —CH$_2$CH$_2$NHCH$_2$(6-quinolyl);
Compound of Formula (IX): L is CO, T is NH, R is —CH$_2$CH=NO(phenyl);
Compound of Formula (IX): L is CO, T is NH, R is —CH$_2$CH=NOCH$_2$(phenyl);
Compound of Formula (IX): L is CO, T is NH, R is —CH$_2$CH=NOCH$_2$(4-NO$_2$-phenyl);
Compound of Formula (IX): L is CO, T is NH, R is —CH$_2$CH=NOCH$_2$(4-quinolyl);
Compound of Formula (IX): L is CO, T is NH, R is —CH$_2$CH=NOCH$_2$(2-quinolyl);
Compound of Formula (IX): L is CO, T is NH, R is —CH$_2$CH=NOCH$_2$(3-quinolyl);
Compound of Formula (IX): L is CO, T is NH, R is —CH$_2$CH=NOCH$_2$-(6-quinolyl);
Compound of Formula (IX): L is CO, T is NH, R is —CH$_2$CH=NOCH$_2$-(1-naphthyl);
Compound of Formula (IX): L is CO, T is NH, R is —CH$_2$CH=NOCH$_2$-(2-naphthyl);
Compound of Formula (IX): L is CO, T is NH, R is —CH$_2$CH$_2$NHOCH$_2$-(phenyl);
Compound of Formula (IX): L is CO, T is NH, R is —CH$_2$CH$_2$NHOCH$_2$-(4-NO$_2$-phenyl);
Compound of Formula (IX): L is CO, T is NH, R is —CH$_2$C(O)-phenyl;
Compound of Formula (IX): L is CO, T is NH, R is —CH$_2$C(O)-(4-F-phenyl);
Compound of Formula (IX): L is CO, T is NH, R is —CH$_2$CH=NNHC(O)phenyl;
Compound of Formula (IX): L is CO, T is NH, R is —CH$_2$CH$_2$CH$_2$-(3-quinolyl);
Compound of Formula (IX): L is CO, T is NH, R is —CH$_2$-(2-(3-quinolyl)cyclopropyl);
Compound of Formula (IX): L is CO, T is NH, R is —CH$_2$—C≡C—H;
Compound of Formula (IX): L is CO, T is NH, R is —CH$_2$—C≡C-(3-quinolyl);
Compound of Formula (IX): L is CO, T is NH, R is —CH$_2$—C≡C-(6-nitro-3-quinolyl);
Compound of Formula (IX): L is CO, T is NH, R is —CH$_2$—C≡C-phenyl;
Compound of Formula (IX): L is CO, T is NH, R is —CH$_2$—C≡C-naphthyl;
Compound of Formula (IX): L is CO, T is NH, R is —CH$_2$—C≡C-(2-naphthyl);
Compound of Formula (IX): L is CO, T is NH, R is —CH$_2$—C≡C-(6-methoxy-2-naphthyl);
Compound of Formula (IX): L is CO, T is NH, R is —CH$_2$—C≡C-(6-chloro-2-naphthyl);
Compound of Formula (IX): L is CO, T is NH, R is —CH$_2$—C≡C-(6-quinolyl);
Compound of Formula (IX): L is CO, T is NH, R is —CH$_2$—C≡C-(2-methyl-6-quinolyl);
Compound of Formula (IX): L is CO, T is NH, R is —CH$_2$—C≡C-(5-(N-(2-pyridyl)amino)carbonyl)furanyl);
Compound of Formula (IX): L is CO, T is NH, R is —CH$_2$—C≡C-(1-phenylethenyl);
Compound of Formula (IX): L is CO, T is NH, R is —CH$_2$—C≡C—Br;
Compound of Formula (IX): L is CO, T is NH, R is —CH$_2$-(2,2-dimethyl-1,3-dioxolan-4-yl);
Compound of Formula (IX): L is CO, T is NH, R is —CH$_2$CH(OH)-phenyl;
Compound of Formula (IX): L is CO, T is NH, R is —CH$_2$CH(OH)CH$_2$OH;
Compound of Formula (IX): L is CO, T is NHNH$_2$, R is —CH$_2$CH=CH$_2$;
Compound of Formula (IX): L is CO, T is NHNH$_2$, R is —CH$_2$CH=CH-(3-quinolyl);
Compound of Formula (IX): L is CO, T is NHNH$_2$, R is —CH$_2$CH$_2$CH$_2$-(3-quinolyl);
Compound of Formula (IX): L is CO, T is NH$_2$, R is —CH$_2$CH=CH-naphthyl;
Compound of Formula (IX): L is CO, T is NH$_2$, R is —CH$_2$CH=CH-(3-(2-furanyl)-6-quinolyl);
Compound of Formula (IX): L is CO, T is NH$_2$, R is —CH$_2$CH=CH-(8-chloro-3-quinolyl);
Compound of Formula (IX): L is CO, T is NH$_2$, R is —CH$_2$CH=CH-(4-chloro-2-trifluoromethyl-6-quinolyl);
Compound of Formula (IX): L is CO, T is NH$_2$, R is —CH$_2$CH=CH-(9-fluorenone-2-yl);
Compound of Formula (IX): L is CO, T is NH$_2$, R is —CH$_2$CH=CH-(6-benzoyl-2-naphthyl);
Compound of Formula (IX): L is CO, T is NH$_2$, R is —CH$_2$CH=CH-(7-methoxy-2-naphthyl);
Compound of Formula (IX): L is CO, T is NH$_2$, R is —CH$_2$CH=CH-(3-phenyl-6-quinolyl);
Compound of Formula (IX): L is CO, T is NH$_2$, R is —CH$_2$CH=CH-(3-(2-pyridyl)-6-quinolyl);

Compound of Formula (IX): L is CO, T is NH₂, R is —CH₂CH=CH-(3-(2-thiophenyl)-6-quinolyl);
Compound of Formula (IX): L is CO, T is NH₂, R is —CH₂CH=CH-(4-methylnaphthyl);
Compound of Formula (IX): L is CO, T is NH₂, R is —CH₂CH=CH-(6-β-D-galactopyranosyl-2-naphthyl);
Compound of Formula (IX): L is CO, T is NH₂, R is —CH₂CH=CH-(7-quinolyl);
Compound of Formula (IX): L is CO, T is NH₂, R is —CH₂CH=CH-(4-fluoronaphthyl);
Compound of Formula (IX): L is CO, T is NH₂, R is —CH₂CH=CH-(3-biphenyl);
Compound of Formula (IX): L is CO, T is NH₂, R is —CH₂CH=CH-(5-nitronaphthyl);
Compound of Formula (IX): L is CO, T is NH₂, R is —CH₂CH=CH-(4-pyrrolylphenyl);
Compound of Formula (IX): L is CO, T is NH₂, R is —CH₂CH=CH-(6-methoxy-2-naphthyl);
Compound of Formula (IX): L is CO, T is NH₂, R is —CH₂CH=CH-(3,5-dichlorophenyl);
Compound of Formula (IX): L is CO, T is NH₂, R is —CH₂-(3-iodophenyl);
Compound of Formula (IX): L is CO, T is NH₂, R is —CH₂-(3-(2-furanyl)phenyl);
Compound of Formula (IX): L is CO, T is NH₂, R is —CH₂CH=CH-(6-hydroxy-2-naphthyl);
Compound of Formula (IX): L is CO, T is NH₂, R is —CH₂CH=CH-(6-(2-bromoethoxy)-2-naphthyl);
Compound of Formula (IX): L is CO, T is NH₂, R is —CH₂CH=CH-(6'(2-(tetrazolyl)ethoxy-2-naphthyl),
Compound of Formula (IX): L is CO, T is NH₂, R is —CH₂CH=CH-naphthyl;
Compound of Formula (IX): L is CO, T is NH, R is —CH₂—C≡C-(2-phenylethenyl);
Compound of Formula (IX): L is CO, T is NH, R is —CH₂—CH=CH-(5-(3-isoxazolyl)-2-thiophenyl);
Compound of Formula (IX): L is CO, T is NH, R is —CH₂—CH=CH-(1,3-dimethyl-2,4-dioxo-5-pyrimidinyl); and
Compound of Formula (IX): L is CO, T is NH, R is —CH₂—CH=CH-(5—(2-pyridyl)aminocarbonyl-2-furanyl).

Preferred compounds of formula IX are those selected from the group consisting of:
Compound of Formula (IX): L is CO, T is O, R is —CH₂CH=CH₂;
Compound of Formula (IX): L is CO, T is O, R is —CH₂CH=CH-Phenyl;
Compound of Formula (IX): L is CO, T is O, R is —CH₂CH=CH-(3-quinolyl);
Compound of Formula (IX): L is CO, T is NH, R is —CH₂CH=CH₂;
Compound of Formula (IX): L is CO, T is NH, R is —CH₂CH=CH-Phenyl;
Compound of Formula (IX): L is CO, T is NH, R is —CH₂CH=CH-(3-quinolyl);
Compound of Formula (IX): L is CO, T is N(CH₃), R is —CH₂CH=CH₂;
Compound of Formula (IX): L is CO, T is N(CH₃), R is —CH₂CH=CH-(3-quinolyl);
Compound of Formula (IX): L is CO, T is N(CH₂CH₂N(CH₃)₂), R is —CH₂CH=CH₂;
Compound of Formula (IX): L is CO, T is N(CH₂CH₂N(CH₃)₂), R is —CH₂CH=CH-(3-quinolyl);
Compound of Formula (IX): L is CO, T is NH, R is —CH₂CH=CH-(3-pyridyl);
Compound of Formula (IX): L is CO, T is NH, R is —CH₂CH=CH-(2-naphthyl);
Compound of Formula (IX): L is CO, T is NH, R is —CH₂CH=CH-(4-isoquinolinyl);
Compound of Formula (IX): L is CO, T is NH, R is —CH₂CH=CH-(3,4-methylenedioxyphenyl);
Compound of Formula (IX): L is CO, T is NH, R is —CH₂CH=CH-(8-quinolyl);
Compound of Formula (IX): L is CO, T is NH, R is —CH₂CH=CH-(6-quinolyl);
Compound of Formula (IX): L is CO, T is NH, R is —CH₂CH=CH-(6-nitroquinolyl);
Compound of Formula (IX): L is CO, T is NH, R is —CH₂CH=CH-(5-quinolyl);
Compound of Formula (IX): L is CO, T is NH, R is —CH₂CH=CH-(6-amino-3-quinolyl);
Compound of Formula (IX): L is CO, T is NH, R is —CH₂CH=CH-(1,8-naphthyridin-3-yl);
Compound of Formula (IX): L is CO, T is NH, R is —CH₂CH=CH-(6-(acetylamino)-3-quinolyl);
Compound of Formula (IX): L is CO, T is NH, R is —CH₂CH=CH-(6-quinoxalinyl);
Compound of Formula (IX): L is CO, T is NH, R is —CH₂CH=CH-(6-hydroxy-3-quinolyl);
Compound of Formula (IX): L is CO, T is NH, R is —CH₂CH=CH-(6-methoxy-3-quinolyl);
Compound of Formula (IX): L is CO, T is NH, R is —CH₂CH=CH-(5-nitro-3-quinolyl);
Compound of Formula (IX): L is CO, T is NH, R is —CH₂CH=CH-(8-nitro-3-quinolyl);
Compound of Formula (IX): L is CO, T is NH, R is —CH₂CH=CH-(2-quinolyl);
Compound of Formula (IX): L is CO, T is NH, R is —CH₂CH=CH-(4-quinolyl);
Compound of Formula (IX): L is CO, T is NH, R is —CH₂CH=CH-(4-carboxyl-3-quinolyl);
Compound of Formula (IX): L is CO, T is NH, R is —CH₂CH=CH-(6-fluoro-3-quinolyl);
Compound of Formula (IX): L is CO, T is NH, R is —CH₂CH=CH-(6-methoxycarbonyl-3-quinolyl);
Compound of Formula (IX): L is CO, T is NH, R is —CH₂CH=CH-(6-aminocarbonyl-3-quinolyl);
Compound of Formula (IX): L is CO, T is NH, R is —CH₂CH=CH-(6-cyano-3-quinolyl);
Compound of Formula (IX): L is CO, T is NH, R is —CH₂CH=CH-(3-bromo-6-quinolyl);
Compound of Formula (IX): L is CO, T is NH, R is —CH₂CH₂CH₂-(3-quinolyl);
Compound of Formula (IX): L is CO, T is NH, R is —CH₂-(2-(3-quinolyl)cyclopropyl);
Compound of Formula (IX): L is CO, T is NH, R is —CH₂—C≡C—H;
Compound of Formula (IX): L is CO, T is NH, R is —CH₂—C≡C-(3-quinolyl);
Compound of Formula (IX): L is CO, T is NH, R is —CH₂—C≡C-(6-nitro-3-quinolyl);
Compound of Formula (IX): L is CO, T is NH, R is —CH₂—C≡C-phenyl;
Compound of Formula (IX): L is CO, T is NH, R is —CH₂—C≡C-naphthyl;
Compound of Formula (IX): L is CO, T is NH, R is —CH₂—C≡C-(2-naphthyl);
Compound of Formula (IX): L is CO, T is NH, R is —CH₂—C≡C-(6-methoxy-2-naphthyl);
Compound of Formula (IX): L is CO, T is NH, R is —CH₂—C≡C-(6-chloro-2-naphthyl );
Compound of Formula (IX): L is CO, T is NH, R is —CH₂—C≡C-(6-quinolyl);
Compound of Formula (IX): L is CO, T is N(NH₂), R is —CH₂CH=CH₂;

Compound of Formula (IX): L is CO, T is N(NH$_2$), R is
—CH$_2$CH=CH-(3-quinolyl);
Compound of Formula (IX): L is CO, T is N(NH$_2$), R is
—CH$_2$CH$_2$CH$_2$-(3-quinolyl);
Compound of Formula (IX): L is CO, T is NH$_2$, R is
—CH$_2$CH=CH-naphthyl;
Compound of Formula (IX): L is CO, T is NH$_2$, R is
—CH$_2$CH=CH-(3-(2-pyridyl)-6-quinolyl);
Compound of Formula (IX): L is CO, T is NH$_2$, R is
—CH$_2$CH=CH-(7-quinolyl); and
Compound of Formula (IX): L is CO, T is NH, R is
—CH$_2$—CH=CH-(5-(3-isoxazolyl)-2-thiophenyl).

In another embodiment of the invention is a process for the preparation of 6-O-substituted macrolide compounds having the Formula:

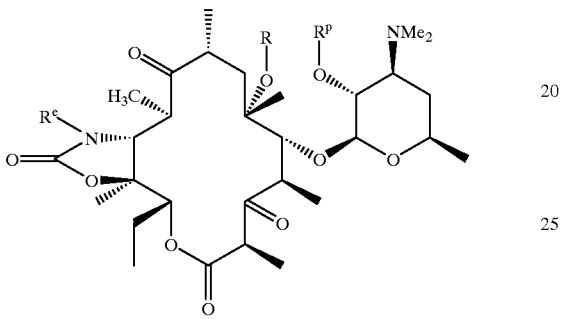

wherein
R and RP
R is selected from the group consisting of
(1) methyl substituted with a moiety selected from the group consisting of
 (a) CN,
 (b) F,
 (c) —CO$_2$R$^{10}$ wherein R$^{10}$ is C$_1$–C$_3$-alkyl or aryl substituted C$_1$–C$_3$-alkyl, or heteroaryl substituted C$_1$–C$_3$-alkyl,
 (d) S(O)$_n$R$^{10}$ where n is 0, 1 or 2 and R$^{10}$ is as previously defined,
 (e) NHC(O)R$^{10}$ where R$^{10}$ is as previously defined,
 (f) NHC(O)NR$^{11}$R$^{12}$ wherein R$^{11}$ and R$^{12}$ are independently selected from hydrogen, C$_1$–C$_3$-alkyl, C$_1$–C$_3$-alkyl substituted with aryl, substituted aryl, heteroaryl, substituted heteroaryl,
 (g) aryl,
 (h) substituted aryl,
 (i) heteroaryl, and
 (j) substituted heteroaryl,
(2) C$_2$–C$_{10}$-alkyl,
(3) C$_2$–C$_{10}$-alkyl substituted with one or more substituents selected from the group consisting of
 (a) halogen,
 (b) hydroxy,
 (c) C$_1$–C$_3$-alkoxy,
 (d) C$_1$–C$_3$-alkoxy-C$_1$–C$_3$-alkoxy,
 (e) oxo,
 (f) —N$_3$,
 (g) —CHO,
 (h) O—SO$_2$-(substituted C$_1$–C$_6$-alkyl),
 (i) —NR$^{13}$R$^{14}$ wherein R$^{13}$ and R$^{14}$ are selected from the group consisting of
  (i) hydrogen,
  (ii) C$_1$–C$_{12}$-alkyl,
  (iii) substituted C$_1$–C$_{12}$-alkyl,
  (iv) C$_1$–C$_{12}$-alkenyl,
  (v) substituted C$_1$–C$_{12}$-alkenyl,
  (vi) C$_1$–C$_{12}$-alkynyl,
  (vii) substituted C$_1$–C$_{12}$-alkynyl,
  (viii) aryl,
  (ix) C$_3$–C$_8$-cycloalkyl,
  (x) substituted C$_3$–C$_8$-cycloalkyl,
  (xi) substituted aryl,
  (xii) heterocycloalkyl,
  (xiii) substituted heterocycloalkyl,
  (xiv) C$_1$–C$_{12}$-alkyl substituted with aryl,
  (xv) C$_1$–C$_{12}$-alkyl substituted with substituted aryl,
  (xvi) C$_1$–C$_{12}$-alkyl substituted with heterocycloalkyl,
  (xvii) C$_1$–C$_{12}$-alkyl substituted with substituted heterocycloalkyl,
  (xviii) C$_1$–C$_{12}$-alkyl substituted with C$_3$–C$_8$-cycloalkyl,
  (xix) C$_1$–C$_{12}$-alkyl substituted with substituted C$_3$–C$_8$-cycloalkyl,
  (xx) heteroaryl,
  (xxi) substituted heteroaryl,
  (xxii) C$_1$–C$_{12}$-alkyl substituted with heteroaryl, and
  (xxiii) C$_1$–C$_{12}$-alkyl substituted with substituted heteroaryl, or
 R$^{13}$ and R$^{14}$ are taken together with the atom to which they are attached form a 3–10 membered heterocycloalkyl ring which may be substituted with one or more substituents independently selected from the group consisting of
  (i) halogen,
  (ii) hydroxy,
  (iii) C$_1$–C$_3$-alkoxy,
  (iv) C$_1$–C$_3$-alkoxy-C$_1$–C$_3$-alkoxy,
  (v) oxo,
  (vi) C$_1$–C$_3$-alkyl,
  (vii) halo-C$_1$–C$_3$-alkyl, and
  (vii) C$_1$–C$_3$-alkoxy-C$_1$–C$_3$-alkyl,
 (j) —CO$_2$R$^{10}$ wherein R$^{10}$ is as previously defined,
 (k) —C(O)NR$^{11}$R$^{12}$ wherein R$^{11}$ and R$^{12}$ are as previously defined,
 (l) =N—O—R$^{10}$ wherein R$^{10}$ is as previously defined,
 (m) —C≡N,
 (n) O—S(O)$_n$R$^{10}$ wherein n is 0, 1 or 2 and R$^{10}$ is as previously defined,
 (o) aryl,
 (p) substituted aryl,
 (q) heteroaryl,
 (r) substituted heteroaryl,
 (s) C$_3$–C$_8$-cycloalkyl,
 (t) substituted C$_3$–C$_8$-cycloalkyl,
 (u) C$_1$–C$_{12}$-alkyl substituted with heteroaryl,
 (v) heterocycloalkyl,
 (w) substituted heterocycloalkyl,
 (x) NHC(O)R$^{10}$ where R$^{10}$ is as previously defined,
 (y) NHC(O)NR$^{11}$R$^{12}$ wherein R$^{11}$ and R$^{12}$ are as previously defined,
 (z) =N—NR$^{13}$R$^{14}$ wherein R$^{13}$ and R$^{14}$ are as previously defined,
 (aa) =N—R$^9$ wherein R$^9$ is as previously defined,
 (bb) =N—NHC(O)R$^{10}$ wherein R$^{10}$ is as previously defined, and
 (cc) =N—NHC(O)NR$^{11}$R$^{12}$ wherein R$^{11}$ and R$^{12}$ are as previously defined;

(4) $C_3$-alkenyl substituted with a moiety selected from the group consisting of
  (a) halogen,
  (b) —CHO,
  (c) —$CO_2R^{10}$ where $R^{10}$ is as previously defined,
  (d) —C(O)—$R^9$ where $R^9$ is as previously defined,
  (e) —C(O)$NR^{11}R^{12}$ wherein $R^{11}$ and $R^{12}$ are as previously defined,
  (f) —C≡N,
  (g) aryl,
  (h) substituted aryl,
  (i) heteroaryl,
  (j) substituted heteroaryl,
  (k) $C_3$–$C_7$-cycloalkyl, and
  (l) $C_1$–$C_{12}$-alkyl substituted with heteroaryl,
(5) $C_4$–$C_{10}$-alkenyl;
(6) $C_4$–$C_{10}$-alkenyl substituted with one or more substituents selected from the group consisting of
  (a) halogen,
  (b) $C_1$–$C_3$-alkoxy,
  (c) oxo,
  (d) —CHO,
  (e) —$CO_2R^{10}$ where $R^{10}$ is as previously defined,
  (f) —C(O)$NR^{11}R^{12}$ wherein $R^{11}$ and $R^{12}$ are as previously defined,
  (g) —$NR^{13}R^{14}$ wherein $R^{13}$ and $R^{14}$ are as previously defined,
  (h) =N—O—$R^{10}$ where $R^{10}$ is as previously defined,
  (i) —C≡N,
  (j) O—$S(O)_nR^{10}$ where n is 0, 1 or 2 and $R^{10}$ is as previously defined,
  (k) aryl,
  (l) substituted aryl,
  (m) heteroaryl,
  (n) substituted heteroaryl,
  (o) $C_3$–$C_7$-cycloalkyl,
  (p) $C_1$–$C_{12}$-alkyl substituted with heteroaryl,
  (q) $NHC(O)R^{10}$ where $R^{10}$ is as previously defined,
  (r) $NHC(O)NR^{11}R^{12}$ wherein $R^{11}$ and $R^{12}$ are as previously defined,
  (s) =N—$NR^{13}R^{14}$ wherein $R^{13}$ and $R^{14}$ are as previously defined,
  (t) =N—$R^9$ wherein $R^9$ is as previously defined,
  (u) =N—$NHC(O)R^{10}$ where $R^{10}$ is as previously defined, and
  (v) =N—$NHC(O)NR^{11}R^{12}$ wherein $R^{11}$ and $R^{12}$ are as previously defined;
(7) $C_3$–$C_{10}$-alkynyl; and
(8) $C_3$–$C_{10}$-alkynyl substituted with one or more substituents selected from the group consisting of
  (a) trialkylsilyl,
  (b) aryl,
  (c) substituted aryl,
  (d) heteroaryl, and
  (e) substituted heteroaryl;

$R^e$ is H or W—$R^d$, wherein W is absent or is selected from the group consisting of —O—, —NH—CO—, —N=CH— and —NH—, and $R^d$ is selected from the group consisting of (1) hydrogen,
(2) $C_1$–$C_6$-alkyl optionally substituted with one or more substituents selected from the group consisting of
  (a) aryl,
  (b) substituted-aryl,
  (c) heteroaryl,
  (d) substituted-heteroaryl,
  (e) hydroxy,
  (f) $C_1$–$C_6$-alkoxy,
  (g) $NR^7R^8$ wherein $R^7$ and $R^8$ are independently selected from hydrogen and $C_1$–$C_6$-alkyl, or $R^7$ and $R^8$ are taken with the nitrogen atom to which they are connected to form a 3- to 7-membered ring which, when the ring is a 5- to 7-membered ring, may optionally contain a hetero function selected from the group consisting of —O—, —NH—, —N($C_1$–$C_6$-alkyl-)—, —N(aryl)—, —N(aryl-$C_1$–$C_6$-alkyl-)—, —N(substituted-aryl-$C_1$–$C_6$-alkyl-)—, —N(heteroaryl)—, —N(heteroaryl-$C_1$–$C_6$-alkyl-)—, —N(substituted-heteroaryl-$C_1$–$C_6$-alkyl-)—, and —S— or —$S(O)_n$—, wherein n is 1 or 2, and
  (h) —$CH_2$—M—$R^9$
  wherein M is selected from the group consisting of:
    (i) —C(O)—NH—,
    (ii) —NH—C(O)—,
    (iii) —NH—,
    (iv) —N=,
    (v) —N($CH_3$)—,
    (vi) —NH—C(O)—O—
    (vii) —NH—C(O)—NH—
    (viii) —O—C(O)—NH—
    (ix) —O—C(O)—O—
    (x) —O—,
    (xi) —$S(O)_n$—, wherein n is 0, 1 or 2,
    (xii) —C(O)—O—,
    (xiii) —O—C(O)—, and
    (xiv) —C(O)—, and
  $R^9$ is selected from the group consisting of:
    (i) $C_1$–$C_6$-alkyl, optionally substituted with a substituent selected from the group consisting of
      (aa) aryl,
      (bb) substituted-aryl,
      (cc) heteroaryl, and
      (dd) substituted-heteroaryl,
    (ii) aryl,
    (iii) substituted-aryl,
    (iv) heteroaryl,
    (v) substituted-heteroaryl, and
    (vi) heterocycloalkyl,
(3) $C_3$–$C_7$-cycloalkyl,
(4) aryl,
(5) substituted-aryl,
(6) heteroaryl, and
(7) substituted-heteroaryl; the method comprising.

(a) treating a compound having the formula

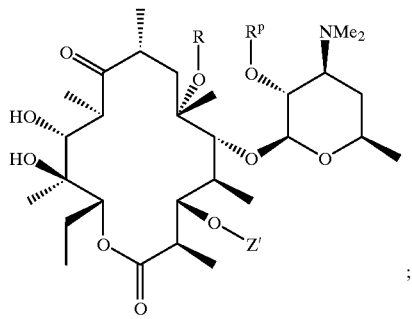

wherein
R is as previously defined, RP is a hydroxy protecting group and Z' is 4"-hydroxy-protected cladinose, with sodium hexamethyldisilazide and carbonyldiimidazole to give a compound having the formula

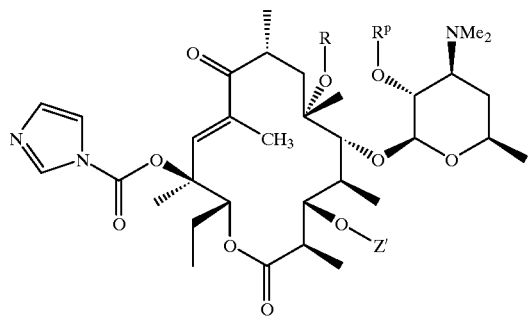

(b) treating the compound from step (a) with a reagent selected from the group consisting of ammonia, $R^e$—$NH_2$, hydrazine, substituted hydrazine, hydroxylamine, and substituted hydroxylamine to give a compound having the formula

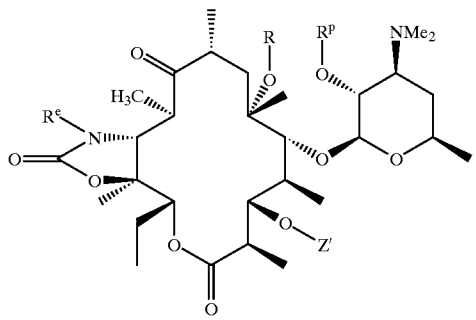

wherein
$R^e$ is H or W—$R^d$, wherein W is absent or is selected from the group consisting of —O—, —NH—CO—, —N=CH— and —NH—, and $R^d$ is as defined previously;
(c) optionally treating the compound from step (b) wherein $R^e$ is H with an alkylating agent having the formula $R^d$-halogen, wherein $R^d$ is as defined previously, to give a compound of the formula shown in step (b) wherein $R^e$ is W—$R^d$, W is absent and $R^d$ is as defined previously;

(d) optionally treating the compound from step (b) wherein $R^e$ is W—$R^d$ and W is —NH— and $R^d$ is H, with an alkylating agent selected from the group consisting of $R^d$-halogen, wherein $R^d$ is as defined previously, to give a compound of the formula shown in step (b) wherein $R^e$ is W—$R^d$, W is —NH— and $R^d$ is as defined above;

(e) optionally treating the compound from step (b) wherein $R^e$ is W—$R^d$ and W is —NH— and $R^d$ is H, with an acylating agent selected from the group consisting of $R^d$—C(CO)-halogen or $(R^d$—C(CO)—O$)_2$ to give a compound wherein $R^e$ is W—$R^d$, W is —NH—CO— and $R^d$ is as defined above;

(f) optionally treating the compound from step (b) wherein $R^e$ is W—$R^d$ and W is —NH— and $R^d$ is H, with an aldehyde having the formula $R^d$—CHO, wherein $R^d$ as defined above to give a compound wherein $R^e$ is W—$R^d$, W is —N=CH— and $R^d$ is as defined above;

(g) removing the cladinose moiety by hydrolysis with acid to give a compound having the formula

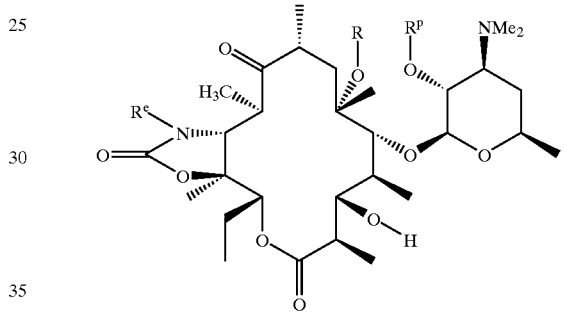

(h) oxidizing the 3-hydroxyl group; and
(i) optionally deprotecting, and isolating the desired compound.

In a preferred embodiment of the process immediately above, R is an allyl or propargyl group substituted with a moiety selected from the group consisting of 1-phenylethenyl, 2-chlorophenyl, 2-fluorenyl, 2-methyl-6-quinolyl, 2-naphthyl, 2-phenylethenyl, 2-quinolyl, 3-(2-furanyl)-6-quinolyl, 3-(2-pyridyl)-6-quinolyl, 3-quinolyl, 3-(2-thiophenyl)-6-quinolyl, 3-biphenyl, 3-bromo-6-quinolyl, 3-carbazolyl, 3-chloro-6-quinolyl, 3-cyano-6-quinolyl, 3-fluoro-6-quinolyl, 3-hydroxy-2-(N-(2-methoxyphenyl)amido)-7-naphthyl, 3-iodophenyl, 3-methoxy-6-quinolyl, 3-nitrophenyl, 3-phenyl-6-quinolyl, 3-quinolyl, 4-benzoxazolyl, 4-carboxyl-3-quinolyl, 4-chloro-2-trifluoromethyl-6-quinolyl, 4-chlorophenyl, 4-fluoronaphthyl, 4-fluorophenyl, 4-isoquinolinyl, 4-methoxyphenyl, 4-methylnaphthyl, 4-pyridyl, 4-pyrrolylphenyl, 4-quinolyl, 5-(2-pyridyl)aminocarbonyl-2-furanyl, 5-(3-isoxazolyl)-2-thiophenyl, 5-benzimidazolyl, 5-indolyl, 5-isoquinolyl, 5-nitro-3-quinolyl, 5-nitronaphthyl, 5-(N-(2-pyridyl)amino)carbonyl)furanyl, 5-quinolyl, 6-(acetylamino)-3-quinolyl, 6-(2-(tetrazolyl) ethoxy-2-naphthyl, 6-(2-bromoethoxy)-2-naphthyl, 6-amino-3-quinolyl, 6-aminocarbonyl-3-quinolyl, 6-β-D-galactopyranosyl-2-naphthyl, 6-benzoyl-2-naphthyl, 6-cyano-3-quinolyl, 6-fluoro-3-quinolyl, 6-hydroxy-2-naphthyl, 6-hydroxy-3-quinolyl, 6-methoxy-2-naphthyl, 6-methoxy-3-quinolyl, 6-methoxycarbonyl-3-quinolyl, 6-nitroquinolyl, 6-quinolyl, 6-quinoxalinyl, 7-methoxy-2-naphthyl, 7-nitro-6-quinoxalinyl, 7-quinolyl, 8-chloro-3-quinolyl, 8-nitro-3-quinolyl, 8-quinolyl, 9-oxofluoren-2-yl, 1,3-dimethyl-2,4-dioxo-5-pyrimidinyl, 1,8-naphthyridin-3-yl, 3,4-methylenedioxyphenyl, 3,5-dichlorophenyl, naphthyl, and phenyl, and in step (b) the reagent is selected from the group consisting of ammonia and $R^e$—$NH_2$; optional steps (c), (d) and (e) are omitted; and in step (g) the oxidizing reagent is selected from N-chlorosuccinimide-dimethyl sulfide and carbodiimide-dimethylsulfoxide; and in step (h) the optional deprotection is carried out by stirring in methanol.

In a more preferred embodiment of the process immediately above, R is an allyl or propargyl group substituted with a moiety selected from the group consisting of 2-methyl-6-quinolyl, 2-quinolyl, 3-(2-furanyl)-6-quinolyl, 3-(2-pyridyl)-6-quinolyl, 3-quinolyl, 3-(2-thiophenyl)-6-quinolyl, 3-bromo-6-quinolyl, 3-chloro-6-quinolyl, 3-cyano-6-quinolyl, 3-fluoro-6-quinolyl, 3-methoxy-6-quinolyl, 3-phenyl-6-quinolyl, 3-quinolyl, 4-carboxyl-3-quinolyl, 4-chloro-2-trifluoromethyl-6-quinolyl, 4-isoquinolinyl, 4-quinolyl, 5-isoquinolyl, 5-nitro-3-quinolyl, 5-quinolyl, 6-(acetylamino)-3-quinolyl, 6-amino-3-quinolyl, 6-aminocarbonyl-3-quinolyl, 6-cyano-3-quinolyl, 6-fluoro-3-quinolyl, 6-hydroxy-3-quinolyl, 6-methoxy-3-quinolyl, 6-methoxycarbonyl-3-quinolyl, 6-nitroquinolyl, 6-quinolyl, 7-quinolyl, 8-chloro-3-quinolyl, 8-nitro-3-quinolyl and 8-quinolyl.

In another embodiment of the invention is a process for preparing a compound having the formula

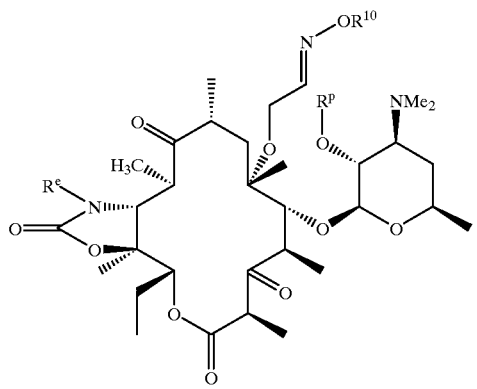

wherein $R^e$ is H or W—$R^d$, wherein W is absent or is selected from the group consisting of —O—, —NH—CO—, —N=CH— and —NH—, and $R^d$ is as defined previously, and $R^{10}$ is H or $C_1$–$C_3$-alkyl, aryl substituted $C_1$–$C_3$-alkyl, or heteroaryl substituted $C_1$–$C_3$-alkyl, the method comprising (a) treating a compound having the formula

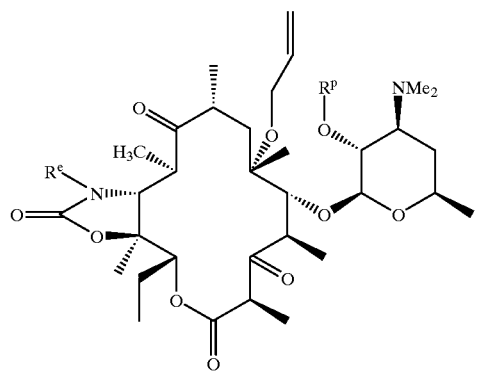

with ozone to give a compound having the formula

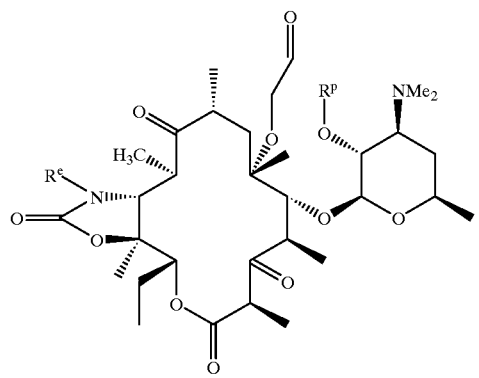

(b) treating the compound of step (a) with a hydroxylamine compound having the formula $NH_2$—O—$R^{10}$, wherein $R^{10}$ is as previously defined; and (c) optionally deprotecting, and isolating the desired compound.

In a preferred embodiment of the process immediately above, $R^e$ is H.

In another embodiment of the invention is a process for preparing a compound having the formula

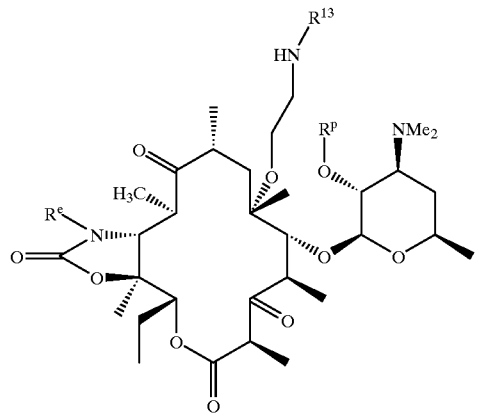

wherein $R^e$ is H or W—$R^d$, wherein W is absent or is selected from the group consisting of —O—, —NH—CO—, —N=CH— and —NH—, and $R^d$ is as defined above, is the method comprising (a) reductively aminating a compound having the formula

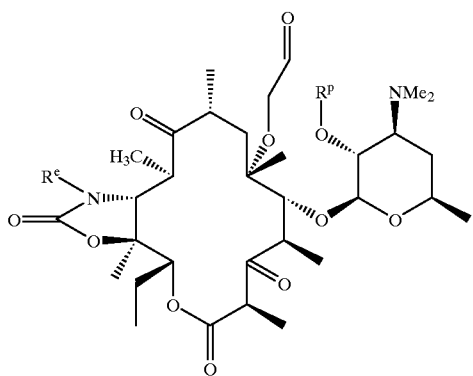

with an amine compound having the formula $NH_2$—$R^{13}$, wherein $R^{13}$ is as previously defined; and
(b) optionally deprotecting, and isolating the desired compound.

In another embodiment of the present invention are compounds having formula IV

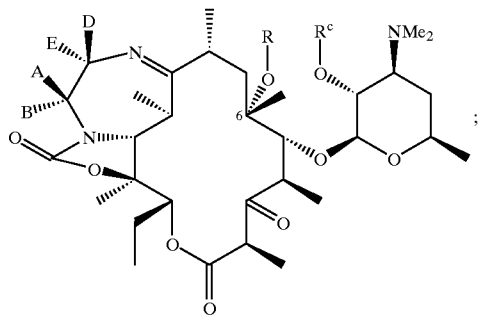

(IV)

wherein
R, $R^c$, A, B, D and E are as defined previously.

In a more preferred embodiment of the compounds of formula IV of the invention are compounds having the formula VII,

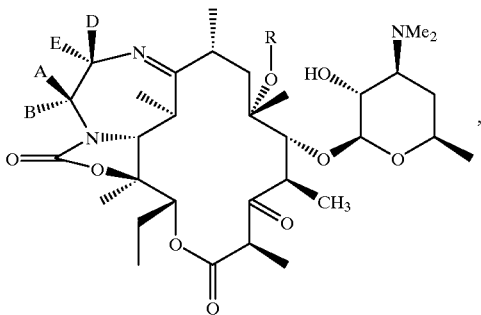

(VII)

wherein
A, B, D, E, and R are defined previously.

Compounds representative of the embodiment of formula VII include, but are not limited to:

Compound of Formula (VII): A, B, D, and E are H, R is allyl;
Compound of Formula (VII): A, B, D, and E are H, R is —$CH_2CH_2CH_3$;
Compound of Formula (VII): A, B, D, and E are H, R is —$CH_2CH_2NH_2$;
Compound of Formula (VII): A, B, D, and E are H, R is —$CH_2CH$=$NOH$;
Compound of Formula (VII): A, B, D, and E are H, R is —$CH_2CH_2CH_2OH$;
Compound of Formula (VII): A, B, D, and E are H, R is —$CH_2F$;
Compound of Formula (VII): A, B, D, and E are H, R is —$CH_2CN$;
Compound of Formula (VII): A, B, D, and E are H, R is —$CH_2CH(OH)CN$;
Compound of Formula (VII): A, B, D, and E are H, R is —$CH_2$-phenyl;
Compound of Formula (VII): A, B, D, and E are H, R is —$CH_2$-(4-pyridyl);
Compound of Formula (VII): A, B, D, and E are H, R is —$CH_2$-(4-quinolyl);
Compound of Formula (VII): A, B, D, and E are H, R is —$CH_2CH$=$CH$-(4-pyridyl);
Compound of Formula (VII): A, B, D, and E are H, R is —$CH_2CH$=$CH$-(4-chlorophenyl);
Compound of Formula (VII): A, B, D, and E are H, R is —$CH_2CH$=$CH$-(4-fluorophenyl);
Compound of Formula (VII): A, B, D, and E are H, R is —$CH_2CH$=$CH$-(4-methoxyphenyl);
Compound of Formula (VII): A, B, D, and E are H, R is —$CH_2CH_2CH_2$-phenyl;
Compound of Formula (VII): A, B, D, and E are H, R is —$CH_2CH$=$CH$-(4-pyridyl);
Compound of Formula (VII): A, B, D, and E are H, R is —$CH_2CH_2CH_2$-(4-pyridyl);
Compound of Formula (VII): A, B, D, and E are H, R is —$CH_2CH$=$CH$-(4-quinolyl);
Compound of Formula (VII): A, B, D, and E are H, R is —$CH_2CH_2CH_2$-(4-quinolyl);
Compound of Formula (VII): A, B, D, and E are H, R is —$CH_2CH$=$CH$-(5-quinolyl);
Compound of Formula (VII): A, B, D, and E are H, R is —$CH_2CH_2CH_2$-(5-quinolyl);
Compound of Formula (VII): A, B, D, and E are H, R is —$CH_2CH$=$CH$-(4-benzoxazolyl);
Compound of Formula (VII): A, B, D, and E are H, R is —$CH_2CH$=$CH$-(4-benzimidazolyl);
Compound of Formula (VII): A, B, D, and E are H, R is —$CH_2CH$=$CH$-(8-quinolyl);
Compound of Formula (VII): A, B, D, and E are H, R is —$CH_2CH_2NHCH_2$-phenyl;
Compound of Formula (VII): A, B, D, and E are H, R is —$CH_2CH_2NHCH_2$-(4-pyridyl);
Compound of Formula (VII): A, B, D, and E are H, R is —$CH_2CH_2NHCH_2$-(4-quinolyl);
Compound of Formula (VII): A, B, D, and E are H, R is —$CH_2CH_2NHCH(CH_2$-phenyl$)C(O)OCH_3$;
Compound of Formula (VII): A, B, D, and E are H, R is —$CH_2CH_2NHCH_2CH_2$-(2-chlorophenyl);
Compound of Formula (VII): A, B and E are H, D is benzyl, R is allyl;
Compound of Formula (VII): A is benzyl, B, D and E are H, R is allyl;
Compound of Formula (VII): A and E are phenyl, B and D and are H, R is allyl;
Compound of Formula (VII): A is methyl, B, D and E are H, R is allyl;
Compound of Formula (VII): A and D are methyl, B and E are H, R is allyl;
Compound of Formula (VII): A and E taken together is —$CH_2CH_2CH_2$—, B and D are H, R is allyl;

Compound of Formula (VII): A, B, D, and E are H, R is —CH₂CH=CH-(3-quinolyl); and Compound of Formula (VII): A, B, D, and E are H, R is 3-(3-quinolyl)propyl.

Preferred compounds of formula VII are those in the group consisting of:

Compound of Formula (VII): A, B, D, and E are H, R is allyl;

Compound of Formula (VII): A, B, D, and E are H, R is —CH₂CH=CH-(3-quinolyl); and Compound of Formula (VII): A, B, D, and E are H, R is —CH₂CH₂CH₂-(3-quinolyl).

In another embodiment of the invention is the process for preparing a compound having the formula IV (IV)

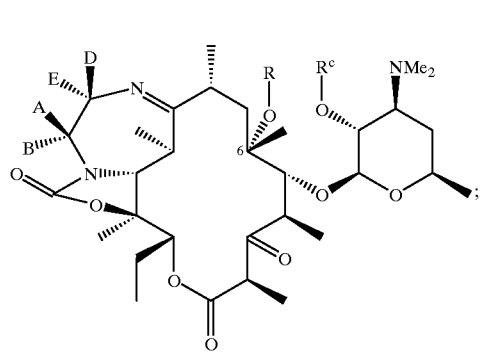

wherein $R^c$, R, A, B, D and E are as defined previously, the method comprising:

(a) treating a compound having the formula (II)

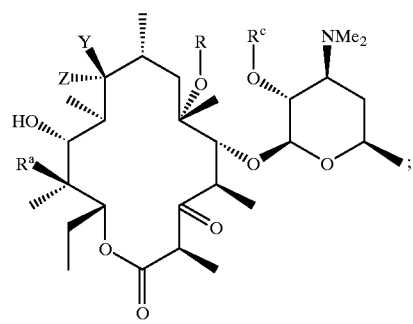

wherein

R is as defined previously, and Rc is a hydroxy protecting group, by treatment with methanesulfonic anhydride in pyridine, then treating the methansulfonyl derivative with an amine base to give a compound having the formula

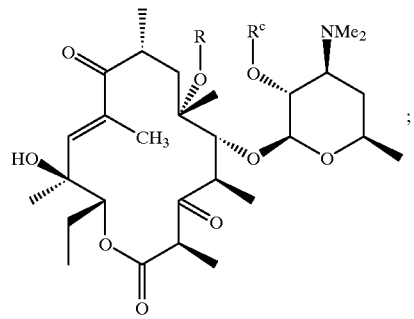

(b) treating the compound from step (a) with an alkali metal hydride base and carbonyldiimidazole to give a compound having the formula

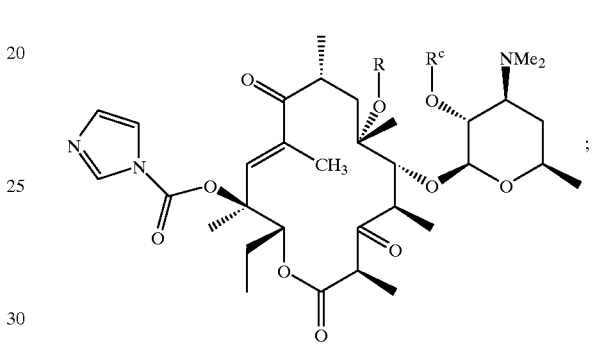

(c) treating the compound of step (b) with a diamine having the formula

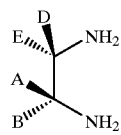

wherein

A, B, D and E are as defined previously, to give a compound having the formula

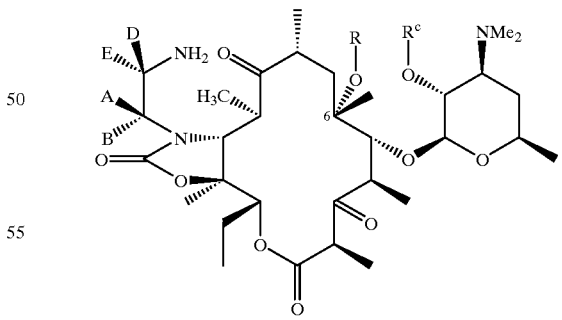

(d) cyclizing the compound of step (c) with dilute mineral or organic acid, optionally deprotecting, and isolating the desired compound.

An alternate to the process described immediately above is that process wherein steps (c) and (d) are replaced by the steps (c)–(f) consisting of (c) treating the compound of step (b) with an amine having the formula

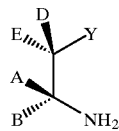

wherein

A, B, D and E are as defined therein, and Y is hydroxy, to give a compound having the formula

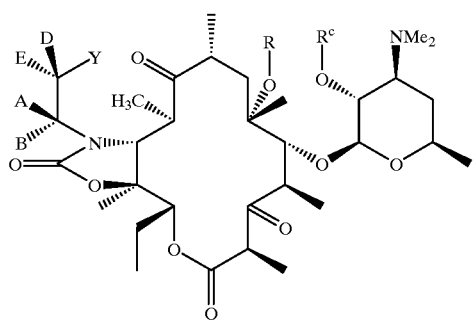

(d) treating the compound of step (c) with triphenylphosphine and diphenylphosphoryl azide and diethylazodicarboxylate in tetrahydrofuran to give the analogous compound of wherein Y is $N_3$, and removing the deprotecting group to give the analogous compound wherein Y is $N_3$ and $R^c$ is H;

(e) treating the compound of step (d) with a reducing agent selected from the group consisting of triphenylphosphine-water, hydrogen with a catalyst, sodium borohydride, and dialkylaluminum hydride, to give the compound having the formula

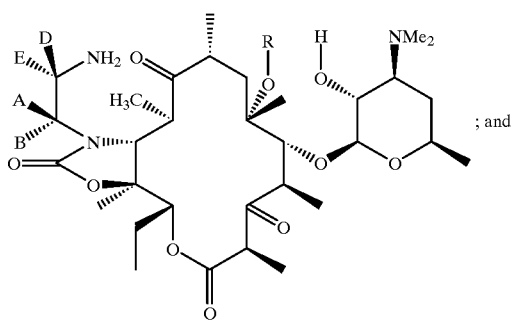

(f) cyclizing the compound of step (e) with dilute mineral or organic acid, and isolating the desired compound.

In another embodiment of the present invention are compounds having formula IV-A

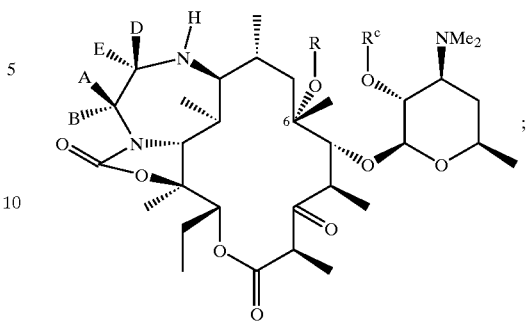

wherein
R, $R^c$, A, B, D and E are as defined previously.

In a preferred embodiment are compounds having formula IV-A wherein $R^c$ is H, and R, A, B, D and E are as defined previously.

In another embodiment of the present invention are compounds having formula V

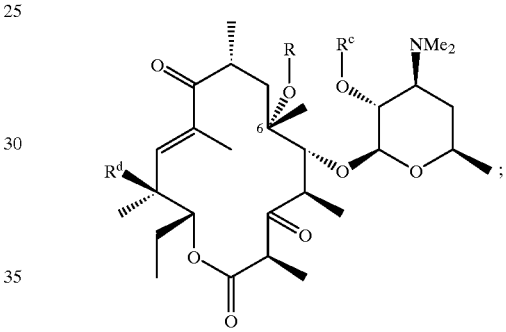

wherein
R, $R^c$ and $R^d$ are as defined previously.

In a preferred embodiment of the compounds of formula V of the invention are compounds having the formula VI

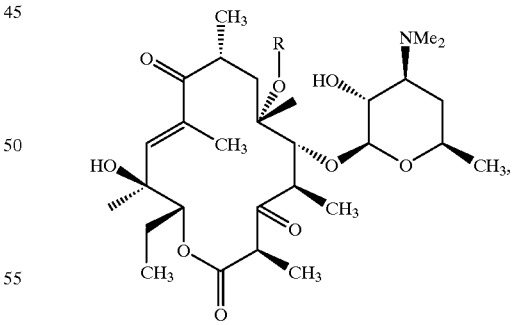

wherein
R is as defined previously.

Compounds representative of compounds of formula VI include, but are not limited to:
Compound of formula (VI): R is —$CH_2CH_2CH_3$,
Compound of formula (VI): R is —$CH_2CH$=$CH$,
Compound of formula (VI): R is —$CH_2CH$=$CH$-Phenyl,
Compound of formula (VI): R is —$CH_2CH_2CH_2$-Phenyl,
Compound of formula (VI): R is —$CH_2CH$=NOH, Compound of formula (VI): R is —CH$_2$CH$_2$NH$_2$,
Compound of formula (VI): R is —CH$_2$CH$_2$NHCH$_2$-Phenyl,
Compound of formula (VI): R is —CH$_2$CH$_2$NHCH$_2$-(4-pyrdidyl),
Compound of formula (VI): R is —CH$_2$CH$_2$NHCH$_2$-(4-quinolyl),
Compound of formula (VI): R is —CH$_2$CH(OH)CN,
Compound of formula (VI): R is —CH$_2$CH$_2$NHCH(CO$_2$CH$_3$)CH$_2$-Phenyl,
Compound of formula (VI): R is CH$_2$CN,
Compound of formula (VI): R is —CH$_2$CH=CH-(4-methoxyphenyl),
Compound of formula (VI): R is —CH$_2$CH=CH-(4-chlorophenyl),
Compound of formula (VI): R is —CH$_2$CH=CH-(4-fluorophenyl),
Compound of formula (VI): R is —CH$_2$CH=CH-(3-quinolyl),
Compound of formula (VI): R is —CH$_2$CH=CH-(8-quinolyl), and
Compound of formula (VI): R is —CH$_2$CH$_2$NHCH$_2$CH$_2$-(2-chlorophenyl).

Another embodiment of the invention is the process for preparing a compound having the formula

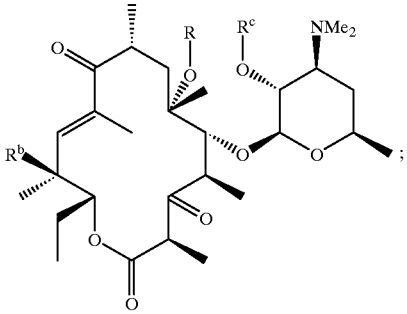

(V)

wherein
R and R$^c$ are as defined previously and R$^b$ is selected from the group consisting of hydroxy, —O—C(O)—NH$_2$ and —O—C(O)-imidazolyl; the method comprising:
(a) treating a compound having the formula

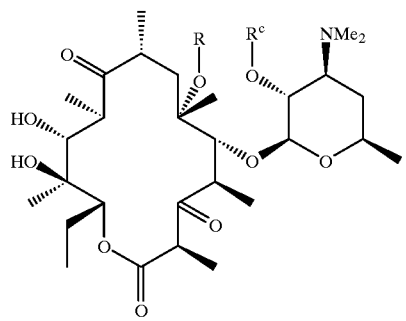

wherein
R$^c$ is a hydroxy protecting group and R is as previously defined with a reagent combination selected from
(1) an alkali metal hydride and a phosgene reagent selected from phosgene, diphosgene and triphosgene under anhydrous conditions, followed by aqueous base catalyzed decarboxylation, and (2) reaction with methanesulfonic anhydride in pyridine, followed by treatment with an amine base, to give the compound of formula V wherein R$^b$ is hydroxy;
(b) optionally treating the compound of formula V of step (b) wherein R$^b$ is hydroxy with an alkali metal hydride base and carbonyldiimidazole to give the compound of formula V wherein R$^b$ is —O—C(O)-imidazolyl;
(c) optionally treating the compound of formula V of step (a) wherein R$^b$ is —O—C(O)-imidazolyl with an amine to give the compound of formula V wherein R$^b$ is —O—C(O)—NH$_2$; and
(d) optionally deprotecting and isolating the desired compound.

Definitions

As used throughout this specification and the appended claims, the following terms have the meanings specified.

The terms "C$_1$–C$_3$-alkyl", "C$_1$–C$_6$-alkyl", and "C$_1$–C$_{12}$-alkyl" as used herein refer to saturated, straight- or branched-chain hydrocarbon radicals derived from a hydrocarbon moiety containing between one and three, one and six, and one and twelve carbon atoms, respectively, by removal of a single hydrogen atom. Examples of C$_1$–C$_3$-alkyl radicals include methyl, ethyl, propyl and isopropyl, examples of C$_1$–C$_6$-alkyl radicals include, but are not limited to, methyl, ethyl, propyl, isopropyl, n-butyl, tert-butyl, neopentyl and n-hexyl. Examples of C$_1$–C$_{12}$-alkyl radicals include, but are not limited to, all the foregoing examples as well as n-heptyl, n-octyl, n-nonyl, n-decyl, n-undecyl and n-docecyl.

The term "C$_1$–C$_6$-alkoxy" as used herein refers to an C$_1$–C$_6$-alkyl group, as previously defined, attached to the parent molecular moiety through an oxygen atom. Examples of C$_1$–C$_6$-alkoxy, but are not limited to, methoxy, ethoxy, propoxy, isopropoxy, n-butoxy, tert-butoxy, neopentoxy and n-hexoxy.

The term "C$_1$–C$_{12}$-alkenyl" denotes a monovalent group derived from a hydrocarbon moiety containing from two to twelve carbon atoms and having at least one carbon-carbon double bond by the removal of a single hydrogen atom. Alkenyl groups include, for example, ethenyl, propenyl, butenyl, 1-methyl-2-buten-1-yl, and the like.

The term "C$_1$–C$_{12}$-alkynyl" as used herein refers to a monovalent group derived from a hydrocarbon containing from two to twelve carbon atoms and having at least one carbon-carbon triple bond by the removal of a single hydrogen atom. Representative alkynyl groups include ethynyl, 2-propynyl (propargyl), 1-propynyl and the like.

The term "alkylene" denotes a divalent group derived from a straight or branched chain saturated hydrocarbon by the removal of two hydrogen atoms, for example methylene, 1,2-ethylene, 1,1-ethylene, 1,3-propylene, 2,2-dimethylpropylene, and the like.

The term "C$_1$–C$_3$-alkylamino" as used herein refers to one or two C$_1$–C$_3$-alkyl groups, as previously defined, attached to the parent molecular moiety through a nitrogen atom. Examples of C$_1$–C$_3$-alkylamino include, but are not limited to methylamino, dimethylamino, ethylamino, diethylamino, and propylamino.

The term "oxo" denotes a group wherein two hydrogen atoms on a single carbon atom in an alkyl group as defined above are replaced with a single oxygen atom (i.e. a carbonyl group).

The term "aprotic solvent" as used herein refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heteroaryl compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4th ed., edited by John A. Riddick et al., Vol. II, in the Techniques of Chemistry Series, John Wiley & Sons, New York, 1986.

The term "aryl" as used herein refers to a mono- or bicyclic carbocyclic ring system having one or two aromatic rings including, but not limited to, phenyl, naphthyl, tetrahydronaphthyl, indanyl, indenyl and the like. Aryl groups (including bicyclic aryl groups) can be unsubstituted or substituted with one, two or three substituents independently selected from loweralkyl, substituted loweralkyl, haloalkyl, alkoxy, thioalkoxy, amino, alkylamino, dialkylamino, acylamino, cyano, hydroxy, halo, mercapto, nitro, carboxaldehyde, carboxy, alkoxycarbonyl and carboxamide. In addition, substituted aryl groups include tetrafluorophenyl and pentafluorophenyl.

The term "$C_3$–$C_{12}$-cycloalkyl" denotes a monovalent group derived from a monocyclic or bicyclic saturated carbocyclic ring compound by the removal of a single hydrogen atom. Examples include cyclopropyl, cyclobutyl, cyclopentyl, cyclohexyl, bicyclo[2.2.1]heptyl, and bicyclo[2.2.2]octyl.

The terms "halo" and "halogen" as used herein refer to an atom selected from fluorine, chlorine, bromine and iodine.

The term "alkylamino" refers to a group having the structure —NHR' wherein R' is alkyl, as previously defined, Examples of alkylamino include methylamino, ethylamino, iso-propylamino and the like.

The term "dialkylamino" refers to a group having the structure —NR'R" wherein R' and R" are independently selected from alkyl, as previously defined. Additionally, R' and R" taken together may optionally be —$(CH_2)_k$— where k is an integer of from 2 to 6. Examples of dialkylamino include, dimethylamino, diethylaminocarbonyl, methylethylamino, piperidino, and the like.

The term "haloalkyl" denotes an alkyl group, as defined above, having one, two, or three halogen atoms attached thereto and is exemplified by such groups as chloromethyl, bromoethyl, trifluoromethyl, and the like.

The term "alkoxycarbonyl" represents an ester group; i.e. an alkoxy group, attached to the parent molecular moiety through a carbonyl group such as methoxycarbonyl, ethoxycarbonyl, and the like.

The term "thioalkoxy" refers to an alkyl group as previously defined attached to the parent molecular moiety through a sulfur atom.

The term "carboxaldehyde" as used herein refers to a group of formula —CHO.

The term "carboxy" as used herein refers to a group of formula —$CO_2H$.

The term "carboxamide" as used herein refers to a group of formula —CONHR'R" wherein R' and R" are independently selected from hydrogen or alkyl or R' and R" taken together may optionally be —$(CH_2)_k$— where k is an integer of from 2 to 6.

The term "heteroaryl", as used herein, refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

The term "heterocycloalkyl" as used herein, refers to a non-aromatic partially unsaturated or fully saturated 3- to 10-membered ring system, which includes single rings of 3 to 8 atoms in size and bi- or tri-cyclic ring systems which may include aromatic six-membered aryl or heteroaryl rings fused to a non-aromatic ring. These heterocycloalkyl rings include those having from one to three heteroatoms independently selected from oxygen, sulfur and nitrogen, in which the nitrogen and sulfur heteroatoms may optionally be oxidized and the nitrogen heteroatom may optionally be quaternized.

Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

Specific heterocycloalkyl rings considered useful in preparing compounds of the invention include: 3-methyl-4-(3-methylphenyl)piperazine, 3-methylpiperidine, 4-(bis-(4-fluorophenyl)methyl)piperazine, 4-(diphenylmethyl) piperazine, 4-(ethoxycarbonyl)piperazine, 4-(ethoxycarbonylmethyl)piperazine, 4-(phenylmethyl) piperazine, 4-(1-phenylethyl)piperazine, 4-(1,1-dimethylethoxycarbonyl)piperazine, 4-(2-(bis-(2-propenyl) amino)ethyl)piperazine, 4-(2-(diethylamino)ethyl) piperazine, 4-(2-chlorophenyl)piperazine, 4-(2-cyanophenyl)piperazine, 4-(2-ethoxyphenyl)piperazine, 4-(2-ethylphenyl)piperazine, 4-(2-fluorophenyl)piperazine, 4-(2-hydroxyethyl)piperazine, 4-(2-methoxyethyl) piperazine, 4-(2-methoxyphenyl)piperazine, 4-(2-methylphenyl)piperazine, 4-(2-methylthiophenyl) piperazine, 4-(2-nitrophenyl)piperazine, 4-(2-nitrophenyl) piperazine, 4-(2-phenylethyl)piperazine, 4-(2-pyridyl) piperazine, 4-(2-pyrimidinyl)piperazine, 4-(2,3-dimethylphenyl)piperazine, 4-(2,4-difluorophenyl) piperazine, 4-(2,4-dimethoxyphenyl)piperazine, 4-(2, 4dimethylphenyl)piperazine, 4-(2,5-dimethylphenyl) piperazine, 4-(2,6-dimethylphenyl)piperazine, 4-(3-chlorophenyl)piperazine, 4-(3- methylphenyl)piperazine, 4-(3-trifluoromethylphenyl)piperazine , 4-(3 ,4-dichlorophenyl)piperazine, 4-(3,4-dimethoxyphenyl) piperazine, 4-(3,4-dimethylphenyl)piperazine, 4-(3,4-methylenedioxyphenyl)piperazine, 4-(3,4,5-trimethoxyphenyl)piperazine, 4-(3,5-dichlorophenyl) piperazine, 4-(3,5-dimethoxyphenyl)piperazine, 4-(4-(phenylmethoxy)phenyl)piperazine, 4-(4-(1,1-dimethylethyl)phenylmethyl)piperazine, 4-(4-chloro-3-trifluoromethylphenyl)piperazine, 4-(4-chlorophenyl)-3-methylpiperazine, 4-(4-chlorophenyl)piperazine, 4-(4-chlorophenyl)piperazine, 4-(4-chlorophenylmethyl) piperazine, 4-(4-fluorophenyl)piperazine, 4-(4-methoxyphenyl)piperazine, 4-(4-methylphenyl)piperazine, 4-(4-nitrophenyl)piperazine, 4-(4-trifluoromethylphenyl) piperazine, 4-cyclohexylpiperazine, 4-ethylpiperazine, 4-hydroxy-4-(4-chlorophenyl)methylpiperidine, 4-hydroxy-4-phenylpiperidine, 4-hydroxypyrrolidine, 4-methylpiperazine, 4-phenylpiperazine, 4-piperidinylpiperazine, 4-((2-furanyl)carbonyl)piperazine, 4-((1,3-dioxolan-5-yl)methyl)piperazine, 6-fluoro-1,2,3,4-tetrahydro-2-methylquinoline, 1,4-diazacycloheptane, 2,3-dihydroindolyl, 3,3-dimethylpiperidine, 4,4-ethylenedioxypiperidine, 1,2,3,4-tetrahydroisoquinoline, 1,2,3,4-tetrahydroquinoline, azacyclooctane, decahydroquinoline, piperazine, piperidine, pyrrolidine, thiomorpholine, and triazole.

The term "heteroarylalkyl" as used herein, refers to a heteroaryl group as defined above attached to the parent molecular moiety through an alkylene group wherein the alkylene group is of one to four carbon atoms. "Hydroxy-protecting group", as used herein, refers to an easily removable group which is known in the art to protect a hydroxyl group against undesirable reaction during synthetic procedures and to be selectively removable. The use of hydroxy-protecting groups is well known in the art for protecting groups against undesirable reactions during a synthetic procedure and many such protecting groups are known, cf., for example, T. H. Greene and P. G. M. Wuts, *Protective Groups in Organic Synthesis,* 2nd edition, John Wiley & Sons, New York (1991). Examples of hydroxy-protecting groups include, but are not limited to, methylthiomethyl, tert-dimethylsilyl, tert-butyldiphenylsilyl, ethers such as methoxymethyl, and esters including acetyl benzoyl, and the like.

The term "ketone protecting group", as used herein, refers to an easily removable group which is known in the art to protect a ketone group against undesirable reactions during synthetic procedures and to be selectively removable. The use of ketone-protecting groups is well known in the art for protecting groups against undesirable reactions during a synthetic procedure and many such protecting groups are known, cf., for example, T. H. Greene and P. G. M. Wuts, *Protective Groups in Organic Synthesis,* 2nd edition, John Wiley & Sons, New York (1991). Examples of ketone-protecting groups include, but are not limited to, ketals, oximes, O-substituted oximes for example O-benzyl oxime, O-phenylthiomethyl oxime, 1-isopropoxycyclohexyl oxime, and the like.

A the term "protected-hydroxy" refers to a hydroxy group protected with a hydroxy protecting group, as defined above, including benzoyl, acetyl, trimethylsilyl, triethylsilyl, methoxymethyl groups, for example.

The term "

The term "protogenic organic solvent" as used herein refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. 11, in the Techniques of Chemistry Series, John Wiley & Sons, New York, 1986.

The term "substituted aryl" as used herein refers to an aryl group as defined herein substituted by independent replacement of one, two or three of the hydrogen atoms thereon with Cl, Br, F, I, OH, CN, $C_1$–$C_3$-alkyl, $C_1$–$C_6$-alkoxy, $C_1$–$C_6$-alkoxy substituted with aryl, haloalkyl, thioalkoxy, amino, alkylamino, dialkylamino, mercapto, nitro, carboxaldehyde, carboxy, alkoxycarbonyl and carboxamide. In addition, any one substitutent may be an aryl, heteroaryl, or heterocycloalkyl group. Also, substituted aryl groups include tetrafluorophenyl and pentafluorophenyl.

The term "substituted heteroaryl" as used herein refers to a heteroaryl group as defined herein substituted by independent replacement of one, two or three of the hydrogen atoms thereon with Cl, Br, F, I, OH, CN, $C_1$–$C_3$-alkyl, $C_1$–$C_6$-alkoxy, $C_1$–$C_6$-alkoxy substituted with aryl, haloalkyl, thioalkoxy, amino, alkylamino, dialkylamino, mercapto, nitro, carboxaldehyde, carboxy, alkoxycarbonyl and carboxamide. In addition, any one substitutent may be an aryl, heteroaryl, or heterocycloalkyl group.

The term "substituted heterocycloalkyl" as used herein, refers to a heterocycloalkyl group, as defined above, substituted by independent replacement of one, two or three of the hydrogen atoms thereon with Cl, Br, F, I, OH, CN, $C_1$–$C_3$-alkyl, $C_1$–$C_6$-alkoxy, $C_1$–$C_6$-alkoxy substituted with aryl, haloalkyl, thioalkoxy, amino, alkylamino, dialkylamino, mercapto, nitro, carboxaldehyde, carboxy, alkoxycarbonyl and carboxamide. In addition, any one substitutent may be an aryl, heteroaryl, or heterocycloalkyl group.

Numerous asymmetric centers may exist in the compounds of the present invention. Except where otherwise noted, the present invention contemplates the various stereoisomers and mixtures thereof. Accordingly, whenever a bond is represented by a wavy line, it is intended that a mixture of stereo-orientations or an individual isomer of assigned or unassigned orientation may be present.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in *J. Pharmaceutical Sciences,* 66: 1–19 (1977), incorporated herein by reference. The salts can be prepared in situ during the final isolation and purification of the compounds of the invention. or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid. oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters includes formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, *Pro-drugs as Novel Delivery Systems*, Vol. 14 of the A.C.S. Symposium Series, and in Edward B. Roche, ed., *Bioreversible Carriers in Drug Design*, American Pharmaceutical Association and Pergamon Press, 1987, both of which are incorporated herein by reference.

Antibacterial Activity

Representative compounds of the present invention were assayed in vitro for antibacterial activity as follows: Twelve petri dishes containing successive aqueous dilutions of the test compound mixed with 10 mL of sterilized Brain Heart Infusion (BHI) agar (Difco 0418-01-5) were prepared. Each plate was inoculated with 1:100 (or 1:10 for slow-growing strains, such as Micrococcus and Streptococcus) dilutions of up to 32 different microorganisms, using a Steers replicator block. The inoculated plates were incubated at 35–37° C. for 20 to 24 hours. In addition, a control plate, using BHI agar containing no test compound, was prepared and incubated at the beginning and end of each test.

An additional plate containing a compound having known susceptibility patterns for the organisms being tested and belonging to the same antibiotic class as the test compound was also prepared and incubated as a further control, as well as to provide test-to-test comparability. Erythromycin A was used for this purpose.

After incubation, each plate was visually inspected. The minimum inhibitory concentration (MIC) was defined as the lowest concentration of drug yielding no growth, a slight haze, or sparsely isolated colonies on the inoculum spot as compared to the growth control. The results of this assay, shown below in Table 2 demonstrate the antibacterial activity of the compounds of the invention.

TABLE 1

Antibacterial Activity (MIC's) of Selected Compounds

| Microorganism | Organism code | Ery. A standard | Example 1 | Example 2 | Example 3 | Example 5 | Example 7 | Example 8 | Example 9 |
|---|---|---|---|---|---|---|---|---|---|
| *Staphylococcus aureus* ATCC 6538P | AA | 0.2 | 12.5 | 3.1 | 25 | 6.2 | 3.1 | 25 | 3.1 |
| *Staphylococcus aureus* A5177 | BB | 3.1 | 50 | 3.1 | >100 | 6.2 | 3.1 | 25 | 1.56 |
| *Staphylococcus aureus* A-5278 | CC | >100 | >100 | >100 | >100 | >100 | >100 | >100 | >100 |
| *Staphylococcus aureus* CMX 642A | DD | 0.39 | 50 | 3.1 | 100 | 12.5 | 3.1 | 6.2 | 6.2 |
| *Staphylococcus aureus* NCTC10649M | EE | 0.39 | 6.2 | 1.56 | 25 | 12.5 | 3.1 | 6.2 | 0.78 |
| *Staphylococcus aureus* CMX 553 | FF | 0.39 | 25 | 3.1 | 25 | 12.5 | 3.1 | 50 | 3.1 |
| *Staphylococcus aureus* 1775 | GG | >100 | >100 | >100 | >100 | >100 | >100 | >100 | >100 |
| *Staphylococcus epidermidis* 3519 | HH | 0.39 | 50 | 6.2 | 50 | 6.2 | 3.1 | 100 | 3.1 |
| *Enterococcus faecium* ATCC 8043 | II | 0.05 | 12.5 | 6.2 | 25 | 6.2 | 1.56 | 6.2 | 0.78 |
| *Streptococcus bovis* A-5169 | JJ | 0.02 | 25 | 3.1 | 25 | 1.56 | 0.78 | 3.1 | 0.05 |
| *Streptococcus agalactiae* CMX 508 | KK | 0.05 | 6.2 | 1.56 | 25 | 1.56 | 0.78 | 6.2 | 0.39 |
| *Streptococcus pyogenes* EES61 | LL | 0.05 | —* | 3.1 | 100 | 3.1 | 1.56 | 6.2 | 0.39 |
| *Streptococcus pyogenes* 930 | MM | >100 | >100 | >100 | >100 | >100 | >100 | >100 | >100 |
| *Streptococcus pyogenes* PIU 2548 | NN | 6.2 | 12.5 | 3.1 | 100 | 6.2 | 3.1 | 12.5 | 0.78 |
| *Micrococcus luteus* ATCC 9341 | OO | 0.05 | 3.1 | 1.56 | 12.5 | 0.78 | 0.39 | 6.2 | 0.2 |
| *Micrococcus luteus* ATCC 4698 | PP | 0.2 | 6.2 | 3.1 | 100 | 6.2 | 1.56 | 12.5 | 0.78 |
| *Escherichia coli* JUHL | QQ | >100 | >100 | >100 | >100 | >100 | >100 | >100 | 25 |
| *Escherichia coli* SS | RR | 0.78 | 12.5 | 3.1 | 50 | 6.2 | 3.1 | 6.2 | 0.39 |
| *Escherichia coli* DC-2 | SS | >100 | >100 | >100 | >100 | >100 | 100 | >100 | 25 |
| *Candida albicans* CCH 442 | TT | >100 | >100 | >100 | >100 | >100 | >100 | >100 | >100 |
| *Mycobacterium smegmatis* ATCC 114 | UU | 3.1 | >100 | 25 | 100 | >100 | 100 | 100 | 6.2 |
| *Nocardia Asteroides* ATCC9970 | VV | 0.1 | 6.2 | 0.2 | 12.5 | 6.2 | 0.78 | 12.5 | 0.2 |
| *Haemophilis Influenzae* DILL AMP R | WW | 4 | >128 | — | — | >128 | — | — | 16 |
| *Streptococcus Pneumonia* ATCC6303 | XX | 0.06 | 4 | — | — | 8 | — | — | 0.25 |
| *Streptococcus Pneumonia* GYR 1171 | YY | 0.06 | 4 | — | — | 4 | — | — | 0.25 |
| *Streptococcus Pneumonia* 5979 | ZZ | >128 | >128 | — | — | >128 | — | — | >64 |
| *Streptococcus Pneumonia* 5649 | ZZA | 16 | 8 | — | — | 16 | — | — | 4 |

| Organism code | Example 10 | Example 12 | Example 14 | Example 15 | Example 16 | Example 17 | Example 18 | Example 71 | Example 72 | Example 73 | Example 74 |
|---|---|---|---|---|---|---|---|---|---|---|---|
| AA | 6.2 | 6.2 | 1.56 | 6.2 | 1.56 | 1.56 | 0.2 | 0.78 | 0.1 | 0.39 | 0.2 |
| BB | 6.2 | 3.1 | 1.56 | 6.2 | 1.56 | 1.56 | 0.2 | 0.39 | 0.1 | 0.39 | 0.2 |
| CC | >100 | >100 | >100 | >100 | >100 | 50 | >100 | >100 | >100 | 100 | >100 |
| DD | 6.2 | 6.2 | 3.1 | 6.2 | 1.56 | 1.56 | 0.2 | 1.56 | 0.1 | 0.39 | 0.2 |
| EE | 6.2 | 6.2 | 3.1 | 6.2 | 1.56 | 1.56 | 0.2 | 0.78 | 0.1 | 0.39 | 0.2 |
| FF | 6.2 | 6.2 | 3.1 | 6.2 | 1.56 | 1.56 | 0.2 | 3.1 | 0.2 | 0.39 | 0.2 |

TABLE 1-continued

Antibacterial Activity (MIC's) of Selected Compounds

| Organism code | | | | | | | | | | | |
|---|---|---|---|---|---|---|---|---|---|---|---|
| GG | >100 | >100 | >100 | >100 | >100 | 50 | >100 | >100 | 100 | 100 | >100 |
| HH | 6.2 | 12.5 | 1.56 | 6.2 | 1.56 | 1.56 | 0.2 | 3.1 | 0.1 | 0.39 | 0.2 |
| II | 6.2 | 1.56 | 0.78 | 1.56 | 0.78 | 1.56 | 0.2 | 1.56 | 0.05 | 0.1 | 0.1 |
| JJ | 0.2 | 0.2 | 0.2 | 0.2 | 0.2 | 0.39 | — | 0.2 | 0.01 | 0.05 | 0.05 |
| KK | 1.56 | 0.78 | 0.2 | 0.2 | 0.39 | 0.78 | 0.2 | 0.2 | 0.01 | 0.05 | 0.05 |
| LL | 0.39 | 0.39 | 0.39 | 0.39 | 0.39 | 0.78 | 0.2 | 0.39 | <0.005 | 0.05 | 0.05 |
| MM | >100 | >100 | 50 | 100 | >100 | 25 | 100 | >100 | 50 | 12.5 | 50 |
| NN | 1.56 | 1.56 | 0.78 | 3.1 | 0.78 | 0.78 | 0.1 | 0.39 | 0.2 | 0.2 | 0.39 |
| OO | 0.2 | 0.39 | 0.39 | 0.78 | 0.2 | 0.39 | — | — | 0.01 | 0.1 | 0.05 |
| PP | 1.56 | 0.78 | 0.78 | 3.1 | 0.78 | 0.78 | 0.2 | 0.78 | 0.1 | 0.2 | 0.2 |
| QQ | >100 | >100 | >100 | >100 | >100 | >100 | >100 | >100 | — | >100 | >100 |
| RR | 1.56 | 0.39 | 6.2 | 6.2 | 6.2 | 12.5 | 0.39 | 3.1 | 0.78 | 3.1 | 3.1 |
| SS | >100 | >100 | >100 | >100 | >100 | >100 | >100 | >100 | >100 | >100 | >100 |
| TT | >100 | >100 | >100 | >100 | >100 | 50 | >100 | >100 | >100 | >100 | >100 |
| UU | 12.5 | — | 3.1 | 6.2 | 3.2 | 3.1 | — | 25 | 0.78 | 0.78 | 0.39 |
| VV | 1.56 | 0.39 | 3.1 | 1.56 | 1.56 | 3.1 | 0.1 | 0.39 | 0.1 | 0.39 | 0.39 |
| WW | 64 | 32 | 128 | >64 | 128 | 64 | 16 | 64 | 8 | 16 | 4 |
| XX | 2 | 0.25 | 1 | 1 | 1 | 1 | 0.03 | 0.25 | 0.06 | 0.125 | 0.125 |
| YY | 2 | — | 0.25 | 1 | 0.25 | 0.5 | — | 0.25 | 0.06 | 0.125 | 0.125 |
| ZZ | >128 | >128 | 128 | 32 | 128 | 32 | 128 | >128 | 64 | 64 | 32 |
| ZZA | 4 | 2 | 2 | 1 | 2 | 2 | 0.25 | 1 | 0.5 | 1 | 0.5 |

| Organism code | Example 75 | Example 102 | Example 103 | Example 104 | Example 171 | Example 172 | Example 173 | Example 174 | Example 175 | Example 176 | Example 179 |
|---|---|---|---|---|---|---|---|---|---|---|---|
| AA | 0.1 | 0.78 | 0.1 | 0.05 | 0.1 | 100 | 12.5 | 3.1 | 0.2 | 1.56 | 6.2 |
| BB | 0.1 | 1.56 | 0.1 | 0.05 | 0.05 | 100 | 50 | 3.1 | 0.39 | 0.78 | 6.2 |
| CC | >100 | >100 | >100 | >100 | >100 | 100 | 100 | >100 | 25 | >100 | >100 |
| DD | 0.1 | 1.56 | 0.1 | 0.05 | 0.05 | 100 | 12.5 | 3.1 | 0.78 | 1.56 | 6.2 |
| EE | 0.1 | 0.78 | 0.1 | 0.1 | 0.02 | 100 | 12.5 | 3.1 | 0.78 | 0.78 | 6.2 |
| FF | 0.1 | 1.56 | 0.1 | 0.1 | 0.05 | >100 | 12.5 | 3.1 | 0.78 | 0.78 | 6.2 |
| GG | >100 | >100 | >100 | >100 | >100 | 100 | 100 | >100 | 12.5 | 100 | >100 |
| HH | 0.1 | 1.56 | 0.1 | 0.05 | 0.2 | 100 | 12.5 | 3.1 | 0.78 | 0.78 | 12.5 |
| II | 0.1 | 0.78 | 0.05 | 0.05 | 0.05 | 100 | 1.56 | 3.1 | 0.02 | 0.2 | 1.56 |
| JJ | <0.005 | 0.2 | 0.01 | 0.01 | <=0.005 | 25 | 0.78 | 0.2 | 0.02 | 0.05 | 0.39 |
| KK | 0.01 | 0.2 | 0.02 | 0.01 | 0.02 | 50 | 0.78 | 0.39 | 0.02 | 0.05 | 0.39 |
| LL | 0.02 | 0.2 | 0.02 | <=0.005 | <=0.005 | 50 | 0.78 | 0.39 | 0.01 | 0.05 | 0.39 |
| MM | 3.1 | >100 | 100 | 1.56 | 25 | 50 | 50 | >100 | 3.1 | 50 | >100 |
| NN | 0.1 | 0.2 | 0.1 | 0.1 | 0.2 | 25 | 3.1 | 1.56 | 0.39 | 0.2 | 0.78 |
| OO | 0.02 | 0.2 | 0.01 | <=0.005 | 0.01 | 50 | 0.78 | 0.39 | 0.05 | 0.05 | 1.56 |
| PP | 0.2 | 0.78 | 0.1 | 0.05 | 0.39 | 100 | 3.1 | 0.78 | 0.1 | 0.2 | 3.1 |
| QQ | 50 | >100 | 100 | 50 | 25 | >100 | >100 | >100 | >100 | >100 | >100 |
| RR | 0.39 | 1.56 | 0.39 | 0.39 | 0.39 | >100 | 50 | 12.5 | 0.78 | 3.1 | 6.2 |
| SS | >100 | >100 | 100 | 50 | 25 | >100 | >100 | >100 | >100 | >100 | >100 |
| TT | 100 | >100 | >100 | >100 | >100 | >100 | 100 | >100 | >100 | >100 | >100 |
| UU | 0.39 | 25 | 0.2 | 0.39 | 0.78 | 50 | 3.1 | 3.1 | 0.78 | 0.78 | 12.5 |
| VV | 0.05 | 1.56 | 0.02 | 0.01 | 0.05 | 25 | 6.2 | 0.78 | 0.39 | 1.56 | 3.1 |
| WW | 2 | 64 | 4 | 2 | 2 | >128 | 128 | 128 | 64 | 64 | >128 |
| XX | 0.03 | 0.5 | 0.03 | 0.03 | 0.03 | 16 | 2 | 1 | 0.03 | 0.25 | 0.5 |
| YY | 0.03 | 0.25 | 0.03 | 0.03 | 0.03 | 16 | 2 | 1 | 0.03 | 0.25 | 0.5 |
| ZZ | 64 | >64 | 128 | 16 | >16 | 64 | 32 | >128 | 8 | 64 | >128 |
| ZZA | 0.5 | 0.25 | 0.25 | 0.25 | 1 | 32 | 4 | 2 | 2 | 0.25 | 0.5 |

| Organism code | Example 180 | Example 181 | Example 182 | Example 183 | Example 184 | Example 185 | Example 186 | Example 187 | Example 188 | Example 189 | Example 190 |
|---|---|---|---|---|---|---|---|---|---|---|---|
| AA | 0.1 | 6.2 | 0.39 | 25 | 3.1 | 0.1 | 0.1 | 0.1 | 0.1 | 0.2 | 0.05 |
| BB | 0.1 | 6.2 | 0.2 | 25 | 1.56 | 0.1 | 0.01 | 0.1 | 0.1 | 0.1 | 0.05 |
| CC | >100 | >100 | >100 | >100 | >100 | >100 | >100 | >100 | >100 | >100 | >100 |
| DD | 0.1 | 6.2 | 0.39 | 25 | 3.1 | 0.1 | 0.1 | 0.1 | 0.1 | 0.2 | 0.05 |
| EE | 0.1 | 6.2 | 0.39 | 25 | 3.1 | 0.1 | 0.1 | 0.1 | 0.2 | 0.1 | 0.02 |
| FF | 0.1 | 6.2 | 0.39 | 25 | 1.56 | 0.1 | 0.01 | 0.1 | 0.1 | 0.1 | 0.02 |
| GG | >100 | >100 | >100 | >100 | >100 | >100 | >100 | >100 | >100 | >100 | >100 |
| HH | 0.1 | 12.5 | 0.78 | 25 | 3.1 | 0.1 | 0.1 | 0.1 | 0.1 | 0.2 | 0.05 |
| II | 0.05 | 0.78 | 0.1 | 3.1 | 0.2 | 0.05 | 0.05 | 0.02 | 0.05 | 0.05 | 0.02 |
| JJ | 0.02 | 0.1 | 0.01 | 0.78 | 0.1 | <=0.005 | <=0.005 | <=0.005 | <=0.005 | <=0.005 | <=0.005 |
| KK | 0.05 | 0.2 | 0.05 | 1.56 | 0.1 | 0.01 | 0.01 | 0.02 | <=0.005 | <=0.005 | <=0.005 |
| LL | 0.02 | 0.1 | 0.01 | 1.56 | 0.1 | 0.01 | 0.01 | 0.01 | 0.01 | <=0.005 | <=0.005 |
| MM | 25 | >100 | 100 | >100 | 25 | >100 | 3.1 | 25 | 25 | 50 | 12.5 |
| NN | 0.2 | 0.78 | 0.39 | 3.1 | 1.56 | 0.2 | 0.1 | 0.1 | 0.1 | 0.2 | 0.1 |
| OO | 0.02 | 0.78 | 0.02 | 6.2 | 0.39 | 0.01 | <=0.005 | 0.01 | 0.02 | 0.02 | 0.01 |
| PP | 0.1 | 1.56 | 0.39 | 25 | 0.78 | 0.1 | 0.1 | 0.02 | 0.2 | 0.1 | 0.1 |
| QQ | >100 | >100 | >100 | >100 | >100 | 100 | >100 | 100 | >100 | 100 | 100 |
| RR | 0.2 | 1.56 | 0.39 | 25 | 12.5 | 0.39 | 0.39 | 0.39 | 0.78 | 0.39 | 0.2 |
| SS | >100 | >100 | >100 | >100 | >100 | 100 | >100 | >100 | >100 | 50 | 100 |
| TT | >100 | >100 | >100 | >100 | >100 | >100 | >100 | >100 | >100 | >100 | >100 |
| UU | 0.2 | 12.5 | 0.39 | >100 | 6.2 | 3.1 | 0.2 | 0.78 | 0.78 | 0.78 | 0.78 |

TABLE 1-continued

Antibacterial Activity (MIC's) of Selected Compounds

| | | | | | | | | | | | |
|---|---|---|---|---|---|---|---|---|---|---|---|
| VV | 0.1 | 0.39 | 0.2 | 1.56 | 3.1 | 0.1 | 0.1 | 0.1 | 0.39 | 0.05 | 0.1 |
| WW | 4 | 64 | 8 | >128 | >128 | 8 | 16 | 2 | 8 | 8 | 4 |
| XX | 0.03 | 1 | 0.125 | 2 | 1 | 0.03 | 0.03 | 0.03 | 0.03 | 0.125 | 0.06 |
| YY | 0.03 | 1 | 0.25 | 2 | 0.5 | 0.03 | 0.015 | 0.03 | 0.03 | 0.06 | 0.03 |
| ZZ | 128 | >128 | >128 | >128 | 32 | >128 | >128 | >16 | >64 | >32 | >128 |
| ZZA | 0.25 | 2 | 2 | 2 | 2 | 0.5 | 1 | 0.25 | 1 | 0.5 | 0.5 |

| Organism code | Example 191 | Example 192 | Example 193 | Example 194 | Example 195 | Example 196 | Example 197 | Example 198 | Example 199 | Example 200 | Example 201 |
|---|---|---|---|---|---|---|---|---|---|---|---|
| AA | 0.05 | 0.1 | 0.05 | 0.05 | 0.05 | 0.1 | 0.1 | 0.05 | 0.1 | 0.1 | 0.1 |
| BB | 0.05 | 0.1 | 0.1 | 0.05 | — | — | 0.1 | 0.05 | 0.1 | 0.1 | 0.1 |
| CC | >100 | >100 | >100 | >100 | >100 | >100 | >100 | >100 | >100 | >100 | >100 |
| DD | 0.05 | 0.1 | 0.1 | 0.05 | 0.05 | 0.1 | 0.1 | 0.05 | 0.1 | 0.1 | 0.1 |
| EE | 0.1 | 0.2 | 0.1 | 0.1 | 0.05 | 0.1 | 0.2 | 0.05 | 0.1 | 0.1 | 0.1 |
| FF | 0.05 | 0.1 | 0.1 | 0.05 | 0.05 | 0.1 | 0.2 | 0.02 | 0.1 | 0.1 | 0.1 |
| GG | >100 | >100 | >100 | >100 | >100 | >100 | >100 | >100 | >100 | >100 | >100 |
| HH | 0.05 | 0.1 | 0.1 | 0.05 | 0.05 | 0.2 | 0.1 | 0.1 | 0.1 | 0.1 | 0.1 |
| II | 0.05 | 0.02 | 0.02 | 0.02 | 0.05 | 0.05 | 0.05 | 0.02 | <=0.05 | 0.02 | 0.05 |
| JJ | — | 0.01 | 0.01 | <=0.005 | 0.01 | <=0.005 | <=0.005 | <=0.005 | <=0.05 | 0.01 | 0.01 |
| KK | 0.05 | 0.01 | 0.01 | 0.01 | 0.05 | <=0.005 | <=0.005 | <=0.005 | <=0.05 | 0.02 | 0.01 |
| LL | 0.02 | 0.01 | <=0.005 | 0.01 | 0.02 | <=0.005 | <=0.005 | <=0.005 | — | — | 0.01 |
| MM | 3.1 | 50 | 25 | 0.78 | 1.56 | >100 | 100 | 0.39 | 50 | 50 | 1.56 |
| NN | 0.1 | 0.1 | 0.05 | 0.05 | 0.1 | 0.2 | 0.1 | 0.1 | 0.1 | 0.2 | 0.2 |
| OO | 0.01 | 0.01 | 0.01 | 0.01 | 0.01 | 0.01 | 0.02 | <=0.005 | 0.05 | 0.01 | 0.05 |
| PP | 0.1 | 0.2 | 0.1 | 0.1 | 0.1 | 0.1 | 0.2 | 0.1 | 0.1 | 0.2 | 0.1 |
| QQ | 50 | >100 | 100 | 50 | 50 | >100 | 100 | 50 | 100 | 50 | 50 |
| RR | 0.2 | 0.2 | 0.2 | 0.39 | 0.2 | 0.39 | 0.2 | 0.1 | 0.39 | 0.39 | 0.2 |
| SS | 100 | 100 | >100 | 100 | 50 | >100 | 100 | 50 | >100 | 12.5 | 50 |
| TT | >100 | >100 | >100 | >100 | >100 | >100 | >100 | >100 | >100 | >100 | >100 |
| UU | 0.39 | 3.1 | 0.39 | 0.78 | 0.39 | 0.2 | 1.56 | 0.39 | 0.78 | 0.78 | 6.2 |
| VV | 0.02 | 0.1 | 0.05 | <=0.005 | 0.05 | 0.1 | 0.1 | 0.02 | 0.1 | 0.1 | 0.2 |
| WW | 2 | 4 | 4 | 1 | 8 | 2 | 1 | 4 | 2 | 2 |
| XX | 0.03 | 0.03 | 0.03 | <=0.004 | 0.03 | 0.03 | 0.03 | <=0.004 | 0.008 | <=0.004 | 0.03 |
| YY | 0.03 | 0.03 | 0.015 | <=0.004 | 0.015 | 0.03 | 0.03 | <=0.004 | 0.008 | <=0.004 | 0.03 |
| ZZ | 2 | >128 | >128 | 64 | 4 | >128 | 64 | 4 | >128 | >128 | 16 |
| ZZA | 0.25 | 0.25 | 0.25 | 0.25 | 0.25 | 0.25 | 0.5 | 0.125 | 0.25 | 0.25 | 1 |

| Organism code | Example 202 | Example 203 | Example 204 | Example 205 | Example 206 | Example 207 | Example 208 | Example 209 | Example 210 | Example 211 | Example 212 |
|---|---|---|---|---|---|---|---|---|---|---|---|
| AA | — | 0.2 | 0.1 | — | 0.78 | 0.1 | 0.1 | 0.05 | 0.1 | 0.05 | 0.39 |
| BB | — | 0.39 | 0.1 | — | 0.39 | 0.1 | 0.39 | — | — | 0.05 | 0.39 |
| CC | — | >100 | >100 | — | >100 | >100 | >100 | >100 | >100 | >100 | >100 |
| DD | — | 0.2 | 0.1 | — | 0.78 | 0.1 | 0.2 | 0.1 | 0.1 | 0.1 | 0.39 |
| EE | — | 0.2 | 0.1 | — | 0.78 | 0.1 | 0.2 | 0.1 | 0.1 | 0.1 | 0.39 |
| FF | — | 0.39 | 0.1 | — | 0.78 | 0.1 | 0.2 | 0.1 | 0.1 | 0.1 | 0.39 |
| GG | — | >100 | >100 | — | >100 | >100 | >100 | >100 | >100 | >100 | >100 |
| HH | — | 0.2 | 0.1 | — | 0.78 | 0.1 | 0.2 | 0.1 | 0.1 | 0.05 | 0.39 |
| II | — | 0.2 | 0.05 | — | 0.39 | 0.02 | 0.1 | 0.02 | 0.02 | 0.01 | 0.1 |
| JJ | — | <=0.005 | 0.01 | — | 0.1 | <=0.005 | 0.01 | 0.01 | <=0.005 | 0.01 | <=0.005 |
| KK | — | 0.01 | 0.01 | — | 0.39 | <=0.005 | 0.01 | 0.01 | <=0.005 | 0.01 | 0.1 |
| LL | — | 0.01 | 0.01 | — | 0.39 | 0.01 | 0.01 | 0.01 | 0.01 | 0.01 | 0.05 |
| MM | — | 1.56 | 3.1 | — | >100 | 1.56 | 0.78 | 3.1 | 0.78 | 3.1 | 25 |
| NN | — | 0.39 | 0.2 | — | 1.56 | 0.2 | 0.39 | 0.1 | 0.2 | 0.1 | 0.39 |
| OO | — | 0.02 | 0.02 | — | 0.2 | 0.01 | 0.01 | 0.01 | 0.02 | 0.01 | 0.05 |
| PP | — | 0.39 | 0.1 | — | 1.56 | 0.1 | 0.1 | 0.2 | 0.2 | 0.1 | 0.39 |
| QQ | — | 100 | >100 | — | >100 | 25 | 25 | 100 | 50 | 25 | >100 |
| RR | — | 0.39 | 0.78 | — | 25 | 0.2 | 0.39 | 0.2 | 0.2 | 0.2 | 0.39 |
| SS | — | 100 | >100 | — | >100 | 50 | 50 | >100 | >100 | 50 | >100 |
| TT | — | >100 | >100 | — | >100 | >100 | >100 | >100 | >100 | >100 | >100 |
| UU | — | 6.2 | 0.78 | — | 3.1 | 0.39 | 0.78 | 0.78 | 0.78 | 0.39 | 0.78 |
| VV | — | 0.39 | 0.1 | — | 3.1 | 0.02 | 0.2 | 0.02 | 0.02 | 0.05 | 0.2 |
| WW | | 4 | 4 | | >128 | 2 | 2 | 2 | 2 | 2 | 8 |
| XX | 0.03 | 0.03 | 0.06 | 0.03 | 0.5 | 0.015 | 0.03 | 0.03 | 0.015 | <=0.004 | 0.125 |
| YY | 0.03 | 0.03 | 0.06 | 0.06 | 0.5 | 0.015 | 0.03 | 0.03 | <=0.004 | <=0.004 | 0.25 |
| ZZ | 32 | 16 | 8 | >64 | >128 | 64 | 4 | 4 | 4 | 16 | 128 |
| ZZA | 2 | 2 | 0.5 | 4 | 4 | 0.5 | 1 | 0.5 | 0.25 | 0.25 | 1 |

| Organism code | Example 213 | Example 214 | Example 215 | Example 216 | Example 217 | Example 218 | Example 219 | Example 221 | Example 222 | Example 223 | Example 224 |
|---|---|---|---|---|---|---|---|---|---|---|---|
| AA | 0.2 | 6.2 | 0.05 | 0.2 | 0.2 | 0.1 | 0.2 | 0.2 | 0.2 | 0.2 | 0.39 |
| BB | 0.2 | 25 | 0.1 | 0.2 | 0.39 | 0.1 | 0.2 | 0.39 | 0.1 | 0.2 | 0.2 |
| CC | >100 | >100 | >100 | >100 | >100 | >100 | 100 | >100 | >100 | >100 | >100 |
| DD | 0.2 | 12.5 | 0.1 | 0.2 | 0.39 | 0.1 | 0.2 | 0.39 | 0.39 | 0.2 | 0.2 |
| EE | 0.2 | 12.5 | 0.1 | 0.2 | | 0.1 | 0.2 | 0.2 | 0.2 | 0.2 | 0.2 |

TABLE 1-continued

Antibacterial Activity (MIC's) of Selected Compounds

| | | | | | | | | | | | |
|---|---|---|---|---|---|---|---|---|---|---|---|
| FF | 0.2 | 12.5 | 0.1 | 0.2 | 0.2 | 0.1 | 0.2 | 0.2 | 0.2 | 0.2 | 0.2 |
| GG | >100 | >100 | >100 | >100 | >100 | >100 | 100 | >100 | >100 | >100 | >100 |
| HH | 0.2 | 25 | 0.1 | 0.2 | 0.39 | 0.1 | 0.2 | 0.2 | 0.2 | 0.39 | 0.39 |
| II | 0.1 | 25 | 0.05 | 0.05 | 0.2 | 0.05 | 0.05 | 0.05 | 0.02 | 0.05 | 0.01 |
| JJ | 0.05 | 6.2 | 0.01 | 0.01 | 0.02 | 0.01 | <=0.005 | <=0.005 | <=0.005 | <=0.005 | 0.01 |
| KK | 0.05 | 3.1 | 0.01 | 0.02 | 0.02 | 0.01 | 0.02 | 0.02 | 0.02 | <=0.005 | <=0.005 |
| LL | 0.02 | 1.56 | 0.01 | 0.02 | 0.02 | 0.01 | 0.02 | 0.01 | <=0.005 | <=0.005 | 0.01 |
| MM | 100 | 12.5 | 0.78 | 0.78 | 0.78 | 6.2 | 3.1 | >100 | >100 | >100 | >100 |
| NN | 0.39 | 25 | 0.1 | 0.2 | 0.78 | 0.2 | 0.2 | 0.39 | 0.39 | 0.1 | 0.2 |
| OO | 0.05 | 12.5 | 0.01 | 0.05 | 0.1 | 0.05 | 0.05 | 0.02 | 0.01 | 0.05 | 0.02 |
| PP | 0.2 | 12.5 | 0.2 | 0.1 | 0.39 | 0.05 | 0.2 | 0.2 | 0.2 | 0.2 | 0.2 |
| QQ | 100 | >100 | 25 | 100 | 50 | 50 | 100 | 12.5 | 25 | 50 | 25 |
| RR | 0.39 | 3.1 | 0.2 | 0.39 | 0.39 | 0.39 | 0.78 | 0.1 | 0.1 | 0.2 | 0.2 |
| SS | >100 | >100 | >100 | >100 | >100 | >100 | >100 | 12.5 | 25 | 100 | 25 |
| TT | >100 | >100 | >100 | >100 | >100 | >100 | >100 | >100 | >100 | >100 | >100 |
| UU | 0.39 | 100 | 0.78 | 0.78 | 12.5 | 0.78 | 0.39 | 3.1 | 0.78 | 3.1 | 3.1 |
| VV | 0.39 | 50 | 0.02 | 0.1 | 0.78 | 0.05 | 0.05 | 0.2 | 0.2 | 0.2 | 0.1 |
| WW | 4 | 64 | 2 | 2 | 2 | | 2 | 2 | 4 | 4 | 4 |
| XX | 0.03 | 1 | 0.015 | 0.015 | 0.03 | 0.015 | 0.03 | 0.03 | 0.03 | 0.03 | 0.03 |
| YY | 0.03 | 1 | <=0.004 | 0.015 | 0.03 | 0.015 | 0.03 | 0.06 | 0.06 | 0.03 | 0.03 |
| ZZ | >128 | >128 | 16 | 0.5 | 2 | 4 | 2 | >128 | >128 | >128 | >128 |
| ZZA | 1 | 32 | 0.25 | 0.25 | 2 | 0.25 | 0.25 | 2 | 2 | 0.5 | 2 |

| Organism code | Example 225 | Example 226 | Example 227 | Example 228 | Example 229 | Example 230 | Example 231 | Example 232 | Example 233 | Example 234 | Example 235 |
|---|---|---|---|---|---|---|---|---|---|---|---|
| AA | 0.2 | 0.1 | 0.2 | 0.39 | 0.2 | 0.1 | 0.1 | 0.1 | 0.1 | 0.1 | 0.2 |
| BB | 0.39 | 0.1 | 0.2 | 0.78 | 0.2 | 0.1 | 0.1 | 0.1 | 0.1 | 0.1 | 0.2 |
| CC | >100 | >100 | >100 | >100 | >100 | >100 | >100 | >100 | >100 | >100 | >100 |
| DD | 0.39 | 0.1 | 0.2 | 0.78 | 0.2 | 0.1 | 0.1 | 0.2 | 0.2 | 0.2 | 0.2 |
| EE | 0.39 | 0.1 | 0.2 | 0.78 | 0.2 | 0.1 | 0.1 | 0.2 | 0.2 | 0.2 | 0.2 |
| FF | 0.2 | 0.1 | 0.2 | 0.78 | 0.2 | 0.2 | 0.05 | 0.1 | 0.1 | 0.1 | 0.2 |
| GG | >100 | >100 | >100 | >100 | >100 | >100 | >100 | >100 | >100 | >100 | >100 |
| HH | 0.2 | 0.1 | 0.2 | 0.78 | 0.2 | 0.1 | 0.2 | 0.2 | 0.2 | 0.1 | 0.2 |
| II | 0.05 | 0.05 | 0.05 | 0.1 | 0.05 | 0.05 | 0.02 | 0.02 | 0.05 | 0.05 | 0.05 |
| JJ | 0.01 | 0.01 | <=0.005 | 0.02 | <=0.005 | <=0.005 | 0.02 | 0.02 | 0.02 | <=0.005 | 0.01 |
| KK | 0.01 | 0.02 | 0.05 | <=0.005 | 0.02 | <=0.005 | 0.02 | 0.02 | 0.02 | 0.05 | 0.01 |
| LL | 0.01 | 0.01 | 0.02 | 0.01 | 0.01 | <=0.005 | 0.02 | 0.02 | 0.02 | 0.01 | 0.01 |
| MM | >100 | 6.2 | 50 | 25 | 50 | >100 | 100 | >100 | 100 | 100 | 25 |
| NN | 0.39 | 0.39 | 0.39 | 0.78 | 0.2 | 0.05 | 0.1 | 0.2 | 0.1 | 0.2 | 0.2 |
| OO | 0.02 | 0.02 | 0.05 | 0.2 | 0.02 | 0.05 | 0.02 | 0.02 | 0.02 | 0.01 | 0.05 |
| PP | 0.2 | 0.1 | 0.39 | 0.39 | 0.05 | 0.2 | 0.1 | 0.2 | 0.2 | 0.1 | 0.39 |
| QQ | 12.5 | 6.2 | 6.2 | >100 | >100 | 100 | 100 | 25 | 50 | 50 | >100 |
| RR | 0.2 | 0.2 | 0.2 | 0.78 | 0.39 | 0.39 | 0.39 | 0.39 | 0.39 | 0.39 | 0.78 |
| SS | 12.5 | 12.5 | 25 | >100 | >100 | >100 | 100 | >100 | 50 | 50 | >100 |
| TT | >100 | >100 | >100 | >100 | >100 | >100 | >100 | >100 | >100 | >100 | >100 |
| UU | 3.1 | 0.78 | 1.56 | 3.1 | 1.56 | 0.78 | 0.78 | 0.39 | 0.78 | 0.78 | 0.78 |
| VV | 0.2 | 0.05 | 0.05 | 0.78 | 0.2 | 0.05 | 0.05 | 0.05 | 0.05 | 0.1 | 3.1 |
| WW | 4 | 2 | 2 | 8 | 2 | 2 | 2 | 2 | 2 | 2 | 4 |
| XX | 0.03 | 0.03 | 0.03 | 0.125 | <=0.004 | 0.03 | 0.03 | 0.03 | 0.03 | 0.03 | 0.03 |
| YY | 0.06 | 0.03 | 0.03 | 0.125 | <=0.004 | 0.015 | 0.03 | 0.03 | 0.03 | 0.03 | 0.03 |
| ZZ | >128 | >128 | >64 | >128 | >128 | 128 | >128 | >128 | 64 | >128 | 32 |
| ZZA | 2 | 2 | 2 | 1 | 0.125 | 0.25 | 0.5 | 0.5 | 0.25 | 0.25 | 0.5 |

| Organism code | Example 236 | Example 237 | Example 238 | Example 239 | Example 240 | Example 241 | Example 242 | Example 243 | Example 244 | Example 245 | Example 246 |
|---|---|---|---|---|---|---|---|---|---|---|---|
| AA | 0.2 | 0.39 | 0.2 | 6.2 | 3.1 | 3.1 | 0.2 | 0.05 | 0.1 | 0.1 | 0.78 |
| BB | 0.2 | 0.39 | 0.2 | 6.2 | 3.1 | — | — | 0.05 | 0.2 | 0.2 | 0.78 |
| CC | >100 | >100 | >100 | >100 | >100 | >100 | >100 | >100 | >100 | >100 | >100 |
| DD | 0.2 | 0.39 | 0.39 | 6.2 | 6.2 | 6.2 | 0.2 | 0.05 | 0.2 | 0.2 | 0.78 |
| EE | 0.2 | 0.39 | 0.39 | 6.2 | 3.1 | 6.2 | 0.2 | 0.1 | 0.2 | 0.2 | 0.78 |
| FF | 0.2 | 0.39 | 0.39 | 6.2 | 3.1 | 6.2 | 0.2 | 0.05 | 0.1 | 0.2 | 0.78 |
| GG | 100 | >100 | >100 | >100 | >100 | >100 | >100 | >100 | >100 | >100 | >100 |
| HH | 0.2 | 0.39 | 0.39 | 6.2 | 3.1 | 6.2 | 0.39 | 0.1 | 0.2 | 0.1 | 0.78 |
| II | 0.05 | 0.1 | 0.05 | 1.56 | 0.78 | 1.56 | 0.1 | 0.02 | 0.05 | 0.05 | 0.2 |
| JJ | 0.05 | 0.05 | 0.02 | 0.39 | 0.39 | 0.39 | 0.02 | 0.02 | 0.01 | 0.05 | 0.1 |
| KK | 0.05 | 0.05 | 0.02 | 0.39 | 0.39 | 1.56 | 0.05 | 0.02 | <=0.005 | 0.02 | 0.2 |
| LL | 0.01 | 0.05 | 0.02 | 0.39 | 0.39 | 0.78 | 0.01 | 0.02 | 0.02 | 0.02 | 0.2 |
| MM | 25 | >100 | >100 | >100 | >100 | >100 | >100 | 6.2 | 1.56 | 0.78 | >100 |
| NN | 0.2 | 0.2 | 0.2 | 1.56 | 0.78 | 6.2 | 0.2 | 0.1 | 0.2 | 0.1 | 0.39 |
| OO | 0.05 | 0.05 | 0.05 | 0.39 | 0.39 | 0.78 | 0.05 | 0.02 | 0.02 | 0.05 | 0.2 |
| PP | 0.2 | 0.39 | 0.2 | 1.56 | 1.56 | 3.1 | 0.39 | 0.02 | 0.2 | 0.2 | 0.78 |
| QQ | 50 | >100 | 100 | >100 | >100 | >100 | >100 | 50 | 50 | 50 | >100 |
| RR | 0.39 | 0.39 | 0.39 | 6.2 | 3.1 | 1.56 | 0.78 | 0.2 | 0.1 | 0.05 | 0.78 |
| SS | >100 | >100 | >100 | >100 | >100 | >100 | >100 | 50 | 25 | 25 | >100 |
| TT | >100 | >100 | >100 | >100 | >100 | >100 | >100 | >100 | >100 | >100 | >100 |

TABLE 1-continued

Antibacterial Activity (MIC's) of Selected Compounds

| | | | | | | | | | | | |
|---|---|---|---|---|---|---|---|---|---|---|---|
| UU | 0.39 | 0.78 | 0.2 | 50 | 6.2 | 100 | 0.78 | 0.39 | 0.78 | 0.78 | 50 |
| VV | 0.2 | 0.39 | 0.1 | 3.1 | 1.56 | 6.2 | 0.39 | 0.05 | 0.02 | 0.05 | 0.78 |
| WW | 4 | 16 | 8 | 64 | 32 | 16 | 8 | 4 | 2 | 2 | 16 |
| XX | 0.03 | 0.03 | 0.03 | 0.25 | 0.25 | 0.5 | 0.03 | 0.03 | 0.03 | 0.03 | 0.25 |
| YY | 0.03 | 0.03 | 0.03 | 0.25 | 0.25 | 0.25 | 0.03 | 0.03 | 0.03 | 0.03 | 0.125 |
| ZZ | 32 | >128 | >64 | >128 | >128 | >128 | >128 | 128 | 64 | 64 | >128 |
| ZZA | 0 | 0.5 | 0.25 | 1 | 1 | 4 | 0.25 | 0.25 | 0.5 | 0.5 | 0.5 |

| Organism code | Example 247 | Example 248 | Example 249 | Example 250 | Example 251 | Example 252 | Example 253 | Example 254 | Example 255 | Example 256 | Example 257 |
|---|---|---|---|---|---|---|---|---|---|---|---|
| AA | 0.05 | 0.05 | 0.1 | 0.2 | 0.1 | 0.1 | 0.05 | 0.1 | 0.1 | 0.05 | 0.2 |
| BB | 0.05 | 0.05 | 0.1 | 0.2 | 0.1 | 0.1 | 0.05 | 0.1 | 0.2 | 0.05 | 0.2 |
| CC | >100 | >100 | >100 | >100 | >100 | >100 | >100 | >100 | >100 | >100 | >100 |
| DD | 0.05 | 0.05 | 0.2 | 0.2 | 0.1 | 0.1 | 0.05 | 0.1 | 0.2 | 0.05 | 0.2 |
| EE | 0.05 | 0.05 | 0.2 | 0.2 | 0.1 | 0.1 | 0.1 | 0.1 | 0.2 | 0.05 | 0.2 |
| FF | 0.05 | 0.02 | 0.1 | 0.2 | 0.1 | 0.1 | 0.05 | 0.1 | 0.2 | 0.02 | 0.2 |
| GG | >100 | >100 | >100 | 100 | >100 | >100 | >100 | >100 | >100 | >100 | >100 |
| HH | 0.05 | 0.05 | 0.1 | 0.2 | 0.1 | 0.1 | 0.05 | 0.1 | 0.1 | 0.1 | 0.2 |
| II | 0.02 | 0.02 | 0.05 | 0.05 | 0.1 | 0.05 | 0.05 | 0.02 | 0.05 | 0.02 | 0.1 |
| JJ | <=0.005 | 0.02 | 0.01 | 0.01 | 0.02 | 0.02 | 0.02 | <=0.005 | 0.02 | 0.01 | 0.01 |
| KK | 0.01 | <=0.005 | 0.02 | 0.05 | 0.02 | 0.02 | 0.01 | 0.02 | 0.02 | 0.05 |
| LL | 0.01 | <=0.005 | 0.02 | 0.01 | 0.05 | 0.05 | 0.01 | 0.01 | 0.02 | 0.01 | 0.01 |
| MM | 0.39 | 0.39 | 100 | 6.2 | 6.2 | 3.1 | 0.78 | 0.78 | 50 | 25 | 100 |
| NN | 0.1 | 0.1 | 0.1 | 0.2 | 0.2 | 0.1 | 0.05 | 0.1 | 0.2 | 0.2 | 0.2 |
| OO | 0.01 | 0.02 | 0.01 | 0.2 | 0.02 | 0.02 | 0.01 | 0.02 | 0.05 | 0.01 | 0.05 |
| PP | 0.02 | 0.1 | 0.1 | 0.2 | 0.2 | 0.2 | 0.1 | 0.1 | 0.2 | 0.1 | 0.2 |
| QQ | 25 | 50 | 100 | 100 | >100 | >100 | 50 | 25 | 100 | 100 | >100 |
| RR | 0.2 | 0.39 | 0.39 | 0.39 | 1.56 | 0.78 | 0.2 | 0.2 | 0.2 | 0.2 | 0.78 |
| SS | 25 | 50 | >100 | >100 | >100 | >100 | 50 | 100 | >100 | >100 | >100 |
| TT | >100 | >100 | >100 | >100 | >100 | >100 | >100 | >100 | >100 | >100 | >100 |
| UU | 0.39 | 0.39 | 0.39 | 0.78 | 0.2 | 0.2 | 0.2 | 0.78 | 3.1 | 1.56 | 0.39 |
| VV | 0.01 | 0.02 | 0.1 | 0.1 | 0.05 | 0.05 | 0.02 | 0.01 | 0.05 | 0.05 | 0.2 |
| WW | 1 | 1 | 4 | 4 | 16 | 2 | 2 | 2 | | 2 | 8 |
| XX | <=0.004 | 0.03 | 0.03 | 0.03 | 0.125 | 0.03 | 0.015 | <=0.004 | 0.03 | 0.03 | 0.125 |
| YY | <=0.004 | 0.03 | 0.03 | 0.03 | 0.25 | 0.03 | 0.03 | <=0.004 | 0.03 | 0.03 | 0.125 |
| ZZ | 4 | 4 | >128 | 16 | >128 | 4 | 1 | 2 | 16 | 16 | 128 |
| ZZA | 0.25 | 0.25 | 0.25 | 0.5 | 1 | 0.25 | 0.25 | 0.25 | 0.25 | 0.25 | 0.5 |

| Organism code | Example 258 | Example 259 | Example 260 | Example 261A | Example 261B | Example 262 | Example 263 | Example 264 | Example 265 | Example 266 | Example 267 |
|---|---|---|---|---|---|---|---|---|---|---|---|
| AA | 0.78 | 6.2 | 25 | 6.2 | 3.1 | 0.78 | 0.1 | 0.01 | 0.1 | 0.2 | 0.05 |
| BB | 0.39 | 6.2 | 25 | 6.2 | 3.1 | 0.78 | 0.1 | 0.01 | 0.1 | 0.2 | 0.05 |
| CC | >100 | >100 | >100 | >100 | >100 | >100 | >100 | >100 | 50 | >100 | >100 |
| DD | 0.78 | 12.5 | 25 | 12.5 | 6.2 | 0.78 | 0.1 | 0.01 | 0.1 | 0.2 | 0.05 |
| EE | 0.39 | 6.2 | 25 | 12.5 | 3.1 | 0.78 | 0.1 | 0.01 | 0.1 | 0.2 | 0.05 |
| FF | 0.78 | 6.2 | 25 | 12.5 | 3.1 | 0.78 | 0.05 | 0.01 | 0.1 | 0.2 | 0.05 |
| GG | >100 | >100 | >100 | >100 | >100 | >100 | >100 | >100 | 25 | >100 | >100 |
| HH | 0.78 | 6.2 | 25 | 6.2 | 6.2 | 0.78 | 0.1 | 0.05 | 0.1 | 0.2 | 0.05 |
| II | 0.39 | 0.78 | 3.1 | 1.56 | 0.78 | 0.39 | 0.02 | 0.01 | 0.05 | 0.1 | 0.05 |
| JJ | 0.05 | 0.39 | 0.78 | 0.39 | 0.39 | <=0.005 | 0.01 | <=0.005 | <=0.005 | 0.01 | <=0.005 |
| KK | 0.1 | 0.78 | 0.78 | 0.39 | 0.39 | 0.05 | 0.02 | 0.01 | <=0.005 | 0.01 | <=0.005 |
| LL | 0.05 | 0.39 | 0.78 | 0.39 | 0.39 | 0.1 | 0.02 | 0.01 | 0.01 | 0.01 | <=0.005 |
| MM | >100 | >100 | >100 | >100 | >100 | >100 | 50 | 3.1 | 6.2 | 6.2 | 1.56 |
| NN | 0.2 | 1.56 | 12.5 | 1.56 | 0.78 | 0.78 | 0.2 | 0.2 | 0.1 | 0.2 | 0.1 |
| OO | 0.1 | 0.78 | 1.56 | 0.78 | 0.39 | 0.1 | 0.02 | <=0.005 | 0.01 | 0.02 | <=0.005 |
| PP | 0.39 | 1.56 | 3.1 | 3.1 | 1.56 | 0.39 | 0.2 | 0.1 | 0.05 | 0.2 | 0.05 |
| QQ | >100 | >100 | >100 | >100 | >100 | >100 | >100 | 100 | >100 | >100 | 25 |
| RR | 0.78 | 1.56 | 6.2 | 6.2 | 6.2 | 1.56 | 0.78 | 0.1 | 0.78 | 0.78 | 0.2 |
| SS | >100 | >100 | >100 | >100 | >100 | >100 | >100 | 100 | >100 | >100 | 25 |
| TT | >100 | >100 | >100 | >100 | >100 | >100 | >100 | >100 | 50 | >100 | >100 |
| UU | 12.5 | 12.5 | >100 | 25 | 25 | 6.2 | 0.78 | 0.78 | 0.2 | 0.39 | 0.39 |
| VV | 0.39 | 3.1 | 50 | 6.2 | 6.2 | 0.39 | 0.2 | 0.01 | 0.2 | 0.1 | 0.02 |
| WW | 32 | 128 | 64 | 64 | 32 | 16 | 4 | 2 | 4 | 4 | 2 |
| XX | 0.03 | 1 | 2 | 1 | 0.5 | 0.03 | 0.015 | 0.03 | 0.015 | 0.06 | 0.03 |
| YY | 0.03 | 1 | 1 | 1 | 0.5 | 0.03 | 0.015 | 0.015 | 0.015 | 0.03 | 0.03 |
| ZZ | >128 | >128 | >64 | >128 | >128 | >128 | >128 | >128 | 32 | 2 | 8 |
| ZZA | 0.125 | 4 | 16 | 2 | 1 | 0.5 | 0.25 | 0.5 | 0.25 | 0.25 | 0.25 |

| Organism code | Example 268 | Example 269 | Example 270 | Example 271 | Example 272 | Example 273 | Example 274 | Example 275 | Example 276 | Example 277 | Example 278 |
|---|---|---|---|---|---|---|---|---|---|---|---|
| AA | 0.39 | — | 0.1 | 0.39 | 0.2 | 0.2 | 0.1 | 0.2 | 0.39 | 1.56 | 0.05 |
| BB | 0.39 | — | 0.1 | 0.78 | 0.1 | 0.2 | 0.1 | 0.2 | 0.78 | 1.56 | 0.05 |
| CC | 25 | — | >100 | >100 | 100 | >100 | >100 | >100 | 50 | >100 | >100 |
| DD | 0.39 | — | 0.1 | 0.39 | 0.2 | 0.2 | 0.1 | 0.2 | 0.39 | 1.56 | 0.05 |

TABLE 1-continued

Antibacterial Activity (MIC's) of Selected Compounds

| | | | | | | | | | | | |
|---|---|---|---|---|---|---|---|---|---|---|---|
| EE | 0.39 | — | 0.2 | 0.78 | 0.2 | 0.2 | 0.1 | 0.2 | 0.78 | 1.56 | 0.05 |
| FF | 0.39 | — | 0.1 | 0.39 | 0.1 | 0.2 | 0.05 | 0.2 | 0.78 | 1.56 | 0.05 |
| GG | 25 | — | >100 | 100 | 50 | >100 | >100 | >100 | 25 | >100 | >100 |
| HH | 0.39 | — | 0.1 | 0.39 | 0.2 | 0.2 | 0.1 | 0.2 | 0.78 | 1.56 | 0.1 |
| II | 0.2 | — | 0.05 | 0.39 | 0.05 | 0.1 | 0.05 | 0.1 | 0.2 | 0.78 | 0.05 |
| JJ | 0.1 | — | 0.05 | 0.1 | 0.02 | 0.02 | 0.01 | 0.01 | 0.02 | 0.39 | 0.01 |
| KK | 0.1 | — | 0.05 | 0.2 | 0.02 | 0.02 | 0.01 | 0.05 | 0.1 | 0.2 | 0.01 |
| LL | 0.1 | — | 0.05 | 0.1 | 0.05 | 0.05 | 0.01 | 0.02 | 0.02 | 0.2 | <=0.005 |
| MM | 25 | — | 3.1 | 6.2 | 3.1 | 12.5 | 6.2 | 12.5 | 25 | 50 | 1.56 |
| NN | 0.39 | — | 0.2 | 0.39 | 0.2 | 0.39 | 0.1 | 0.2 | 0.39 | 1.56 | 0.2 |
| OO | 0.1 | — | 0.02 | 0.2 | 0.05 | 0.05 | 0.01 | 0.02 | 0.1 | 0.39 | 0.01 |
| PP | 0.39 | — | 0.2 | 0.78 | 0.2 | 0.39 | 0.1 | 0.2 | 0.39 | 3.1 | 0.1 |
| QQ | >100 | — | 50 | >100 | >100 | >100 | >100 | >100 | >100 | >100 | 25 |
| RR | 3.1 | — | 0.39 | 3.1 | 0.78 | 0.78 | 0.2 | 0.78 | 6.2 | 6.2 | 0.39 |
| SS | >100 | — | 50 | >100 | >100 | >100 | >100 | >100 | >100 | >100 | 12.5 |
| TT | >100 | — | >100 | >100 | >100 | >100 | >100 | >100 | 100 | >100 | >100 |
| UU | 0.39 | — | 0.39 | 1.56 | 0.2 | 0.78 | 0.78 | 0.39 | 0.78 | 3.1 | 0.78 |
| VV | 0.39 | — | 0.1 | 0.78 | 0.2 | 0.39 | 0.05 | 0.2 | 1.56 | 3.1 | 0.02 |
| WW | 16 | | 16 | 64 | 32 | 8 | 4 | 8 | 8 | >128 | 4 |
| XX | 0.125 | 0.06 | 0.03 | 0.25 | 0.03 | 0.03 | <=0.004 | 0.03 | 0.125 | 0.5 | 0.03 |
| YY | 0.125 | 0.06 | 0.03 | 0.25 | 0.03 | 0.03 | <=0.004 | 0.03 | 0.125 | 0.5 | 0.03 |
| ZZ | 8 | 2 | 2 | 8 | 16 | 16 | 8 | 4 | 16 | 32 | 128 |
| ZZA | 1 | 0.5 | 0.25 | 1 | 0.25 | 0.5 | 0.25 | 0.5 | 0.5 | 4 | 0.5 |

| Organism code | Example 279 | Example 280 | Example 281 | Example 282 | Example 283 | Example 284 | Example 285 | Example 286 | Example 287 | Example 288 | Example 289 |
|---|---|---|---|---|---|---|---|---|---|---|---|
| AA | 0.39 | 0.39 | 0.78 | 0.2 | 0.1 | 0.2 | 3.1 | 6.2 | 0.1 | 0.1 | 0.2 |
| BB | 0.39 | 0.39 | 0.78 | 0.1 | 0.1 | 0.2 | 3.1 | 6.2 | 0.1 | 0.2 | 0.2 |
| CC | 50 | 50 | >100 | 100 | 100 | 50 | >100 | >100 | >100 | >100 | >100 |
| DD | 0.78 | 0.39 | 0.78 | 0.2 | 0.1 | 0.2 | 3.1 | 6.2 | 0.1 | 0.39 | 0.2 |
| EE | 0.39 | 0.39 | 0.78 | 0.2 | 0.1 | 0.2 | 3.1 | 6.2 | 0.1 | 0.39 | 0.2 |
| FF | 0.39 | 0.39 | 0.78 | 0.1 | 0.1 | 0.2 | 3.1 | 6.2 | 0.02 | 0.39 | 0.2 |
| GG | 50 | 25 | >100 | 100 | 50 | 50 | >100 | >100 | >100 | 100 | >100 |
| HH | 0.39 | 0.39 | 0.78 | 0.2 | 0.2 | 0.2 | 3.1 | 6.2 | 0.1 | 0.39 | 0.2 |
| II | 0.2 | 0.2 | 0.39 | 0.05 | 0.05 | 0.05 | 0.39 | 1.56 | 0.05 | 0.39 | 0.2 |
| JJ | 0.05 | 0.05 | 0.05 | 0.01 | 0.01 | 0.02 | 0.2 | 0.39 | 0.02 | 0.01 | 0.02 |
| KK | 0.02 | 0.05 | 0.1 | 0.02 | 0.02 | 0.02 | 0.2 | 0.2 | 0.02 | 0.02 | 0.1 |
| LL | — | 0.1 | 0.1 | <=0.005 | <=0.005 | <=0.005 | 0.05 | 0.78 | 0.02 | 0.1 | 0.1 |
| MM | 25 | 12.5 | 50 | 25 | 3.1 | 25 | 100 | 100 | 3.1 | 12.5 | >100 |
| NN | 0.39 | 0.39 | 0.39 | 0.1 | 0.2 | 0.2 | 0.78 | 1.56 | 0.1 | 0.39 | 0.39 |
| OO | 0.05 | 0.1 | 0.2 | 0.05 | 0.01 | 0.05 | 0.39 | 1.56 | 0.02 | 0.02 | 0.05 |
| PP | 0.39 | 0.78 | 0.78 | 0.2 | 0.2 | 0.2 | 0.39 | 3.1 | 0.2 | 0.39 | 0.39 |
| QQ | >100 | >100 | >100 | >100 | >100 | >100 | >100 | >100 | 50 | >100 | >100 |
| RR | 1.56 | 1.56 | 3.1 | 0.78 | 0.78 | 1.56 | 12.5 | 12.5 | 0.39 | 3.1 | 3.1 |
| SS | >100 | >100 | >100 | >100 | >100 | >100 | >100 | >100 | >100 | >100 | >100 |
| TT | >100 | >100 | >100 | >100 | >100 | 50 | >100 | >100 | >100 | >100 | >100 |
| UU | 0.78 | 3.1 | 3.1 | 1.56 | 0.39 | 0.2 | 6.2 | 25 | 0.39 | 0.39 | 1.56 |
| VV | 0.78 | 6.2 | 3.1 | 0.2 | 0.2 | 0.78 | 1.56 | 12.5 | 0.05 | 0.39 | 0.39 |
| WW | 8 | 8 | 32 | 8 | 2 | 4 | >128 | 128 | 2 | 8 | 64 |
| XX | 0.03 | 0.06 | 0.25 | 0.03 | <=0.004 | 0.03 | 0.25 | 1 | 0.03 | 0.125 | 0.25 |
| YY | 0.03 | 0.06 | 0.25 | 0.03 | <=0.004 | 0.03 | 0.25 | 0.5 | 0.03 | 0.125 | 0.25 |
| ZZ | 32 | 16 | 64 | 16 | 4 | 32 | 64 | 64 | 4 | 16 | >128 |
| ZZA | 0.5 | 1 | 1 | 0.25 | 0.125 | 0.25 | 1 | 2 | 0.5 | 1 | 1 |

| Organism code | Example 290 | Example 291 | Example 292 | Example 293 |
|---|---|---|---|---|
| AA | 0.1 | 0.05 | 0.1 | 0.39 |
| BB | 0.1 | 0.05 | 0.1 | 0.39 |
| CC | 50 | >100 | >100 | >100 |
| DD | 0.1 | 0.05 | 0.1 | 0.39 |
| EE | 0.1 | 0.05 | 0.1 | 0.39 |
| FF | 0.1 | 0.05 | 0.1 | 0.39 |
| GG | 25 | >100 | >100 | >100 |
| HH | 0.1 | 0.05 | 0.05 | 0.39 |
| II | 0.05 | 0.02 | 0.02 | 0.1 |
| JJ | <=0.005 | <=0.005 | <=0.005 | 0.02 |
| KK | <=0.005 | <=0.005 | 0.02 | 0.05 |
| LL | 0.01 | <=0.005 | 0.01 | 0.02 |
| MM | 6.2 | 3.1 | 12.5 | >100 |
| NN | 0.1 | 0.1 | 0.05 | 0.78 |
| OO | 0.01 | <=0.005 | 0.02 | 0.05 |
| PP | 0.05 | 0.05 | 0.1 | 0.2 |
| QQ | >100 | 25 | 50 | >100 |
| RR | 0.78 | 0.1 | 0.2 | 0.78 |
| SS | >100 | 50 | 100 | >100 |
| TT | 50 | >100 | >100 | >100 |

TABLE 1-continued

Antibacterial Activity (MIC's) of Selected Compounds

| | | | | |
|---|---|---|---|---|
| UU | 0.2 | 0.39 | 0.78 | 12.5 |
| VV | 0.2 | 0.01 | 0.02 | 0.78 |
| WW | 4 | 2 | 2 | 16 |
| XX | 0.015 | <=0.004 | 0.03 | 0.03 |
| YY | 0.015 | <=0.004 | 0.03 | 0.03 |
| ZZ | 32 | 1 | 16 | >128 |
| ZZA | 0.25 | 0.125 | 0.25 | 0.5 |

*missing data is indicated by

Pharmaceutical Compositions

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be. present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), bucally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye drops are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, bacterial infections are treated or prevented in a patient such as a human or lower mammal by administering to the patient a therapeutically effective amount of a compound of the invention, in such amounts and for such time as is necessary to achieve the desired result. By a "therapeutically effective amount" of a compound of the invention is meant a sufficient amount of the compound to treat bacterial infections, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; the activity of the specific compound employed: the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compounds of this invention administered to a human or other mammal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 2000 mg of the compound(s) of this invention per day in single or multiple doses.

Abbreviations

Abbreviations which have been used in the descriptions of the scheme and the examples that follow are: AIBN for azobisisobutyronitrile; $Bu_3SnH$ for tributyltin hydride; CDI for carbonyldiimidazole; DBU for 1,8-diazabicyclo[5.4.0]undec-7-ene; DEAD for diethylazodicarboxylate; DMF for dimethylformamide; DMSO for dimethylsulfoxide; DPPA for diphenylphosphoryl azide; Et$_3$N for triethylamine; EtOAc for ethyl acetate; Et$_2$O for diethyl ether; EtOH for ethanol; HOAc for acetic acid; MeOH for methanol; NaN(TMS)$_2$ for sodium bis(trimethylsilyl)amide; NMMO for N-methylmorpholine N-oxide; TEA for triethylamine; THF for tetrahydrofuran; and TPP for triphenylphosphine.

Synthetic Methods

The compounds and processes of the present invention will be better understood in connection with the following synthetic schemes I–VI (to be found following the text describing the schemes) which illustrate the methods by which the compounds of the invention may be prepared. The compounds of the present invention are prepared by the representative methods described below. The groups A, B, D, E, W, X, Y, Z, R$^a$, R$^b$, R$^c$, and R$^d$ are as defined above unless otherwise noted below.

The preparation of the compounds of the invention of formula VIII from erythromycin A is outlined in Schemes Ia and Ib. The preparation of protected erythromycin A is described in the following United States patents, U.S. Pat. No. 4,990,602; U.S. Pat. No. 4,331,803, U.S. Pat. No. 4,680,368, and U.S. Pat. No. 4,670,549 which are incorporated by reference. Also incorporated by reference is European Patent Application EP 260,938. In general, the C-9-carbonyl group of compound I is protected as an oxime, (V is =N—O—R$^3$ or =N—O—C(R$^8$)(R$^9$)—O—R$^3$ where R$^3$ is defined above and R$^8$ and R$^9$ are each independently selected from the group consisting of (a) hydrogen, (b) unsubstituted C$_1$–C$_{12}$-alkyl, (c) C$_1$–C$_{12}$-alkyl substituted with aryl, and (d) C$_1$–C$_{12}$-alkyl substituted with substituted aryl, or R$^9$ and R$^{10}$ taken together with the carbon to which they are attached form a C$_3$–C$_{12}$-cycloalkyl ring). An especially preferred carbonyl protecting group V is O-(1-isopropoxycyclohexyl)oxime.

The 2'- and 4"-hydroxy groups of 2 are protected by reaction with a suitable hydroxy protecting reagent, such as those described by T. W. Greene and P. G. M. Wuts in *Protective Groups in Organic Synthesis*, 2nd ed., John Wiley & Son, Inc., 1991, which is incorporated by reference. Hydroxy protecting groups include, for example, acetic anhydride, benzoic anhydride, benzyl chloroformate, hexamethyldisilazane, or a trialkylsilyl chloride in an aprotic solvent. Examples of aprotic solvents are dichloromethane, chloroform, DMF, tetrahydrofuran (THF), N-methyl pyrrolidinone, dimethylsulfoxide, diethylsulfoxide, N,N-dimethylformamide, N,N-dimethylacetamide, hexamethylphosphoric triamide, a mixture thereof or a mixture of one of these solvents with ether, tetrahydrofuran, 1,2-dimethoxyethane, acetonitrile, ethyl acetate, acetone and the like. Aprotic solvents do not adversely affect the reaction, and are preferably dichloromethane, chloroform, DMF, tetrahydrofuran (THF), N-methyl pyrrolidinone or a mixture thereof. Protection of 2'- and 4"-hydroxy groups of 2 may be accomplished sequentially or simultaneously to provide compound 3 where RP is a hydroxy protecting group. A preferred protecting group RP is trimethylsilyl.

The 6-hydroxy group of compound 3 is then alkylated by reaction with an alkylating agent in the presence of base to give compound 4. Alkylating agents include alkyl chlorides, bromides, iodides or alkyl sulfonates. Specific examples of alkylating agents include allyl bromide, propargyl bromide, benzyl bromide, 2-fluoroethyl bromide, 4-nitrobenzyl bromide, 4-chlorobenzyl bromide, 4-methoxybenzyl bromide, α-bromo-p-tolunitrile, cinnamyl bromide, methyl 4-bromocrotonate, crotyl bromide, 1-bromo-2-pentene, 3-bromo-1-propenyl phenyl sulfone, 3-bromo-1-trimethylsilyl-1-propyne, 3-bromo-2-octyne, 1-bromo-2-butyne, 2-picolyl chloride, 3-picolyl chloride, 4picolyl chloride, 4-bromomethyl quinoline, bromoacetonitrile, epichlorohydrin, bromofluoromethane, bromonitromethane, methyl bromoacetate, methoxymethyl chloride, bromoacetamide, 2-bromoacetophenone, 1-bromo-2-butanone, bromo chloromethane, bromomethyl phenyl sulfone, 1,3-dibromo-1-propene, and the like. Examples of alkyl sulfonates are: allyl 0-tosylate, 3-phenylpropyl-O-trifluoromethane sulfonate, n-butyl —O-methanesulfonate and the like. Examples of the solvents used are aprotic solvents such as dimethylsulfoxide, diethylsulfoxide, N,N-dimethylformamide, N,N-dimethylacetamide, N-methyl-2-pyrrolidone, hexamethylphosphoric triamide, a mixture thereof or a mixture of one of these solvents with ether, tetrahydrofuran, 1,2-dimethoxyethane, acetonitrile, ethyl acetate, acetone and the like. Examples of the base which can be used include potassium hydroxide, cesium hydroxide, tetraalkylammonium hydroxide, sodium hydride, potassium hydride, potassium isopropoxide, potassium tert-butoxide, potassium isobutoxide and the like.

The deprotection of the 2'- and 4"-hydroxyl groups is then carried out according to methods described in literature, for example, by T. W. Greene and P. G. M. Wuts in *Protective Groups in Organic Synthesis*, 2nd ed., John Wiley & Son, Inc., 1991, which is incorporated herein by reference. The conditions used for the deprotection of the 2'- and 4"-hydroxyl groups usually results in the conversion of X to =N—OH. (For example, using acetic acid in acetonitrile and water results in the deprotection of the 2'- and 4"-hydroxyl groups and the conversion of X from =N—O—R$^3$ or =N—O—C(R$^8$)(R$^9$)—O'R$^3$ where R$^3$, R$^8$ and R$^9$ are as defined above to =N—OH.) If this is not the case, the conversion is carried out in a separate step.

The deoximation reaction can be carried out according to the methods described in the literature, for example by Greene (op. cit.) and others. Examples of the deoximating agent are inorganic sulfur oxide compounds such as sodium hydrogen sulfite, sodium pyrosulfate, sodium thiosulfate, sodium sulfate, sodium sulfite, sodium hydrosulfite, sodium metabisulfite, sodium dithionate, potassium thiosulfate, potassium metabisulfite and the like. Examples of the solvents used are protic solvents such as water, methanol, ethanol, propanol, isopropanol, trimethylsilanol or a mixture of one or more of the mentioned solvents and the like. The deoximation reaction is more conveniently carried out in the presence of an organic acid such as formic acid, acetic acid and trifluoroacetic acid. The amount of acid used is from about 1 to about 10 equivalents of the amount of compound 5 used. In a preferred embodiment, the deoximation is carried out using an organic acid such as formic acid in ethanol and water to give the desired product 6.

The conversion of the 6-substituted erythromycin derivative to the 6-substituted ketolide is described in scheme 1b. The cladinose moiety of macrolide 6 is removed either by mild aqueous acid hydrolysis or by enzymatic hydrolysis to give 7. Representative acids include dilute hydrochloric acid, sulfuric acid, perchloric acid, chloroacetic acid, dichloroacetic acid or trifluoroacetic acid. Suitable solvents for the reaction include methanol, ethanol, isopropanol, butanol and the like. Reaction times are typically 0.5 to 24 hours. The reaction temperature is preferably −10 to 35° C. The 2'-hydroxy group of 7 is protected using a suitable hydroxy protecting reagent such as acetic anhydride, benzoyl anhydride, benzyl chloroformate or trialkylsilyl chloride in an aprotic solvent, as defined above, preferably dichloromethane, chloroform, DMF, tetrahydrofuran (THF), N-methyl pyrrolidinone or a mixture thereof. A particularly preferred protecting group RP is benzoate. It is possible to reverse the order of the steps for removing the cladinose and protecting the hydroxy groups without affecting the yield of the process.

The 3-hydroxy group of 8 is oxidized to the ketone 9 using a modified Swern oxidation procedure. Suitable oxidizing agents are N-chlorosuccinimide-dimethyl sulfide or carbodiimide-dimethylsulfoxide. In a typical example, 8 is added into a pre-formed N-chlorosuccinimide and dimethyl sulfide complex in a chlorinated solvent such as methylene chloride at −10 to 25° C. After being stirred for 0.5–4 hours, a tertiary amine such as triethylamine or Hunig's base is added to produce the corresponding ketone. The 2' hydroxy protecting group of 9 is then removed by standard methods to give the desired ketolide VIII. When RP is an ester such as acetate or benzoate, the compound may be deprotected by treatment with methanol or ethanol. When RP is a trialkylsilyl group, the compound may be deprotected by treatment with fluoride in THF or acetonitrile.

The oxime derivative may then be prepared by reaction of compound VIII wherein X is O with hydroxylamine hydrochloride in the presence of base, or hydroxylamine in the presence of acid as described in U.S. Pat. No. 5,274,085, to form the compounds wherein $R^1$ is H. Reaction with the substituted hydroxylamine $R^1ONH_2$, results in the formation of compounds in which $R^1$ is other than H. Alternatively, compounds wherein $R^1$ is other than H may be prepared by initial formation of the unsubstituted oxime as described above followed by reaction with $R^1X'$ wherein X' is a suitable leaving group such as halogen.

The preparation of the compounds of this invention of formula (IX) wherein L is CO and T is —NH— or —N(W—$R^d$)— is outlined in Schemes 1c and 4. According to Scheme 1c, the 6-O-substituted compound 6 is first protected with a suitable hydroxy protecting group to give compound 6A, by the procedures referenced above. Compound 6A is then treated with sodium hexamethyldisilazide and carbonyldiimidazole to give compound 6B. In particular, treatment of compound 6B, with aqueous ammonia results in formation of the cyclic carbamate 6C wherein $R^e$ is H. Likewise, reaction of compound 6B with an amino compound of the formula $H_2N$—W—$R^d$ results in formation of the cyclic carbamate in which $R^e$ is —W—$R^d$.

Alternate or additional procedures may be used to prepare compounds of formula (IX) wherein L is CO and T is —N(W—$R^d$)—. For example, treatment of a compound 6C wherein $R^e$ is H with an alkylating agent having the formula $R^d$-halogen, wherein $R^d$ is as defined previously, gives a compound 6C wherein $R^e$ is W—$R^d$, W is absent and $R^d$ is as defined previously.

Reaction of compound 6B with a hydrazine compound of the formula $H_2N$—NH—$R^d$ results in formation of the cyclic carbamate gives a compound 6C wherein $R^e$ is W—$R^d$, W is —NH— and $R^d$ is as defined above. When unsubstituted hydrazine is the reagent the final product is a compound 6C wherein $R^e$ is —N(W—$R^d$)— wherein (W—$R^d$) is (NH$_2$).

Treatment of a compound 6C wherein $R^e$ is —N(W—$R^d$)— wherein (W—$R^d$) is (NH$_2$) with an alkylating agent having the formula $R^d$-halogen, wherein $R^d$ is as defined previously, gives a compound 6C wherein $R^e$ is W—$R^d$, W is —NH— and $R^d$ is as defined previously.

Treatment of compound 6C with an acylating agent selected from the group consisting of $R^d$—C(CO)-halogen or ($R^d$—C(CO)—O)$_2$ gives a compound 6C wherein $R^e$ is W is —NH—CO— and $R^d$ is as defined previously.

Treatment of a compound 6C wherein $R^e$ is —N(W—$R^d$)— wherein (W—$R^d$) is (NH$_2$) with an aldehyde $R^d$—CHO, wherein $R^d$ is as defined previously gives a compound 6C wherein W is —N═CH— and $R^d$ is as defined previously.

Treatment of a compound of formula (IX) wherein L is CO and T is —N(W—$R^d$)— wherein (W—$R^d$) is (NH$_2$), with an alkylating agent having the formula $R^d$-halogen, wherein $R^d$ is as defined previously, gives the compound formula (IX) wherein L is CO, T is —N(W—$R^d$)—, W is absent and $R^d$ is as defined.

Reaction of compound 6B with a hydroxylamine compound of the formula $H_2N$—O—$R^d$ results in formation of the cyclic carbamate in which $R^e$ is —O—$R^d$.

Removal of the cladinose moiety by acid hydrolysis as described previously gives the compound 6D wherein Z' is H. Compound 6D is then oxidized to 6E by the modified Swern oxidation procedure described for Scheme 1b above for converting compound 8 to ketone 9.

Deprotection of the 2'-hydroxy group as described above provides the desired ketolide IX.

According to the alternate procedure shown in Scheme 1d, the compound 2A, which is the 9-oxime compound of erythromycin A, is subjected to acid hydrolysis with dilute mineral or organic acid as described previously to remove the cladinose moiety and give compound 7A. The oxime compound 7A is then converted to the protected oxime compound 7B wherein V is ═N—O—$R^1$ (shown) or ═N—O—C($R^5$)($R^6$)—O—$R^1$ where $R^1$, $R^5$ and $R^6$ are as defined previously, by reaction with the appropriately substituted oxime protecting reagent. The 3 and 2'-hydroxy groups of 7B are then protected as described previously, preferably with a trimethylsilyl protecting group, to give compound 7C. Compound 7C is then alkylated as described previously for Scheme 1a to give compound 7D, and compound 7D is first deoximated as described above for Scheme 1a then the deoximated product is converted to the compound 7E by the procedures described for preparation of compound 6C from compound 6A in Scheme 1c. Compound 7E is then deprotected and oxidized to the 3-ketolide derivative compound of formula IX, wherein X is O, L is CO and T is —NH— or —N(W—$R^d$)— by procedures described previously.

Scheme 1a
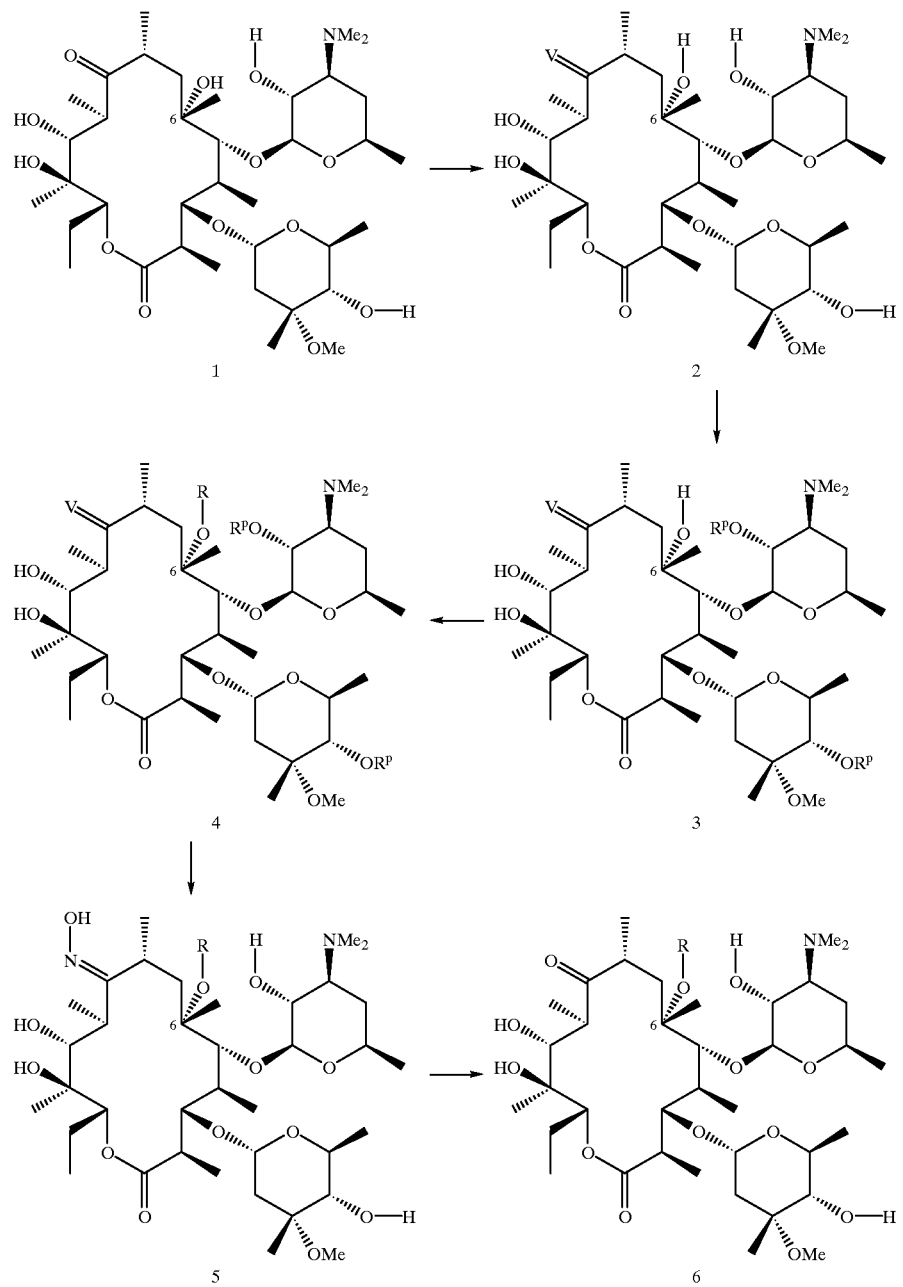

Scheme 1b
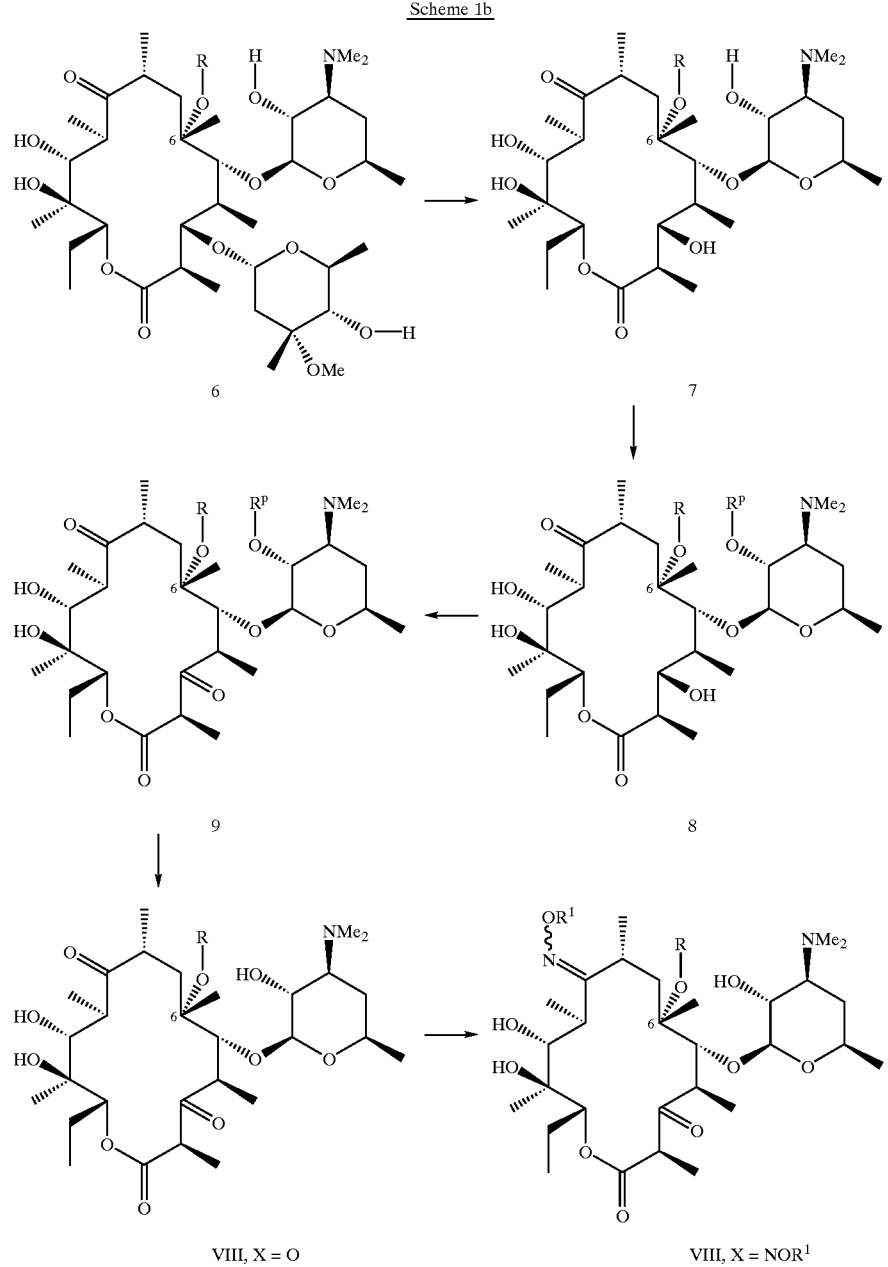

Scheme 1c
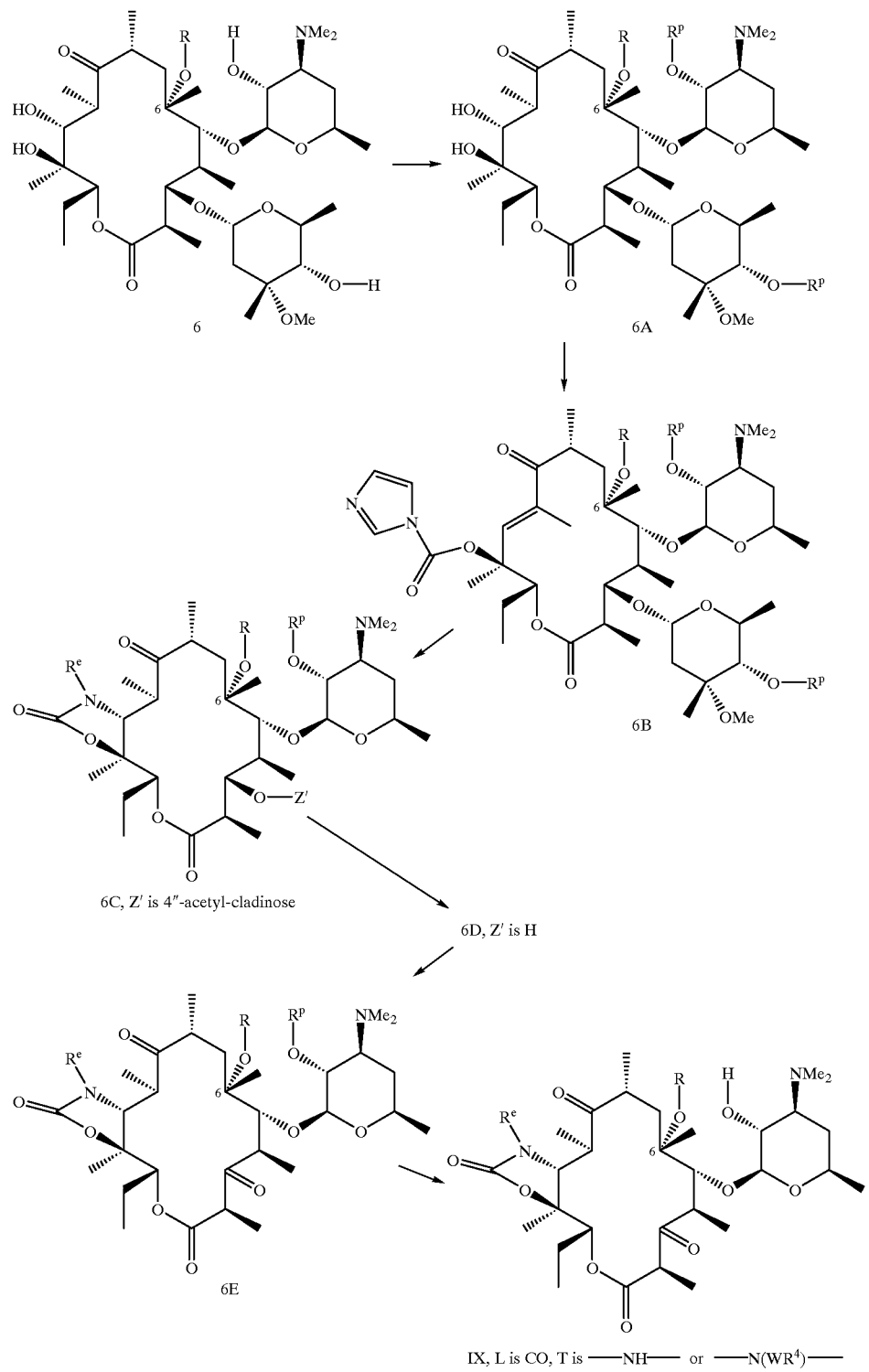

Scheme 1d

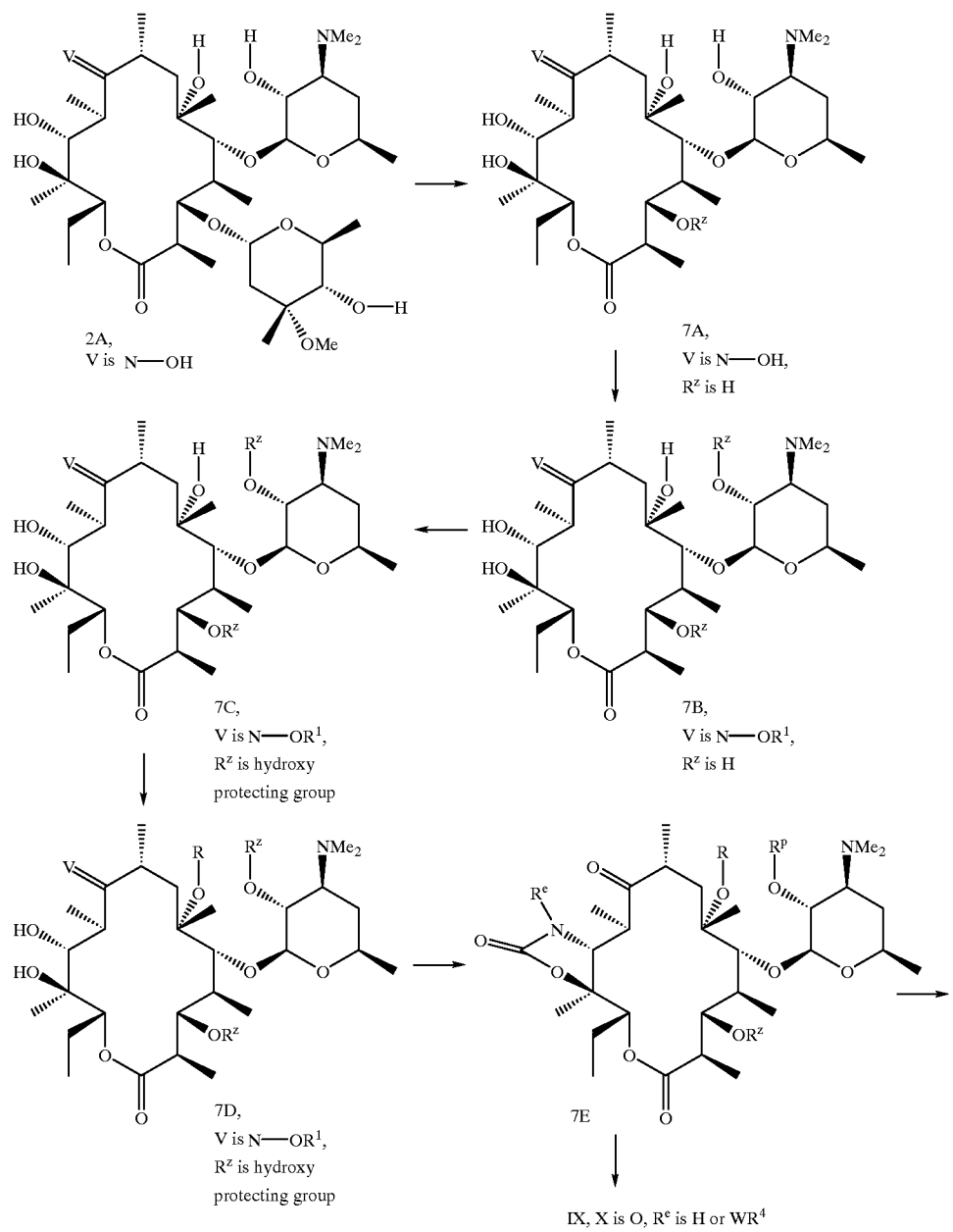

The preparation of the compounds of this invention of formula (IX) wherein L is CO and T is O and compounds of formula VI is outlined in Scheme 2. In Scheme 2, the preparation follows the procedure described by Baker et al., J. Org. Chem., 1988, 53, 2340, which is incorporated herein by reference. In particular, the 2' protected ketolide derivative 9, prepared as described in Scheme 1 above, is converted to the cyclic carbonate 10 by reaction with carbonyldiimidazole and sodium hexamethyldisilazide. Deprotection as described above gives compound IX wherein L is CO and T is O.

Compounds of formula VI are prepared from 9 by reaction with sodium hydride or lithium hydride and phosgene, diphosgene or triphosgene under anhydrous conditions followed by aqueous work up (aqueous base catalyzed decarboxylation). Alternatively, 9 is converted to its corresponding mesylate by reaction with methanesulfonic anhydride in pyridine. The mesylate is then converted to 11 by treatment with an amine base such as DBU or dimethylaminopyridine in acetone or acetonitrile. The 2' protecting group is the removed as described above to give compound VI.

Compounds of formula VI are also prepared from 10 by treatment with an amine base such as 1,8-diazobicyclo [5.5.0]undec-7-ene (DBU) or 4-dimethylaminopyridine (DMAP) in a solvent such as benzene or acetonitrile, or by reaction with sodium or lithium hydride in tetrahydrofuran or N,N-dimethylformamide (DMF) to give 11 which is then deprotected as described above to give the desired compound.

Compounds of formula VII are prepared as described in Schemes 3a and 3b. In accordance with Scheme 3a, ketolide 11, prepared as in Scheme 2, is converted to 12 by reaction with carbonyldiimidazole and an alkali metal hydride base, such as sodium hydride, lithium hydride or potassium hydride in a suitable aprotic solvent at from about 0° C. to ambient temperature. Compound 12 may also be prepared by reaction of diol 9, or cyclic carbonate 10, prepared as described in Scheme 2 above, by reaction with carbonyldiimidazole and sodium or lithium hydride under similar conditions. Compound 12 is then reacted with diamine 13 having substituents A, B, D and E as defined above, in a suitable solvent such as aqueous acetonitrile, DMF or aqueous DMF, to give the bicyclic compound 14. Compound 14 is then cyclized by treatment with dilute acid, such as acetic acid or HCl in a suitable organic solvent such as ethanol or propanol and deprotected as described above to give the tricyclic ketolide VII. Alternatively, the 2'-protecting group of the bicyclic ketolide 14 may be removed prior to cyclization using the methods described in Scheme 1. Compounds of formula IV or VII may be reduced to compounds of formula IV-A by treatment with a reducing agent selected from hydrogen in the presence of palladium catalyst, alkyl borohydride and lithium aluminum hydride in a suitable organic solvent.

Scheme 3b illustrates an alternative preparation of compounds of formula VII. Starting material 12 is reacted with a beta-aminoalcohol 15 (Y=OH) in a suitable solvent system such as aqueous acetonitrile, DMF or aqueous DMF at 0–70° C. to give 16 which is converted to the azide with a Mitsunobu reaction using triphenylphosphine and diphenylphosphoryl azide and DEAD in tetrahydrofuran. Alternatively, the hydroxy group in 16 may be activated by treatment with sulfonyl chloride, alkyl or aryl sulfonic anhydride or trifluoromethanesulfonic anhydride in an aprotic solvent. The activated hydroxy group is then converted to the corresponding azide by reaction with lithium azide or sodium azide in an aprotic solvent. The 2'-protecting group is then removed as described above, and the azide is reduced to the amine 17. Suitable reducing reagents are triphenylphosphine-water, hydrogen with a catalyst, sodium borohydride, or dialkylaluminum hydride in the appropriate solvent for these reactions, as is well known in the art. Compound 17 is then cyclized as described in Scheme 3a above.

Compounds of formula IX wherein L is CO and T is NH or N—W—$R^d$ are prepared as shown in Scheme 4. The preparation follows the procedure described by Baker et al., *J. Org. Chem.*, 1988, 53, 2340, which is incorporated herein by reference. In particular, treatment of compound 12, prepared as described in Scheme 3 above with aqueous ammonia results in formation of the cyclic carbamate 18 wherein $R^e$ is H. Likewise, reaction of compound 12 with an amino compound of the formula $H_2N$—W—$R^d$ results in formation of the cyclic carbamate in which $R^e$ is —W—$R^d$.

Deprotection of the 2'-hydroxy group as described above provides the desired ketolide IX. In particular, treatment of compound 6B with aqueous ammonia results in formation of the cyclic carbamate 6C wherein $R^e$ is H. Likewise, reaction of compound 6B with an amino compound of the formula $H_2N$—W—$R^d$ results in formation of the cyclic carbamate in which $R^e$ is —W—$R^d$.

Scheme 2

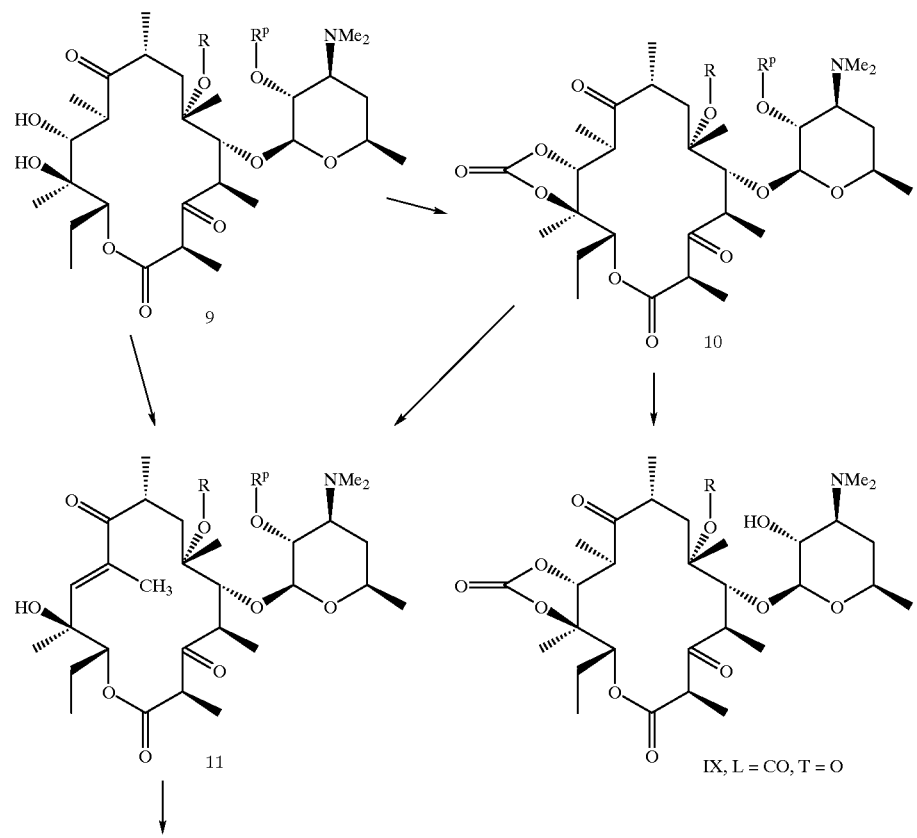

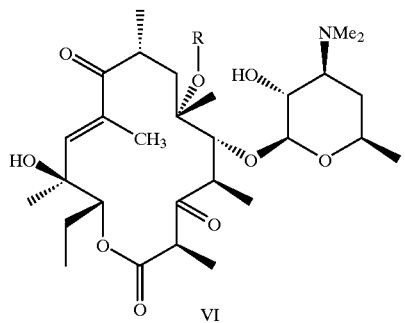
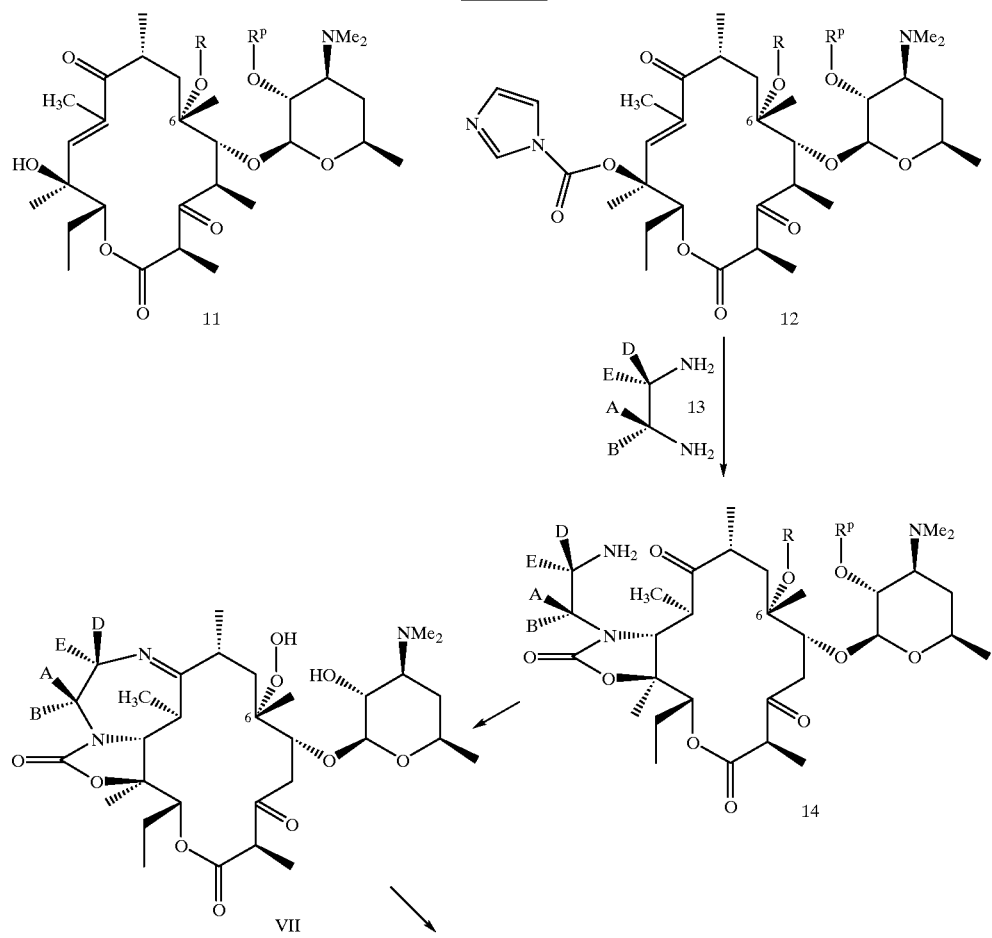
Scheme 3a

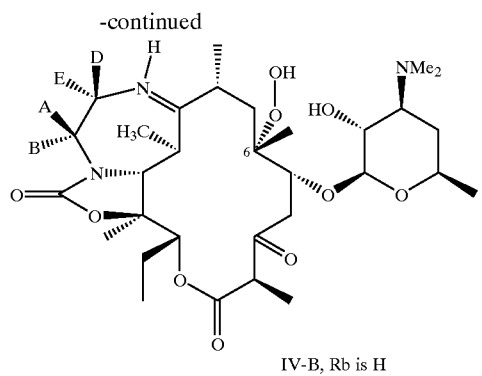
IV-B, Rb is H
Scheme 3b
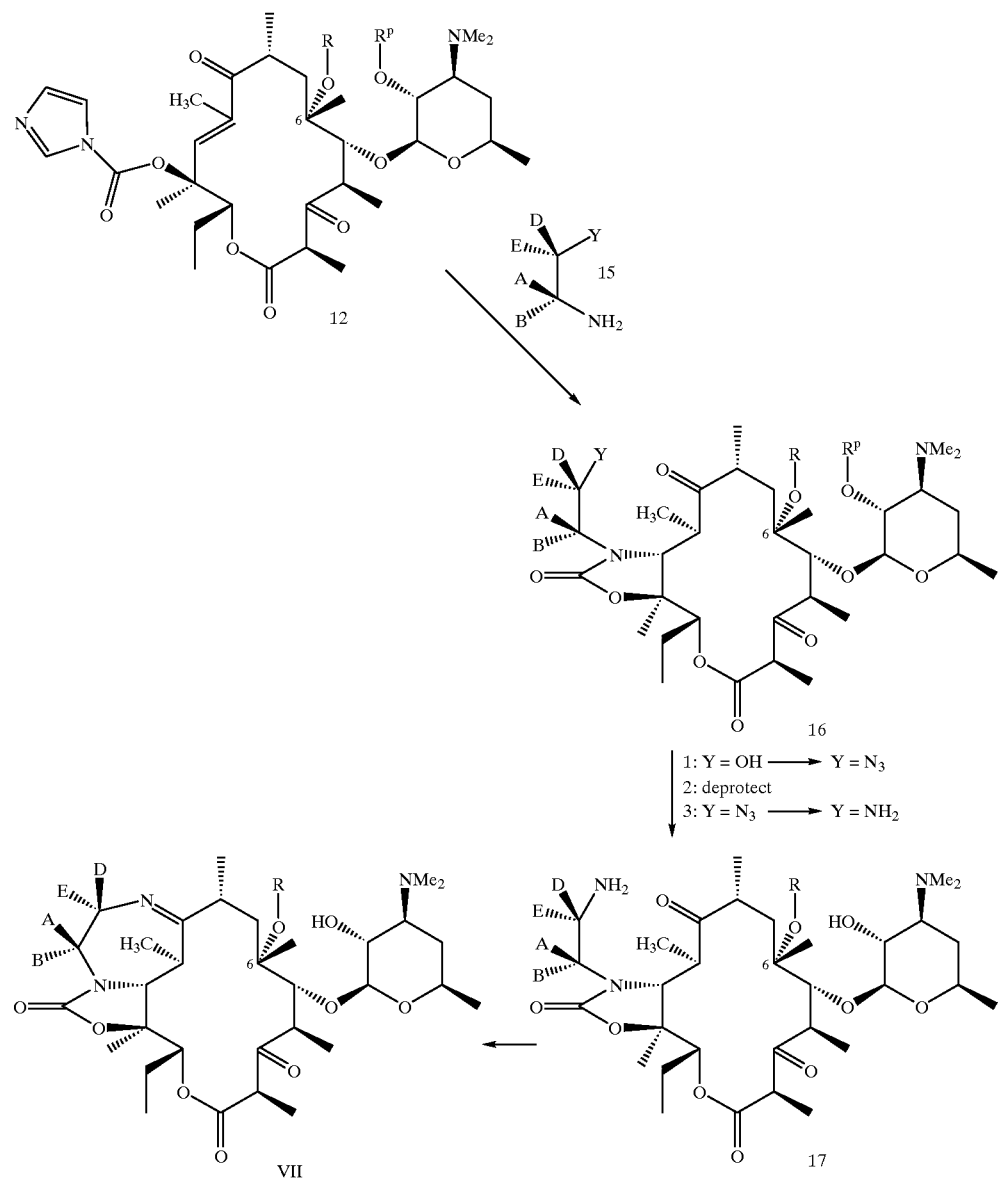

Scheme 4

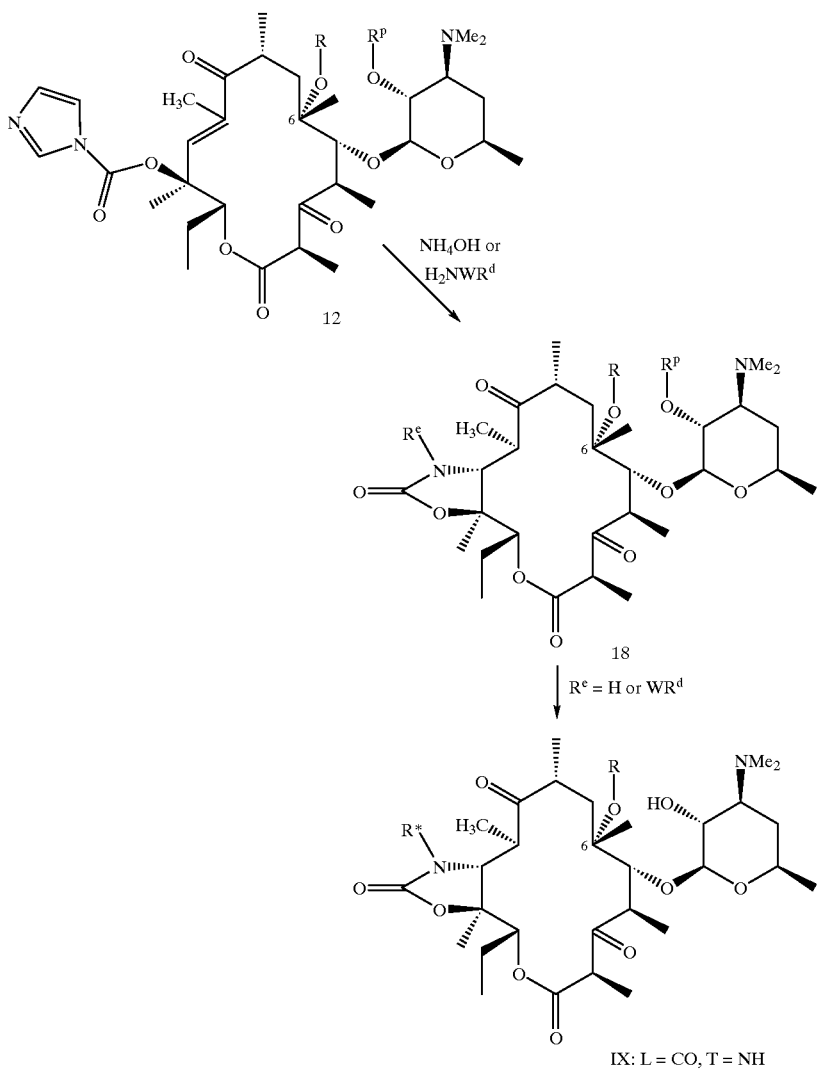

The desired 6-O-substituted compound may be prepared directly as described above or obtained from chemical modification of an initially prepared 6-O-substituted compound. Representative examples of further elaboration of the 6-position are shown in Scheme 5. For example, compound 20 where R is 6-O—$CH_2CH$=$CH_2$ and M' represents the macrolide ring system can be further derivatized. The double bond of the allyl compound can be (a) catalytically reduced to give the 6-O-propyl compound 27; (b) treated with osmium tetroxide to give the 2,3-dihydroxypropyl compound 31 which in turn may be functionalized, such as by esterification with an acylating agent such as an acyl halide or acyl anhydride, at each oxygen atoms to give 32; (c) oxidized with m-chloroperoxybenzoic acid in an aprotic solvent to give the epoxy methyl compound 29 which can be opened with nucleophilic compounds, for example, amines or N-containing heteroaryl compounds, to give compounds with N-containing side chains 30; (d) oxidized under Wacker conditions as described by Henry in "Palladium Catalyzed Oxidation of Hydrocarbons", Reidel Publishing Co., Dordrecht, Holland (1980), to give the 6-O—$CH_2$—C(O)—$CH_3$ compound 28; and (e) ozonized to give the aldehyde 21 which can in turn be (1) converted to oximes 22 and 24 by reaction with $H_2NOR^3$ or $H_2NOH$ respectively, or (2) reductively aminated, such as with a suitable amine in the presence of a borohydride reducing agent or by formation of the imine and subsequent catalytic reduction, to give the amine 23. Reaction of the oxime 24 with diisopropyl carbodiimide in an aprotic solvent in the presence of CuCl gives the nitrile 25. Reaction of 20 with an aryl halide under Heck conditions (Pd(II) or Pd(O), phosphine, and amine or inorganic base, see Organic Reactions, 1982, 27, 345–390) gives 26. Reduction of the double bond in 26, for example using $H_2$ and palladium on carbon gives 33.

Scheme 6 describes alternate procedures for preparing compounds of formula XI wherein L is CO, T is —NH— or —N(W—$R^d$)— and R is substituted alkenyl. The 6-O-allyl erythromycin compound 33 is converted to the compound of formula XI wherein L is CO, T is —NH— or —N(W—$R^d$)— and R is allyl by removing the cladinose and oxidation of the 3-hydroxy group as described in earlier Schemes. Subsequent reaction of the compound of formula XI wherein L is CO, T is —NH— or —N(W—R$^d$)— and R is allyl with a compound having the formula R-halogen, wherein R is aryl, substituted aryl, heteroaryl or substituted heteroaryl, under Heck conditions with (Pd(II) or Pd(O), phosphine, and amine or inorganic base, (see *Organic Reactions,* 1982, 27, 345–390) gives the desired product of formula XI wherein L is CO, T is N(R$^d$) and R is substituted alkenyl.

Alternately, compound 33 is converted to the 6-O-(substituted alkenyl) compound of formula 34 by reaction with an aryl halide, a substituted aryl halide, an heteroaryl halide or substituted heteroaryl halide under Heck conditions with (Pd(II) or Pd(O), phosphine, and amine or inorganic base, as just described. Compound 34 may then be converted to the desired product of formula XI wherein L is CO, T is —NH— or —N(W—R$^d$)—, and R is substituted alkenyl by removing the cladinose and oxidation of the 3-hydroxy group as described in earlier Schemes.

Scheme 5

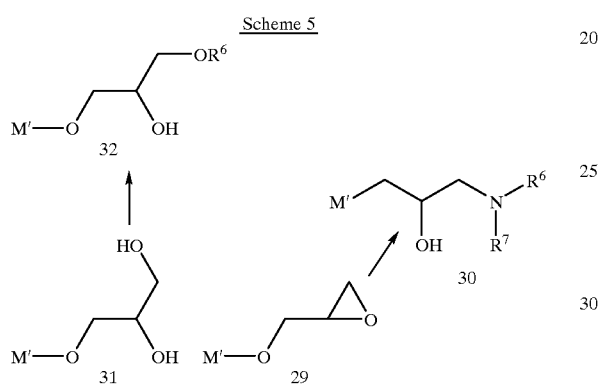

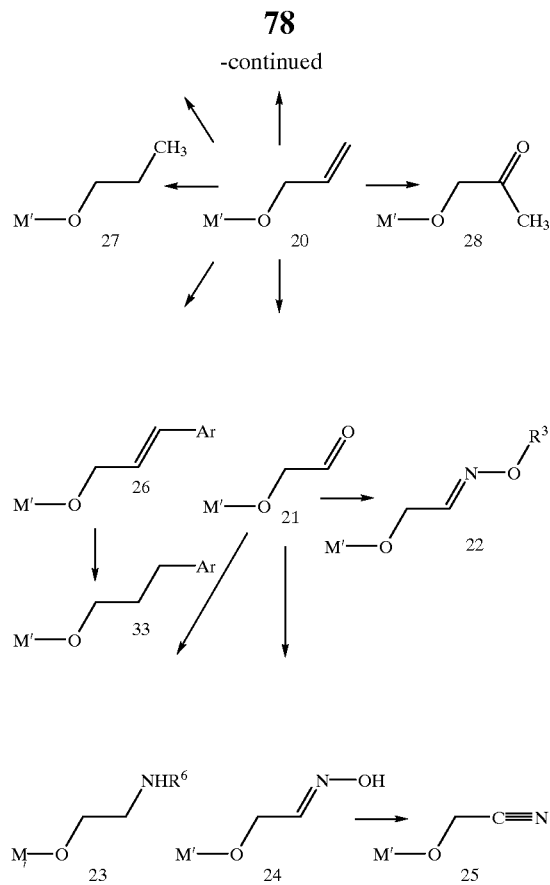

Scheme 6

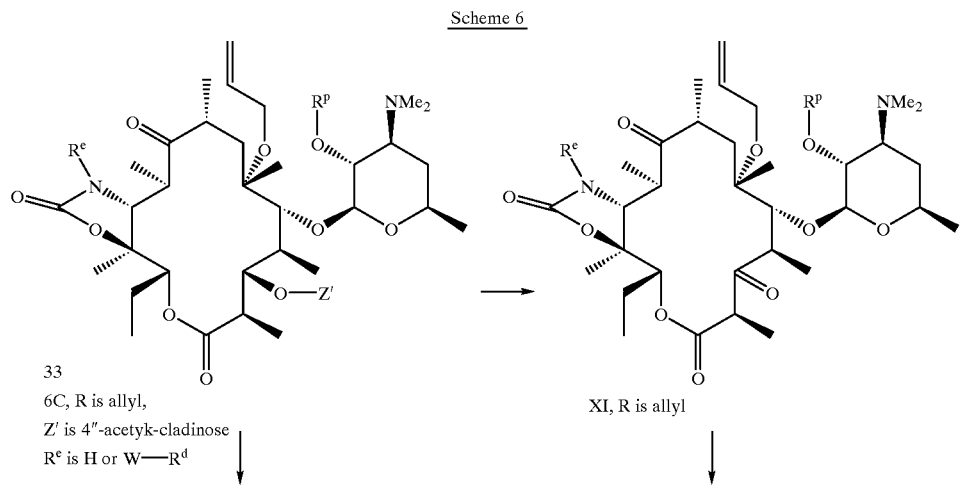

33
6C, R is allyl,
Z' is 4″-acetyk-cladinose
R$^e$ is H or W—R$^d$

XI, R is allyl

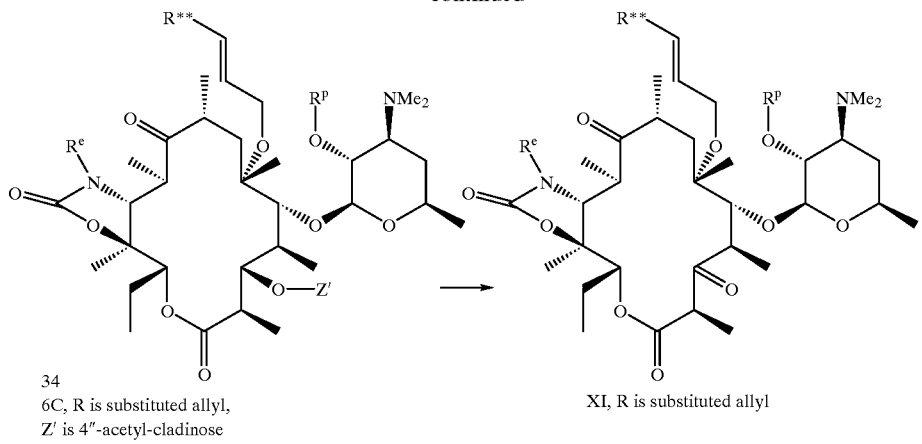

34
6C, R is substituted allyl,
Z' is 4"-acetyl-cladinose

XI, R is substituted allyl

Representative examples of still further elaboration of the 6-position are shown in Scheme 7. The desired 6-O-substituted compound may be prepared by chemical modification of an initially prepared 6-O-propargyl compound. For example, compound 35 where R is 6-O—$CH_2$—C≡CH and M' represents the macrolide ring system can be further derivatized. The triple bond of the alkyne compound 35 can be treated with an aryl halide, a substituted aryl halide, an heteroaryl halide or substituted heteroaryl halide in the presence of Pd(triphenylphosphine)$_2$Cl$_2$ and CuI in the presence of an organic amine, such as triethylamine, to give the compound 36. Compound 35 may also be treated with a boronic acid derivative HB(OR$^{zz}$), wherein R$^{zz}$ is H or $C_1$–$C_{10}$-alkyl, in an aprotic solvent at 0° C. to ambient temperature to give compounds 37, which are then treated with Pd(triphenylphosphine)$_4$ and an aryl halide, a substituted aryl halide, an heteroaryl halide or substituted heteroaryl halide under Suzuki reaction conditions to give compounds 38. Compound 35 may also be treated with N-halosuccinimide in acetic acid to give compounds 39. Also, compound 35 may be treated with a substituted alkenyl halide, such as Ar—CH=CH-halogen, wherein Ar is aryl, substituted aryl, heteroaryl or substituted heteroaryl, in the presence of Pd(triphenylphosphine)$_2$Cl$_2$ and CuI in the presence of an organic amine, such as triethylamine, to give the appropriately substituted compounds 41. Further, compound 36 can be selectively reduced to the corresponding cis-olefin compound 40 by catalytic hydrogenation in ethanol at atmospheric pressure in the presence of 5% Pd/BaSO$_4$ and quinoline (Rao et al., J. Org. Chem., (1986), 51: 4158–4159).

Scheme 8 describes alternate procedures for preparing compounds of formula XI wherein L is CO, T is —NH— or —N(W—R$^d$)—, and R is substituted alkynyl. The 6-O-propargyl erythromycin compound 42 may be converted to the compound of formula XI wherein L is CO, T is N(R$^d$) and R is propargyl by removing the cladinose and oxidation of the 3-hydroxy group as described in earlier Schemes. Subsequent reaction of the compound of formula XI wherein L is CO, T is N(R$^d$) and R is propargyl with a compound having the formula R-halogen, wherein R is aryl, substituted aryl, heteroaryl or substituted heteroaryl, in the presence of Pd(triphenylphosphine)$_2$Cl$_2$ and CuI in the presence of an organic amine, such as triethylamine, gives the desired product of formula XI wherein L is CO, T is —NH— or —N(W—R$^d$)—, and R is substituted alkynyl.

Compound 42 is converted to the 6-O-(substituted alkynyl) compound of formula 43 by reaction with a compound having the formula R-halogen, wherein R is aryl, substituted aryl, heteroaryl or substituted heteroaryl, in the presence of Pd(triphenylphosphine)$_2$Cl$_2$ and CuI in the presence of an organic amine, such as triethylamine, as just described. Compound 43 is then converted to the desired product of formula XI wherein L is CO, T is —NH— or —N(W—R$^d$)—, and R is substituted alkynyl by removing the cladinose and oxidation of the 3-hydroxy group as described in earlier Schemes.

Scheme 7

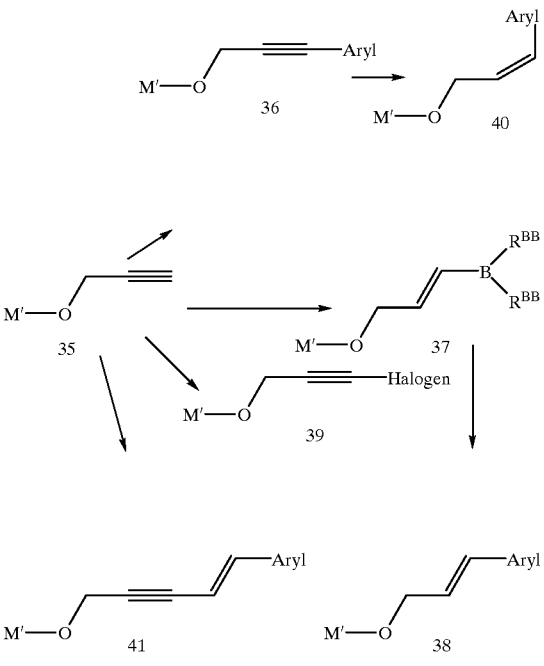

Scheme 8

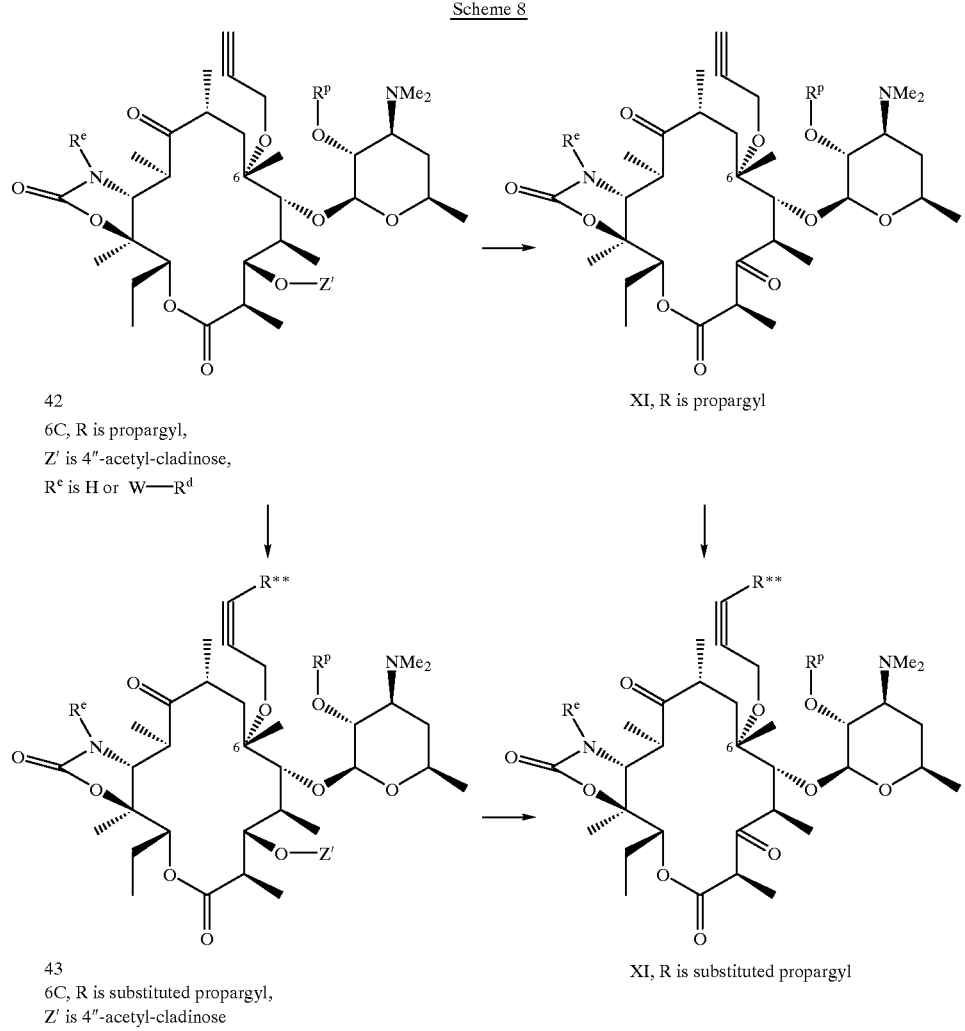

42
6C, R is propargyl,
Z' is 4''-acetyl-cladinose,
R$^e$ is H or W—R$^d$

XI, R is propargyl 43
6C, R is substituted propargyl,
Z' is 4''-acetyl-cladinose XI, R is substituted propargyl The foregoing may be better understood by reference to the following examples which are presented for illustration and not to limit the scope of the inventive concept.

EXAMPLE 1

Compound of Formula (VII): X is O, R is allyl

Step 1a: Compound 4 from Scheme 1a. V is N—O-(1-isopropoxycyclohexyl), R is allyl, R$^p$ is trimethylsilyl To a 0° C. solution of 2',4''-bis-O-trimethylsilylerythromycin A 9-[O-(1-isopropoxycyclohexyl)oxime (1.032 g, 1.00 mmol), prepared according to the method of U.S. Pat. No. 4,990,602 in 5 mL of DMSO and 5 mL of THF was added freshly distilled allyl bromide (0.73 mL, 2.00 mmol). After approximately 5 minutes, a solution of potassium tert-butoxide (1M 2.0 mL, 2.0 mL) in 5 mL of DMSO and 5 mL of THF was added dropwise over 4 hours. The reaction mixture was taken up in ethyl acetate and washed with water and brine. The organic phase was concentrated in vacuo to give the desired compound (1.062 g) as a white foam.

Step 1b: Compound 5 from Scheme 1a: V is NOH, R is allyl

To a solution of the compound resulting from step 1a (1.7 g) in 17 mL of acetonitrile and 8.5 mL of water was added 9 mL of acetic acid at ambient temperature. After several hours at ambient temperature, the reaction mixture was diluted with 200 mL of toluene and concentrated in vacuo. The residue obtained was found to contain unreacted starting material, so additional acetonitrile (15 mL), water (70 mL) and HOAc (2 mL) was added. After 2 hours, an additional 1 mL aliquot of HOAc was added. After approximately three more hours, the reaction mixture was placed in the freezer overnight. The reaction mixture was allowed to warm to ambient temperature, diluted with 200 mL of toluene and concentrated in vacuo. The residue was chased twice with toluene and dried to constant weight (1.524 g).

Step 1c: Compound 6 from Scheme 1a: R is allyl

The compound resulting from step 1b (1.225 g) in 16 mL of 1:1 ethanol-water was treated with NaHSO$_3$ (700 mg) and formic acid (141 µL) and warmed at 86° C. for 2.5 hours. The reaction mixture was allowed to cool to ambient temperature, diluted with 5–6 mL of water, basified with 1 N NaOH to pH 9–10 and extracted with ethyl acetate. The combined organic extracts were washed with brine (2×), dried over MgSO$_4$, filtered and concentrated in vacuo. The crude material was purified by column chromatography eluting with 1% MeOH in methylene chloride containing 1% ammonium hydroxide to give 686 mg (57%) of the title compound. $^{13}$C NMR (CDCl$_3$) δ 219.3 (C-9), 174.8 (C-1), 135.5 (C-17), 116.3 (C-18), 101.9 (C-1'), 95.9 (C-1''), 79.7

(C-5), 78.8 (C-6), 78.5 (C-3), 74.1 (C-12), 72.4 (C-3"), 70.6 (C-11), 68.1 (C-5'), 65.5 (C-16), 65.1 (C2'), 49.0 (C-3" O—$CH_3$), 45.0 (C-2), 44.1 (C-8), 39.7 ($NMe_2$), 37.9 (C-4), 37.1 (C-10), 34.6 (C-2"), 28.4 (C-4'), 21.0, 20.6 (C-3" CH3, C-6' $CH_3$), 20.8 (C-14), 18.3 (C-6"), 18.1 (C-8 $CH_3$), 15.7, 15.6 (C-2 $CH_3$, C-6 $CH_3$), 11.9 (C-10 $CH_3$), 10.1 (C-15), 8.9 (C-4 $CH_3$). MS (FAB)+ m/e 774 (M+H)$^+$, 812 (M+K)$^+$.

Step 1d: Compound 7 from Scheme 1b; R is allyl

To a suspension of the compound prepared in step 1c (7.73 g, 10.0 mmol) in ethanol (25 mL) and water (75 mL) was added aqueous 1 M HCl (18 mL) over 10 minutes. The reaction mixture was stirred for 9 hours at ambient temperature and then was left standing in the refrigerator overnight. Aqueous 2 M NaOH (9 mL, 18 mmol) which resulted in the formation of a white precipitate. The mixture was diluted with water and filtered. The solid was washed with water and dried under vacuum to give the descladinosyl compound 7 (3.11 g).

Step 1e: Compound 8 from Scheme 1b; R is allyl, RP is benzoyl

To a solution of the product of step 1d (2.49 g, 4.05 mmol) in dichloromethane (20 mL) was added benzoic anhydride (98%, 1.46 g, 6.48 mmol) and triethylamine (0.90 mL, 6.48 mmol) and the white suspension was stirred for 26 hours at ambient temperature. Aqueous 5% sodium carbonate was added and the mixture was stirred for 20 minutes. The mixture was extracted with dichloromethane. The organic phase was washed with aqueous 5% sodium bicarbonate and brine, dried over sodium sulfate and concentrated in vacuo to give a white foam. Chromatography on silica gel (30% acetone-hexanes) gave the title compound (2.46 g) as a white solid.

Step 1f: Compound 9 from Scheme 1b; R is allyl, RP is benzoyl; same as Compound of Formula (II), $R^a$ is OH, $R^c$ is benzoyl To a -10° C. solution under $N_2$ of N-chlorosuccinimide (0.68 g, 5.07 mmol) in dichloromethane (20 mL) was added dimethylsulfide (0.43 mL, 5.92 mmol) over 5 minutes. The resulting white slurry was stirred for 20 minutes at -10° C. and then a solution of the compound resulting from step 1e (2.43 g, 3.38 mmol) in dichloromethane (20 mL) was added and the reaction mixture was stirred for 30 minutes at -10 to -5° C. Triethylamine (0.47 mL, 3.38 mmol) was added dropwise over 5 minutes and the reaction mixture was stirred for 30 minutes at 0° C. The reaction mixture was extracted with dichloromethane. The organic phase was washed twice with aqueous 5% sodium bicarbonate and once with brine, dried over sodium sulfate, and concentrated in vacuo to give a white foam. Chromatography on silica gel (30% acetone-hexanes) gave the title compound (2.27 g) as a white foam.

Step 1g: Compound of Formula (VIII): X is O, R is allyl

A solution of the compound resulting from step 1f (719 mg, 1.0 mmol) in methanol (20 mL) was stirred at reflux for 6 hours. The reaction mixture was concentrated in vacuo and the residue was purified by chromatography on silica gel (95:5:0.5 dichloromethane-methanol-ammonia) to give the desired compound (577 mg) as a white foam. $^{13}$C NMR ($CDCl_3$) δ 219.2 (C-9), 206.0 (C-3), 169.8 (C-1), 135.3, 117.5, 102.8, 78.4, 78.0, 75.9, 74.4, 70.3, 69.5, 69.0, 65.9, 64.6, 50.6, 45.4, 45.1, 40.2, 38.6, 37.8, 31.6, 28.4, 21.8, 21.3, 20.3, 18.1, 16.5, 14.7, 12.8, 12.3, 10.6. MS (FAB)+ m/e 614 (M+H)$^+$.

EXAMPLE 2

Compound of Formula (VIII): X is NOH, R is allyl

To a solution of the compound resulting from Example 1 (122 mg, 0.2 mmol) in ethanol was added hydroxylamine hydrochloride (76 mg, 1.1 mmol) and triethylamine (56 µL, 0.4 mmol) and the reaction mixture was stirred overnight at 80° C. The reaction mixture was concentrated and the residue was taken up in ethyl acetate. The organic phase was washed with aqueous 5% sodium bicarbonate and brine, dried over sodium sulfate, and concentrated in vacuo. Chromatography on silica gel (95:5:0.5 dichloromethane-methanol-ammonia) gave the E oxime (42 mg) and the Z oxime (38 mg) as white foams. $^{13}$C NMR ($CDCl_3$) δ 206.3 (C-3), 170.1 (C-9), 169.8 (C-1), 136.1, 116.5, 102.7, 78.6, 78.2, 75.5, 74.1, 70.3, 70.2, 69.4, 65.9, 64.7, 50.6, 45.2, 40.2, 37.3, 33.1, 28.4, 25.4, 21.9, 21.3, 20.3, 18.6, 16.5, 14.9, 14.7, 12.8, 10.7. MS (FAB)+ m/e 629 (M+H)$^+$.

EXAMPLE 3

Compound of Formula (VIII): X is O, R is propyl

A solution of the compound resulting from Example 1 (122 mg, 0.2 mmol) in ethanol was flushed with nitrogen and 10% palladium on carbon (20 mg) was added. The mixture was then flushed with hydrogen and the reaction mixture was stirred overnight under positive hydrogen pressure. The reaction mixture was filtered and concentrated in vacuo to give a glass. Chromatography on silica gel (95:5:0.5 dichloromethane-methanol-ammonia) gave the title compound as a white solid. $^{13}$C NMR ($CDCl_3$) δ 220.2 (C-9), 206.5 (C-3), 169.9 (C-1), 102.7, 78.1, 77.7, 75.7, 74.1, 70.3, 69.4, 65.9, 64.5, 50.6, 45.4, 44.7, 40.2, 38.8, 37.5, 28.4, 22.3, 21.9, 21.3, 20.3, 18.3, 16.5, 14.9, 14.7, 12.4, 10.6, 10.2. MS (FAB)+ m/e 616 (M+H)$^+$.

EXAMPLE 4

Compound of Formula (VII): X is O, R is —$CH_2CHO$

Step 4a: Compound of Formula (VIII): X is O, R is —$CH_2CHO$ N-oxide

Ozone was passed through a -78° C. solution in dichloromethane (100 mL) of the compound resulting from Example 1 (2.45 g, 4.0 mmol) for 45 minutes. The reaction mixture was then flushed with nitrogen for 10 minutes. Dimethyl sulfide (1.46 mL, 20 mmol) was added at -78° C. and the reaction mixture was stirred for 30 minutes at 0° C. The reaction mixture was concentrated in vacuo to give a white foam (2.78 g) which was used without further purification.

Step 4b: Compound of Formula (VIII): X is O, R is —$CH_2CHO$

The desired compound was prepared by heating a solution in THF (40 mL) of the compound resulting from step 4a (2.78 g, 4.0 mmol) and triphenyphosphine (2.62 g, 10.0 mmol) at 55° C. for 2.5 hours. The reaction mixture was concentrated in vacuo to give a white foam. Chromatography on silica gel (1:1 acetone-hexane, then 75:25:0.5 acetone-hexane-triethylamine) gave the desired compound (1.29 g) as a white solid. MS (FAB)+ m/e 616 (M+H)$^+$.

EXAMPLE 5

Compound of Formula (VIII): X is O, R is —$CH_2CH$=NOH

To a solution in methanol (5 mL) of the compound prepared in Example 4 (46 mg, 0.08 mmol) was added triethylamine (31 µL, 0.225 mmol) and hydroxylamine hydrochloride (7.7 mg, 0.112 mmol) and the reaction mixture was stirred for 6 hours at ambient temperature. The reaction mixture was taken up in ethyl acetate and washed with aqueous 5% sodium bicarbonate and brine, dried over sodium sulfate, and concentrated in vacuo to give a clear glass. Chromatography on silica gel (95:5:0.5 dichloromethane-methanol-ammonia) gave the title compound (29 mg) as a white solid. MS (FAB)+ m/e 631 (M+H)+.

EXAMPLE 6

Compound of Formula (VIII): X is NOH, R is —CH$_2$CH=NOH

The title compound (7.0 mg) was obtained from the chromatography described in Example 5. MS (FAB)+m/e 631 (M+H)+. MS (FAB)+ m/e 645 (M+H)+.

EXAMPLE 7

Compound of Formula (VIII): X is O, R is —CH$_2$CN

To a solution under nitrogen of the compound prepared in Example 5 (168 mg, 0.267 mmol) in THF (5 mL) was added diisopropylcarbodiimide (83 µL, 0.534 mmol) and CuCl (2.7 mg, 0.027 mmol) and the reaction mixture was stirred overnight at ambient temperature. The reaction mixture was taken up in ethyl acetate and washed with aqueous 5% sodium bicarbonate and brine, dried over sodium sulfate, and concentrated in vacuo to give a clear glass. Chromatography on silica gel (95:5:0.5 dichloromethane-methanol-ammonia) gave the title compound (63 mg) as a white solid. $^{13}$C NMR (CDCl$_3$) δ 219.5(C-9), 205.6 (C-3), 169.9 (C-1), 103.4, 81.3, 78.2, 77.4, 77.1, 74.0, 70.2, 69.7, 69.1, 65.9, 51.1, 48.6, 46.7, 44.3, 40.2, 38.0, 37.6, 28.2, 23.5, 21.2, 19.7, 17.8, 16.1, 14.4, 11.9, 10.5, 10.5. MS (FAB)+ m/e 613 (M+H)+.

EXAMPLE 8

Compound of Formula (VIII): X is O, R is —CH$_2$CH$_2$NH$_2$

To a solution in methanol (10 mL) of the compound prepared in Example 4 (170 mg, 0.276 mmol) was added ammonium acetate (212 mg, 2.76 mmol) and the mixture was cooled to 0° C. Sodium cyanoborohydride (34 mg, 0.553 mmol) was added and the reaction mixture was stirred for 30 hours at 0° C. The reaction mixture was taken up in ethyl acetate and washed with aqueous 5% sodium carbonate, aqueous 2% tris(hydroxymethyl)aminomethane, and brine, dried over sodium sulfate, filtered, and concentrated in vacuo. Chromatography on silica gel (90:10:0.5 dichloromethane-methanol-ammonia) gave the title compound (90 mg) as a white solid. $^{13}$C NMR (CDCl$_3$) δ 217.0 (C-9), 206.3 (C-3), 170.6 (C-1), 102.7, 78.9, 78.5, 75.1, 74.9, 70.3, 69.4, 67.8, 65.9, 63.1, 50.8, 45.8, 44.9, 41.7, 40.3, 38.8, 38.2, 28.4, 22.2, 21.3, 20.7, 19.2, 16.6, 14.9, 12.8, 12.4, 10.9. MS (FAB)+ m/e 617 (M+H)+.

EXAMPLE 9

Compound of Formula (VIII): X is O, R is —CH$_2$CH$_2$NHCH$_2$-Phenyl

To a 0° C. solution in methanol (10 mL) of the compound prepared in Example 4 (121.3 mg, 0.200 mmol) was added acetic acid (114 µL, 2.00 mmol) and benzylamine (218 µL, 2.00 mmol) and the mixture was stirred for 10 minutes. Sodium cyanoborohydride (24.8 mg, 0.400 mmol) was added and the reaction mixture was stirred for 16 hours. Additional sodium cyanoborohydride (24.8 mg, 0.400 mmol) was then added and stirring was continued for 5 hours. The reaction mixture was taken up in ethyl acetate and washed with aqueous 5% sodium carbonate, aqueous 2% tris(hydroxymethyl)aminomethane, and brine, dried over sodium sulfate, filtered, and concentrated in vacuo. Chromatography on silica gel (95:5:0.5 dichloromethane-methanol-ammonia) followed by a second chromatography (50:50:0.5 acetone-hexanes-triethylamine) gave the title compound (82 mg) as a white foam. $^{13}$C NMR (CDCl$_3$) δ 216.6 (C-9), 206.3 (C-3), 170.5 (C-1), 139.0, 128.6, 128.3, 126,9, 102.4, 78.9, 78.4, 75.1, 74.8, 70.2, 69.4, 67.8, 65.9, 61.7, 53.2, 50.7, 48.2, 45.6, 44.8, 40.2, 38.8, 38.0, 28.3, 21.9, 21.3, 20.6, 18.8, 16.6, 14.6, 12.6, 12.3, 10.7. MS (FAB)+ m/e 707 (M+H)+.

EXAMPLE 10

Compound of Formula (VIII): X is O, R is —CH$_2$CH$_2$NHCH$_2$CH$_2$-Phenyl

To a 0° C. solution in methanol (10 mL) of the compound prepared in Example 4 (121.3 mg, 0.200 mmol) was added acetic acid (114 µL, 2.00 mmol) and phenethylamine (218 µL, 2.00 mmol) and the mixture was stirred for 10 minutes. Sodium cyanoborohydride (24.8 mg, 0.400 mmol) and the reaction mixture was stirred for 16 hours. The reaction mixture was taken up in ethyl acetate and washed with aqueous 5% sodium carbonate, aqueous 2% tris (hydroxymethyl)aminomethane, and brine, dried over sodium sulfate, filtered, and concentrated in vacuo. Chromatography on silica gel (90:10:0.5 dichloromethane-methanol-ammonia) gave the title compound (60.1 mg) as a white foam. MS (FAB)+ m/e 721 (M+H)+.

EXAMPLE 11

Compound of Formula (VIII): X is O, R is —CH$_2$CH$_2$NHCH(CO$_2$CH$_3$)CH$_2$-Phenyl To a 0° C. solution in methanol (10 mL) of the compound prepared in Example 4 (121.3 mg, 0.200 mmol) was added L-phenylalanine methyl ester hydrochloride (129 mg, 0.600 mmol) and the mixture was stirred for 10 minutes. Sodium cyanoborohydride (24.8 mg, 0.400 mmol) and the reaction mixture was stirred for 22 hours. The reaction mixture was taken up in ethyl acetate and washed with aqueous 5% sodium carbonate, aqueous 2% tris(hydroxymethyl) aminomethane, and brine, dried over sodium sulfate, filtered, and concentrated in vacuo. Chromatography on silica gel (95:5:0.5 dichloromethane-methanol-ammonia) gave the title compound (60.1 mg) as a white foam. $^{13}$C NMR (CDCl$_3$) δ 217.8 (C-9), 206.4 (C-3), 170.5 (C-1). 170.4, 137.5, 129.4, 128.2, 126,4, 102.4, 78.8, 78.4, 75.2, 74.9, 70.2, 69.4, 68.5, 65.9, 63.1, 61.6, 51.4, 50.7, 47.1, 45.5, 44.7, 40.2, 39.2, 38.4, 28.4, 21.8, 21.2, 20.6, 18.7, 16.6, 14.7, 12.6, 12.2, 10.7. MS (FAB)+ m/e 779 (M+H)+.

EXAMPLE 12

Compound of Formula (VIII): X is O, R is —CH$_2$CH$_2$NHCH$_2$-(4-pyridyl)

The desired compound was prepared according to the method of Example 10, except substituting 4-aminomethylpyridine for phenethylamine. $^{13}$C NMR (CDCl$_3$) δ 217.8 (C-9), 206.2 (C-3), 170.6 (C-1), 149.7, 148.2, 123.3, 102.5, 78.9, 78.4, 75.0, 74.9, 70.2, 69.5, 68.4, 65.9, 61.7, 52.4, 50.7, 48.7, 45.7, 44.8, 40.2, 39.2, 38.5, 38.2, 28.4, 21.8, 21.3, 20.6, 18.7, 16.6, 14.6, 12.6, 12.2, 10.7. MS (FAB)+ m/e 708 (M+H)$^+$.

EXAMPLE 13

Compound of Formula (VIII): X is O, R is —CH$_2$CH$_2$NHCH$_2$-(4-quinolyl)

To a solution of the compound prepared in Example 8 (90 mg, 0.15 mmol) in methanol (2 mL) was added 4-quinolinecarboxaldehyde (23 mg, 0.15 mmol), acetic acid (8.6 μL, 0.15 mmol), and sodium cyanoborohydride (9.4 mg, 0.15 mmol) and the reaction mixture was stirred for 15 hours. The reaction mixture was taken up in ethyl acetate and washed with aqueous 5% sodium carbonate, aqueous 2% tris(hydroxymethyl)aminomethane, and brine, dried over sodium sulfate, filtered, and concentrated in vacuo. Chromatography on silica gel (90:10:0.5 dichloromethane-methanol-ammonia) gave the title compound (32 mg) as an off-white solid. MS (FAB)+ m/e 758 (M+H)$^+$.

EXAMPLE 14

Compound of Formula (VIII): X is O, R is —CH$_2$CH=CH-Phenyl

Step 14a: Compound 9 from Scheme 2: X is O, R is —CH$_2$CH=CH-Phenyl, Rp is benzoyl To a solution under nitrogen of the compound prepared in Example 1, step 6, (717 mg, 1.00 mmol), palladium(II) acetate (22 mg, 0.100 mmol), and triphenyphosphine (52 mg, 0.200 mmol) in acetonitrile (5 mL) was added iodobenzene (220 μL, 2.00 mmol) and triethylamine (280 μL, 2.00 mmol) and the mixture was cooled to −78° C., degassed, and sealed. The reaction mixture was then warmed to 60° C. for 0.5 hours and stirred at 80° C. for 12 hours. The reaction mixture was taken up in ethyl acetate and washed twice with aqueous 5% sodium bicarbonate, once with aqueous 2% tris(hydroxymethyl)aminomethane, and once with brine, dried over sodium sulfate, filtered, and concentrated in vacuo. Chromatography on silica gel (95:5:0.5 dichloromethane-methanol-ammonia) gave the title compound (721 mg) as an off-white foam.

Step2 14b: Compound of Formula (VIII): X is O, R is —CH$_2$CH=CH-Phenyl

Deprotection of the compound prepared in step 14a was accomplished by heating in methanol according to the procedure of Example 1, step g. $^{13}$C NMR (CDCl$_3$) δ 219.4 (C-9), 206.0 (C-3), 169.8 (C-1), 137.0, 132.6, 128.3, 127.3, 126.7, 126.6, 102.7, 78.4, 78.2, 75.9, 74.3, 70.3, 69.5, 69.1, 65.9, 64.2, 50.6, 45.4, 45.3, 40.2, 38.7, 37.7, 28.3, 21.9, 21.2, 20.3, 18.1, 16.5, 14.6, 13.0, 12.3, 10.8. MS (FAB)+ m/e 690 (M+H)$^+$.

EXAMPLE 15

Compound of Formula (VIII): X is O, R is —CH$_2$CH$_2$CH$_2$-Phenyl

A solution of the compound prepared in Example 14 (170 mg, 0.247 mmol) in methanol (10 mL) was flushed with nitrogen. 10% Palladium on carbon (50 mg) was added and the mixture was flushed with hydrogen and stirred for 18 hours under positive hydrogen pressure. The reaction mixture was filtered through celite and the filter cake was rinsed with dichloromethane. The filtrate was concentrated in vacuo to give a colorless glass. The glass was taken up in ether, hexane was added and the solvents were removed in vacuo to give the tide compound (67 mg) as a white solid. $^{13}$C NMR (CDCl$_3$) δ 220.2 (C-9), 206.5 (C-3), 170.0 (C-1), 142.3, 128.4, 128.1, 125.4, 102.6, 78.2, 78.0, 75.6, 74.2, 70.3, 69.5, 69.4, 65.9, 62.1, 50.6, 45.4, 44.6, 40.2, 38.8, 37.5, 32.1, 30.3, 28.4, 21.9, 21.3, 20.2, 18.4, 16.5, 14.9, 12.4, 10.6. MS (FAB)+ m/e 692 (M+H)$^+$.

EXAMPLE 16

Compound of Formula (VIII): X is O, R is —CH$_2$CH=CH-(4-methoxvphenyl)

The desired compound was prepared according to the method of Example 14, except substituting 4-iodoanisole for iodobenzene. MS (FAB)+ m/e 720 (M+H)$^+$.

EXAMPLE 17

Compound of Formula (VIII): X is O, R is —CH$_2$CH=CH-(4-chlorophenyl)

The desired compound was prepared according to the method of Example 14, except substituting 1-chloro-4-iodobenzene for iodobenzene. $^{13}$C NMR (CDCl$_3$) δ 219.6 (C-9), 206.0 (C-3), 169.8 (C-1), 139.6, 135.5, 131.3, 128.5, 127.9, 127.3, 102.7, 78.4, 78.2, 75.9, 74.2, 70.3, 69.5, 69.2, 65.9, 64.1, 50.6, 45.4, 45.3, 40.2, 38.6, 37.6, 28.4, 21.8, 21.2, 20.3, 18.0, 16.5, 14.6, 13.0, 12.2, 10.8. MS (FAB)+ m/e 724 (M+H)$^+$.

EXAMPLE 18

Compound of Formula (VIII): X is O, R is —CH$_2$CH=CH-(3-quinolyl)

Step 18a: Compound 9 from Scheme 2, X is O, R is —CH$_2$CH=CH-(3-!quinolyl), Rp is benzoyl A mixture of the compound prepared in Example 1, step f, (1.80 g, 0.25 mmol), palladium(II)acetate (11 mg, 0.05 mmol), and tri-o-tolylphosphine (30 mg, 0.10 mmol) and 3-bromoquinoline (68 μL, 0.5 mmol) in acetonitrile (2 mL) was cooled to −78° C., degassed, and sealed. The reaction mixture was then warmed to 50° C. for 2 hours and stirred at 80° C. for 16 hours. The reaction mixture was taken up in ethyl acetate and washed with aqueous 5% sodium carbonate, aqueous 2% tris(hydroxymethyl)aminomethane, and brine, dried over sodium sulfate, filtered, and concentrated in vacuo. Chromatography on silica gel (98:2 dichloromethane-methanol) gave the title compound (186 mg) as an off-white foam. MS (FAB)+ m/e 845 (M+H)$^+$.

Step 18b: Compound of Formula (VIII): X is O, R is —CH$_2$CH=CH-(3-quinolyl)

Deprotection of the compound prepared in step 18a was accomplished by heating in methonal according to the procedure of Example 1, step g. $^{13}$C NMR (CDCl$_3$) δ 219.7 (C-9) 205,9 (C-3) 169.8 (C-1), 152.1, 150.0, 147.5, 140.2, 132.6, 130.0, 129.2, 129.1, 128.8, 128.1, 127.9, 126.5, 102.8, 78.5, 78.2, 75.9, 74.2, 70.2, 69.4, 69.2, 65.9, 64.1, 50.6, 45.4, 45.3, 40.2, 38.7, 37.6, 28.4, 21.8, 21.2, 20.3, 18.0, 16.5, 14.6, 13.0, 12.2, 10.8. MS (FAB)+ m/e 741 (M+H)$^+$.

Using the procedures described in the preceding examples and schemes and methods known in the synthetic organic chemistry art, the following compounds of Formula VIII wherein X is O can be prepared. These compounds having the R substituent as described in the table below are of the formula

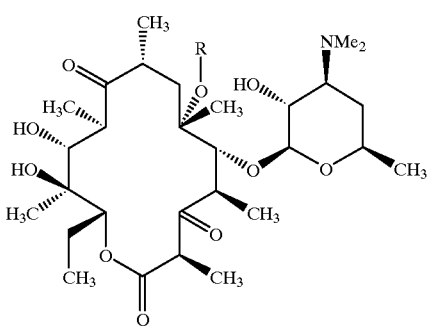

| Ex. No. | substitutent |
|---|---|
| 19 | R is —CH$_2$CH$_2$CH$_2$OH |
| 20 | R is —CH$_2$C(O)OH |
| 21 | R is —CH$_2$CH$_2$NHCH$_3$ |
| 22 | R is —CH$_2$CH$_2$NHCH$_2$OH |
| 23 | R is —CH$_2$CH$_2$N(CH$_3$)$_2$ |
| 24 | R is —CH$_2$CH$_2$(1-morpholinyl) |
| 25 | R is —CH$_2$C(O)NH$_2$ |
| 26 | R is —CH$_2$NHC(O)NH$_2$ |
| 27 | R is —CH$_2$NHC(O)CH$_3$ |
| 28 | R is —CH$_2$F |
| 29 | R is —CH$_2$CH$_2$OCH$_3$ |
| 30 | R is —CH$_2$CH$_3$ |
| 31 | R is —CH$_2$CH=CH(CH$_3$)$_2$ |
| 32 | R is —CH$_2$CH$_2$CH(CH$_3$)CH$_3$ |
| 33 | R is —CH$_2$CH$_2$OCH$_2$CH$_2$OCH$_3$ |
| 34 | R is —CH$_2$SCH$_3$ |
| 35 | R is —cyclopropyl |
| 36 | R is —CH$_2$OCH$_3$ |
| 37 | R is —CH$_2$CH$_2$F |
| 38 | R is —CH$_2$-cyclopropyl |
| 39 | R is —CH$_2$CH$_2$CHO |
| 40 | R is —C(O)CH$_2$CH$_2$CH$_3$ |
| 41 | R is —CH$_2$-(4-nitrophenyl) |
| 42 | R is —CH$_2$-(4-chlorophenyl) |
| 43 | R is —CH$_2$-(4-methoxyphenyl) |
| 44 | R is —CH$_2$-(4-cyanophenyl) |
| 45 | R is —CH$_2$CH=CHC(O)OCH$_3$ |
| 46 | R is —CH$_2$CH=CHC(O)OCH$_2$CH$_3$ |
| 47 | R is —CH$_2$CH=CHCH$_3$ |
| 48 | R is —CH$_2$CH=CHCH$_2$CH$_3$ |
| 49 | R is —CH$_2$CH=CHCH$_2$CH$_2$CH$_3$ |
| 50 | R is —CH$_2$CH=CHSO$_2$-phenyl |
| 51 | R is —CH$_2$C≡C—Si(CH$_3$)$_3$ |
| 52 | R is —CH$_2$C≡CCH$_2$CH$_2$CH$_2$CH$_2$CH$_2$CH$_3$ |
| 53 | R is —CH$_2$C≡CCH$_3$ |
| 54 | R is —CH$_2$-(2-pyridyl) |
| 55 | R is —CH$_2$-(3-pyridyl) |
| 56 | R is —CH$_2$-(4-pyridyl) |
| 57 | R is —CH$_2$-(4-quinolyl) |
| 58 | R is —CH$_2$NO$_2$ |
| 59 | R is —CH$_2$C(O)OCH$_3$ |
| 60 | R is —CH$_2$C(O)-phenyl |
| 61 | R is —CH$_2$C(O)CH$_2$CH$_3$ |
| 62 | R is —CH$_2$Cl |
| 63 | R is —CH$_2$S(O)$_2$-phenyl |
| 64 | R is —CH$_2$CH=CHBr |
| 65 | R is —CH$_2$CH=CH-(4-quinolyl) |
| 66 | R is —CH$_2$CH$_2$CH$_2$-(4-quinolyl) |
| 67 | R is —CH$_2$CH=CH-(5-quinolyl) |
| 68 | R is —CH$_2$CH$_2$CH$_2$-(5-quinolyl) |
| 69 | R is —CH$_2$CH=CH-(4-benzoxazolyl) |
| 70 | R is —CH$_2$CH=CH-(7-benzimidazolyl) |

EXAMPLE 71

Compound of Formula (IX): L is CO, T is O, R is —CH$_2$CH=CH$_2$

Step 71a: Compound 10 from Scheme 2; R is R is —CH$_2$CH=CH$_2$, R$^p$ is benzoyl To a −35° C. solution under nitrogen in THF (60 mL) of the compound prepared in Example 1, step f, (3.58 g, 5.00 mmol) was added sodium hexamethyldisilazide (1.0 M in THF, 5.5 mL, 5.5 mmol) and the resulting white suspension was stirred for 30 minutes. A solution of carbonyldiimidazole (4.05 g, 25 mmol) in THF (40 mL) was added dropwise over 20 minutes at −35° C. and then the cold bath was removed and the reaction mixture was stirred for 30 minutes. The reaction mixture was taken up in ethyl acetate and washed with aqueous 5% sodium bicarbonate and brine, dried over sodium sulfate, filtered, and concentrated in vacuo. Chromatography on silica gel (30% acetone-hexane) gave the title compound (2.6 g) as a white foam. MS (FAB)+ m/e 744 (M+H)$^+$.

Step 71b: Compound of Formula (IX): L is CO, T is O, R is —CH$_2$CH=CH$_2$

Deprotection of the compound prepared in step 71a was accomplished by heating in methanol according to the procedure of Example 1, step g. $^{13}$C NMR (CDCl$_3$) δ 212.1 (C-9), 205.0 (C-3), 168.9 (C-1), 153.8, 134.4, 118.4, 103.1, 84.7, 80.5, 78.7, 77.1, 76.9, 70.3. 69.5, 65.9, 64.8, 50.8, 46.5, 44.1, 40.2, 38.8, 38.1-, 28.4, 22.7, 21.2, 20.5, 18.3, 14.5, 13.6, 12.6, 10.6. MS (FAB)+ m/e 640 (M+H)$^+$.

EXAMPLE 72

Compound of Formula (IX): L is CO, T is O, R is —CH$_2$CH=CH-Phenyl

Step 72a: Compound 10 from Scheme 2: R is —CH$_2$CH=CH-Phenyl, R$^p$ is benzoyl

A solution of the compound prepared in Example 14, step a (150 mg, 0.20 mmol) in THF (5 mL) was cooled to −35° C. and flushed with nitrogen. Lithium hexamethyldisilazide (1.0 M in THF, 0.22 mL, 0.22 mmol) over 2 minutes at −35° C. The reaction mixture was stirred for 10 minutes at −35° C. and then a solution of carbonyldiimidazole (162 mg, 1.00 mmol) in THF (3 mL) was added dropwise over 2 minutes. The cold bath was removed and the reaction mixture was stirred for 30 minutes. The reaction mixture was cooled to 0° C. and aqueous 0.5 M KH$_2$PO$_4$ was added. The mixture was extracted with ethyl acetate and the organic phase was washed with brine, dried over sodium sulfate, and concentrated in vacuo. Chromatography on silica gel (30% acetone-hexane) gave the title compound (87 mg) as a white solid. MS (FAB)+ m/e 820 (M+H)$^+$.

Step 72b: Compound of Formula (IX): L is CO, T is O, R is —CH$_2$CH=CH-Phenyl

Deprotection of the compound prepared in step 72a was accomplished by heating in methanol according to the procedure of Example 1, step g. $^{13}$C NMR (CDCl$_3$) δ 212.4 (C-9). 205.2 (C-3), 168.3 (C-1), 153.3, 136.4, 134.9, 128.3, 127.6, 127.0, 124.7, 103.2, 84.5. 80.8, 78.7, 78.0, 70.3, 69.6, 65.9, 64.5, 50.9, 46.9, 44.4, 40.2, 39.1, 37.8, 28.3, 23.0, 21.2, 20.4, 18.1, 14.8, 14.4, 13.7, 12.6, 10.8. MS (FAB)+ m/e 716 (M+H)$^+$.

EXAMPLE 73

Compound of Formula (IX): L is CO, T is O, R is —CH$_2$CH$_2$CH$_2$-Phenyl

Step 73a: Compound 8 from Scheme 1b: R is —CH$_2$CH$_2$CH$_2$-Phenyl, Rp is benzoyl The desired compound was prepared by reaction of the compound of Example 15 with benzoic anhydride according to the procedure of Example 1, step e.

Step 73b: Compound 10 from scheme 1b: R is —CH$_2$CH$_2$CH$_2$-Phenyl, R$^p$ is benzoyl A solution of the compound prepared in step 73a (104 mg, 0.13 mmol) in THF (5 mL) was cooled to −35° C. and flushed with nitrogen. Sodium hexamethyldisilazide (1.0 M in THF, 0.16 mL, 0.16 mmol) over 1 minute at −35° C. The reaction mixture was stirred for 10 minutes at −35° C. and then a solution of carbonyldiimidazole (105 mg, 0.65 mmol) in THF (3 mL) was added dropwise over 1 minute. The cold bath was removed and the reaction mixture was stirred for 30 minutes. The mixture was extracted with ethyl acetate and the organic phase was washed with aqueous 5% sodium bicarbonate and brine, dried over sodium sulfate, and concentrated in vacuo to give a colorless glass. Chromatography on silica gel (30% acetone-hexane) gave the title compound (63 mg) as a white solid. MS (FAB)+ m/e 822 (M+H)$^+$.

Step 73c: Compound of Formula (IX): L is CO, T is O, R is —CH$_2$CH$_2$CH$_2$-Phenyl Deprotection of the compound prepared in step 73b was accomplished by heating in methanol according to the procedure of Example 1, step g. $^{13}$C NMR (CDCl$_3$) δ 211.8 (C-9), 205.1 (C-3), 169.6 (C-1), 153.6, 141.9, 128.5, 128.1, 125.5, 102.7, 84.6, 80.5, 78.3, 76.0, 70.2, 69.5, 65.9, 62.4, 50.7, 45.5, 44.5, 40.2, 38,6, 37.9, 31.9, 30.4, 28.4, 22.6, 21.2, 20.3, 18.5, 14.6, 13.4, 13.3, 12.6, 10.4. MS (FAB)+ m/e 718 (M+H)$^+$.

EXAMPLE 74

Compound of Formula (IX): L is CO, T is O, R is —CH$_2$CH=CH-(4-chlorophenyl)

Step 74a: Compound 10 from Scheme 1b: R is —CH$_2$CH=CH-(4-chlorophenyl), R$^p$ is benzoyl A solution of the compound of formula 10 (R is —CH$_2$CH=CH-(4-chlorophenyl), Rp is benzoyl), prepared as in Example 17, (165 mg, 0.20 mmol) in THF (5 mL) was cooled to −35° C. and flushed with nitrogen. Lithium hexamethyldisilazide (1.0 M in THF, 0.22 mL, 0.22 mmol) over 2 minutes at −35° C. The reaction mixture was stirred for 10 minutes at −35° C. and then a solution of carbonyldiimidazole (105 mg, 0.65 mmol) in THF (3 mL) was added dropwise over 2 minutes. The cold bath was removed and the reaction mixture was stirred for 30 minutes. The mixture was extracted with ethyl acetate and the organic phase was washed with aqueous 5% sodium bicarbonate and brine, dried over sodium sulfate, and concentrated in vacuo to give a colorless glass (219 mg) which was used without further purification. MS (FAB)+ m/e 854 (M+H)$^+$.

Step 74b: Compound of Formula (IX): L is CO, T is O, R is —CH$_2$CH=CH-(4-chlorophenyl)

Deprotection of the compound prepared in step 74a was accomplished by heating in methanol according to the procedure of Example 1, step g. $^{13}$C NMR (CDCl$_3$) δ 212.4 (C-9), 205.1 (C-3), 168.6 (C-1), 153.3, 135.0, 133.5, 133.2, 128.5, 128.3, 125.5, 103.2, 84.5, 80.7, 78.8, 78.0, 70.3, 69.6, 66.0, 64.3, 50.9, 46.9, 44.4, 40.2, 39.1, 37.8, 28.4, 23.0, 21.2, 20.4, 18.1, 14.8, 14.4, 13.6, 12.6, 10.7. MS (FAB)+ m/e 750 (M+H)$^+$.

EXAMPLE 75

Compound of Formula (IX): L is CO, T is O, R is —CH$_2$CH=CH-(3-quinolyl)

The compound formula 10 (R is —CH$_2$CH=CH-(3-quinolyl), Rp is benzoyl), prepared as in Example 18, was converted to the title compound using the procedure of Example 71, steps a and b. $^{13}$C NMR (CDCl$_3$) δ 212.4 (C-9), 205.2 (C-3), 168.7 (C-1), 153.4, 150.3, 147.6, 132.7, 131.1, 129.6, 129.0, 128.9, 128.4, 128.1, 127.7, 126.6, 103.2, 84.5, 80.6, 78.9, 77.5, 77.0, 70.3, 69.6, 65.9, 64.3, 50.9, 46.9, 44.5, 40.3, 39.0, 37.8, 28.4, 22.8, 21.2, 20.4, 18.1, 14.7, 14.4, 13.5, 12.6, 10.6. MS (FAB)+ m/e 767 (M+H)$^+$.

Using the procedures described in the preceding examples and schemes and methods known in the synthetic organic chemistry art, the following compounds of Formula IX wherein L is CO and T is O can be prepared. These compounds having the R substituent as described in the table below are of the formula

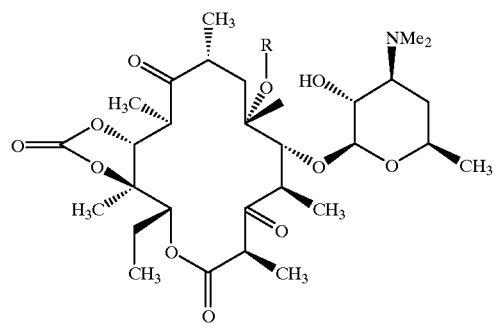

| Ex. No. | Substituent |
|---|---|
| 76 | R is —CH$_2$CH$_2$CH$_3$. |
| 77 | R is —CH$_2$CH$_2$NH$_2$. |
| 78 | R is —CH$_2$CH=NOH. |
| 79 | R is —CH$_2$CH$_2$CH$_2$OH |
| 80 | R is —CH$_2$F |
| 81 | R is —CH$_2$CH$_2$-phenyl |
| 82 | R is —CH$_2$CH$_2$-(4-pyridyl) |
| 83 | R is —CH$_2$CH$_2$-(4-quinolyl) |
| 84 | R is —CH$_2$CH(OH)CN |
| 85 | R is —CH(C(O)OCH$_3$)CH$_2$-phenyl |
| 86 | R is —CH$_2$CN |
| 87 | R is —CH$_2$CH=CH-(4-methoxyphenyl) |
| 88 | R is —CH$_2$CH=CH-(4-fluorophenyl) |
| 89 | R is —CH$_2$CH=CH-(8-quinolyl) |
| 90 | R is —CH$_2$CH$_2$NHCH$_2$-phenyl |
| 91 | R is —CH$_2$-phenyl |
| 92 | R is —CH$_2$-(4-pyridyl) |
| 93 | R is —CH$_2$-(4-quinolyl) |
| 94 | R is —CH$_2$CH=CH-(4-pyridyl) |
| 95 | R is —CH$_2$CH$_2$CH$_2$-(4-pyridyl) |
| 96 | R is —CH$_2$CH=CH-(4-quinolyl) |
| 97 | R is —CH$_2$CH$_2$CH$_2$-(4-quinolyl) |
| 98 | R is —CH$_2$CH=CH-(5-quinolyl) |
| 99 | R is —CH$_2$CH$_2$CH$_2$-(5-quinolyl) |
| 100 | R is —CH$_2$CH=CH-(4-benzoxazolyl) |
| 101 | R is —CH$_2$CH=CH-(4-benzimidazolyl) |

EXAMPLE 102

Compound of Formula (IX): L is CO, T is NH, R is —CH$_2$CH=CH$_2$

Step 102a: Compound 11 from Scheme 2: R is —CH$_2$CH=CH$_2$, R$^p$ is benzoyl

To a solution of compound 10 (R is —CH$_2$CH=CH$_2$, R$^p$ is benzoyl), prepared as in Example 71, step a, (2.59 g, 3.48 mmol) in benzene (100 mL) was added 1,8-diazabicyclo [5.4.0]undec-7-ene (DBU, 5.0 mL, 34 mmol). The reaction mixture was flushed with nitrogen, warmed to 80° C., and stirred for 3.5 hours. The reaction mixture was cooled to 0° C. and aqueous 0.5 M NaH$_2$PO$_4$ (100 mL) was added. The mixture was extracted twice with ethyl acetate and the combined organic layers were washed with brine, dried over sodium sulfate and concentrated in vacuo to give a white foam. Chromatography on silica gel (30% acetone-hexanes) gave the title compound (1.74 g) as a white solid. MS (FAB+ m/e 700 (M+H)$^+$.

Step 102b: Compound 12 from Scheme 3a: R is —CH$_2$CH=CH$_2$, R$^p$ is benzoyl

A solution in THF (30 mL) of the compound prepared in step 102a (1.74 g, 2.49 mmol) was cooled to −10° C. and flushed with nitrogen. Sodium hydride (80% in mineral oil, 150 mg, 5.00 mmol) was added and the reaction mixture was stirred for 10 minutes. A solution of carbonyldiimidazole (1.22 g, 7.50 mmol) in THF (20 mL) was added over 10 minutes at −10° C. The cold bath was removed and the reaction mixture was stirred for 1 hour. The reaction mixture was extracted with ethyl acetate and the organic phase was washed with aqueous 5% sodium bicarbonate and brine, dried over sodium sulfate, and concentrated in vacuo to give a white foam. Chromatography on silica gel (30% acetone-hexanes) gave the title compound (1.58 g) as a white solid. MS (FAB)+ m/e 794 (M+H)+.

Step 102c: Compound 18 from Scheme 4: R is —CH$_2$CH═CH$_2$, R$^p$ is benzoyl

The compound prepared in step 102b (1.19 g, 1.5 mmol) was dissolved in THF (2 mL) and acetonitrile (20 mL) and the solution was flushed with nitrogen. Aqueous ammonium hydroxide (28%, 21 mL) was added and the reaction mixture was stirred under nitrogen for 24 hours. The reaction mixture was extracted with ethyl acetate and the organic phase was washed with aqueous 5% sodium bicarbonate and brine, dried over sodium sulfate, and concentrated in vacuo to give a white foam. Chromatography on silica gel (30% acetone-hexanes) gave the title compound (0.56 g) as a white solid. MS (FAB)+ m/e 743 (M+H)+.

Step 102d: Compound of Formula (IX): L is CO, T is NH, R is —CH$_2$CH═CH$_2$

The title compound was prepared by deprotection of the compound prepared in step 102c by heating in methanol according to the procedure of Example 1, step g. $^{13}$C NMR (CDCl$_3$) δ 216.9 (C-9), 205.3 (C-3), 169.5 (C-1), 158.0, 134.4, 118.2, 102.8, 83.7, 78.4, 77.1, 76.1, 70.2, 69.5, 65.9, 64.7, 57.8, 50.8, 45.9, 45.1, 40.2, 38.9, 37.3, 28.3, 22.6, 21.2, 20.2, 18.1, 14.5, 13.8, 13.7, 10.6. MS (FAB)+ m/e 639 (M+H)+.

EXAMPLE 103

Compound of Formula (IX): L is CO, T is NH, R is —CH$_2$CH═CH-Phenyl

The desired compound was prepared using the procedure of Example 18, except substituting the compound prepared in Example 102, step c, (which is the compound 18 of Scheme 4, wherein R is allyl and R$^p$ is benzoyl) for the compound of Example 1, step f, used therein, and substituting iodobenzene for 3-bromoquinoline. $^{13}$C NMR (CDCl$_3$) δ 217.1 (C-9), 205.3 (C-3), 169.5 (C-1), 157.4, 136.5, 133.7, 128.6, 127.8, 126.5, 125.4, 102.9, 83.4, 78.4, 77.7, 76.4, 70.3, 69.5, 65.9, 64.3, 58.2, 50.9, 46.3, 45.1, 40.2, 39.1, 37.3, 31.5, 28.3, 22.8, 21.2, 20.3, 18.1, 14.4, 14.2, 13.7, 10.8. MS (FAB)+ m/e 715 (M+H)+.

EXAMPLE 104

Compound of Formula (IX): L is CO, T is NH, R is —CH$_2$CH═CH-(3-quinolyl)

The desired compound was prepared using the procedure of Example 18, except substituting the compound prepared in Example 102, step c, (which is the compound 18 of Scheme 4, wherein R is allyl and R$^p$ is benzoyl) for the compound of Example 1, step f, used therein. $^{13}$C NMR (CDCl$_3$) δ 217.4 (C-9), 205.3 (C-3), 169.6 (C-1), 157.7, 149.7, 147.6, 132.5, 129.9. 129.6, 129.2, 129.1, 128.6, 128.1, 126.7, 102.9, 83.5, 78.8, 77.5, 76.5, 70.2, 69.5, 65.9, 64.3, 58.2, 50.9, 46.3, 45.1, 40.2, 39.1, 37.4, 28.2, 22.6, 21.2, 20.2, 18.1, 14.4, 14.2, 13.7, 10.7. MS (FAB)+ m/e 766 (M+H)+.

Using the procedures described in the preceding examples and schemes and methods known in the synthetic organic chemistry art, the following compounds of Formula IX wherein L is CO and T is NH can be prepared. These compounds having the R substituent as described in the table below are of the formula:

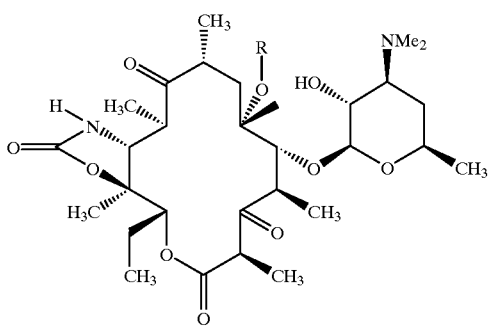

| Ex. No. | Substituent |
|---|---|
| 105 | R is —CH$_2$CH$_2$CH$_3$. |
| 106 | R is —CH$_2$CH$_2$NH$_2$. |
| 107 | R is —CH$_2$CH═NOH. |
| 108 | R is —CH$_2$CH$_2$CH$_2$OH |
| 109 | R is —CH$_2$F |
| 110 | R is —CH$_2$CH$_2$NHCH$_2$-phenyl |
| 111 | R is —CH$_2$CH$_2$NHCH$_2$-(4-pyridyl) |
| 112 | R is —CH$_2$CH$_2$NHCH$_2$-(4-quinolyl) |
| 113 | R is —CH$_2$CH(OH)CN |
| 114 | R is —CH(C(O)OCH$_3$)CH$_2$-phenyl |
| 115 | R is —CH$_2$CN |
| 116 | R is —CH$_2$CH═CH-(4-chlorophenyl) |
| 117 | R is —CH$_2$CH═CH-(4-fluorophenyl) |
| 118 | R is —CH$_2$CH═CH-(4-methoxyphenyl) |
| 119 | R is —CH$_2$CH$_2$CH$_2$-(4-ethoxyphenyl) |
| 120 | R is —CH$_2$CH═CH-(3-quinolyl) |
| 121 | R is —CH$_2$CH$_2$NHCH$_2$CH$_2$-(2-chlorophenyl) |
| 122 | R is —CH$_2$-phenyl |
| 123 | R is —CH$_2$-(4-pyridyl) |
| 124 | R is —CH$_2$-(4-quinolyl) |
| 125 | R is —CH$_2$CH═CH-(4-pyridyl) |
| 126 | R is —CH$_2$CH$_2$CH$_2$-(4-pyridyl) |
| 127 | R is —CH$_2$CH═CH-(4-quinolyl) |
| 128 | R is —CH$_2$CH$_2$CH$_2$-(4-quinolyl) |
| 129 | R is —CH$_2$CH═CH-(5-quinolyl) |
| 130 | R is —CH$_2$CH$_2$CH$_2$-(5-quinolyl) |
| 131 | R is —CH$_2$CH═CH-(4-benzoxazolyl) |
| 132 | R is —CH$_2$CH═CH-(4-benzimidazolyl) |
| 133 | R is —CH$_2$CH═CH-(8-quinolyl) |

EXAMPLE 134

Compound of Formula (VII): A, B, D, and E are H, R is allyl

Step 134a: Compound of Formula 14 (Scheme 3a): A, B, D, and E are H, R is allyl, R$^p$ is benzoyl To a solution under nitrogen of a compound of formula 12 (R is allyl, Rp is benzoyl, 385 mg, 0.485 mmol), prepared as in Example 102, step b, in acetonitrile was added ethylenediamine (291 mg, 4.85 mmol) and the reaction mixture was stirred for 67 hours. The reaction mixture was extracted with ethyl acetate and the organic phase was washed with aqueous 5% sodium bicarbonate and brine, dried over sodium sulfate, and concentrated in vacuo to give the title compound (401 mg) as colorless oil which was used without further purification.

Step 134b: Compound of Formula (VII): A, B, D, and E are H, R is allyl

The crude oil prepared in step 134a was dissolved in methanol (5 mL), acetic acid (60 μL) was added, and the reaction mixture was stirred for 15 hours at ambient temperature. The reaction mixture was extracted with ethyl acetate and the organic phase was washed with aqueous 5% sodium bicarbonate and brine, dried over sodium sulfate, and concentrated in vacuo to give a slightly yellow glass (347 mg). Chromatography on silica gel (95:5:0.5 dichloromethane-methanol-ammonia) gave the title compound (126 mg) as a white foam. MS m/e 664 (M+H)$^+$.

Using the procedures described in the preceding examples and schemes and methods known in the synthetic organic chemistry art, the following compounds of Formula VII wherein A, B, D and E are H can be prepared. These compounds having the R substituent as described in the table below are of the formula:

| Ex. No. | Substituent |
|---|---|
| 135 | R is —CH$_2$CH$_2$CH$_3$. |
| 136 | R is —CH$_2$CH$_2$NH$_2$. |
| 137 | R is —CH$_2$CH=NOH. |
| 138 | R is —CH$_2$CH$_2$CH$_2$OH |
| 139 | R is —CH$_2$F |
| 140 | R is —CH$_2$CN |
| 141 | R is —CH$_2$CH(OH)CN |
| 142 | R is —CH$_2$-phenyl |
| 143 | R is —CH$_2$-(4-pyridyl) |
| 144 | R is —CH$_2$-(4-quinolyl) |
| 145 | R is —CH$_2$CH=CH-(4-pyridyl) |
| 146 | R is —CH$_2$CH=CH-(4-chlorophenyl) |
| 147 | R is —CH$_2$CH=CH-(4-fluorophenyl) |
| 148 | R is —CH$_2$CH=CH-(4-methoxyphenyl) |
| 149 | R is —CH$_2$CH$_2$CH$_2$-phenyl |
| 150 | R is —CH$_2$CH=CH-(4-pyridyl) |
| 151 | R is —CH$_2$CH$_2$CH$_2$-(4-pyridyl) |
| 152 | R is —CH$_2$CH=CH-(4-quinolyl) |
| 153 | R is —CH$_2$CH$_2$CH$_2$-(4-quinolyl) |
| 154 | R is —CH$_2$CH=CH-(5-quinolyl) |
| 155 | R is —CH$_2$CH$_2$CH$_2$-(5-quinolyl) |
| 156 | R is —CH$_2$CH=CH-(4-benzoxazolyl) |
| 157 | R is —CH$_2$CH=CH-(4-benzimldazolyl) |
| 158 | R is —CH$_2$CH=CH-(8-quinolyl) |
| 159 | R is —CH$_2$CH$_2$NHCH$_2$-phenyl |
| 160 | R is —CH$_2$CH$_2$NHCH$_2$-(4-pyridyl) |
| 161 | R is —CH$_2$CH$_2$NHCH$_2$-(4-quinolyl) |
| 162 | R is —CH$_2$CH$_2$NHCH(CH$_2$-phenyl)C(O)OCH$_3$ |
| 163 | R is —CH$_2$CH$_2$NHCH$_2$CH$_2$-(2-chlorophenyl) |

EXAMPLE 164

Compound of Formula (VII): A, B and E are H, D is benzyl, R is allyl

Step 614a: 2-(R)-(BOC-amino)-3-phenyl-1-propanol

To a 5.2 g (23.8 mmol) sample of di-t-butyl dicarbonate in 20 mL of methylene chloride held at 0° C. was added (R)-2-amino-3-phenyl-1-propanol (3.0 g, 19.8 mmol, Aldrich), and the reaction mixture was stirred 1.5 hours at room temperature. The solvent was removed, and the residue was dried under high vacuum and taken directly to the next step.

Step 164b: 2-(R)-(BOC-amino)-1-O-methanesulfonyloxy-3-phenylpropane

The material from step 164a was dissolved in 20 mL of methylene chloride and 5 mL of THF, and the solution was cooled to 0° C. Triethylamine (4.1 mL, 29.4 mmol) was added, then methanesulfonyl chloride (1.9 mL, 24.5 mmol) was added slowly. The mixture was stirred 45 minutes at room temperature, then the solvent was removed under vacuum. The residue was dissolved in ethyl acetate, and the solution was washed with water and brine, dried (Na$_2$SO$_4$) and filtered. The solvent was removed under vacuum to afford 6.38 g of the title compound. MS m/z (M+H)$^+$: 330, MS m/z (M+NH$_4$)$^+$: 347.

Step 164c: 1-azido-2-(R)-(BOC-amino)-3-phenylpropane

The compound from step 164b above (6.36 g, 193 mmol) was dissolved in 25 mL of DMF, and 2.5 g (38 mmol) of NaN$_3$ was added. The reaction mixture was stirred for 24 hours at 62° C. The solution was cooled to room temperature, then extracted with ethyl acetate. The organic extract was washed with water and brine, dried (Na$_2$SO$_4$) and filtered. The solvent was removed under vacuum to afford 4.34 g of the title compound. MS m/z (M+H)$^+$: 277, MS m/z (M+NH$_4$)$^+$: 294.

Step 164d: 1-azido-2-(R)-amino-3-phenylpropane

The compound from step 164c (4.3 g,15.6 mmol) was dissolved in 30 mL of 4 N HCl in ethanol, and the reaction mixture was stirred for 1.5 hours at room temperature. The solvent was stripped and chased with ether. The residue was dissolved in water, NaCl was added, and the mixture was extracted with ethyl ether, which was discarded. The aqueous layer was adjusted to pH 12 with K$_2$CO$_3$, saturated with NaCl, then extracted with CHCl$_3$. The organic extract was washed with brine, dried (Na$_2$SO$_4$) and filtered. The solvent was removed under vacuum to afford 2.17 g of the title compound. MS m/z (M+H)$^+$: 177, MS m/z (M+NH$_4$)$^+$: 194.

Step 164e: 1,2-(R)-diamino-3-phenylpropane

A sample of the compound from step 164d (1.2 g, 6.8 mmol) was hydrogenated (4 atm) in ethanol over 1.2 g of 10% Pd/C for 21.5 hours at room temperature. The mixture was filtered to remove the catalyst, and the solvent was removed to afford the title compound (1.055 g). MS m/z (M+H)$^+$: 151, MS m/z (M+NH$_4$)$^+$: 168.

Step 164f: Compound 14 from Scheme 3a; A, B and E are H, D is benzyl, R is allyl, R$^p$ is benzoyl The desired compound is prepared by stirring a solution of compound prepared as in Example 102, step b, (which is the compound 12 from Scheme 3a, wherein R is allyl, Rp is benzoyl), and 1,2-(R)-diamino-3-phenylpropane, prepared as in step 164e above, in aqueous acetonitrile for an amount of time sufficient to consume substantially all of the starting material.

Step 164g: Compound 14 from Scheme 3a: A, B and E are H, D is benzyl, R is allyl, Rp is H The title compound is prepared by deprotection of the compound prepared in step 164f by heating in methanol according to the procedure of Example 1, step g.

Step 164h: Compound of Formula (VII): A, B and E are H, D is benzyl, R is allyl

The desired compound is prepared by heating a solution of the compound prepared in step 164g in ethanol-acetic acid.

EXAMPLE 165

Compound of Formula (VII): A is benzyl, B, D and E are H, R is allyl

Step 165a: Compound 16 from Scheme 3b: A is benzyl, B, D and E are H, Y is OH, R is allyl, R$^p$ is benzoyl The desired compound is prepared according to the method of Example 164, step f, except substituting (S)-2-amino-3-phenyl-1-propanol (Aldrich Chemical Co.) for 1,2-(R)-diamino-3-phenylpropane Step 165b: Compound 16 from Scheme 3b: A is benzyl, B, D and E are H, Y is $N_3$, R is allyl, $R^p$ is benzoyl The desired compound is prepared by treating a solution in THF of the compound of step 165a with triphenylphosphine, diethylazodicarboxylate, and diphenylphosphorylazide.

Step 165c: Compound 16 from Scheme 3b: A is benzyl, B, D and E are H, Y is $N_3$, R is allyl, $R^p$ is H The desired compound is prepared by deprotection of the compound prepared in step 165b by heating in methanol according to the procedure of Example 1, step g.

Step 165d: Compound 17 from Scheme 3b: R is allyl

The desired compound is prepared by refluxing a solution in THF of the product of step 165d and triphenylphosphine.

Step 165e: Compound of Formula (VII): A is benzyl, B, D and E are H, R is allyl

The desired compound is prepared by heating a solution of the compound prepared in step 165d in ethanol-acetic acid.

EXAMPLE 166

Compound of Formula (VII): A and E are phenyl, B and D and are H, R is allyl

The desired compound is prepared according to the method of Example 164, steps f–h, except substituting 1,2-diphenyl-1,2-ethylenediamine (Aldrich Chemical Co.) for 1,2-(R)-diamino-3-phenylpropane

EXAMPLE 167

Compound of Formula (VII): A is methyl, B, D and E are H, R is allyl

The desired compound is prepared according to the method of Example 165, except substituting (S)-2-amino-1-propanol (Aldrich Chemical Co.) for (S)-2-amino-3-phenyl-1-propanol.

EXAMPLE 168

Compound of Formula (VII): A and D are methyl, B and E are H, R is allyl

Step 168a: meso-2,3-bis(methanesulfonyloxy)butane

Samples of meso-2,3-butanediol (10 g, 111 mmol, Aldrich) and triethylamine (92.8 mL, 666 mmol) were dissolved in methylene chloride. The solution was cooled to −78° C., and methanesulfonyl chloride (25.8 mL, 333 mmol) was added dropwise. A precipitate formed. The mixture was diluted with additional methylene chloride, and the mixture was stirred for 20 minutes at −78° C. and at 0° C. for 2 hours. The reaction mixture was warmed to room temperature, diluted with additional solvent, and washed with $H_2O$, aqueous $NaHCO_3$ and aqueous NaCl. The organic solution was dried over $MgSO_4$, and the solvent was removed to afford the title compound (25.01 g). $^1$H NMR (300 MHz, $CDCl_3$): δ 4.91 (q, 2H), 3.10 (s, 6H), 1.45 (d, 6H).

Step 168b: meso-2,3-diazidobutane

A sample of the compound from step 168a (25 g) was dissolved in 250 mL of DMF, and $NaN_3$ (40 g) was added. The mixture was stirred vigorously at 85° C. for 24 hours, then cooled to room temperature. The mixture was diluted with 800 mL of ether, washed with $H_2O$, aqueous $NaHCO_3$ and aqueous NaCl, then dried over $MgSO_4$. The solution was filtered and concentrated to afford the title compound (13.00 g). $^1$H NMR (300 MHz, $CDCl_3$): δ 3.50 (m, 2H), 1.30 (d, 6H).

Step 168c: meso-2,3-butanediamine

A sample of the compound from step 168b (13.0 g, 125 mmol) was dissolved in ethanol and hydrogenated at 4 atm over 10% Pd/C for 20 hours at room temperature. The catalyst was removed by filtration, and the solvent was removed under vacuum to afford the title compound. $^1$H NMR (300 MHz, $CDCl_3$): δ 2.70 (m, 2H), 1.45 (br, 4H), 1.05 (d, 6H).

MS (m/z): 89 $(M+H)^+$.

Step 168d: Compound of Formula (VII): A and D are methyl, B and E are H, R is allyl The desired compound is prepared according to the method of Example 164, steps c–h, except substituting meso-2,3-butanediamine, prepared as in step 168c, for the 1,2-(R)-diamino-3-phenylpropane thereof.

EXAMPLE 169

Compound of Formula (VII): A and E taken together is —$CH_2CH_2CH_2$—, B and D are H, R is allyl The desired compound is prepared according to the method of Example 168, except substituting 1,2-cyclopentane diol (Aldrich Chemical Co.) for meso 2,3-butanediol.

EXAMPLE 170

Compound of Formula (VII): A, B, D, and E are H, R is —$CH_2CH$=$CH$-(3-quinolyl)

The desired compound was prepared by coupling 3-bromoquinoline with the product of Example 134 according to the method of Example 18. MS (FAB)+ m/e 791 $(M+H)^+$.

EXAMPLE 171

Compound of Formula (VII): A, B, D, and E are H, R is —$CH_2CH_2CH_2$-(3-quinolyl)

To a sample of the compound from Example 170 (110 mg) in methanol (10 mL) flushed with nitrogen was added 10% Pd/C (50 mg), and the mixture was stirred at room temperature under 1 atm of hydrogen for 16 hours. The mixture was filtered and concentrated, and the residue was purified by chromatography on silica gel eluting with 95:5:0.5 to 90:10:0.5 dichloromethane/methanol/dimethylamine to give the title compound (106 mg). High Res. MS m/e $(M+H)^+$ Calcd for $C_{44}H_{64}N_4O_9$: 793.4752; Found 793.4766.

EXAMPLE 172

Compound of Formula (VIII): X is O, R is $CH_2$-(3-iodophenyl)

Following the procedures of Example 1, except substituting 3-iodobenzyl bromide for the allyl bromide of step 1f, the title compound was prepared. MS (FAB)+ m/e 949 $(M+H)^+$.

EXAMPLE 173

Compound of Formula (VIII): X is O, R is $CH_2$-(2-naphthyl)

Following the procedures of Example 1, except substituting (2-naphthyl)methyl bromide for the allyl bromide of step 1a and acetic anhydride for the benzoic anhydride in step 1e, the title compound was prepared. MS (FAB)+ m/e 714 (M+H)$^+$; Anal. Calcd. for $C_{40}H_{59}NO_{10}$: C, 67.30; H, 8.33; N, 1.96; Found: C, 66.91; H, 8.29; N, 1.64.

EXAMPLE 174

Compound of Formula (VIII): X is O, R is $CH_2$—CH=CH-(4-fluorophenyl)

Following the procedures of Example 172, except substituting 4-fluoro-1-iodobenzene for the iodobenzene of step 14a, the title compound was prepared.

EXAMPLE 175

Compound of Formula (VIII): X is O, R is $CH_2$—CH(OH)—CN

The title compound was obtained by chromatographic separation from the reaction mixture of the crude product of Example 8. MS (FAB)+ m/e 643 (M+H)$^+$.

EXAMPLE 176

Compound of Formula (IX): L is CO, T is NH, R is —$CH_2$-(2-naphthyl)

Step 176a. Compound 6 from Scheme 1a: R is —$CH_2$-(2-naphthyl)

Following the procedures of Example 1, steps a–c, except substituting (2-naphthyl)methyl bromide for the allyl bromide of step 1a, the title compound was prepared. MS (FAB)+ m/e 874 (M+H)$^+$.

Step 176b. Compound 6A from Scheme 1c; R is —$CH_2$-(2-naphthyl), Rp is acetyl

The compound from step 176a (2.0 g) was treated according to the procedure of Example 1 step e, except substituting acetic anhydride for the benzoic anhydride of that example. MS (FAB)+ m/e 958 (M+H)$^+$.

Step 176c. Compound 6B from Scheme 1c: R is —$CH_2$-(2-naphthyl), Rp is acetyl

The compound of step 176b (500 mg) was treated with NaH and carbonyldiimidazole according to the procedure of Example 102 step b to afford the title compound (58 mg). MS (FAB)+ m/e 1034 (M+H)$^+$.

Step 176d. Compound 6C from Scheme 1c: R is —$CH_2$-(2-naphthyl), Rp is acetyl, $R^d$ is H The compound of step 176c (58 mg) was treated with ammonia in acetonitrile according to the procedure of Example 102 step c to afford the title compound. MS (FAB)+ m/e 983 (M+H)$^+$.

Step 176e. Compound of formula (IX): L is CO, T is NH, R is —$CH_2$-(2-naphthyl)

The compound of step 176d was treated according to the procedures of Example 1 steps 1d, 1f and 1g, to give the title compound. MS (FAB)+ m/e 739 (M+H)$^+$.

EXAMPLE 177

Compound of Formula (III); Rc is acetyl, L is CO, T is NH, R is —$CH_2CH=CH_2$

Step 177a. Compound 6A from Scheme 1c: R is —$CH_2CH=CH_2$, $R^p$ is acetyl

To a sample of the compound from Example 1 step c (405.2 g, 528 mmol) in dichloromethane (20 mL) was added dimethylaminopyridine(0.488 g, 4 mmol) and acetic anhydride (3.39 mL, 36 mmol), and the mixture was stirred at room temperature for 3 hours. The mixture was diluted with methylene chloride, then washed with 5% aqueous sodium bicarbonate and brine and dried over $Na_2SO_4$. The residue was dried and recrystallized from acetonitrile to give the title compound (491 g). MS m/e 857 (M+H)$^+$.

Step 177b. Compound 6B from Scheme 1c: R is —$CH_2CH=CH_2$, $R^p$ is acetyl

To a sample of the compound from step 177a (85.8 g, 100 mmol) in dry THF (500 mL) cooled to −40° C. and flushed with nitrogen was added sodium bis(trimethylsilyl)amide (125 mL, 125 mmol) over 20 minutes, and the mixture was stirred at −40° C. for 40 minutes. To this mixture was added a solution of carbonyldiimidazole (3.65 g, 22.56 mmol) in 5:3 THF/DMF (800 mL) under nitrogen at −40° C. over 30 minutes, and the mixture was stirred at −20° C. for 30 minutes. The mixture was stirred at room temperature for 27 hours, then diluted with ethyl acetate. The mixture was washed with 5% sodium bicarbonate and brine, dried over $Na_2SO_4$, and concentrated to give the title compound (124 g), which was taken directly to the next step.

Step 177c. Compound 6C from Scheme 1c: R is —$CH_2CH=CH_2$, $R^p$ is acetyl, $R^d$ is H The compound from step 177b (124 g) was dissolved in 9:1 acetonitrile/THF (1100 mL), ammonium hydroxide (28%, 200 mL) was added, and the mixture was stirred at room temperature under nitrogen for 8 days. The solvent was removed, and the residue was dissolved in ethyl acetate. This solution was washed with 5% sodium bicarbonate and brine, dried over $Na_2SO_4$, and concentrated to give the title compound. MS (FAB)+ m/e 882 (M+H)$^+$.

Step 177d. Compound 6D from Scheme 1c: R is —$CH_2CH=CH_2$, $R^p$ is acetyl, $R^d$ is H To a sample of the compound from step 177c (69.0 g, 78.2 mmol) suspended in ethanol (200 mL) and diluted with water (400 mL) was added HCl (0.972 N, 400 mL) dropwise over 20 minutes. The mixture was stirred for 4 hours, and additional HCl was added (4 N, 100 mL) over 20 minutes. The mixture was stirred for 18 hours, cooled to 0° C., then NaOH (4 N, 200 mL) was added over 30 minutes to approximately pH 9. The title compound was isolated by filtration (35.56 g).

Step 177e. Compound 6E from Scheme 1c: R is —$CH_2CH=CH_2$, $R^p$ is acetyl, $R^d$ is H; (Compound of Formula (III): Rc is acetyl, L is CO, T is NH, R is —$CH_2CH=CH_2$)

To a −10° C. solution under nitrogen of N-chlorosuccinimide (2.37 g, 17.8 mmol) in dichloromethane (80 mL) was added dimethylsulfide (1.52 mL, 20.8 mmol) over 5 minutes. The resulting white slurry was stirred for 10 minutes at −10° C., a solution of the compound from step 177d (8.10 g, 11.9 mmol) in dichloromethane (60 mL) was added and the reaction mixture was stirred for 30 minutes at −10 to −5° C. Triethylamine (1.99 mL, 14.3 mmol) was added dropwise over 10 minutes and the reaction mixture was stirred for 1 hour at 0° C. The reaction mixture was extracted with dichloromethane. The organic phase was washed with aqueous 5% sodium bicarbonate and brine, dried over sodium sulfate, and concentrated in vacuo to give a white foam. Chromatography on silica gel (eluting with 50:50:0.5 acetone/hexanes/ammonium hydroxide) gave the title compound (8.27 g) as a white foam. Anal. Calcd. for $C_{35}H_{56}N_2O_{11}$: C, 61.75; H, 8.29; N, 4.11; Found: C, 62.25; H, 8.50; N, 4.28.

EXAMPLE 178

Alternate Preparation of Compound of Formula (IX): L is CO, T is NH, R is —$CH_2CH=CH$-(3-quinolyl)

Step 178a. (Compound of Formula (III): Rc is acetyl, L is CO, T is NH, R is —$CH_2CH=CH$-(3-quinolyl))

A mixture of the compound from Example 177 (46.36 g, 68.2 mmol), palladium(II)acetate (3.055 g, 13.6 mmol), and tri-o-tolylphosphine (8.268 g, 27.2 mmol) in acetonitrile (400 mL) was flushed with nitrogen. To this solution was added 3-bromoquinoline (18.45 mL, 136 mmol) and triethylamine (18.92 mL, 13.6 mmol) via syringe. The reaction mixture was heated at 50° C. for 1 hour and stirred at 90° C. for 4 days. The reaction mixture was taken up in ethyl acetate and washed with aqueous 5% sodium bicarbonate and brine, dried over sodium sulfate, filtered, and concentrated in vacuo. Chromatography on silica gel (eluting with 50:50:0.5 acetone/hexanes/ammonium hydroxide) gave the title compound (46.56 g) as a white foam. MS m/e 808 $(M+H)^+$.

Step 178b: Compound of Formula (IX): L is CO, T is NH, R is —$CH_2CH$=CH-(3-quinolyl)

Deprotection of a sample of the compound prepared in step 178a (42.43 g) was accomplished by stirring overnight in methanol according to the procedure of Example 1, step g to give the title product (32.95 g). MS m/e 766 $(M+H)^+$.

EXAMPLE 179

Compound of Formula (IX): L is CO, T is N($CH_3$), R is —$CH_2CH$=$CH_2$

Step 179a: Compound 18 from Scheme 4: R* is methyl, R is —$CH_2CH$=$CH_2$, $R^p$ is benzoyl A sample of the compound from Example 102, step 102b (Compound (12) from Scheme 3a; R is —$CH_2CH$=$CH_2$, $R^p$ is benzoyl, 320 mg, 0.400 mmol) was dissolved in acetonitrile (10 mL) and the solution was flushed with nitrogen. Aqueous methylamine (40%, 0.344 mL) was added and the reaction mixture was stirred under nitrogen for 4 days. The reaction mixture was extracted with ethyl acetate and the organic phase was washed with aqueous 5% sodium bicarbonate and brine, dried over sodium sulfate, and concentrated in vacuo to give a white foam. Chromatography on silica gel (30% acetone-hexanes) gave the title compound (277 mg) as a white solid. MS m/e 757 $(M+H)^+$.

Step 179b. Compound of Formula (IX): L is CO, T is N($CH_3$), R is —$CH_2CH$=$CH_2$ Deprotection of a sample of the compound prepared in step 179a (110 mg) was accomplished by stirring overnight in methanol according to the procedure of Example 1, step g, to give the title product (48 mg). Anal. Calcd. for $C_{34}H_{56}N_2O_{10}O$: C, 62.56; H, 8.65; N, 4.29; Found: C, 62.23; H, 8.72; N, 4.13.

EXAMPLE 180

Compound of Formula (IX): L is CO, T is N($CH_3$), R is —$CH_2CH$=CH-(3-quinolyl)

Following the procedure of Example 178, except substituting the compound of Example 179 step a for the starting material compound therein (from Example 177), the title compound was prepared.

EXAMPLE 181

Compound of Formula (IX): L is CO, T is N($CH_2CH_2N(CH_3)_2$), R is —$CH_2CH$=$CH_2$ Step 181a. Compound 18 from Scheme 4: R* is 2-(dimethylamino)ethyl, R is —$CH_2CH$=$CH_2$, $R^p$ is benzoyl Following the procedures of Example 179, except substituting N,N-dimethylethylenediamine for the methylamine thereof, the title compound was prepared (285 mg). MS m/e 814 $(M+H)^+$.

Step 181a. Compound of Formula (IX): L is CO, T is $N(CH_2CH_2N(CH_3)_2)_2$, R is —$CH_2CH$=$CH_2$ Deprotection of a sample of the compound prepared in step 181a (110 mg) was accomplished by heating overnight in methanol according to the procedure of Example 1, step g, to give the title product (28 mg).

EXAMPLE 182

Compound of Formula (IX): L is CO, T is N ($CH_2CH_2N(CH_3)_2$), R is —$CH_2CH$=CH-(3-quinolyl)

Following the procedures of Example 178, except substituting the compound of Example 181 step a (162 mg) for the starting material compound therein (from Example 177), the title compound was prepared (33.4 mg).

EXAMPLE 183

Compound of Formula (IX): L is CO, T is N ($CH_2CH$=$CH_2$), R is —$CH_2CH$=$CH_2$ Step 183a. Compound 18 from Scheme 4: R* is —$CH_2CH$=$CH_2$, R is —$CH_2CH$=$CH_2$, $R^p$ is benzoyl Following the procedures of Example 179, except substituting allylamine for the methylamine thereof, the title compound was prepared.

Step 183b. Compound of Formula (IX): L is CO, T is N($CH_2CH$=$CH_2$), R is —$CH_2CH$=$CH_2$ Deprotection of a sample of the compound prepared in step 183a (78 mg) was accomplished by heating overnight in methanol according to the procedure of Example 1, step g, to give the title product (33 mg).

EXAMPLE 184

Compound of Formula (IX): L is CO, T is T is N ($CH_2CH$=CH-(3-quinolyl)), R is —$CH_2CH$=CH-(3-quinolyl)

Following the procedures of Example 178, except substituting the compound of Example 183 step a for the starting material compound therein (from Example 177), the title compound was prepared. H. Res. M.S. Calcd. for $C_{54}H_{69}N_4O_{10}$: 933.5014; Found 933.5052.

EXAMPLES 185–219

Following the procedures of Example 178, except substituting the reagent below for the 3-bromoquinoline of Example 178, the compounds 185–219 shown in the table below the following compounds 185–219 shown in the table below were prepared. These compounds of Formula IX wherein L is CO and T is O having the R substituent as described in the table below are of the formula

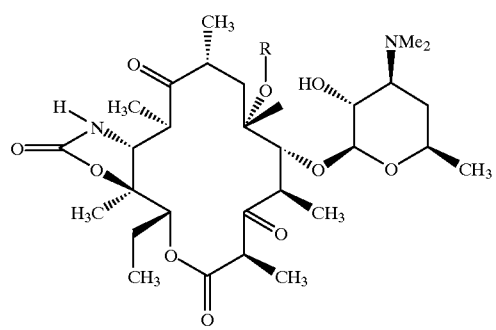
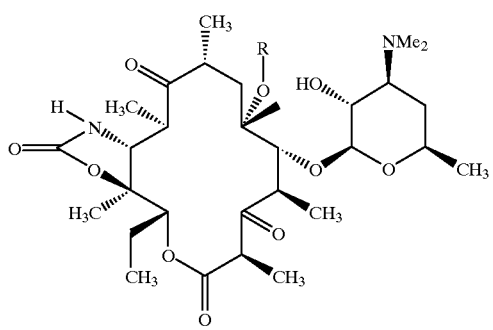

Examples 185–219

| Ex. No. | reagent | substituent | data |
|---|---|---|---|
| 185 | 3-bromopyridine | R is —CH₂CH=CH-(3-pyridyl) | MS 716 (M + H)⁺ |
| 186 | 2-bromonaphthalene | R is —CH₂CH=CH-(2-naphthyl) | MS 765 (M + H)⁺ |
| 187 | 4-bromoisoquinoline | R is —CH₂CH=CH-(4-isoquinolinyl) | H. Res. M.S. Calcd. for $C_{42}H_{60}N_3O_{10}$: 766.4279; Found 776.4271. |
| 188 | 4-bromo-1,2-methylenedioxy-benzene | R is —CH₂CH=CH-(3,4-methylenedioxyphenyl) | H. Res. M.S. Calcd. for $C_{40}H_{58}N_2O_{12}$: 759.4068; Found 759.4083. |
| 189 | 8-bromoquinoline | R is —CH₂CH=CH-(8-quinolyl) | MS 766 (M + H)⁺ |
| 190 | 5-bromoindole | R is —CH₂CH=CH-(5-indolyl) | H. Res. M.S. Calcd. for $C_{41}H_{59}N_3O_{10}$: 754.4279; Found 754.4294. |
| 191 | 3-bromo-6-chloro-quinoline | R is —CH₂CH=CH-(6-chloro-3-quinolyl) | H. Res. M.S. Calcd. for $C_{42}H_{58}N_3O_{10}$: 800.3889; Found 800.3880. |
| 192 | 3,4-ethylenedioxy-benzene | R is —CH₂CH=CH-(3,4-ethylenedioxyphenyl) | H. Res. M.S. Calcd. for $C_{41}H_{60}N_3O_{12}$: 773.4225; Found 773.4204. |
| 193 | 1-iodo-3-nitro-benzene | R is —CH₂CH=CH-(3-nitrophenyl) | H. Res. M.S. Calcd. for $C_{39}H_{58}N_3O_{12}$: 760.4020; Found 760.4004. |
| 194 | 6-bromoquinoline | R is —CH₂CH=CH-(6-quinolyl) | MS 766 (M + H)⁺ |
| 195 | 3-bromo-6-nitro-quinoline | R is —CH₂CH=CH-(6-nitroquinolyl) | H. Res. M.S. Calcd. for $C_{42}H_{59}N_4O_{12}$: 811.4129; Found 811.4122. |
| 196 | 5-bromoquinoline | R is —CH₂CH=CH-(5-quinolyl) | H. Res. M.S. Calcd. for $C_{42}H_{60}N_3O_{10}$: 766.4279; Found 766.4281. |
| 197 | 2-methyl-6-bromo-quinoline | R is —CH₂CH=CH-(2-methyl-6-quinolyl) | Anal. Calcd. for $C_{43}H_{61}N_3O_{10}$: C, 66.22; H, 7.88; N, 5.39; Found: C, 66.43; H, 8.12; N, 5.18. |
| 198 * | 3-bromoquinoline | Compound of Formula (III): L is CO, T is NH, $R^c$ is acetyl; R is —CH₂CH=CH-(3-quinolyl) | H. Res. M.S. Calcd. for $C_{44}H_{61}N_3O_{10}$: 808.4379; Found 808.4381. |
| 199 | 5-bromoisoquinoline | R is —CH₂CH=CH-(5-isoquinolyl) | H. Res. M.S. Calcd. for $C_{42}H_{59}N_3O_{10}$: 766.4279; Found 766.4301. |
| 200 | 6-bromo-7-nitro-quinoxaline | R is —CH₂CH=CH-(7-nitro-6-quinoxalinyl) | H. Res. M.S. Calcd. for $C_{44}H_{57}N_5O_{12}$: 812.4082; Found 812.4064. |
| 201 | 6-amino-3-bromo-quinoline | R is —CH₂CH=CH-(6-amino-3-quinolyl) | H. Res. M.S. Calcd. for $C_{42}H_{60}N_4O_{10}$: 781.4388; Found 781.4386. |
| 202 | 3-bromo-1,8-naphthyridine | R is —CH₂CH=CH-(1,8-naphthyridin-3-yl) | H. Res. M.S. Calcd. for $C_{41}H_{58}N_4O_{10}$: 781.4388; Found 781.4386. |
| 203 | 6-(acetylamino)-3-bromoquinoline | R is —CH₂CH=CH-(6-(acetylamino)-3-quinolyl) | H. Res. M.S. Calcd. for $C_{44}H_{62}N_4O_{11}$: 823.4493; Found 823.4479. |
| 204 | 3-bromocarbazole | R is —CH₂CH=CH-(3-carbazolyl) | H. Res. M.S. Calcd. for $C_{45}H_{61}N_3O_{10}$: 804.4435; Found 803.4437. |
| 205 | 5-bromobenzimidazole | R is —CH₂CH=CH-(5-benzimidazolyl) | H. Res. M.S. Calcd. for $C_{40}H_{58}N_4O_{10}$: 755.4231; Found 755.4224. |

-continued

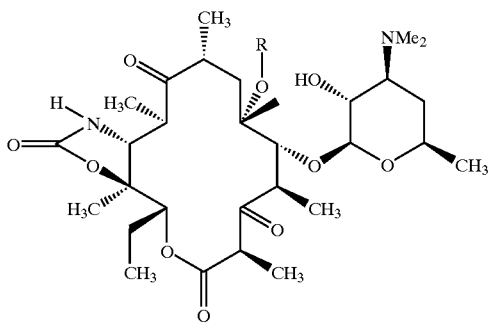

Examples 185–219

| Ex. No. | reagent | substituent | data |
|---|---|---|---|
| 206 | 7-bromo-3-hydroxy-N-(2-methoxy-phenol)-2-napthyl-amide | R is —CH$_2$CH=CH-(-3-hydroxy-2-(N-(2-methoxy-phenyl)amido)-7-naphthyl) | H. Res. M.S. Calcd. for C$_{51}$H$_{67}$N$_3$O$_{13}$: 930.4752; Found 930.4754. |
| 207 | 6-bromo-quinoxaline | R is —CH$_2$CH=CH-(6-quinoxalinyl) | H. Res. M.S. Calcd. for C$_{41}$H$_{59}$N$_4$O$_{13}$: 767.4231; Found 767.4236. |
| 208 | 3-bromo-6-hydroxyl-quinoline | R is —CH$_2$CH=CH-(6-hydroxy-3-quinolyl) | H. Res. M.S. Calcd. for C$_{42}$H$_{60}$N$_3$O$_{11}$: 782.4228; Found 782.4207. |
| 209 | 3-bromo-6-methoxyquinoline | R is —CH$_2$CH=CH-(6-methoxy-3-quinolyl) | H. Res. M.S. Calcd. for C$_{43}$H$_{62}$N$_3$O$_{11}$: 796.4384; Found 796.4379. |
| 210 | 3-bromo-5-nitro-quinoline | R is —CH$_2$CH=CH-(5-nitro-3-quinolyl) | H. Res. M.S. Calcd. for C$_{42}$H$_{59}$N$_4$O$_{12}$: 811.4129; Found 811.4146. |
| 211 | 3-bromo-8-nitro-quinoline | R is —CH$_2$CH=CH-(8-nitro-3-quinolyl) | Anal. Calcd. for C$_{42}$H$_{58}$N$_4$O$_{12}$: C, 62.21; H, 7.21; N, 6.91; Found: C, 62.56; H, 7.48; N, 6.61. |
| 212 | 2-chloroquinoline | R is —CH$_2$CH=CH-(2-quinolyl) | MS (M + H)$^+$ 766. |
| 213 | 4-chloroquinoline | R is —CH$_2$CH=CH-(4-quinolyl) | MS 766 (M + H)$^+$ |
| 214 | 3-bromoquinoline-6-carboxylic acid | R is —CH$_2$CH=CH-(4-carboxyl-3-quinolyl) | MS (M + H)$^+$ 810. |
| 215 | 3-bromo-6-fluoro-quinoline | R is —CH$_2$CH=CH-(6-fluoro-3-quinolyl) | Anal. Calcd. for C$_{42}$H$_{58}$FN$_3$O$_{10}$: C, 64.35; H, 7.46; N, 5.36; Found: C, 64.53; H, 7.69; N, 5.18. |
| 216 | 3-bromoquinoline-6-carboxylic acid methyl ester | R is —CH$_2$CH=CH-(6-methoxycarbonyl-3-quinolyl) | MS (M + H)$^+$ 824. |
| 217 | 3-bromoquinoline-6-carboxamide | R is —CH$_2$CH=CH-(6-aminocarbonyl-3-quinolyl) | MS (M + H)$^+$ 809. |

-continued

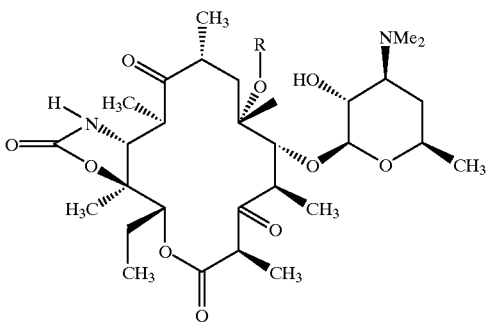

Examples 185–219

| Ex. No. | reagent | substituent | data |
|---|---|---|---|
| 218 | 3-bromo-6-cyano-quinoline | R is —CH$_2$CH=CH-(6-cyano-3-quinolyl) | MS (M + H)$^+$ 791. |
| 219 | 3-bromo-6-iodo-quinoline | R is —CH$_2$CH=CH-(3-bromo-6-quinolyl) | MS (M + H)$^+$ 844. |

* without deprotection step

EXAMPLE 220

Compound of Formula (IX): L is CO, T is NH, R is —CH$_2$C(O)H

The compound from Example 102 (14.0 g) was dissolved in CH$_2$Cl$_2$ (200 mL) and the solution was cooled to −78° C. under a nitrogen atmosphere. Ozone was then bubbled through the solution until a blue color persisted. The reaction was then purged with N$_2$ until colorless and dimethylsulfide (14 mL) was added, and the reaction mixture was warmed to 0° C. After stirring for 90 min, the reaction mixture was concentrated under reduced pressure to give a light-yellow foam. This material was dissolved in THF (300 mL) and treated with triphenylphosphine (8 g) at reflux for 6 hours, then the reaction mixture was concentrated under reduced pressure. Chromatography (1:1 acetone/hexanes to 3:1 acetone/hexanes with 0.5% TEA) gave the product (6.6 g) as an off-white foam. MS(CI) m/e 641 M+H)$^+$.

EXAMPLE 221

Compound of Formula (IX): L is CO, T is NH, R is —CH$_2$CH$_2$NHCH$_2$Phenyl

The compound from Example 220 (120 mg, 0.187 mmol) and benzylamine (40 μL, 0.366 mmol, 2 equiv) were dissolved in 3 mL of dry dichloromethane. Molecular sieves (4 Å) were added and the reaction was stirred overnight. The reaction was then filtered and concentrated under reduced pressure. The resulting imine was dissolved in MeOH (5 mL), a catalytic amount of 10% Pd on carbon was added, and the reaction was stirred rapidly under 1 atm of H$_2$ pressure for 20 hours. The mixture was then filtered through a Celite pad, and the solution concentrated under reduced pressure. Chromatography (SiO$_2$, 5% MeOH/dichloromethane with 0.2% NH$_4$OH) gave the desired material (84 mg) as a white solid. $^{13}$C NMR (CDCl$_3$) δ 218.3, 205.6, 170.3, 157.9, 140.2, 128.2, 126.8, 102.4, 83.5, 78.2, 76.9, 75.1, 70.1, 69.5, 65.9, 62.0, 58.4, 53.8, 50.6, 48.2, 45.3, 44.8, 40.1, 39.0, 37.4, 28.2, 22.4, 21.2, 20.6, 18.3, 14.6, 13.6, 13.5, 12.7, 10.3. MS(CI) m/e 732 (M+H)$^+$.

EXAMPLE 222

Compound of Formula (IX): L is CO, T is NH, R is —$CH_2CH_2NHCH_2CH_2$Phenyl

The title compound was prepared from the compound of Example 220 (108 mg, 0.169 mmol) and phenethylamine (42 μL, 0.334 mmol, 2 equiv) using the procedure described for Example 221. Chromatography ($SiO_2$, 5% MeOH/dichloromethane with 0.5% $NH_4OH$) gave the desired material (82 mg) as a white solid. $^{13}C$ NMR ($CDCl_3$) δ 218.1, 205.5, 170.3, 158.0, 140.2, 128.8, 128.2, 125.8, 102.4, 83.6, 78.3, 76.9, 75.1, 70.1, 69.5, 65.9, 61.9, 58.3, 51.5, 50.6, 48.8, 45.2, 44.9, 40.1, 38.9, 37.4, 36.5, 28.2, 22.4, 21.2, 20.6, 18.3, 14.6, 13.6, 13.4, 12.8, 103. 12803. MS me 746 (M+H)$^+$. Anal Calcd for $C_{40}H_{63}N_3O_{10}$. Found C 64.26, H 8.47, N 5.43.

EXAMPLE 223

Compound of Formula (IX): L is CO, T is NH, R is —$CH_2CH_2NHCH_2CH_2CH_2$Phenyl The title compound was prepared from the compound of Example 220 (100 mg, 0.156 mmol) and 3-phenyl-1-propylamine (40 μL, 0.282 mmol, 1.8 equiv) using the procedure described for Example 221. Chromatography ($SiO_2$, 5% MeOH/dichloromethane with 0.5% $NH_4OH$) gave the desired material (45 mg) as a white solid. $^{13}C$ NMR ($CDCl_3$) δ 218.6, 205.7, 170.4, 158.1, 142.3, 128.4, 128.2, 125.6, 102.4, 83.7, 78.3, 77.0, 75.2, 70.2, 69.5, 65.9, 62.0, 58.4, 50.6, 49.2, 49.0, 45.3, 44.9, 40.2, 39.0, 37.5, 33.7, 31.7, 28.2, 22.4, 21.2, 20.7, 18.3, 14.6, 13.6, 13.5, 12.8, 10.3. MS(CI) m/e 760 (M+H)$^+$. Anal Calcd for $C_{41}H_{65}N_3O_{10}$.

EXAMPLE 224

Compound of Formula (IX): L is CO, T is NH, R is —$CH_2CH_2NHCH_2CH_2CH_2CH_2$Phenyl The title compound was prepared from the compound of Example 220 (170 mg, 0.266 mmol) and 4-phenyl-1-butylamine (68 μL, 0.431 mmol, 1.6 equiv) using the procedure described for Example 22 1. Chromatography ($SiO_2$, 5% MeOH/dichloromethane with 0.2% $NH_4OH$) gave the desired material (87 mg) as a white solid. $^{13}C$ NMR ($CDCl_3$) δ 218.6, 205.6, 170.4, 158.1, 142.6, 128.4, 128.1, 125.5, 102.4, 83.7, 78.3, 77.0, 75.2, 70.2, 69.5, 65.9, 61.9, 58.4, 50.6, 50.0, 49.0, 45.3, 44.9, 40.2, 39.0, 37.5, 35.8, 29.7, 29.1, 28.2, 22.4, 21.2, 20.7, 18.3, 14.6, 13.6, 13.5, 12.7, 10.3. MS(CI) m/e 774 (M+H)$^+$. Anal Calcd for $C_{42}H_{67}N_3O_{10}$. Found C 64.80, H 8.63, N 5.35.

EXAMPLE 225

Compound of Formula (IX): L is CO, T is NH, R is —$CH_2CH_2NHCH_2CH_2CH_2$-(3-quinolyl)

The compound from Example 220 (135 mg, 0.211 mmol) and 3-(3-quinolyl)-1-propylamide (70 mg, 0.376 mmol, 1.8 equiv) were dissolved in 4 mL of dry dichloromethane. Molecular sieves (4 Å) were added and the reaction was stirred overnight. The reaction was then filtered and concentrated under reduced pressure. The resulting imine was dissolved in MeOH (5 mL) and treated with $NaCNBH_3$ (about 100 mg) and enough AcOH to turn bromocresol green indicator from blue to yellow. After stirring for 4 hours, the reaction mixture was poured into saturated $NaHCO_3$ solution and extracted into dichloromethane. The organic portion was washed with saturated $NaHCO_3$, $H_2O$ and brine, dried ($Na_2SO_4$) and concentrated under reduced pressure. Chromatography ($SiO_2$, 5% MeOH/dichloromethane with 0.5% $NH_4OH$ to 10% MeOH/dichloromethane with 1% $NH_4OH$) gave the desired material (71 mg) as a white solid. $^{13}C$ NMR ($CDCl_3$) δ 218.8, 205.7, 170.5, 158.2, 152.2, 146.8, 135.0, 134.2, 129.1, 128.4, 128.2, 127.4, 126.4, 102.5, 83.8, 78.4, 77.2, 75.2, 70.2, 69.6, 65.9, 62.0, 58.4, 50.7, 49.5, 49.1, 45.4, 44.9, 40.2, 39.1, 37.6, 31.4, 30.9, 28.3, 22.6, 21.3, 20.7, 18.3, 14.7, 13.6, 13.5, 12.8, 10.3. MS(CI) m/e 811 (M+H)$^+$. Anal Calcd for $C_{44}H_{66}N_4O_{10}$. Found C 65.50, H 8.51, N 6.66.

EXAMPLE 226

Compound of Formula (IX): L is CO, T is NH, R is —$CH_2CH_2NHCH_2$(3-quinolyl)

The title compound was prepared from the compound of Example 220 (150 mg, 0.234 mmol) and 3-(aminomethyl)quinoline (100 mg, 0.633 mmol, 2.7 equiv) using the procedure described for Example 225. Chromatography ($SiO_2$, 5% MeOH/dichloromethane with 0.5% $NH_4OH$) gave the desired material (82 mg) as a white solid. $^{13}C$ NMR ($CDCl_3$) δ 218.8, 205.5, 170.4, 158.1, 151.6, 147.3, 134.5, 133.0, 129.0, 128.7, 128.0, 127.6, 126.3, 102.4, 83.7, 78.3, 76.9, 75.1, 70.1, 69.4, 65.8, 61.8, 58.4, 51.3, 50.5, 48.5, 45.3, 44.8, 40.1, 39.0, 37.4, 28.2, 22.3, 21.2, 20.6, 18.2, 14.6, 13.6, 13.4, 12.7, 10.2. MS(CI) m/e 783 (M+H)$^+$. Anal Calcd for $C_{42}H_{62}N_4O_{10}$. Found C 64.32, H 8.01, N 7.11.

The 3-(aminomethyl)quinoline reagent was prepared as follows:

Step 226a. 3-(hydroxymethyl)quinoline

Quinoline 3-carboxaldehyde (1.0 g, 6.37 mmol) was dissolved in 20 mL of EtOH and treated with $NaBH_4$ (70 mg). After stirring for 1 hour, the solution was treated with 2 mL of 1N HCl, and after stirring for 10 min the reaction mixture was treated with enough 1N NaOH to make the solution basic. The reaction mixture was extracted with $Et_2O$ and the organic portion was washed with $H_2O$ and brine. The organic portion was dried over $Na_2SO_4$ and concentrated under reduced pressure to give the title compound. MS(CI) m/e 160 (M+H)$^+$.

Step 226b. 3-(azidomethyl)quinoline 3-(hydroxymethyl)quinoline (0.36 g, 2.26 mmol) and triphenyl phosphine (621 mg, 2.37 mmol, 1.05 equiv) were dissolved in 10 mL of dry THF followed by cooling to 0° C. The reaction mixture was treated with diphenylphosphoryl azide (570 μL, 2.63 mmol, 1.16 equiv) followed by the dropwise addition of diethylazodicarboxylate (405 μL, 2.57 mmol, 1.14 equiv). The reaction mixture was allowed to warm to room temperature overnight. The reaction mixture was then concentrated under reduced pressure. Chromatography ($SiO_2$, 2:1 Hexanes/EtOAc) gave the desired material (350 mg) as a colorless oil. MS(CI) m/e 185 (M+H)$^+$.

Step 226c. 3-(aminomethyl)quinoline 3-(azidomethyl)quinoline (250 mg, 1.36 mmol) and triphenylphosphine (880 mg, 3.36 mmol, 2.5 equiv) were dissolved in 10 mL THF. The reaction mixture was treated with 0.5 mL of $H_2O$ and refluxed for 6 hours. The reaction mixture was cooled and partitioned between $Et_2O$ and 1N HCl. The aqueous portion was then treated with 1N NaOH until basic and extracted into EtOAc. The organic portion was dried over $Na_2SO_4$ and concentrated under reduced pressure to give the title compound (104 mg) as a brown oil. MS(CI) m/e 159 (M+H)$^+$.

EXAMPLE 227

Compound of Formula (IX): L is CO, T is NH, R is —$CH_2CH_2NHCH_2$(6-quinolyl)

The title compound was prepared from the compound of Example 220 (116 mg, 0.181 mmol) and 3-(aminomethyl)

quinoline (40 mg, 0.25 mmol, 1.4 equiv) using the procedure described for Example 221. Chromatography (SiO$_2$, 5% MeOH/dichloromethane with 0.5% NH$_4$OH) gave the desired material (62 mg) as a white solid. $^{13}$C NMR (CDCl$_3$) 218.7, 205.6, 170.4, 158.1, 149.8, 147.8, 138.9, 136.0, 130.3, 129.4, 128.3, 126.2, 121.0, 102.5, 83.7, 78.4, 77.0, 75.2, 70.2, 69.5, 65.9, 62.1, 58.5, 53.7, 50.6, 48.6, 45.4, 44.9, 40.2, 39.1, 37.5, 28.3, 22.4, 21.3, 20.7, 18.3, 14.7, 13.7, 13.5, 12.8, 10.3. MS(CI) m/e 783 (M+H)$^+$. Anal Calcd for C$_{42}$H$_{62}$N$_4$O$_{10}$.

The 6-(aminomethyl)quinoline reagent was prepared as follows:

Step 227a. 6-(hydroxymethyl)quinoline

Quinoline 6-carboxylic acid (1.73 g, 10.0 mmol) was suspended in 40 mL of THF, under N$_2$ at 0° C., and treated with N-ethyl morpholine (1.3 mL, 10.2 mmol, 1.02 equiv) followed by the dropwise addition of ethyl chloroformate (1.1 mL, 11.5 mmol, 1.15 equiv). After stirring for 15 min, the solution was filtered, and the resulting salts were rinsed with additional THF. The filtrate was then added to a rapidly stirring solution of NaBH$_4$ (760 mg, 20 mmol) in H$_2$O (50 mL). After stirring for 20 min, the reaction mixture was quenched with saturated NH$_4$Cl solution and extracted with EtOAc (2×50 mL). The organic portion was washed with brine, dried over Na$_2$SO$_4$, and concentrated under reduced pressure. Chromatography (SiO$_2$, 1:3 Hexanes/EtOAc) gave the desired material (1.03 g) as a colorless oil. MS(CI) m/e 160 (M+H)$^+$.

Step 227b. 6-(azidomethyl)quinoline 6-(hydroxymethyl)quinoline (0.51 g, 3.21 mmol) and triphenyl phosphine (880 mg, 3.36 mmol, 1.05 equiv) were dissolved in 15 mL of dry THF followed by cooling to 0° C. The reaction mixture was treated with diphenylphosphoryl azide (0.81 mL, 3.74 mmol, 1.16 equiv) followed by the dropwise addition of diethylazodicarboxylate (0.57 mL, 3.62 mmol, 1.13 equiv). The reaction mixture was allowed to warm to room temperature overnight, then concentrated under reduced pressure. Chromatography (SiO$_2$, 30% EtOAc/Hexanes) gave the desired material (320 mg) as a colorless oil. MS(CI) m/e 185 (M+H)$^+$.

Step 227c. 6-(aminomethyl)quinoline 6-(azidomethyl)quinoline (320 mg) and triphenylphosphine (880 mg) were dissolved in 7 mL THF. The reaction mixture was treated with 0.5 mL of H$_2$O and refluxed for 7 hours. The reaction mixture was cooled and partitioned between Et$_2$O and 1N HCl. The aqueous portion was then treated with 1N NaOH until basic and extracted into EtOAc. The organic portion was dried over Na$_2$SO$_4$ and concentrated under reduced pressure to give the title compound (70 mg) as a brown oil. MS(CI) m/e 159 (M+H)$^+$.

EXAMPLE 228

Compound of Formula (IX): L is CO, T is NH, R is —CH$_2$CH=NO(phenyl)

The compound from Example 220 (200 mg, 0.313 mmol) and O-phenylhydroxylamine-HCl (138 mg, 0.948 mmol, 3.0 equiv) were dissolved in 4 mL of MeOH. Triethylamine (118 μL, 0.847 mmol, 2.7 equiv) was added and the reaction was stirred at reflux for 3 hours. The reaction was cooled and quenched with saturated NaHCO$_3$ solution. The reaction mixture was extracted with dichloromethane (2×25 mL) and the combined organic portions were washed with H$_2$O and brine. The organic portion was dried over Na$_2$SO$_4$ and concentrated under reduced pressure. Chromatography (SiO$_2$, 5% MeOH/dichloromethane with 0.2% NH$_4$OH) gave the desired material (150 mg, 3:2 mixture of oxime isomers) as a violet-colored solid. $^{13}$C NMR (CDCl$_3$) δ 218.1, 217.4, 205.0, 169.9, 169.8, 159.1, 159.1, 157.9, 157.6, 152.9, 150.8, 129.1, 129.0, 122.2, 122.1, 114.8, 114.6, 103.2, 103.1, 83.5, 83.4, 79.8, 79.6, 77.1. 77.0, 76.9, 70.2, 69.6, 65.8, 60.3, 58.1, 58.0, 58.0, 50.9, 50.9, 46.6. 46.6, 44.8, 44.7, 40.1, 38.7, 38.5, 37.4, 37.4, 28.2, 22.2, 22.1, 21.1, 21.1, 20.5, 20.1, 18.0, 17.9, 14.6, 14.5, 14.5, 14.4, 13.5, 13.5, 10.4, 10.2. MS(CI) m/e 732 (M+H)$^+$. Anal Calcd for C$_{38}$H$_{57}$N$_3$O$_{11}$. Found C 62.30, H 7.76, N 5.74.

EXAMPLE 229

Compound of Formula (IX): L is CO, T is NH, R is —CH$_2$CH=NOCH$_2$(phenyl)

The title compound was prepared from the compound of Example 220 (201 mg, 0.314 mmol) and O-benzylhydroxylamine.HCl (150 mg, 0.940 mmol, 3.0 equiv) using the procedure described for Example 228. Chromatography (SiO$_2$, 5% MeOH/dichloromethane with 0.2% NH$_4$OH) gave the desired material (170 mg, 2:1 mixture of oxime isomers) as a white solid. $^{13}$C NMR (CDCl$_3$) δ 218.1, 217.2, 205.1, 170.0, 169.8, 158.0, 157.9, 150.5, 147.8, 138.1, 137.8, 128.4, 128.0, 127.8, 103.3, 103.3, 83.7, 83.7, 79.6, 79.5, 77.5, 77.3, 77.0, 76.9, 76.1, 76.0, 70.4, 69.7, 66.0, 60.5, 58.2, 58.1, 58.0, 51.0, 51.0, 46.8, 46.5, 45.0, 44.9, 40.3, 38.9, 38.7, 37.6, 28.4, 22.5, 22.4, 21.3, 20.6, 20.2, 18.2, 18.1, 14.8, 14.7, 14.6, 14.4, 13.7, 13.7, 10.6, 10.5. MS(CI) m/e 746 (M+H)$^+$. Anal Calcd for C$_{39}$H$_{59}$N$_3$O$_{11}$. Found C 62.89 H 8.04, N 5.42.

EXAMPLE 230

Compound of Formula (IX): L is CO, T is NH, R is —CH$_2$CH=NOCH$_2$(4-NO$_2$-phenyl)

The title compound was prepared from the compound of Example 220 (200 mg, 0.313 mmol) and O-(4-nitrobenzyl)hydroxylamine.HCl (192 mg, 0.938 mmol, 3.0 equiv) using the procedure described for Example 228. Chromatography (SiO$_2$, 5% MeOH/dichloromethane with 0.2% NH$_4$OH) gave the desired material (184 mg, 2:1 mixture of oxime isomers) as a white solid. $^{13}$C NMR (CDCl$_3$) δ 218.2, 217.3, 205.0, 169.9, 169.7, 157.8, 151.2, 148.7, 147.4, 145.7, 145.5, 128.4, 128.1, 123.6, 123.5, 103.2, 83.6, 83.5, 79.6, 79.4, 77.1, 76.9, 76.8, 74.5, 74.3, 70.2, 69.6, 65.8, 60.2, 58.0, 57.9, 57.8, 51.0, 50.9, 46.8, 46.6, 44.9, 44.7, 40.2, 38.7, 38.5, 37.5, 37.4, 28.2, 22.4, 22.2, 21.2, 21.2, 20.5, 20.1, 18.1, 17.9, 14.8, 14.5, 14.4, 13.5, 10.5, 10.3. MS(CI) m/e 791 (M+H)$^+$.

EXAMPLE 231

Compound of Formula (IX): L is CO, T is NH, R is —CH$_2$CH=NOCH$_2$(4-quinolyl)

The compound from Example 220 (200 mg, 0.313 mmol) and O-(4-quinolyl)methylhydroxylamine (200 mg, 0.86 mmol, 2.7 equiv) were dissolved in 4 mL of MeOH. Catalytic pTSA.H$_2$O was added and the reaction was stirred at reflux for 2 hours. The reaction was cooled and quenched with saturated NaHCO$_3$ solution. The reaction mixture was extracted with dichloromethane (2×25 mL) and the combined organic portions were washed with H$_2$O and brine. The organic portion was dried over Na$_2$SO$_4$ and concentrated under reduced pressure. Chromatography (SiO$_2$, 5% MeOH/dichloromethane with 0.2% NH$_4$OH) gave the desired material (226 mg, 2:1 mixture of oxime isomers) as a white solid. $^{13}$C NMR (CDCl$_3$) δ 218.1, 217.3, 205.0, 205.0, 170.0, 169.8, 158.0, 157.9, 151.3, 150.3, 148.7, 148.0, 143.2, 143.2, 130.1, 130.0, 129.1, 129.1, 126.7, 126.2, 126.2, 123.4, 123.3, 119.9, 119.6, 103.2, 83.7, 83.6, 79.7, 79.5, 77.4, 77.2, 77.1, 77.0, 76.9, 72.6, 72.3, 70.3, 69.6, 65.8, 60.3, 58.1, 58.0, 57.9, 51.0, 50.9, 46.8, 46.6, 44.9, 44.8, 40.2, 38.8, 38.5, 37.5, 37.5, 28.2, 22.4, 22.2, 21.2, 21.2, 20.5, 20.2, 18.1, 18.0, 14.9, 14.6, 14.5, 13.6, 13.6, 10.6, 10.3. MS(CI) m/e 797 (M+H)$^+$. Anal Calcd for $C_{42}H_{60}N_4O_{11}$. Found C 63.46, H 7.80, N 6.87.

The O-(4-quinolyl)methylhydroxylamine reagent was prepared as follows:

Step 231a. N-(4-quinolyl)methoxyphthalimide 4-(hydroxymethyl)quinoline (1.20 g, 7.55 mmol), triphenyl phosphine (2.27 g, 8.66 mmol, 1.15 equiv) and N-hydroxyphthalimide (1.42 g, 8.71 mmol, 1.15 equiv) were dissolved in 40 mL of dry THF. Diethylazodicarboxylate (1.44 mL, 9.15 mmol, 1.21 equiv) was then added dropwise and the reaction was stirred overnight. The reaction mixture was then diluted with 50 mL of Et$_2$O and filtered. The resulting solid was dissolved in dichloromethane and washed with 1N NaOH, H$_2$O and brine. The organic portion was dried over Na$_2$SO$_4$ and concentrated under reduced pressure to give the title compound (2.03 g) as a fluffy white solid. MS(CI) m/e 305 (M+H)$^+$.

Step 231 b. O-(4-quinolyl)methylhydroxylamine

N-(4-quinolyl)methoxy phthalimide (2.00 g) was suspended in 95% EtOH and hydrazine (0.30 mL) was added. The reaction mixture was stirred for 3 h and then filtered. The filtrate was concentrated under reduced pressure and then taken up in a small amount of dichloromethane. The small amount of remaining phthalhydrazide was then removed by filtration. The filtrate was concentrated under reduced pressure to give the title compound (1.44 g) as a yellow oil. MS(CI) m/e 175 (M+H)$^+$.

EXAMPLE 232

Compound of Formula (IX): L is CO, T is NH, R is —CH$_2$CH=NOCH$_2$(2-quinolyl)

The title compound was prepared from the compound of Example 220 (206 mg, 0.322 mmol) and O-(2-quinolyl)methylhydroxylamine (120 mg, 0.681 mmol, 2.1 equiv) using the procedure described for Example 231. Chromatography (SiO$_2$, 5% MeOH/dichloromethane with 0.2% NH$_4$OH) gave the desired material (185 mg, 3:1 mixture of oxime isomers) as a white solid. $^{13}$C NMR (CDCl$_3$) δ 217.9, 217.2, 204.9, 204.9, 169.9, 169.8, 159.0, 158.9, 157.8, 151.0, 148.7, 147.6, 136.5, 129.3, 129.2, 129.0, 127.5, 126.1, 126.0, 119.8, 119.6, 103.1, 83.5, 79.6, 79.4, 77.3, 77.0, 76.9, 76.9, 76.8, 76.7, 70.2, 69.5, 65.8, 60.4, 58.0, 58.0, 50.9, 46.5, 46.4, 44.8, 44.7, 40.1, 38.7, 38.5, 37.4, 37.4, 28.2, 22.3, 22.2, 21.2, 21.1, 20.5, 20.1, 18.1, 18.0, 14.5, 14.4, 14.3, 13.5, 10.4, 10.3. MS(CI) m/e 797 (M+H)$^+$.

The O-(2-quinolyl)methylhydroxylamine reagent was prepared as follows:

Step 232a. N-(2-quinolyl)methoxyphthalimide 2-(hydroxymethyl)quinoline (1.20 g, 7.55 mmol), triphenyl phosphine (1.00 g, 6.29 mmol, 1.05 equiv) and N-hydroxyphthalimide (1.08 g, 6.63 mmol, 1.05 equiv) were dissolved in 25 mL of dry THF. Diethylazodicarboxylate (1.09 mL, 6.93 mmol, 1.10 equiv) was then added dropwise and the reaction was stirred overnight. The reaction mixture filtered to give a white solid. The filtrate was concentrated and a second crop of material was obtained by triturating with Et$_2$O. This was combined with the original solid and recrystallization from EtOH gave the desired product (1.53 g) as a fluffy white solid. MS(CI) m/e 305 (M+H)$^+$.

Step 232b. O-(2-quinolyl)methylhydroxylamine

N-(2-quinolyl)methoxy phthalimide (1.53 g) was suspended in 95% EtOH and hydrazine (0.30 mL) was added. The reaction mixture was stirred for 5 h and then filtered. The filtrate was concentrated under reduced pressure and then taken up in a small amount of dichloromethane. The small amount of remaining phthalhydrazide was then removed by filtration. The filtrate was concentrated under reduced pressure to give the title compound (0.91 g) as a yellow oil. MS(CI) m/e 175 (M+H)$^+$.

EXAMPLE 233

Compound of Formula (IX): L is CO, T is NH, R is —CH$_2$CH=NOCH$_2$(3-quinolyl)

The title compound was prepared from the compound of Example 220 (250 mg, 0.391 mmol) and O-(3-quinolyl)methylhydroxylamine (160 mg, 0.909 mmol, 2.3 equiv) using the procedure described for Example 231. Chromatography (SiO$_2$, 5% MeOH/dichloromethane with 0.2% NH$_4$OH) gave the desired material (202 mg, 2:1 mixture of oxime isomers) as a white solid. $^{13}$C NMR (CDCl$_3$) δ 217.9, 217.1, 205.0, 169.9, 169.7, 157.9, 157.8, 151.0, 150.9, 150.8, 148.4, 147.8, 135.4, 135.2, 130.6, 130.5, 129.3, 129.2, 128.0, 127.9, 127.9, 126.6, 126.5, 103.2, 83.6, 83.5, 79.5, 79.4, 77.2, 76.9, 76.7, 73.7, 73.4, 70.3, 69.6, 65.9, 60.3, 58.1, 57.9, 51.0, 50.9, 46.7, 46.4, 44.9, 44.7, 40.2, 38.8, 38.6, 37.5, 28.2, 22.4, 22.2, 21.2, 20.4, 20.1, 18.1, 18.0, 14.7, 14.6, 14.4, 14.3, 13.6, 13.5, 10.5, 10.3. MS(CI) m/e 797 (M+H)$^+$. Anal Calcd for $C_{42}H_{60}N_4O_{11}$. Found C 63.00 H 7.56 N 6.79.

The O-(3-quinolyl)methylhydroxylamine reagent was prepared as follows:

Step 233a. N-(3-quinolyl)methoxyphthalimide 3-(hydroxymethyl)quinoline (400 mg, 2.52 mmol), triphenyl phosphine (692 mg, 2.64 mmol, 1.05 equiv) and N-hydroxyphthalimide (430 mg, 2.64 mmol, 1.05 equiv) were dissolved in 10 mL of dry THF. Diethylazodicarboxylate (0.44 mL, 2.80 mmol, 1.11 equiv) was then added dropwise and the reaction was stirred overnight. The reaction mixture placed in a freezer for 2 hours, and then filtered to give the desired product (0.69 g) as a fluffy white solid. MS(CI) m/e 305 (M+H)$^+$.

Step 233b. O-(3-quinolyl)methylhydroxylamine

N-(3-quinolyl)methoxy phthalimide (0.69 g) was suspended in 95% EtOH and hydrazine (0.10 mL) was added. The reaction mixture was stirred overnight and then filtered. The filtrate was concentrated under reduced pressure and then taken up in a small amount of dichloromethane. The small amount of remaining phthalhydrazide was then removed by filtration. The filtrate was concentrated under reduced pressure to give the title compound (0.42 g) as a yellow oil. MS(CI) m/e 175 (M+H)$^+$.

EXAMPLE 234

Compound of Formula (IX): L is CO, T is NH, R is —CH$_2$CH=NOCH$_2$(6-quinolyl)

The title compound was prepared from the compound of Example 220 (120 mg, 0.186 mmol) and O-(6-quinolyl)methylhydroxylamine (92 mg, 0.529 mmol, 2.8 equiv) using the procedure described for Example 231. Chromatography (SiO$_2$, 5% MeOH/dichloromethane with 0.2% NH$_4$OH) gave the desired material (89 mg, 3:1 mixture of oxime isomers) as a white solid. $^{13}$C NMR (CDCl$_3$) δ 217.9, 217.1, 204.9, 169.8, 169.6, 157.8, 157.7, 150.6, 150.1, 148.0, 147.8, 136.1, 136.1, 129.6, 129.4, 129.3, 128.0, 126.6, 126.3, 121.0, 103.0, 83.5, 83.4, 79.4, 79.3, 77.4, 77.0, 76.8, 76.7, 76.6, 75.5, 75.3, 70.1, 69.5, 65.7, 60.2, 58.0, 57.9, 57.8, 50.8, 46.6, 46.3, 44.8, 44.6, 40.1, 38.6, 38.4, 37.3, 28.1, 22.3, 22.1, 21.1, 20.4, 20.0, 18.0, 17.8, 14.7, 14.5, 14.3, 13.4, 10.4, 10.2. MS(CI) m/e 797 (M+H)$^+$. Anal Calcd for $C_{42}H_{60}N_4O_{11}$. Found C 63.03 H 7.60 N 6.69.

The O-(6-quinolyl)methylhydroxylamine reagent was prepared as follows:

Step 234a. N-(6-quinolyl)methoxyphthalimide 6-(hydroxymethyl)quinoline (520 mg, 3.27 mmol), triphenyl phosphine (900 mg, 3.44 mmol, 1.05 equiv) and N-hydroxyphthalimide (560 mg, 3.43 mmol, 1.05 equiv) were dissolved in 25 mL of dry THF. Diethylazodicarboxylate (574 µL, 3.63 mmol, 1.11 equiv) was then added dropwise and the reaction was stirred overnight. The reaction mixture filtered to give a white solid. The filtrate was concentrated and a second crop of material was obtained by triturating with Et$_2$O. This was combined with the original solid and recrystallization from EtOH gave the desired product (782 mg) as a fluffy white solid. MS(CI) m/e 305 (M+H)$^+$.

Step 234b. O-(2-quinolyl)methylhydroxylamine

N-(2-quinolyl)methoxy phthalimide (782 mg) was suspended in 95% EtOH and hydrazine (0.15 mL) was added. The reaction mixture was stirred overnight and then filtered. The filtrate was concentrated under reduced pressure and then taken up in a small amount of dichloromethane. The small amount of remaining phthalhydrazide was then removed by filtration. The filtrate was concentrated under reduced pressure to give the title compound (480 mg) as a yellow oil. MS(CI) m/e 175 (M+H)$^+$.

EXAMPLE 235

Compound of Formula (IX): L is CO, T is NH, R is —CH$_2$CH═NOCH$_2$(1-naphthyl)

The title compound was prepared from the compound of Example 220 (117 mg, 0.183 mmol) and O-(1-naphthyl)methylhydroxylamine (80 mg, 0.462 mmol, 2.5 equiv) using the procedure described for Example 231. Chromatography (SiO$_2$, 5% MeOH/dichloromethane with 0.1 % NH$_4$OH) gave the desired material (112 mg, 2:1 mixture of oxime isomers) as a white solid. $^{13}$C NMR (CDCl$_3$) δ 217.8, 217.0, 205.0, 169.9; 169.7, 157.9, 157.8, 150.3, 147.7, 133.7, 133.1, 131.8, 128.7, 128.6, 128.4, 127.1, 126.8, 126.2, 125.6, 125.3, 124.1, 103.1, 103.1, 83.6, 79.5, 79.3, 77.2, 77.0, 76.9, 74.7, 74.3, 70.3, 69.6, 65.9, 60.5, 58.1, 58.0, 51.0, 50.9, 46.6, 46.3, 44.9, 44.8, 40.2, 38.8, 38.6, 37.5, 28.3, 22.4, 22.3, 21.2, 20.5, 20.0, 14.6, 14.5, 14.1, 13.6, 10.5, 10.3. MS(CI) m/e 796 (M+H)$^+$. Anal Calcd for $C_{43}H_{61}N_3O_{11}$. Found C 64.91 H 7.80 N 5.06.

The O-(1-naphthyl)methylhydroxylamine reagent was prepared as follows:

Step 235a. N-(1-naphthyl)methoxyphthalimide 1-(hydroxymethyl)naphthalene (1.00 g, 6.33 mmol), triphenyl phosphine (1.73 g, 6.60 mmol, 1.04 equiv) and N-hydroxyphthalimide (1.08 g, 6.63 mmol, 1.05 equiv) were dissolved in 25 mL of dry THF. Diethylazodicarboxylate (1.09 mL, 6.93 mmol, 1.09 equiv) was then added dropwise and the reaction was stirred overnight. The reaction mixture was diluted with 25 mL of Et$_2$O and placed in a freezer for 2 hours. The reaction mixture was then filtered to give a white solid. Recrystallization from EtOH gave the desired product (1.21 g) as a white solid. MS(CI) m/e 321 (M+NH$_4$)$^+$.

Step 235b. O-(1-naphthyl)methylhydroxylamine

N-(1-naphthyl)methoxy phthalimide (1.21 g) was suspended in 95% EtOH and hydrazine (0.20 mL) was added. The reaction mixture was stirred overnight and then filtered. The filtrate was concentrated under reduced pressure and then taken up in a small amount of dichloromethane. The small amount of remaining phthalhydrazide was then removed by filtration. The filtrate was concentrated under reduced pressure to give the title compound (480 mg) as a colorless oil. MS(CI) m/e 174 (M+H)$^+$.

EXAMPLE 236

Compound of Formula (IX): L is CO, T is NH, R is —CH$_2$CH═NOCH$_2$(2-naphthyl)

The title compound was prepared from the compound of Example 220 (122 mg, 0.191 mmol) and O-(2-naphthyl)methylhydroxylamine (62 mg, 0.358 mmol, 1.9 equiv) using the procedure described for Example 231. Chromatography (SiO$_2$, 5% MeOH/dichloromethane with 0.1 % NH$_4$OH) gave the desired material (100 mg, 3:1 mixture of oxime isomers) as a white solid. $^{13}$C NMR (CDCl$_3$) δ 217.8, 217.0, 204.9, 169.8, 169.6, 157.8, 157.7, 150.3, 147.8, 135.4, 135.1, 133.2, 132.9, 128.0, 127.9, 127.9, 127.5, 127.0, 126.7, 126.1, 125.8, 125.7, 125.7, 125.6, 103.1, 83.5, 83.5, 79.4, 79.3, 77.1, 76.9, 76.8, 76.1, 75.9, 70.2, 69.5, 65.8, 60.3, 58.0, 57.9, 57.9, 50.9, 46.6, 46.3, 44.8, 44.7, 40.1, 38.7, 38.5, 37.4, 28.1, 22.3, 22.1, 21.1, 20.4, 20.0, 18.0, 17.9, 14.6, 14.5, 14.4, 14.2, 13.5, 10.4, 10.2. MS(CI) m/e 796 (M+H)$^+$. Anal Calcd for $C_{43}H_{61}N_3O_{11}$. Found C 64.59 H 7.72 N 5.14.

The O-(2-naphthyl)methylhydroxylamine reagent was prepared as follows:

Step 236a. N-(2-naphthyl)methoxyphthalimide 2-(hydroxymethyl)naphthalene (1.00 g, 6.33 mmol), triphenyl phosphine (1.73 g, 6.60 mmol, 1.04 equiv) and N-hydroxyphthalimide (1.08 g, 6.63 mmol, 1.05 equiv) were dissolved in 25 mL of dry THF. Diethylazodicarboxylate (1.09 mL, 6.93 mmol, 1.09 equiv) was then added dropwise and the reaction was stirred overnight. The reaction mixture was placed in a freezer for 2 h and then filtered, rinsing with Et$_2$O, to give the product (1.38 g) as a white solid. MS(CI) m/e 321 (M+NH$_4$)$^+$.

Step 236b. O-(2-naphthyl)methylhydroxylamine

N-(2-naphthyl)methoxy phthalimide (1.38 g) was suspended in 95% EtOH and hydrazine (0.25 mL) was added. The reaction mixture was stirred overnight and then filtered. The filtrate was concentrated under reduced pressure and then taken up in a small amount of dichloromethane. The small amount of remaining phthalhydrazide was then removed by filtration. The filtrate was concentrated under reduced pressure to give the title compound (821 mg) as a colorless oil. MS(CI) m/e 174 (M+H)$^+$.

EXAMPLE 237

Compound of Formula (IX): L is CO, T is NH, R is —CH$_2$CH$_2$NHOCH$_2$(phenyl)

The compound from Example 229 (120 mg, 0.161 mmol) was dissolved in MeOH (5 mL) and treated with NaCNBH$_3$ (about 120 mg) and enough AcOH to turn bromocresol green indicator from blue to yellow. After stirring for 20 hours, the reaction mixture was poured into saturated NaHCO$_3$ solution and extracted into dichloromethane. The organic portion was washed with saturated NaHCO$_3$, H$_2$O and brine, dried (Na$_2$SO$_4$) and concentrated under reduced pressure. Chromatography (SiO$_2$, 5% MeOH/dichloromethane with 0.2% NH$_4$OH) gave the desired material (51 mg) as a white solid. $^{13}$C NMR (CDCl$_3$) δ 219.0, 205.7, 170.5, 157.8, 138.3, 128.1, 127.5, 102.5, 83.6, 78.6, 77.0, 75.6, 75.2, 70.2, 69.5, 66.0, 58.8, 58.3, 51.4, 50.7, 45.3, 45.0, 40.2, 39.1, 37.7, 28.3, 22.4, 21.3, 20.7, 18.2, 14.7, 13.7, 13.5, 12.8, 10.3. MS(CI) m/e 748 (M+H)$^+$.

EXAMPLE 238

Compound of Formula (IX): L is CO, T is NH, R is —$CH_2CH_2NHOCH_2$(4-$NO_2$-phenyl The compound from Example 230 (64 mg) was dissolved in MeOH (3 mL) and treated with $NaCNBH_3$ (about 100 mg) and enough HCl to turn methyl orange indicator red. After stirring for 20 hours, the reaction mixture was poured into saturated $NaHCO_3$ solution and extracted into dichloromethane. The organic portion was washed with $H_2O$ and brine, dried ($Na_2SO_4$) and concentrated under reduced pressure. Chromatography ($SiO_2$, 5% MeOH/dichloromethane with 0.2% $NH_4OH$) gave the desired material (35 mg) as a white solid. $^{13}$C NMR (CDCl$_3$) δ 219.5, 205.5, 170.5, 157.8, 147.2, 146.8, 128.3, 123.4, 102.4, 83.6, 78.6, 76.8, 75.0, 74.3, 70.1, 69.5, 65.8, 58.4, 58.1, 51.3, 50.6, 45.3, 45.0, 40.1, 38.9, 37.7, 28.2, 22.2, 21.2, 20.7, 18.1, 14.6, 13.5, 13.3, 12.8, 10.2. MS(CI) m/e 793 (M+H)$^+$.

EXAMPLE 239

Compound of Formula (IX): L is CO, T is NH, R is —$CH_2$C(O)-phenyl

Step 239a. Compound of Formula (IX): L is CO, T is NH, R is —$CH_2$C(OH)-phenyl

The compound from Example 220 (550 mg, 0.87 mmol) was dissolved in 16 mL of dry THF and cooled to 0° C. under nitrogen. Phenylmagnesium bromide (3.0 M solution in $Et_2O$, 3.0 mL, 6.0 mmol, 6.9 equiv) was then added dropwise via syringe. The reaction was stirred for 50 min, then quenched by addition of saturated $NH_4Cl$ solution. The reaction mixture was extracted with EtOAc and the organic portion was washed with $H_2O$ and brine, dried ($Na_2SO_4$) and concentrated under reduced pressure. Chromatography ($SiO_2$, 5% MeOH/dichloromethane with 0.2% $NH_4OH$) gave the desired material (295 mg) as a white solid. MS(CI) m/e 719 (M+H)$^+$.

Step 239b. Compound of Formula (18, Scheme 4): R* is H, R$^p$ is Ac, R is —$CH_2$C(OH)-phenyl The compound from the previous step (180 mg, 0.250 mmol) was dissolved in 5 mL of dry dichloromethane and treated with acetic anhydride (25 μL, 0.269 mmol, 1.08 equiv). After stirring overnight, then reaction was quenched by addition of saturated $NaHCO_3$ solution. The reaction mixture was extracted with dichloromethane and the organic portion was washed with brine, dried ($Na_2SO_4$) and concentrated under reduced pressure to give the desired material (160 mg) as a white solid. MS(CI) m/e 761 (M+H)$^+$.

Step 239c. Compound of Formula (18. Scheme 4): R* is H, R$^p$ is Ac, R is —$CH_2$C(O)-phenyl DMSO (145 μL, 2.04 mmol, 14 equiv) was added to a cooled (−78° C.) solution of oxalyl chloride (145 mL, 1.32 mmol, 9 equiv) in 4 mL of dichloromethane under a nitrogen atmosphere. The compound from the previous step (113 mg, 0.149 mmol) was dissolved in 2 mL of dichloromethane and added to the reaction, via cannula, over 15 min. After stirring for 1 hour. $Et_3N$ (0.37 mL, 2.65 mmol, 18 equiv) was added to the reaction mixture and the temperature was slowly raised to −20° C. The was quenched by addition of 5% $KH_2PO_4$ solution and extracted with dichloromethane. The organic portion was washed with 5% $KH_2PO_4$, $H_2O$, and brine, dried ($Na_2SO_4$) and concentrated under reduced pressure. Chromatography ($SiO_2$, 1:1 acetone/hexanes) gave the desired material (42 mg) as a white powder. MS(CI) m/e 759 (M+H)$^+$.

Step 239d. Compound of Formula (IX): L is CO, T is NH, R is —$CH_2$C(O)-phenyl

The compound from the previous step was dissolved in 5 mL of MeOH and left to stirred overnight. The reaction mixture was concentrated under reduced to give the title compound (38 mg) as a white solid. $^{13}$C NMR (CDCl$_3$) δ 215.4, 206.1, 194.4, 169.6, 157.7, 135.5, 133.0, 128.5, 127.6, 103.0, 83.8, 79.6, 77.1, 77.1, 70.2, 69.5, 65.9, 65.4, 57.6, 50.9, 46.0, 44.6, 40.2, 38.9, 37.9, 28.4, 22.4, 21.3, 20.2, 18.9, 14.9, 13.9, 13.7, 13.6, 10.5. MS(CI) m/e 717 (M+H)$^+$.

EXAMPLE 240

Compound of Formula (IX): L is CO, T is NH, R is —$CH_2$C(O)-(4-F-phenyl)

The title compound was prepared from the compound of Example 220 and 4-fluorophenylmagnesium bromide using the reaction sequence of Example 239. $^{13}$C NMR (CDCl$_3$) δ 215.3, 206.0, 192.8, 169.6, 165.7, 157.7, 131.5, 130.2, 115.6, 103.1, 83.8, 79.7, 77.3, 76.8, 70.3, 69.6, 65.8, 65.1, 57.6, 50.9, 46.0, 44.6, 40.2, 38.8, 37.8, 28.3, 22.4, 21.3, 20.2, 18.8, 14.8, 13.9, 13.7, 13.5, 10.4. MS(CI) m/e 735 (M+H)$^+$.

EXAMPLE 241

Compound of Formula (IX): L is CO, T is NH, R is —$CH_2$CH=NNHC(O)phenyl

The compound from Example 220 (100 mg, 0.156 mmol) and benzoic hydrazide (50 mg, 0.370 mmol, 2.4 equiv) were dissolved in 3 mL of dry dichloromethane. Molecular sieves (4 Å) were added and the reaction was stirred overnight. The mixture was filtered, and the filtrate was concentrated under reduced pressure. Chromatography ($SiO_2$, 5% MeOH/dichloromethane with 0.2% $NH_4OH$) gave the desired material (29 mg) as a white solid. $^{13}$C NMR (CDCl$_3$) δ 216.9, 204.2, 169.6, 164.3, 159.0, 148.8, 133.4, 131.2, 128.0, 127.7, 103.2, 83.9, 79.6, 77.6, 76.5, 70.1, 69.5, 65.7, 62.7, 57.8, 50.8, 46.9, 44.4, 40.0, 38.4, 37.3, 28.1, 21.9, 21.1, 20.7, 17.8, 15.0, 14.2, 13.3, 13.1, 10.0. MS(CI) m/e 759 (M+H)$^+$.

EXAMPLE 242

Compound of Formula (IX): L is CO, T is NH, R is —$CH_2CH_2CH_2$(3-quinolyl)

A mixture of the compound from Example 104 (230 mg) and 10% Pd/C (50 mg) in 30 mL of methanol and 15 mL of ethyl acetate was flushed with nitrogen and stirred under 1 atm of hydrogen at room temperature for 22 hours. The mixture was filtered, and the filtrate was concentrated under reduced pressure. Chromatography on silica gel (5% MeOH/dichloromethane with 0.5% $NH_4OH$) gave the desired material (175 mg) as a white solid. Anal Calcd for $C_{42}H_{65}N_3O_{10}$: C, 65.35; H, 8.49; N, 5.44. Found C, 65.73; H, 8.77; N, 5.17.

EXAMPLE 243

Compound of Formula (IX): L is CO, T is NH, R is —$CH_2$(2-(3-quinolyl)cyclopropyl)

To a solution of diazomethane (0.64 M, 3.12 mL, 2.00 mmol) in ether was added a solution of the compound from Example 104 (153 mg, 0.200 mmol) in dichloromethane (5.0 mL) at 0° C. under nitrogen. A small amount (2 mg) of palladium acetate was added, and the mixture was stirred for 20 minutes. Another portion of diazomethane (3 mL) was added, and the mixture was stirred for another hour. The solvents were evaporated, and the residue was purified by chromatography on silica gel (5% MeOH/dichloromethane with 0.5% NH$_4$OH) to give the title compound (100 mg) as a white solid. Anal Calcd for C$_{43}$H$_{61}$N$_3$O$_{10}$: C, 66.22; H, 7.88; N, 5.39. Found C, 66.05; H, 8.08; N, 5.02.

EXAMPLE 244

Compound of Formula (III): R$^c$ is propanoyl, L is CO, T is NH, R is —CH$_2$CH=CH(3-quinolyl)

To a solution of the compound from Example 104 (152 mg) in dichloromethane was added propionic anhydride (52 μL) and triethylamine (56 μL), and the mixture was stirred for 24 hours at room temperature. The mixture was diluted with ethyl acetate, and this was washed with 5% NaHCO$_3$ solution and brine, dried (Na$_2$SO$_4$) and concentrated under reduced pressure. The residue was chromatographed on silica gel (1:1 acetone/hexanes) to give the title compound (119 mg) as a white foam. Anal Calcd for C$_{45}$H$_{63}$N$_3$O$_{11}$: C, 65.75; H, 7.72; N, 5.11. Found C, 65.67; H, 7.92; N, 4.77.

EXAMPLE 245

Compound of Formula (III): R$^c$ is ethylsuccinoyl, L is CO, T is NH, R is —CH$_2$CH=CH(3-quinolyl)

To a solution of the compound from Example 104 (153 mg, 0.200 mmol) in dichloromethane (10 mL) at 0° C. was added ethyl succinyl chloride (29 μL) and triethylamine (56 μL), and the mixture was stirred for 24 hours at room temperature. The mixture was diluted with ethyl acetate, and this was washed with 5% NaHCO$_3$ solution and brine, dried (Na$_2$SO$_4$) and concentrated under reduced pressure. The residue was chromatographed on silica gel (1:1 acetone/hexanes) to give the title compound(110 mg) as a white foam. Anal Calcd for C$_{48}$H$_{67}$N$_3$O$_{13}$.H$_2$O C, 63.21; H, 7.63; N, 4.61. Found C, 63.08; H, 7.50; N, 4.20.

EXAMPLE 246

Compound of Formula (IX): L is CO, T is NH, R is —CH$_2$—C≡C—H

Step 246a. Compound 4 from Scheme 1a: V is N—O-(1-isopropoxycyclohexyl). R is —CH$_2$—C≡C—H, R$^p$ is trimethylsilyl To a solution under nitrogen of 2',4"-bis-O-trimethylsilylerythromycin A 9-[O-(1-isopropoxycyclohexyl)oxime (100 g, 96.9 mmol, prepared according to the method of U.S. Pat. No. 4,990,602) in THF (200 mL) was added anhydrous DMSO (200 mL) and the mixture was cooled to 0° C. To this solution stirred under a N$_2$ atmosphere was added propargyl bromide (27 mL, 240 mmol, 80 wt. % in toluene), followed by a solution of dry KOH (13.6 g, 240 mmol) in anhydrous DMSO (300 mL) over 25 minutes, and the mixture was stirred vigorously for 1 hour at 0° C. Additional KOH (10.9 g, 190 mmol) and propargyl bromide (21 mL, 190 mmol) was added, and the mixture was stirred at 0° C. under N$_2$ for 1.5 hours. This addition of KOH and propargyl bromide was repeated 3 more times at 1.5 hour intervals. The mixture was then extracted with ethyl acetate, and the organic phases were washed with water and brine and dried (MgSO$_4$). Removal of the solvent under vacuum gave the crude product (108 g), which was taken directly to the next step.

Step 246b: Compound 5 from Scheme 1a; R is —CH$_2$—C≡C—H

To the compound from Step 246a (108 g) in CH$_3$CN (300 mL) was added water (150 mL) and acetic acid (glacial, 200 mL), and the mixture was stirred at room temperature for about 20 hours. The solvent was then removed under vacuum at 40° C., and the residue was taken up in EtOAc and washed successively with 5% Na$_2$CO$_3$ and brine. The organic phase was then dried over MgSO$_4$, filtered and concentrated to give the title compound (74 g) as a brown foam, which was taken directly to the next step.

Step 246c: Compound 6 from Scheme 1a: R is —CH$_2$—C≡C—H

The compound from Step 246b (74 g) was dissolved in ethanol (550 mL) and diluted with water (550 mL). To this solution was added sodium nitrite (33 g, 0.48 mol), and the reaction mixture was stirred at room temperature for 15 minutes. Next was added 4M HCl (125 mL, 0.48 mol) at ambient temperature over 15 minutes, the mixture was heated to 70° C. for two hours, then cooled to room temperature. The mixture was extracted with ethyl acetate, and the organic phase was washed with 5% Na$_2$CO$_3$ and brine, then dried over MgSO$_4$, filtered and concentrated. The crude product was purified by chromatography on silica gel, eluting with 1% methanol/dichloromethane containing 0.5% ammonium hydroxide. The compound was crystallized from acetonitrile to give the title compound (27 g).

Step 246d: Compound 6A from Scheme 1c; R$^p$ is acetyl, R is —CH$_2$—C≡C—H

To a solution of 19 grams (246 mmol) the compound from Step 246c in anhydrous dichloromethane (100 mL) was added 4-dimethylaminopyridine (105 mg) and triethylamine (7.16 mL, 52 mmol). The mixture was cooled to about 15° C. in a cold water bath, and acetic anhydride (5.5 milliliters, 59 mmol) was added over 5 minutes. After stirring at 15° C. for 5 minutes, the cold water bath was removed, and the reaction was stirred at ambient temperature for 4 hours. The mixture was diluted with ethyl acetate and washed successively with 5% aqueous sodium carbonate (twice), water (twice) and brine. The organic extracts were dried over magnesium sulfate, filtered and concentrated in vacuo. Drying to constant weight with high vacuum provided the title compound (21 g).

Step 246e: Compound 6B from Scheme 1c; R$^p$ is acetyl, R is —CH$_2$—C≡C—H

To a 0° C. solution of the compound from Step 246d (21 g, 24.5 mmol) in THF (128 mL) and dimethyl sulfoxide (48 mL) was added 1,1'-carbonyldiimidazole (14.3 g, 88.3 mmol). After stirring for 5 minutes, sodium hydride (60% dispersion in mineral oil, 1.3 g, 32.5 mmol) was added portionwise over 1 hour under a nitrogen atmosphere. After complete addition, the cooling bath was removed, and the mixture was stirred at ambient temperature for 3.5 hours. The reaction was recooled to 0° C., diluted with ethyl acetate (~400 mL), and quenched with 5% aqueous sodium bicarbonate (50 mL). The organic layers were washed successively with water and brine, then dried over magnesium sulfate. The solution was filtered and the filtrate was concentrated in vacuo, and dried to constant weight to afford the title compound (23 g), which was taken directly to the next step.

Step 246f: Compound 6C from Scheme 1c: R$^p$ is acetyl, R is —CH$_2$—C≡C—H

A pressure vessel containing the compound from Step 246e (23 g, 24 mmol) in acetonitrile (250 mL) was cooled to −78° C. An equal volume of liquid ammonia (250 milliliters) was condensed into the reaction vessel which was then sealed and allowed to warm to ambient temperature with stirring. After 20 hours the reaction was recooled to −78° C., the pressure vessel was opened and the reaction was allowed to warm to ambient temperature with stirring. When all the liquid ammonia had evaporated, the acetonitrile was removed in vacuo, and the residue was dried to constant weight to provide the title compound (21 g).
Step 246g: Compound 6D from Scheme 1c; $R^p$ is acetyl, R is —$CH_2$—C≡C—H To a 0° C. suspension of the compound from Step 246f (21 g) in 1:1 ethanol/water (200 mL) was added 4 M hydrochloric acid (125 mL) over 10 minutes. After removing the cooling bath, the reaction solution was stirred at ambient temperature for 26 hours. The mixture was diluted with water, cooled to 0° C. and made basic to pH 10 with 2N sodium hydroxide. The mixture was then extracted with ethyl acetate (400 mL), and the organic layers were washed with brine. The organic extracts were dried over magnesium sulfate, filtered, and concentrated in vacuo. Drying to constant weight provided 18 g of the crude product which was crystallized from ethyl acetate/hexanes to give the pure title compound (8.5 g).
Step 246h: Compound 6E from Scheme 1c: $R^p$ is acetyl, R is —$CH_2$—C≡C—H To a −10° C. solution of N-chlorosuccinimide (2.3 g, 0.017 moles) in dichloromethane (100 mL) was added methyl sulfide (1.47 mL, 0.021 moles) over 5 minutes. The reaction was stirred at −10° C. for 10 minutes. A solution of the compound from Step 246g (8.3 g, 0.012 m) in dichloromethane (100 mL) was then added over 30 minutes, and the mixture was stirred for 25 minutes at −10° C. Triethylamine (1.6 mL, 0.021 mol) was added over 5 minutes, and the reaction was stirred at −10° C. for 50 minutes. The reaction was then quenched with 5% aqueous sodium bicarbonate (50 mL), and extracted with dichloromethane (300 mL). The organic layers were washed with 5% aqueous sodium bicarbonate followed by brine, dried over magnesium sulfate, filtered, and concentrated in vacuo. The crude product was purified on silica gel with column chromatography eluting sequentially with 30% acetone/hexanes followed by 50% acetone/hexanes to provide the title compound (7.35 g).
Step 246i: Compound of Formula (IX): L is CO, T is NH, R is —$CH_2$—C≡C—H A sample (72 mg) of the compound from Step 246h was dissolved in methanol (8 mL) and stirred at ambient temperature for 18 hours. After concentrating under vacuum and drying to constant weight under high vacuum 65 mg of the pure title compound was obtained. High Resolution FAB MS: calculated m/e for $(M+H)^+$: $C_{33}H_{53}N_2O_{10}$=637.3700 Observed m/e=637.3718.

EXAMPLE 247

Compound of Formula (IX): L is CO, T is NH, R is —$CH_2$—C≡C-(3-quinolyl)

Step 247a, Compound 6E from Scheme 1c: R is —$CH_2$—C≡C-(3-quinolyl)

A pressure tube equipped with a stir bar was charged with dichlorobis(triphenylphosphine)palladium(II) (6.2 mg), degassed triethylamine (2.5 mL), degassed N,N-dimethylformamide (0.5 mL), then 3-bromoquinoline (93 μL and a sample of the compound from Step 246h (300 mg), and lastly copper (II) iodide (0.84 mg). The reaction was sealed under a nitrogen atmosphere and heated to 60° C. for 2 hours. After cooling to room temperature, the reaction was diluted with 1:1 ether/ethyl acetate and was washed three times with water and brine. The organic extracts were dried over magnesium sulfate, filtered and concentrated in vacuo. Drying with high vacuum provided 374 milligrams of crude product. The crude product was purified with silica gel chromatography using 30% acetone/hexanes to give the title compound (280 mg,78%. MS $(APCI)^+$ m/e 806 $(M+H)^+$.

Step 247b. Compound of Formula (IX): L is CO, T is NH, R is —$CH_2$—C≡C-(3-quinolyl)

The compound form step 247a (270 mg) was dissolved methanol and was stirred at ambient temperature for 18 hours. After concentrating in vacuo and drying to constant weight under high vacuum 260 mg of crude product was obtained. Purification with silica gel chromatography eluting with 98:1:1 dichloromethane/methanol/ammonium hydroxide gave 221 mg of the title compound. High Resolution FAB MS: calculated m/e for $(M+H)^+$: $C_{42}H_{58}N_3O_{10}$=764.4122 Observed m/e=764.4121.

EXAMPLE 248

Compound of Formula (IX): L is CO, T is NH, R is —$CH_2$—C≡C-(6-nitro-3-quinolyl)

Following the procedure of Example 247, except substituting 6-nitro-3-bromoquinoline for 3-bromoquinoline, the title compound was prepared. High Resolution FAB MS: calculated m/e for $(M+H)^+$: $C_{42}H_{57}N_4O_{12}$=809.3973 Observed m/e=809.3966

EXAMPLE 249

Compound of Formula (IX): L is CO, T is NH, R is —$CH_2$—C≡C-phenyl

Following the procedure of Example 247, except substituting iodobenzene for 3-bromoquinoline. High Resolution FAB MS: calculated m/e for $(M+H)^+$: $C_{39}H_{57}N_2O_{10}$=713.4013 Observed m/e=713.3998.

EXAMPLE 250

Compound of Formula (IX): L is CO, T is NH, R is —$CH_2$—C≡C-naphthyl

Following the procedure of Example 247, except substituting 1-iodonaphthalene for 3-bromoquinoline. High Resolution FAB MS: calculated m/e for $(M+H)^+$: $C_{43}H_{59}N_2O_{10}$=763.4170 Observed m/e=763.4161.

EXAMPLE 251

Compound of Formula (IX): L is CO, T is NH, R is —$CH_2$—C≡C-(2-naphthyl)

Following the procedure of Example 247, except substituting 2-bromonaphthalene for 3-bromoquinoline. High Resolution FAB MS: calculated m/e for $(M+H)^+$: $C_{43}H_{59}N_2O_{10}$=763.4170 Observed m/e=763.4150.

EXAMPLE 252

Compound of Formula (IX): L is CO, T is NH, R is —$CH_2$—C≡C-(6-methoxy-2-naphthyl)

Following the procedure of Example 247, except substituting 6-methoxy-2-bromonaphthalene for 3-bromoquinoline. High Resolution FAB MS: calculated m/e for $(M+H)^+$: $C_{44}H_{61}N_2O_{11}$=793.4275 Observed m/e=793.4256.

EXAMPLE 253

Compound of Formula (IX): L is CO, T is NH, R is —$CH_2$—C≡C-(6-chloro-2-naphthyl)

Following the procedure of Example 247, except substituting 6-chloro-3-bromoquinoline for 3-bromoquinoline.

High Resolution FAB MS: calculated m/e for (M+H)$^+$: $C_{42}H_{57}N_3O_{10}Cl$=798.3732 Observed m/e=798.3743.

EXAMPLE 254

Compound of Formula (IX): L is CO, T is NH, R is —CH$_2$—C≡C-(6-quinolyl)

Following the procedure of Example 247, except substituting 6-bromoquinoline for 3-bromoquinoline. High Resolution FAB MS: calculated m/e for (M+H)$^+$: $C_{42}H_{58}N_3O_{10}$=764.4122 Observed m/e=764.4116.

EXAMPLE 255

Compound of Formula (IX): L is CO, T is NH, R is —CH$_2$—C≡C-(2-methyl-6-quinolyl)

Following the procedure of Example 247, except substituting 6-bromo-2-methylquinoline for 3-bromoquinoline. High Resolution FAB MS: calculated m/e for (M+H)$^+$: $C_{43}H_{60}N_3O_{10}$=778.4279 Observed m/e=778.4282.

EXAMPLE 256

Compound of Formula (IX): L is CO, T is NH, R is —CH$_2$—C≡C-(5-(N-(2-pyridyl)amino)carbonyl)furanyl)

Following the procedure of Example 247, except substituting 5-bromo-furan-2-carboxylic acid pyridin-2-yl amide for 3-bromoquinoline. MS (FAB+):(M+H)$^+$ @ m/e 823.

EXAMPLE 257

Compound of Formula (IX): L is CO, T is NH, R is —CH$_2$—C≡C-(1-phenylethenyl)

Following the procedure of Example 247, except substituting alpha-bromostyrene for 3-bromoquinoline. MS (ESI) m/e 739 (M+H)$^+$.

EXAMPLE 258

Compound of Formula (IX): L is CO, T is NH, R is —CH$_2$—C≡C—Br

Step 258a. Compound 6E from Scheme 1c: R is —CH$_2$—C≡C—Br

To a solution under nitrogen of the compound of Example 246, Step h (100 mg) in acetone (1 mL) was added acetic acid (8.4 microliters) at ambient temperature. A second solution containing N-bromosuccinimide (39 mg) and silver nitrate (2.5 mg) in 1 mL of acetone was prepared and then stirred at room temperature under nitrogen for ten minutes and was cooled to 0° C. The first solution was then added to the second solution in one portion, the cooling bath was removed, and the resulting reaction mixture stirred at room temperature under nitrogen for 2 hours. The reaction was then diluted with ethyl acetate, saturated aqueous sodium bicarbonate was added, and the mixture was stirred at room temperature overnight. The organic phase was separated, washed with brine and dried (MgSO$_4$). The solvent was removed, and the residue was purified by chromatography on silica gel, eluting with 40% acetone/hexanes to give the title compound (50 mg, 46%).

Step 258b. Compound of Formula (IX): L is CO, T is NH, R is —CH$_2$—C≡C—Br

A sample (35 mg) of the compound from Step 258a was dissolved in methanol (2 mL) and stirred at ambient temperature for 16 hours. The solvent was removed, and the residue was purified by chromatography on silica gel, eluting with 5:94:1 methanol/dichlormethane/1% NH$_4$OH, to give the title compound (32 mg, 26%). MS (ESI) m/e 715 (M+H)$^+$.

EXAMPLE 259

Compound of Formula (IX): L is CO, T is NH, R is —CH$_2$-(2,2-dimethyl-1,3-dioxolan-4-yl)

Step 259a. Compound 6D from Scheme 1c: R is —CH$_2$CH(OH)CH$_2$OH, R$^p$ is acetyl To a sample of the compound from Example 176, Step d (5.0 g, 7.32 mmol, Compound 6D from Scheme 1c, R is —CH$_2$CH=CH$_2$, Rp is acetyl) and N-methylmorpholine N oxide (1.7 g, 14.5 mmol) in THF (25 mL) at room temperature was added OsO$_4$ (4% in H$_2$O, 0.090 mL. 0.0147 mmol), and the mixture was stirred for 24 hours. The reaction was quenched with sodium bisulfite (1.5 g) and water (10 mL), and the solvents were removed under vacuum. The residue was dissolved in ethyl acetate, which was washed with saturated aqueous sodium bicarbonate, water and brine, and dried (Na$_2$SO$_4$). The solvent was removed to give the title compound (3.17 g).

Step 259b. Compound 6D from Scheme 1c: R is —CH$_2$-(2,2-dimethyl-1,3-dioxolan-4-yl), R$^p$ is acetyl, R$^d$ is H To a sample of the compound from Step 259a (500 mg, 0.70 mmol) and 2,2-dimethoxypropane (0.26 mL, 2.1 mmol, in toluene (7 mL) was added p-toluenesulfonic acid (160 mg, 0.84 mmol), and the mixture was stirred at 55° C. for 3 days. The mixture was diluted with ethyl acetate, and this solution was washed with 10% sodium carbonate solution, water and brine. The organic phase was dried (Na$_2$SO$_4$), and the solvent was removed to give the crude product, which was purified by chromatography on silica gel, eluting with 2:97:1 methanol/chloroform/ammonium hydroxide to give the title compound (363 mg).

Step 259c. Compound 6E from Scheme 1c: R is —CH$_2$-(2, 2-dimethyl-1,3-dioxolan-4-yl), R$^p$ is acetyl, R$^d$ is H A sample of the compound from Step 259b (356 mg, 0.47 mmol) was oxidized with N-chlorosuccinimide and dimethylsulfide according to the procedure of Example 1,Step f, to afford the title compound (371 mg).

Step 259d. Compound of Formula (IX): L is CO, T is NH, R is —CH$_2$-(2,2-dimethyl-1,3-dioxolan-4-yl)

A sample of the compound from Step 259c (100 mg, 0.13 mmol) was stirred in methanol (4 mL) overnight at room temperature. The solvent was removed, and the residue was purified by chromatography on silica gel, eluting with 0.9:98:1 methanol/chloroform/ammonium hydroxide to give the title compound (87 mg). MS m/e 713 (M+H)$^+$.

EXAMPLE 260

Compound of Formula (IX): L is CO, T is NH, R is —CH$_2$CH(OH)CH$_2$OH

A sample of the compound from Example 259 (100 mg, 0.13 mmol) was stirred at reflux with p-toluenesulfonic acid (35 mg, 0.18 mmol) in 4:1 THF/water (2.5 mL) for 3 hours. The mixture was diluted with ethyl acetate, and this solution was washed with 10% sodium carbonate solution, water and brine. The organic phase was dried (Na$_2$SO$_4$), and the solvent was removed to give the crude product, which was purified by chromatography on silica gel, eluting with 2:97:1 methanol/chloroform/ammonium hydroxide to give the title compound (61 mg). MS m/e 689 (M+H)$^+$.

EXAMPLE 261

Compound of Formula (IX): L is CO, T is NH, R is —CH$_2$CH(OH)-phenyl

To a sample of the compound from Example 220 (550 mg, 0.87 mmol) in dry THF (16 mL) at 0° C. under nitrogen was added dropwise a solution of phenyl magnesium bromide (3.0 M, 2.0 mL, 6.0 mmol) in ether. The mixture was stirred for about 1 hour, and the reaction was quenched with saturated ammonium chloride solution. The mixture was extracted with ethyl acetate, and this solution was washed with water and brine and dried ($Na_2SO_4$). The solvent was removed, and the residue was purified by chromatography on silica gel, eluting with 10:90:0.5 methanol/dichloromethane/ammonium hydroxide to give the title compound (235 mg) as two isomers. Isomer A: MS m/e 719 $(M+H)^+$. Isomer B: MS m/e 719 $(M+H)^+$.

EXAMPLE 262

Compound of Formula (IX): L is CO, T is $N(NH_2)$, R is —$CH_2CH=CH_2$

To a sample of the compound from Example 102, Step b (793 mg, 1.0 mmol) in 9:1 acetonitrile/water (10 mL) was added hydrazine (85% aqueous solution, 0.50 mL, 10.0 mmol), and the mixture was stirred at room temperature under nitrogen for 4 days. The mixture was diluted with ethyl acetate, and the organic phase was washed with water and brine and dried ($Na_2SO_4$). The solvent was removed, and the residue was purified by chromatography on silica gel, eluting with 5:95:0.5 methanol/dichloromethane/ammonium hydroxide to give the title compound (91 mg). MS m/e 654 $(M+H)^+$.

EXAMPLE 263

Compound of Formula (IX): L is CO, T is $N(NH_2)$, R is —$CH_2CH=CH$-(3-quinolyl)

Following the procedures of Example 178, except substituting the compound from Example 262 for the compound from Example 177, the title compound was prepared. MS m/e 781 $(M+H)^+$. High Resolution FAB MS: calculated m/e for $(M+H)^+$ of $C_{42}H_{59}N_3O_{10}$: 781.4176; Found: 781.4188.

EXAMPLE 264

Compound of Formula (IX): L is CO, T is $N(NH_2)$, R is —$CH_2CH_2CH_2$-(3-quinolyl)

Following the procedures of Example 3, except substituting the compound from Example 262 for the compound from Example 3, the title compound was prepared. MS m/e 768 $(M+H)^+$. High Resolution FAB MS: calculated m/e for $(M+H)^+$ of $C_{42}H_{61}N_3O_{10}$: 768.4435; Found: 768.4437.

EXAMPLE 265

Compound of Formula (IX): L is CO, T is $NH_2$, R is —$CH_2CH=CH$-naphthyl

Following the procedures of Example 178, except substituting 1-bromonaphthalene for the 3-bromoquinoline of Example 178, the title compound was prepared. MS m/e 764 $(M+H)^+$.

EXAMPLE 266

Compound of Formula (IX): L is CO, T is NH, R is —$CH_2CH=CH$-(3-(2-furanyl)-6-quinolyl)

A mixture of a sample of the 2'-acetylated derivative of the compound of Example 219 (acetylated by the procedure of Example 177, Step a) (177 mg, 0.200 mmol), 2-(tributylstannyl)furan (78 µL, 0.200 mmol) and Pd(triphenylphosphine)$_4$ (23 mg, 0.020 mmol) in dry toluene was heated in a sealed tube at 60° C. to 90° C. for 20 hours. The mixture was then diluted with ethyl acetate, which was washed with aqueous 5% sodium bicarbonate and brine and dried ($Na_2SO_4$). The solvent was removed, and the residue was purified by chromatography on silica gel, eluting with 1:1 acetone/hexanes to give the acetylated title compound. This material was stirred with methanol for 48 hours, and the solvent was removed. The residue was purified by chromatography on silica gel, eluting with 95:5:0.5 dichlormethane/methanol/dimethylamine to give the title compound (102 mg). MS m/e 832 $(M+H)^+$. High Resolution FAB MS: calculated m/e for $(M+H)^+$ of $C_{46}H_{61}N_3O_{11}$: 832.4384; Found: 832.4384.

EXAMPLE 267

Compound of Formula (IX): L is CO, T is $NH_2$, R is —$CH_2CH=CH$-(8-chloro-3-quinolyl)

Following the procedures of Example 178, except substituting 8-chloro-3-bromoquinoline for the 3-bromoquinoline of Example 178, the title compound was prepared. MS m/e 800 $(M+H)^+$. High Resolution FAB MS: calculated m/e for $(M+H)^+$ of $C_{42}H_{58}ClN_3O_{10}$: 800.3889; Found: 800.3890.

EXAMPLE 268

Compound of Formula (IX): L is CO, T is $NH_2$, R is —$CH_2CH=CH$-(4-chloro-2-trifluoromethyl-6-quinolyl)

Following the procedures of Example 178, except substituting 6-bromo-4-chloro-2-trifluoromethylquinoline for the 3-bromoquinoline of Example 178, the title compound was prepared. MS m/e 868 $(M+H)^+$.

EXAMPLE 269

Compound of Formula (IX): L is CO, T is $NH_2$, R is —$CH_2CH=CH$-(2-fluorenyl)

Following the procedures of Example 178, except substituting 2-bromofluorene for the 3-bromoquinoline of Example 178, the title compound was prepared. MS m/e 803 $(M+H)^+$.

EXAMPLE 270

Compound of Formula (IX): L is CO, T is $NH_2$, R is —$CH_2CH=CH$-(9-fluorenone-2-yl)

Following the procedures of Example 178, except substituting 2-iodo-9-fluorenone for the 3-bromoquinoline of Example 178, the title compound was prepared. MS m/e 817 $(M+H)^+$. Anal Calcd for $C_{46}H_{60}N_2O_{11}$ C, 67.63; H, 7.40; N, 3.43. Found C, 68.11; H, 8.08; N, 3.21.

EXAMPLE 271

Compound of Formula (IX): L is CO, T is $NH_2$, R is —$CH_2CH=C$-(6-benzoyl-2-naphthyl)

Following the procedures of Example 178, except substituting 6-benzoyl-2-(trifluoromethylsulfonyloxy) naphthalene (prepared from 6-benzoyl-2-naphthol by reaction with trifluoromethylsulfonic anhydride) for the 3-bromoquinoline of Example 178, the title compound was prepared. MS m/e 869 $(M+H)^+$.

EXAMPLE 272

Compound of Formula (IX): L is CO, T is $NH_2$, R is —$CH_2CH=CH$-(7-methoxy-2-naphthyl)

Following the procedures of Example 178, except substituting 7-methoxy-2-(trifluoromethylsulfonyloxy)

naphthalene (prepared from 7-methoxy-2-naphthol by reaction with trifluoromethylsulfonic anhydride) for the 3-bromoquinoline of Example 178, the title compound was prepared. MS m/e 795 (M+H)$^+$. Anal Calcd for $C_{44}H_{62}N_2O_{11}$.0.5 $H_2O$ C, 65.73; H, 7.90; N, 3.48. Found C, 65.62; H, 8.06; N, 3.49.

EXAMPLE 273

Compound of Formula (IX): L is CO, T is $NH_2$, R is —$CH_2CH$=CH-(3-phenyl-6-quinolyl)

A mixture of a sample of the 2'-acetylated derivative of the compound of Example 219 (acetylated by the procedure of Example 177, Step a) (177 mg, 0.200 mmol), Pd(triphenylphosphine)$_4$ (11.5 mg, 0.010 mmol), CuBr (1.43 mg) and (tributylstannyl)benzene (78.3 μL) in dioxane (2 mL) was heated in a sealed tube at 100° C. for 15 hours. The mixture was then diluted with ethyl acetate, which was washed with aqueous 5% sodium carbonate and brine and dried ($Na_2SO_4$). The solvent was removed, and the residue was purified by chromatography on silica gel to give the acetylated title compound (77 mg). This material was stirred with methanol for 48 hours, and the solvent was removed. The residue was purified by chromatography on silica gel to give the title compound (54.2 mg). MS m/e 842 (M+H)$^+$.

EXAMPLE 274

Compound of Formula (IX): L is CO, T is $NH_2$, R is —$CH_2CH$=CH-(3-(2-pyridyl)-6-quinolyl)

Following the procedures of Example 273, except substituting 2-(tributylstannyl)pyridine for the 2-(tributylstannyl)furan of Example 273, the title compound was prepared. MS m/e 841 (M+H)$^+$.

EXAMPLE 275

Compound of Formula (IX): L is CO, T is $NH_2$, R is —$CH_2CH$=CH-(3-(2-thiophenyl)-6-quinolyl)

Following the procedures of Example 273, except substituting 2-(tributylstannyl)thiophene for the 2-(tributylstannyl)furan of Example 273, the title compound was prepared. MS m/e 848 (M+H)$^+$.

EXAMPLE 276

Compound of Formula (IX): L is CO, T is $NH_2$, R is —$CH_2CH$=CH-(4-methylnaphthyl)

Following the procedures of Example 178, except substituting the 2'-benzoylated compound of Example 102, Step c for the 2'-acetylated compound of Example 177 and substituting 1-bromo-4-methylnaphthalene for the 3-bromoquinoline of Example 178, the title compound was prepared. MS m/e 779 (M+H)$^+$. High Resolution FAB MS: calculated m/e for (M+H)$^+$ of $C_{44}H_{62}N_2O_{10}$: 779.4483; Found: 779.4495.

EXAMPLE 277

Compound of Formula (IX): L is CO, T is $NH_2$, R is —$CH_2CH$=CH-(6-β-D-galactopyranosyl-2-naphthyl)

Following the procedures of Example 178, except substituting the 2'-benzoylated compound of Example 102, Step c for the 2'-acetylated compound of Example 177 and substituting 6-bromo-2-naphthyl-β-D-galactopyranoside (obtained from Sigma Aldrich) for the 3-bromoquinoline of Example 178, the title compound was prepared. MS m/e 943 (M+H)$^+$.

EXAMPLE 278

Compound of Formula (IX): L is CO, T is $NH_2$, R is —$CH_2CH$=CH-(7-quinolyl)

Following the procedures of Example 178, except substituting the 2'-benzoylated compound of Example 102, Step c for the 2'-acetylated compound of Example 177 and substituting 7-(trifluoromethylsulfonyl)quinoline for the 3-bromoquinoline of Example 178, the title compound was prepared. MS m/e 766 (M+H)$^+$.

EXAMPLE 279

Compound of Formula (IX): L is CO, T is $NH_2$, R is —$CH_2CH$=CH-(4-fluoronaphthyl)

Following the procedures of Example 178, except substituting the 2'-benzoylated compound of Example 102, Step c for the 2'-acetylated compound of Example 177 and substituting 1-bromo-4-fluoronaphthalene for the 3-bromoquinoline of Example 178, the title compound was prepared. MS m/e 783 (M+H)$^+$. High Resolution FAB MS: calculated m/e for (M+H)$^+$ of $C_{43}H_{59}FN_2O_{10}$: 783.4227; Found: 783.4223.

EXAMPLE 280

Compound of Formula (IX): L is CO, T is $NH_2$, R is —$CH_2CH$=CH-(3-biphenyl)

Following the procedures of Example 178, except substituting the 2'-benzoylated compound of Example 102, Step c for the 2'-acetylated compound of Example 177 and substituting 3-bromobiphenyl for the 3-bromoquinoline of Example 178, the title compound was prepared. MS m/e 791 (M+H)$^+$. High Resolution FAB MS: calculated m/e for (M+H)$^+$ of $C_{45}H_{63}N_2O_{10}$: 791.4483; Found: 791.4492.

EXAMPLE 281

Compound of Formula (IX): L is CO, T is $NH_2$, R is —$CH_2CH$=CH-(5-nitronaphthyl)

Following the procedures of Example 178, except substituting the 2'-benzoylated compound of Example 102, Step c for the 2'-acetylated compound of Example 177 and substituting 1-bromo-5-nitronaphthalene for the 3-bromoquinoline of Example 178, the title compound was prepared.

EXAMPLE 282

Compound of Formula (IX): L is CO, T is $NH_2$, R is —$CH_2CH$=CH-(4-pyrrolylphenyl)

Following the procedures of Example 178, except substituting the 2'-benzoylated compound of Example 102, Step c for the 2'-acetylated compound of Example 177 and substituting 1-(4-iodophenyl)pyrrole for the 3-bromoquinoline of Example 178, the title compound was prepared. MS m/e 780 (M+H)$^+$. High Resolution FAB MS: calculated m/e for (M+H)$^+$ of $C_{43}H_{61}N_3O_{10}$: 780.4430; Found: 780.4424.

EXAMPLE 283

Compound of Formula (IX): L is CO, T is $NH_2$, R is —$CH_2CH$=CH-(6-methoxy-2-naphthyl)

Following the procedures of Example 178, except substituting the 2'-benzoylated compound of Example 102, Step c for the 2'-acetylated compound of Example 177 and substituting 2-bromo-6-methoxynaphthalene for the 3-bromoquinoline of Example 178, the title compound was prepared. MS m/e 795 (M+H)$^+$. High Resolution FAB MS: calculated m/e for (M+H)$^+$ of $C_{44}H_{62}N_2O_{11}$: 795.4426; Found: 795.4426.

EXAMPLE 284

Compound of Formula (IX): L is CO, T is $NH_2$, R is —$CH_2CH$=CH-(3.5-dichlorophenyl)

Following the procedures of Example 178, except substituting the 2'-benzoylated compound of Example 102, Step c for the 2'-acetylated compound of Example 177 and substituting 1,3-dichloro-5-iodobenzene for the 3-bromoquinoline of Example 178, the title compound was prepared. MS m/e 783 (M+H)$^+$. High Resolution FAB MS: calculated m/e for (M+H)$^+$ of $C_{39}H_{57}Cl_2N_2O_{10}$: 783.3390; Found: 783.3392.

EXAMPLE 285

Compound of Formula (IX): L is CO, T is $NH_2$, R is —$CH_2$-(3-iodophenyl)

Following the procedures of Example 1, steps a–f, except substituting the 3-iodobenzyl bromide for the allyl bromide of Example 1, Step a, to prepare the compound 9 from Scheme 1b, wherein R is 3-iodophenylmethyl and $R^P$ is benzoyl, then treating that compound according to the procedures of Example 102, the title compound was prepared. MS m/e 815 (M+H)$^+$.

EXAMPLE 286

Compound of Formula (IX): L is CO, T is $NH_2$, R is —$CH_2$-(3-(2-furanyl)phenyl)

Following the procedures of Example 266, except substituting the compound of Example 285 for the compound from Example 265, the title compound was prepared. MS m/e 689 (M+H)$^+$.

EXAMPLE 287

Compound of Formula (IX): L is CO, T is $NH_2$, R is —$CH_2CH$=CH-(6-hydroxy-2-naphthyl)

Following the procedures of Example 178, except substituting the 2'-benzoylated compound of Example 102, Step c for the 2'-acetylated compound of Example 177 and substituting 6-bromo-2-naphthol for the 3-bromoquinoline of Example 178, the title compound was prepared. MS m/e 781 (M+H)$^+$.

EXAMPLE 288

Compound of Formula (IX): L is CO, T is $NH_2$, R is —$CH_2CH$=CH-(6-(2-bromoethoxy)-2-naphthyl)

Following the procedures of Example 178, except substituting 6-bromo-2-(2-bromoethoxy)naphthalene for the 3-bromoquinoline of Example 178, the title compound was prepared. MS m/e 887 (M+H)$^+$.

EXAMPLE 289

Compound of Formula (IX): L is CO, T is $NH_2$, R is —$CH_2CH$=CH-(6-(2-(tetrazolyl)ethoxy-2-naphthyl)

To a sample of the compound from Example 288 (371 mg, 0.4 mmol) in acetonitrile (4 mL) was added tetrazole (138 mg, 2 mmol) and triethylamine (0.556 mL, 4 mmol), and the mixture was heated at 60° C. under nitrogen overnight. The volatiles were removed under vacuum, and the residue was dissolved in ethyl acetate. This solution was washed with 5% aqueous sodium bicarbonate and brine, dried ($Na_2SO_4$), and concentrated. The residue was purified by chromatography on silica gel, eluting with 97:3:0.5 dichloromethane/methanol/ammonium hydroxide. This product was stirred in methanol at room temperature for 2 days, then the product was purified by chromatography on silica gel, eluting with 99:1:0.5 dichloromethane/methanol/ammonium hydroxide. MS m/e 877 (M+H)$^+$.

EXAMPLE 290

Compound of Formula (IX): L is CO, T is $NH_2$, R is —$CH_2CH$=CH-naphthyl

Following the procedures of Example 178, except substituting 1-bromonaphthalene for the 3-bromoquinoline of Example 178, the title compound was prepared. MS m/e xxx (M+H)$^+$.

EXAMPLE 291

Compound of Formula (IX): L is CO, T is NH, R is —$CH_2$—C≡C-(2-phenylethenyl)

Following the procedure of Example 247, except substituting beta-bromostyrene for 3-bromoquinoline. MS (ESI) m/e 739 (M+H)$^+$.

EXAMPLE 292

Compound of Formula (IX): L is CO, T is NH, R is —$CH_2$—CH=CH-(5-(3-isoxazolyl)-2-thiophenyl)

Step 292a. Compound 37 from Scheme 7 wherein $R^{BB}$ is OH

To 11.8 mL (11.8 mmol) borane-THF complex (1 molar solution in tetrahydrofuran) at −10° C. was added 2-methyl-2-butene (2.7 mL, 24 mmol). The reaction was stirred at 0° C. for 2 hours and a separately prepared solution containing the compound from Example 246, Step h (Compound 6E from Scheme 1c; $R^P$ is acetyl, R is —$CH_2$—C≡C—H, 2 g, 2.95 mmol) in 10 mL tetrahydrofuran was then added in one portion. The reaction was stirred at 0° C. for 1 hour and was warmed to ambient temperature. After 3 hours the reaction was recooled to 0° C. and 5% aqueous sodium carbonate was added. The mixture was extracted with ethyl acetate, and the organic layers were washed with brine and dried over magnesium sulfate. Concentration and drying in vacuo gave 3.6 grams of crude product which was purified with silica gel chromatography eluting with acetone/hexanes (1:1) to provide the title compound (0.85 g, 40%).

Step 292b. Compound of Formula (IX): L is CO, T is NH, Rc is acetyl, R is —$CH_2$—CH=CH-(5-(3-isoxazolyl)-2-thiophenyl)

A pressure tube equipped with a stir bar was charged with 100 mg (0.138 mmol) of the compound resulting from Step 292a, potassium carbonate (42 mg, 0.3 mmol) 2-bromo-5-(isoxazol-3-yl)thiophene (48 mg, 0.21 mmol), palladium (II) acetate (0.15 mg, 0.7 mmol), 0.75 mL acetone and 0.75 mL water. Two freeze-pump-thaw cycles were performed to degas reaction. The reaction tube was then sealed under nitrogen and heated at 65° C. for 2 hours. The mixture was diluted with ethyl acetate and washed successively with water then brine. Organic extracts were dried over magnesium sulfate, concentrated in vacuo, and dried to constant weight with high vacuum to provide 140 mg of crude product.

Step 292c. Compound of Formula (IX): L is CO, T is NH, R is —CH$_2$—CH=CH-(5-(3-isoxazolyl)-2-thiophenyl)

The compound resulting from Step 292b (140 mg) was dissolved in 5 mL methanol, and the solution was stirred at ambient temperature for 20 hours. The solution was concentrated in vacuo and dried to constant weight. The crude product was purified with silica gel chromatography eluting with 98:1:1 dichloromethane/methanol/ammonium hydroxide to give 34 mg of the title compound. High Resolution FAB MS: calculated m/e for (M+H)$^+$: C$_{40}$H$_{58}$N$_3$O$_{11}$S: 788.3792 Observed: 788.3809.

EXAMPLE 293

Compound of Formula (IX): L is CO, T is NH, R is —CH$_2$—CH=CH-(1,3-dimethyl-2,4-dioxo-5-pyrimidinyl)

Following the procedures of Example 292, except substituting 5-bromo-1,3-dimethyluracil for 2-bromo-5-(isoxazol-3-yl)thiophene, the title compound was prepared. High Resolution FAB MS: calculated m/e for (M+H)$^+$: C$_{39}$H$_{61}$N$_4$O$_{12}$: 777.4286. Observed m/e: 777.4291

EXAMPLE 294

Compound of Formula (IX): L is CO, T is NH, R is —CH$_2$—CH=CH-(5-(2-pyridyl)aminocarbonyl-2-furanyl)

Following the procedures of Example 292, except substituting 5-bromo-furan-2-carboxylic acid pyridin-2-yl-amide for 2-bromo-5-(isoxazol-3-yl)thiophene the title compound was prepared. MS (ESI)+:(M+H)$^+$ @ m/e 825.

What is claimed is:

1. A compound, having the formula,

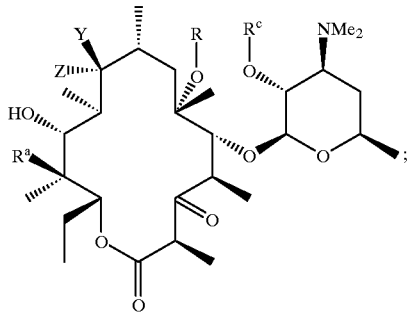

(II)

or a pharmaceutically acceptable salt, ester or prodrug thereof,
wherein either,
Y and Z taken together define a group X,
wherein
X is selected from the group consisting of
(1) =O,
(2) =N—OH,
(3) =N—O—R$^1$ where R$^1$ is selected from the group consisting of
 (a) unsubstituted C$_1$–C$_{12}$-alkyl,
 (b) C$_1$–C$_{12}$-alkyl substituted with aryl,
 (c) C$_1$–C$_{12}$-alkyl substituted with substituted aryl,
 (d) C$_1$–C$_{12}$-alkyl substituted with heteroaryl,
 (e) C$_1$–C$_{12}$-alkyl substituted with substituted heteroaryl,
 (f) C$_3$–C$_{12}$-cycloalkyl, and
 (g) —Si—(R$^2$)(R$^3$)(R$^4$) wherein R$^2$, R$^3$ and R$^4$ are each independently selected from C$_1$–C$_{12}$-alkyl and aryl, and
(4) =N—O—C(R$^5$)(R$^6$)—O—R$^1$ where R$^1$ is as previously defined and R$^5$ and R$^6$ are each independently selected from the group consisting of
 (a) hydrogen,
 (b) unsubstituted C$_1$–C$_{12}$-alkyl,
 (c) C$_1$–C$_{12}$-alkyl substituted with aryl,
 (d) C$_1$–C$_{12}$-alkyl substituted with substituted aryl,
 (e) C$_1$–C$_{12}$-alkyl substituted with heteroaryl, and
 (f) C$_1$–C$_{12}$-alkyl substituted with substituted heteroaryl, or
 R$^5$ and R$^6$ taken together with the atom to which they are attached form a C$_3$–C$_{12}$-cycloalkyl ring;
or,
one of Y and Z is hydrogen and the other is selected from a group consisting of
(1) hydrogen,
(2) hydroxy,
(3) protected hydroxy, and
(4) NR$^7$R$^8$ wherein R$^7$ and R$^8$ are independently selected from hydrogen and C$_1$–C$_6$-alkyl, or R$^7$ and R$^8$ are taken with the nitrogen atom to which they are connected to form a 3- to 7-membered ring which, when the ring is a 5- to 7-membered ring, may optionally contain a hetero function selected from the group consisting of —O—, —NH—, —N(C$_1$–C$_6$-alkyl-)—, —N(aryl)—, —N(aryl-C$_1$–C$_6$-alkyl-)—, —N(substituted-aryl-C$_1$–C$_6$-alkyl-)—, —N(heteroaryl)—, —N(heteroaryl-C$_1$–C$_6$-alkyl-)—, —N(substituted-heteroaryl-C$_1$–C$_6$-alkyl-)—, and —S— or —S(O)$_n$—, wherein n is 1 or 2, R$^a$ is hydrogen or hydroxy;
R$^c$ is hydrogen or a hydroxy protecting group;
R is selected from the group consisting of
(1) methyl substituted with a moiety selected from the group consisting of
 (a) CN,
 (b) F, Cl
 (c) nitro,
 (d) —CHO
 (e) —OR$^9$ wherein R$^9$ is selected from the group consisting of:
  (i) hydrogen
  (ii) C$_1$–C$_6$-alkyl, optionally substituted with a substituent selected from the group consisting of
   (aa) aryl,
   (bb) substituted-aryl,
   (cc) heteroaryl, and
   (dd) substituted-heteroaryl,
  (iii) aryl,
  (iv) substituted-aryl,
  (v) heteroaryl,
  (vi) substituted-heteroaryl, and
  (vii) heterocycloalkyl,
 (f) —C(O)$_l$R$^{10}$ wherein l is 1 or 2 and R$^{10}$ is selected from the group consisting of hydrogen, C$_1$–C$_3$-alkyl, C$_1$–C$_3$-alkyl substituted with aryl, and C$_1$–C$_3$-alkyl substituted with heteroaryl,
 (g) S(O)$_n$R$^9$ where n is 0, 1 or 2 and R$^9$ is as previously defined,
 (h) NHC(O)R$^{10}$ wherein R$^{10}$ is as previously defined,
 (i) NHC(O)NR$^{11}$R$^{12}$ wherein R$^{11}$ and R$^{12}$ are independently selected from hydrogen, C$_1$–C$_3$-alkyl, $C_1$–$C_3$-alkyl substituted with aryl, substituted aryl, heteroaryl, substituted heteroaryl,
(j) aryl,
(k) substituted aryl,
(l) heteroaryl,
(m) substituted heteroaryl,
(n) $C_3$–$C_8$-cycloalkyl, and
(o) substituted $C_3$–$C_8$-cycloalkyl,
(2) $C_2$–$C_{10}$-alkyl substituted with one or more substituents selected from the group consisting of
(a) halogen,
(b) hydroxy,
(c) $C_1$–$C_3$-alkoxy,
(d) $C_1$–$C_3$-alkoxy-$C_1$–$C_3$-alkoxy,
(e) oxo,
(f) —$N_3$,
(g) —CHO,
(h) O—$SO_2$-(substituted $C_1$–$C_6$-alkyl),
(i) —$NR^{13}R^{14}$ wherein $R^{13}$ and $R^{14}$ are selected from the group consisting of
  (i) hydrogen,
  (ii) $C_1$–$C_{12}$-alkyl,
  (iii) substituted $C_1$–$C_{12}$-alkyl,
  (iv) $C_1$–$C_{12}$-alkenyl,
  (v) substituted $C_1$–$C_{12}$-alkenyl,
  (vi) $C_1$–$C_{12}$-alkynyl,
  (vii) substituted $C_1$–$C_{12}$-alkynyl,
  (viii) aryl,
  (ix) $C_3$–$C_8$-cycloalkyl,
  (x) substituted $C_3$–$C_8$-cycloalkyl,
  (xi) substituted aryl,
  (xii) heterocycloalkyl,
  (xiii) substituted heterocycloalkyl,
  (xiv) $C_1$–$C_{12}$-alkyl substituted with aryl,
  (xv) $C_1$–$C_{12}$-alkyl substituted with substituted aryl,
  (xvi) $C_1$–$C_{12}$-alkyl substituted with heterocycloalkyl,
  (xvii) $C_1$–$C_{12}$-alkyl substituted with substituted heterocycloalkyl,
  (xviii) $C_1$–$C_{12}$-alkyl substituted with $C_3$–$C_8$-cycloalkyl,
  (xix) $C_1$–$C_{12}$-alkyl substituted with substituted $C_3$–$C_8$-cycloalkyl,
  (xx) heteroaryl,
  (xxi) substituted heteroaryl,
  (xxii) $C_1$–$C_{12}$-alkyl substituted with heteroaryl, and
  (xxiii) $C_1$–$C_{12}$-alkyl substituted with substituted heteroaryl, or
$R^{13}$ and $R^{14}$ are taken together with the atom to which they are attached form a 3–10 membered heterocycloalkyl ring which may be substituted with one or more substituents independently selected from the group consisting of
  (i) halogen,
  (ii) hydroxy,
  (iii) $C_1$–$C_3$-alkoxy,
  (iv) $C_1$–$C_3$-alkoxy-$C_1$–$C_3$-alkoxy,
  (v) oxo,
  (vi) $C_1$–$C_3$-alkyl,
  (vii) halo-$C_1$–$C_3$-alkyl, and
  (vii) $C_1$–$C_3$-alkoxy-$C_1$–$C_3$-alkyl,
(j) —$CO_2R^{10}$ wherein $R^{10}$ is as previously defined,
(k) —$C(O)NR^{11}R^{12}$ wherein $R^{11}$ and $R^{12}$ are as previously defined,
(l) =N—O—$R^{10}$ wherein $R^{10}$ is as previously defined,
(m) —CN,
(n) $S(O)_nR^9$ where n is 0, 1 or 2 and $R^9$ is as previously defined,
(o) O—$S(O)_nR^{10}$ wherein n is 0, 1 or 2 and $R^{10}$ is as previously defined,
(p) —Si—$(R^2)(R^3)(R^4)$ wherein $R^2$, $R^3$ and $R^4$ are as previously defined,
(q) aryl,
(r) substituted aryl,
(s) heteroaryl,
(t) substituted heteroaryl,
(u) $C_3$–$C_8$-cycloalkyl,
(v) substituted $C_3$–$C_8$-cycloalkyl,
(w) $C_1$–$C_{12}$-alkyl substituted with heteroaryl,
(x) heterocycloalkyl,
(y) substituted heterocycloalkyl,
(z) $NHC(O)R^{10}$ where $R^{10}$ is as previously defined,
(aa) $NHC(O)NR^{11}R^{12}$ wherein $R^{11}$ and $R^{12}$ are as previously defined,
(bb) =N—$NR^{13}R^{14}$ wherein $R^{13}$ and $R^{14}$ are as previously defined,
(cc) =N—$R^9$ wherein $R^9$ is as previously defined,
(dd) =N—$NHC(O)R^{10}$ wherein $R^{10}$ is as previously defined, and
(ee) =N—$NHC(O)NR^{11}R^{12}$ wherein $R^{11}$ and $R^{12}$ are as previously defined;
(3) $C_3$-alkenyl substituted with a moiety selected from the group consisting of
(a) halogen,
(b) —CHO,
(c) —$CO_2R^{10}$ where $R^{10}$ is as previously defined,
(d) —C(O)—$R^9$ where $R^9$ is as previously defined,
(e) —$C(O)NR^{11}R^{12}$ wherein $R^{11}$ and $R^{12}$ are as previously defined,
(f) —CN,
(g) $S(O)_nR^9$ where n is 0, 1 or 2 and $R^9$ is as previously defined,
(h) —Si—$(R^2)(R^3)(R^4)$ wherein $R^2$, $R^3$ and $R^4$ are as previously defined,
(i) aryl,
(j) substituted aryl,
(k) heteroaryl,
(l) substituted heteroaryl,
(m) $C_3$–$C_7$-cycloalkyl, and
(n) $C_1$–$C_{12}$-alkyl substituted with heteroaryl,
(4) $C_4$–$C_{10}$-alkenyl;
(5) $C_4$–$C_{10}$-alkenyl substituted with one or more substituents selected from the group consisting of
(a) halogen,
(b) $C_1$–$C_3$-alkoxy,
(c) oxo,
(d) —CHO,
(e) —$CO_2R^{10}$ where $R^{10}$ is as previously defined,
(f) —$C(O)NR^{11}R^{12}$ wherein $R^{11}$ and $R^{12}$ are as previously defined,
(g) —$NR^{13}R^{14}$ wherein $R^{13}$ and $R^{14}$ are as previously defined,
(h) =N—O—$R^{10}$ where $R^{10}$ is as previously defined,
(i) —CN,
(j) O—$S(O)_nR^{10}$ where n is 0, 1 or 2 and $R^{10}$ is as previously defined,
(k) aryl,
(l) substituted aryl,
(m) heteroaryl,
(n) substituted heteroaryl,
(o) $C_3$–$C_7$-cycloalkyl, (p) $C_1$–$C_{12}$-alkyl substituted with heteroaryl,
(q) NHC(O)$R^{10}$ where $R^{10}$ is as previously defined,
(r) NHC(O)N$R^{11}R^{12}$ wherein $R^{11}$ and $R^{12}$ are as previously defined,
(s) =N—N$R^{13}R^{14}$ wherein $R^{13}$ and $R^{14}$ are as previously defined,
(t) =N—$R^9$ wherein $R^9$ is as previously defined,
(u) =N—NHC(O)$R^{10}$ where $R^{10}$ is as previously defined, and
(v) =N—NHC(O)N$R^{11}R^{12}$ wherein $R^{11}$ and $R^{12}$ are as previously defined;

(6) $C_3$–$C_{10}$-alkynyl; and
(7) $C_3$–$C_{10}$-alkynyl substituted with one or more substituents selected from the group consisting of
(a) trialkylsilyl,
(b) aryl,
(c) substituted aryl,
(d) heteroaryl, and
(e) substituted heteroaryl.

2. A compound according to claim 1 wherein $R^a$ is OH, $R^c$ is benzoyl, and R is allyl.

3. A compound according to claim 1 wherein $R^a$ is hydroxy and $R^c$ is hydrogen.

4. A compound according to claim 1 having the formula VIII,

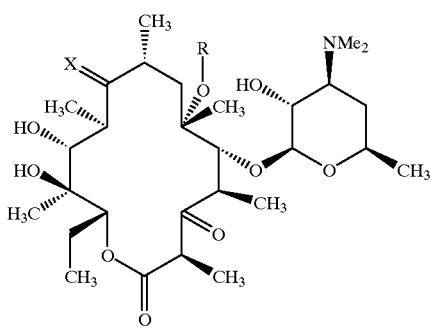

wherein X is O or NOH, and R is as defined therein.

5. A compound according to claim 4 which is selected from the group consisting of:
Compound of Formula (VIII): X is O, R is allyl;
Compound of Formula (VIII): X is NOH, R is allyl.;
Compound of Formula (VIII): X is O, R is propyl;
Compound of Formula (VIII): X is O, R is —$CH_2$CHO;
Compound of Formula (VIII): X is O, R is —$CH_2$CH=NOH;
Compound of Formula (VIII): X is NOH, R is —$CH_2$CH=NOH;
Compound of Formula (VIII): X is O, R is —$CH_2$CN;
Compound of Formula (VIII): X is O, R is —$CH_2CH_2NH_2$;
Compound of Formula (VIII): X is O, R is —$CH_2CH_2NHCH_2$-Phenyl;
Compound of Formula (VIII): X is O, R is —$CH_2CH_2NHCH_2CH_2$-Phenyl;
Compound of Formula (VIII): X is O, R is —$CH_2CH_2NHCH(CO_2CH_3)CH_2$-Phenyl;
Compound of Formula (VIII): X is O, R is —$CH_2CH_2NHCH_2$-(4-pyridyl);
Compound of Formula (VIII): X is O, R is —$CH_2CH_2NHCH_2$-(4-quinolyl);
Compound of Formula (VIII): X is O, R is —$CH_2$CH=CH-Phenyl;
Compound of Formula (VIII): X is O, R is —$CH_2CH_2CH_2$-Phenyl;
Compound of Formula (VIII): X is O, R is —$CH_2$CH=CH-(4-methoxyphenyl);
Compound of Formula (VIII): X is O, R is —$CH_2$CH=CH-(4-chlorophenyl);
Compound of Formula (VIII): X is O, R is —$CH_2$CH=CH-(3-quinolyl);
Compound of Formula (VIII): X is O, R is —$CH_2CH_2CH_2$OH.;
Compound of Formula (VIII): X is O, R is —$CH_2$C(O)OH;
Compound of Formula (VIII): X is O, R is —$CH_2CH_2NHCH_3$;
Compound of Formula (VIII): X is O, R is —$CH_2CH_2NHCH_2$OH;
Compound of Formula (VIII): X is O, R is —$CH_2CH_2$N$(CH_3)_2$;
Compound of Formula (VIII): X is O, R is —$CH_2CH_2$(1-morpholinyl);
Compound of Formula (VIII): X is O, R is —$CH_2$C(O)$NH_2$;
Compound of Formula (VIII): X is O, R is —$CH_2$NHC(O)$NH_2$;
Compound of Formula (VIII): X is O, R is —$CH_2$NHC(O)$CH_3$;
Compound of Formula (VIII): X is O, R is —$CH_2$F;
Compound of Formula (VIII): X is O, R is —$CH_2CH_2OCH_3$;
Compound of Formula (VIII): X is O, R is —$CH_2CH_3$;
Compound of Formula (VIII): X is O, R is —$CH_2$CH=CH$(CH_3)_2$;
Compound of Formula (VIII): X is O, R is —$CH_2CH_2$CH$(CH_3)CH_3$;
Compound of Formula (VIII): X is O, R is —$CH_2CH_2OCH_2CH_2OCH_3$;
Compound of Formula (VIII): X is O, R is —$CH_2SCH_3$;
Compound of Formula (VIII): X is O, R is -cyclopropyl;
Compound of Formula (VIII): X is O, R is —$CH_2OCH_3$;
Compound of Formula (VIII): X is O, R is —$CH_2CH_2$F;
Compound of Formula (VIII): X is O, R is —$CH_2$-cyclopropyl;
Compound of Formula (VIII): X is O, R is —$CH_2CH_2$CHO;
Compound of Formula (VIII): X is O, R is —C(O)$H_2CH_2CH_3$;
Compound of Formula (VIII): X is O, R is —$CH_2$-(4-nitrophenyl);
Compound of Formula (VIII): X is O, R is —$CH_2$-(4-chlorophenyl);
Compound of Formula (VIII): X is O, R is —$CH_2$-(4-methoxyphenyl);
Compound of Formula (VIII): X is O, R is —$CH_2$-(4-cyanophenyl);
Compound of Formula (VIII): X is O, R is —$CH_2$CH=CHC(O)O$CH_3$;
Compound of Formula (VIII): X is O, R is —$CH_2$CH=CHC(O)O$CH_2CH_3$;
Compound of Formula (VIII): X is O, R is —$CH_2$CH=CH$CH_3$;
Compound of Formula (VIII): X is O, R is —$CH_2$CH=CH$CH_2CH_3$;
Compound of Formula (VIII): X is O, R is —$CH_2$CH=CH$CH_2CH_2CH_3$;
Compound of Formula (VIII): X is O, R is —$CH_2$CH=CHS$C_2$-phenyl;
Compound of Formula (VIII): X is O, R is —$CH_2$C≡C—Si$(CH_3)_3$;
Compound of Formula (VIII): X is O, R is —$CH_2$C≡C$CH_2CH_2CH_2CH_2CH_3$;
Compound of Formula (VIII): X is O, R is —$CH_2$C≡C$CH_3$;
Compound of Formula (VIII): X is O, R is —$CH_2$-(2-pyridyl);

Compound of Formula (VIII): X is O, R is —CH$_2$-(3-pyridyl);
Compound of Formula (VIII): X is O, R is —CH$_2$-(4-pyridyl);
Compound of Formula (VIII): X is O, R is —CH$_2$-(4-quinolyl);
Compound of Formula (VIII): X is O, R is —CH$_2$NO$_2$;
Compound of Formula (VIII): X is O, R is —CH$_2$C(O)OCH$_3$;
Compound of Formula (VIII): X is O, R is —CH$_2$C(O)-phenyl;
Compound of Formula (VIII): X is O, R is —CH$_2$C(O)CH$_2$CH$_3$;
Compound of Formula (VIII): X is O, R is —CH$_2$Cl;
Compound of Formula (VIII): X is O, R is —CH$_2$S(O)$_2$-phenyl;
Compound of Formula (VIII): X is O, R is —CH$_2$CH=CHBr;
Compound of Formula (VIII): X is O, R is —CH$_2$CH=CH-(4-quinolyl;
Compound of Formula (VIII): X is O, R is —CH$_2$CH$_2$CH$_2$-(4-quinolyl;
Compound of Formula (VIII): X is O, R is —CH$_2$CH=CH-(5-quinolyl;
Compound of Formula (VIII): X is O, R is —CH$_2$CH$_2$CH$_2$-(5-quinolyl;
Compound of Formula (VIII): X is O, R is —CH$_2$CH=CH-(4-benzoxazolyl;
Compound of Formula (VIII): X is O, R is —CH$_2$CH=CH-(7-benzimidazolyl;
Compound of Formula (VIII): X is O, R is CH$_2$-(3-iodophenyl);
Compound of Formula (VIII): X is O, R is CH$_2$-(2-naphthyl);
Compound of Formula (VIII): X is O, R is CH$_2$—CH=CH-(4-fluorophenyl); and
Compound of Formula (VIII): X is O, R is CH$_2$—CH(OH)—CN.

6. A pharmaceutical composition comprising a therapeutically effective amount of a compound according to claim 1 in combination with a pharmaceutically acceptable carrier.

7. A method for treating a bacterial infection comprising administering a therapeutically effective amount of a compound according to claim 1 in combination with a pharmaceutically acceptable carrier.

8. A process for the preparation of 6-O-substituted macrolide compounds having the formula:

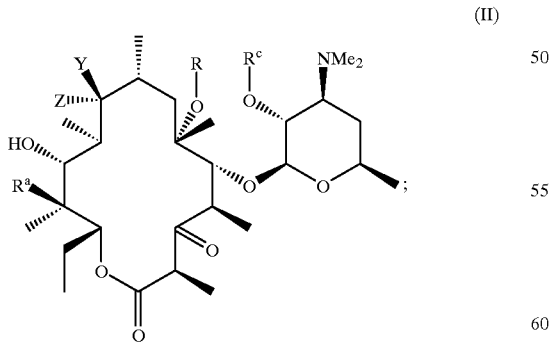

(II)

or a pharmaceutically acceptable salt, ester or prodrug thereof,
wherein either,
Y and Z taken together define a group X,
wherein X is selected from the group consisting of
(1) =O,
(2) =N—OH,
(3) =N—O—R$^1$ where R$^1$ is selected from the group consisting of
(a) unsubstituted C$_1$–C$_{12}$-alkyl,
(b) C$_1$–C$_{12}$-alkyl substituted with aryl,
(c) C$_1$–C$_{12}$-alkyl substituted with substituted aryl,
(d) C$_1$–C$_{12}$-alkyl substituted with heteroaryl,
(e) C$_1$–C$_{12}$-alkyl substituted with substituted heteroaryl,
(f) C$_3$–C$_{12}$-cycloalkyl, and
(g) —Si—(R$^2$)(R$^3$)(R$^4$) wherein R$^2$, R$^3$ and R$^4$ are each independently selected from C$_1$–C$_{12}$-alkyl and aryl, and
(4) =N—O—C(R$^5$)(R$^6$)—O—R$^1$ where R$^1$ is as previously defined and R$^5$ and R$^6$ are each independently selected from the group consisting of
(a) hydrogen,
(b) unsubstituted C$_1$–C$_{12}$-alkyl,
(c) C$_1$–C$_{12}$-alkyl substituted with aryl,
(d) C$_1$–C$_{12}$-alkyl substituted with substituted aryl,
(e) C$_1$–C$_{12}$-alkyl substituted with heteroaryl, and
(f) C$_1$–C$_{12}$-alkyl substituted with substituted heteroaryl, or R$^5$ and R$^6$ taken together with the atom to which they are attached form a C$_3$–C$_{12}$-cycloalkyl ring; or, one of Y and Z is hydrogen and the other is selected from a group consisting of
(1) hydrogen,
(2) hydroxy,
(3) protected hydroxy, and
(4) NR$^7$R$^8$ wherein R$^7$ and R$^8$ are independently selected from hydrogen and C$_1$–C$_6$-alkyl, or R$^7$ and R$^8$ are taken with the nitrogen atom to which they are connected to form a 3- to 7-membered ring which, when the ring is a 5- to 7-membered ring, may optionally contain a hetero function selected from the group consisting of —O—, —NH—, —N(C$_1$–C$_6$-alkyl-)—, —N(aryl)—, —N(aryl-C$_1$–C$_6$-alkyl-)—, —N(substituted-aryl-C$_1$–C$_6$-alkyl-)—, —N(heteroaryl)—, —N(heteroaryl-C$_1$–C$_6$-alkyl-)—, —N(substituted-heteroaryl-C$_1$–C$_6$-alkyl-)—, and —S— or —S(O)$_n$—, wherein n is 1 or 2;

R$^a$ is hydrogen or hydroxy;
R$^c$ is hydrogen or a hydroxy protecting group;
R is selected from the group consisting of
(1) methyl substituted with a moiety selected from the group consisting of
(a) CN,
(b) F, Cl,
(c) nitro,
(d) —CHO,
(e) —OR$^9$ wherein R$^9$ is selected from the group consisting of:
(i) hydrogen
(ii) C$_1$–C$_6$-alkyl, optionally substituted with a substituent selected from the group consisting of
(aa) aryl,
(bb) substituted-aryl,
(cc) heteroaryl, and
(dd) substituted-heteroaryl,
(iii) aryl,
(iv) substituted-aryl, (v) heteroaryl,
(vi) substituted-heteroaryl, and
(vii) heterocycloalkyl,
(f) —C(O)$_L$R$^{10}$ wherein L is 1 or 2 and R$^{10}$ is selected from the group consisting of hydrogen, C$_1$–C$_3$-alkyl, C$_1$–C$_3$-alkyl substituted with aryl, and C$_1$–C$_3$-alkyl substituted with heteroaryl,
(g) S(O)$_n$R$^9$ where n is 0, 1 or 2 and R$^9$ is as previously defined,
(h) NHC(O)R$^{10}$ wherein R$^{10}$ is as previously defined,
(i) NHC(O)NR$^{11}$R$^{12}$ wherein R$^{11}$ and R$^{12}$ are independently selected from the group consisting of hydrogen, C$_1$–C$_3$-alkyl, C$_1$–C$_3$-alkyl substituted with aryl, substituted aryl, heteroaryl, and substituted heteroaryl,
(j) aryl,
(k) substituted aryl,
(l) heteroaryl,
(m) substituted heteroaryl,
(n) C$_3$–C$_8$-cycloalkyl, and
(o) substituted C$_3$–C$_8$-cycloalkyl,
(2) C$_2$–C$_{10}$-alkyl substituted with one or more substituents selected from the group consisting of
(a) halogen,
(b) hydroxy,
(c) C$_1$–C$_3$-alkoxy,
(d) C$_1$–C$_3$-alkoxy-C$_1$–C$_3$-alkoxy,
(e) oxo,
(f) —N$_3$,
(g) —CHO,
(h) O—SO$_2$-(substituted C$_1$–C$_6$-alkyl),
(i) —NR$^{13}$R$^{14}$ wherein R$^{13}$ and R$^{14}$ are selected from the group consisting of
 (i) hydrogen,
 (ii) C$_1$–C$_{12}$-alkyl,
 (iii) substituted C$_1$–C$_{12}$-alkyl,
 (iv) C$_1$–C$_{12}$-alkenyl,
 (v) substituted C$_1$–C$_{12}$-alkenyl,
 (vi) C$_1$–C$_{12}$-alkynyl,
 (vii) substituted C$_1$–C$_{12}$-alkynyl,
 (viii) aryl,
 (ix) C$_3$–C$_8$-cycloalkyl,
 (x) substituted C$_3$–C$_8$-cycloalkyl,
 (xi) substituted aryl,
 (xii) heterocycloalkyl,
 (xiii) substituted heterocycloalkyl,
 (xiv) C$_1$–C$_{12}$-alkyl substituted with aryl,
 (xv) C$_1$–C$_{12}$-alkyl substituted with substituted aryl,
 (xvi) C$_1$–C$_{12}$-alkyl substituted with heterocycloalkyl,
 (xvii) C$_1$–C$_{12}$-alkyl substituted with substituted heterocycloalkyl,
 (xviii) C$_1$–C$_{12}$-alkyl substituted with C$_3$–C$_8$-cycloalkyl,
 (xix) C$_1$–C$_{12}$-alkyl substituted with substituted C$_3$–C$_8$-cycloalkyl,
 (xx) heteroaryl,
 (xxi) substituted heteroaryl,
 (xxii) C$_1$–C$_{12}$-alkyl substituted with heteroaryl, and
 (xxiii) C$_1$–C$_{12}$-alkyl substituted with substituted heteroaryl, or
R$^{13}$ and R$^{14}$ are taken together with the atom to which they are attached form a 3–10 membered heterocycloalkyl ring which may be substituted with one or more substituents independently selected from the group consisting of
 (i) halogen,
 (ii) hydroxy,
 (iii) C$_1$–C$_3$-alkoxy,
 (iv) C$_1$–C$_3$-alkoxy-C$_1$–C$_3$-alkoxy,
 (v) oxo,
 (vi) C$_1$–C$_3$-alkyl,
 (vii) halo-C$_1$–C$_3$-alkyl, and
 (vii) C$_1$–C$_3$-alkoxy-C$_1$–C$_3$-alkyl,
(j) —CO$_2$R$^{10}$ wherein R$^{10}$ is as previously defined,
(k) —C(O)NR$^{11}$R$^{12}$ wherein R$^{11}$ and R$^{12}$ are as previously defined,
(l) =N—O—R$^{10}$ wherein R$^{10}$ is as previously defined,
(m) —CN,
(n) S(O)$_n$R$^9$ where n is 0, 1 or 2 and R$^9$ is as previously defined,
(o) O—S(O)$_n$R$^{10}$ wherein n is 0, 1 or 2 and R$^{10}$ is as previously defined,
(p) —Si—(R$^2$)(R$^3$)(R$^4$) wherein R$^2$, R$^3$ and R$^4$ are as previously defined,
(q) aryl,
(r) substituted aryl,
(s) heteroaryl,
(t) substituted heteroaryl,
(u) C$_3$–C$_8$-cycloalkyl,
(v) substituted C$_3$–C$_8$-cycloalkyl,
(w) C$_1$–C$_{12}$-alkyl substituted with heteroaryl,
(x) heterocycloalkyl,
(y) substituted heterocycloalkyl,
(z) NHC(O)R$^{10}$ where R$^{10}$ is as previously defined,
(aa) NHC(O)NR$^{11}$R$^{12}$ wherein R$^{11}$ and R$^{12}$ are as previously defined,
(bb) =N—NR$^{13}$R$^{14}$ wherein R$^{13}$ and R$^{14}$ are as previously defined,
(cc) =N—R$^9$ wherein R$^9$ is as previously defined,
(dd) =N—NHC(O)R$^{10}$ wherein R$^{10}$ is as previously defined, and
(ee) =N—NHC(O)NR$^{11}$R$^{12}$ wherein R$^{11}$ and R$^{12}$ are as previously defined;
(3) C$_3$-alkenyl substituted with a moiety selected from the group consisting of
(a) halogen,
(b) —CHO,
(c) —CO$_2$R$^{10}$ where R$^{10}$ is as previously defined,
(d) —C(O)—R$^9$ where R$^9$ is as previously defined,
(e) —C(O)NR$^{11}$R$^{12}$ wherein R$^{11}$ and R$^{12}$ are as previously defined,
(f) —CN,
(g) S(O)$_n$R$^9$ where n is 0, 1 or 2 and R$^9$ is as previously defined,
(h) —Si—(R$^2$)(R$^3$)(R$^4$) wherein R$^2$, R$^3$ and R$^4$ are as previously defined,
(i) aryl,
(j) substituted aryl,
(k) heteroaryl,
(l) substituted heteroaryl,
(m) C$_3$–C$_7$-cycloalkyl, and
(n) C$_1$–C$_{12}$-alkyl substituted with heteroaryl,
(4) C$_4$–C$_{10}$-alkenyl;
(5) C$_4$–C$_{10}$-alkenyl substituted with one or more substituents selected from the group consisting of
(a) halogen,
(b) C$_1$–C$_3$-alkoxy,
(c) oxo,
(d) —CHO, (e) —CO₂R¹⁰ where R¹⁰ is as previously defined, (f) —C(O)NR¹¹R¹² wherein R¹¹ and R¹² are as previously defined, (g) —NR¹³R¹⁴ wherein R¹³ and R¹⁴ are as previously defined, (h) =N—O—R¹⁰ where R¹⁰ is as previously defined, (i) —CN, (j) O—S(O)ₙR¹⁰ where n is 0, 1 or 2 and R¹⁰ is as previously defined, (k) aryl, (l) substituted aryl, (m) heteroaryl, (n) substituted heteroaryl, (o) C₃–C₇-cycloalkyl, (p) C₁–C₁₂-alkyl substituted with heteroaryl, (q) NHC(O)R¹⁰ where R¹⁰ is as previously defined, (r) NHC(O)NR¹¹R¹² wherein R¹¹ and R¹² are as previously defined, (s) =N—NR¹³R¹⁴ wherein R¹³ and R¹⁴ are as previously defined, (t) =N—R⁹ wherein R⁹ is as previously defined, (u) =N—NHC(O)R¹⁰ where R¹⁰ is as previously defined, and (v) =N—NHC(O)NR¹¹R¹² wherein R¹¹ and R¹² are as previously defined;

(6) C₃–C₁₀-alkynyl; and (7) C₃–C₁₀-alkynyl substituted with one or more substituents selected from the group consisting of (a) trialkylsilyl, (b) aryl, (c) substituted aryl, (d) heteroaryl, and (e) substituted heteroaryl; the method comprising:

(a) treating a compound having the formula

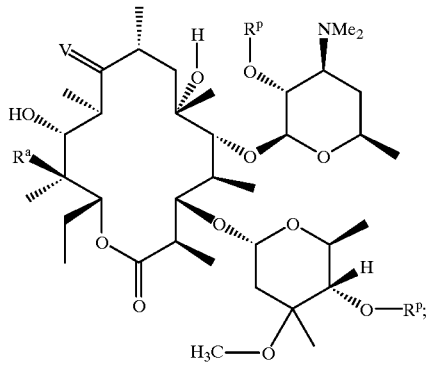

wherein R^p is a hydroxy protecting group and V is =N—O—R¹ or =N—O—C(R⁵)(R⁶)—O—R¹ wherein R¹, R⁵ and R⁶ are as previously defined, with a base in an aprotic solvent followed by treatment with an alkylating agent to give a compound having the formula

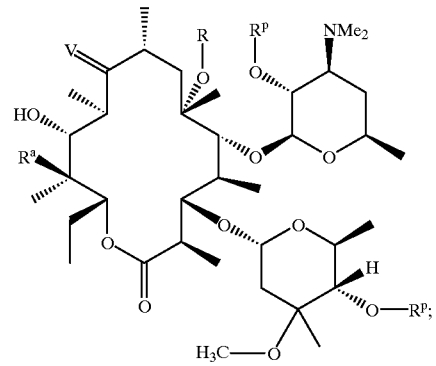

wherein R^a and R^p are as previously defined, V is =N—O—R¹ or =N—O—C(R⁵)(R⁶)—O—R¹ wherein R¹, R⁵ and R⁶ are as previously defined, and R is as defined above;

(b) deprotecting the 2'- and 4"-hydroxyl groups to give a compound of the formula

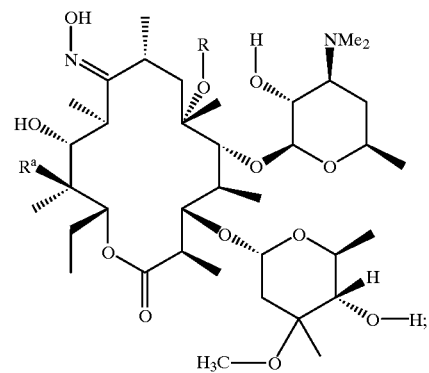

wherein R and R^a are as previously defined, derived from the corresponding alkylating agent;

(c) deoximation in the presence of acid in a suitable solvent to give the desired intermediate having the formula

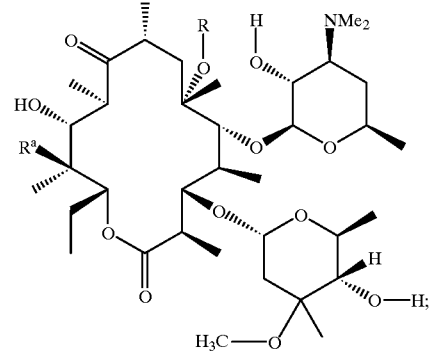

(d) removing the cladinose moiety by hydrolysis with acid, and protecting the 2'-hydroxyl group by treatment with a hydroxy-protecting reagent to give a 3-hydroxy erythromycin compound having the formula

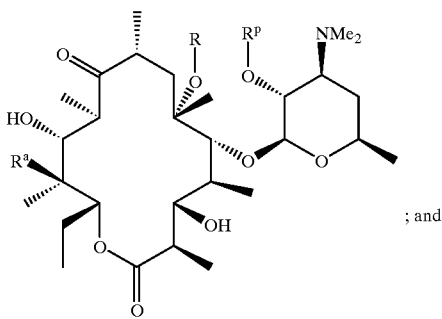

; and (e) oxidizing the 3-hydroxy group, optionally deprotecting the 2'-hydroxyl group, and isolating the desired compound.

9. The process according to claim 8 therein in step (a) the base is selected from the group consisting of potassium hydroxide, cesium hydroxide, tetraalkylammonium hydroxide, sodium hydride, potassium hydride, potassium isopropoxide, potassium tert-butoxide and potassium isobutoxide, the alkylating agent is selected from the group consisting of allyl bromide, propargyl bromide, benzyl bromide, 2-fluoroethyl bromide, 4-nitrobenzyl bromide, 4-chlorobenzyl bromide, 4-methoxybenzyl bromide, α-bromo-p-tolunitrile, cinnamyl bromide, methyl 4-bromocrotonate, crotyl bromide, 1-bromo-2-pentene, 3-bromo-1-propenyl phenyl sulfone, 3-bromo-1-trimethylsilyl-1 -propyne, 3-bromo-2-octyne, 1-bromo-2-butyne, 2-picolyl chloride, 3-picolyl chloride, 4-picolyl chloride, 4-bromomethyl quinoline, bromoacetonitrile, epichlorohydrin, bromofluoromethane, bromonitromethane, methyl bromoacetate, methoxymethyl chloride, bromoacetamide, 2-bromoacetophenone, 1-bromo-2-butanone, bromo chloromethane, bromomethyl phenyl sulfone, 1,3-dibromo-1-propene, allyl O-tosylate, 3-phenylpropyl-O-trifluoromethane sulfonate, and n-butyl-O-methanesulfonate, and the reaction is performed at a temperature from about −15° C. to about 50° C. for a period from 0.5 hours to 10 days; in step (b) deprotection is accomplished by use of acetic acid in water and acetonitrile; and in step (c) the deoximating reagent is an inorganic sulfur oxide compound selected from the group consisting of sodium hydrogen sulfite, sodium pyrosulfate, sodium thiosulfate, sodium sulfate, sodium sulfite, sodium hydrosulfite, sodium metabisulfite, sodium dithionate, potassium thiosulfate, and potassium metabisulfite, or an inorganic nitrite salt in the presence of acid selected from the group consisting of sodium nitrite and potassium nitrite, and the solvent is selected from the group consisting of water, methanol, ethanol, propanol, isopropanol, trimethylsilanol or a mixture of one or more thereof; in step (d) the hydroxy protecting reagent is selected from the group consisting of a trialkysilyl halide, an acyl anhydride or an acyl halide; and in step (e), the oxidizing agent is selected from N-chlorosuccinimide-dimethyl sulfide and carbodiimidedimethylsulfoxide.

* * * * *

UNITED STATES PATENT AND TRADEMARK OFFICE
CERTIFICATE OF CORRECTION

| | |
|---|---|
| PATENT NO. : 6,028,181 | Page 1 of 1 |
| DATED : February 22, 2000 | |
| INVENTOR(S) : Yat Sun Or et al. | |

It is certified that error appears in the above-identified patent and that said Letters Patent is hereby corrected as shown below:

<u>Column 141,</u>
Line 18, replace "to claim 8 therein in step" with -- to claim 8 wherein in step --.

Signed and Sealed this

Twenty-sixth Day of February, 2002

Attest:

JAMES E. ROGAN
*Attesting Officer*    *Director of the United States Patent and Trademark Office*